(12) United States Patent
Seifermann

(10) Patent No.: US 11,825,743 B2
(45) Date of Patent: Nov. 21, 2023

(54) ORGANIC MOLECULES FOR USE IN ORGANIC OPTOELECTRONIC DEVICES

(71) Applicant: SAMSUNG DISPLAY CO., LTD., Yongin-si (KR)

(72) Inventor: Stefan Seifermann, Bühl (DE)

(73) Assignee: Samsung Display Co., Ltd., Yongin-si (KR)

( * ) Notice: Subject to any disclaimer, the term of this patent is extended or adjusted under 35 U.S.C. 154(b) by 734 days.

(21) Appl. No.: 16/485,571

(22) PCT Filed: Sep. 26, 2017

(86) PCT No.: PCT/EP2017/074409
§ 371 (c)(1),
(2) Date: Aug. 13, 2019

(87) PCT Pub. No.: WO2018/153510
PCT Pub. Date: Aug. 30, 2018

(65) Prior Publication Data
US 2019/0393428 A1 Dec. 26, 2019

(30) Foreign Application Priority Data

Feb. 21, 2017 (DE) .......................... 102017103542.7

(51) Int. Cl.
*H10K 85/60* (2023.01)
*C07D 209/86* (2006.01)
(Continued)

(52) U.S. Cl.
CPC ....... *H10K 85/6572* (2023.02); *C07D 209/86* (2013.01); *C07D 209/88* (2013.01);
(Continued)

(58) Field of Classification Search
CPC .. C07D 403/10; C07D 403/14; C07D 519/00; C07D 401/14; C09K 11/06;
(Continued)

(56) References Cited

U.S. PATENT DOCUMENTS 9,899,609 B2 2/2018 Ren et al.
10,193,079 B2 1/2019 Stoessel et al.
(Continued)

FOREIGN PATENT DOCUMENTS

CN 105051014 A 11/2015
CN 105418486 A 3/2016
(Continued)

OTHER PUBLICATIONS

Ming-Shiang Lin "Incorporation of a CN group into mCP: a new bipolar host material for highly efficient blue and white electrophosphorescent devices" J. Mater. Chem., 2012, 22, 16114 (Year: 2012).*

(Continued)

*Primary Examiner* — Michael Y Sun
(74) *Attorney, Agent, or Firm* — Lewis Roca Rothgerber Christie LLP

(57) ABSTRACT

An organic molecule is disclosed comprising:
a first chemical unit having a structure according to Formula I (Continued)

(51) Int. Cl.
| | |
|---|---|
| C07D 495/04 | (2006.01) |
| C09K 11/06 | (2006.01) |
| H10K 50/11 | (2023.01) |
| H10K 101/10 | (2023.01) |

(52) U.S. Cl.
CPC ......... *C07D 403/14* (2013.01); *C07D 487/04* (2013.01); *C07D 491/048* (2013.01); *C07D 495/04* (2013.01); *C09K 11/06* (2013.01); *H10K 85/654* (2023.02); *H10K 85/657* (2023.02); *C09K 2211/1018* (2013.01); *H10K 50/11* (2023.02); *H10K 2101/10* (2023.02)

(58) Field of Classification Search
CPC ........ C09K 2211/1018; H01L 51/0072; H01L 51/5012; H01L 51/0508; H01L 51/42; H01L 51/0067; Y02E 10/549; H05B 33/14
See application file for complete search history.

(56) References Cited

U.S. PATENT DOCUMENTS

| | | | |
|---|---|---|---|
| 11,358,951 B2 | 6/2022 | Miyata et al. | |
| 2016/0126474 A1 | 5/2016 | Hyunjung et al. | |
| 2016/0126478 A1* | 5/2016 | Zheng | H01L 51/0067 548/440 |

FOREIGN PATENT DOCUMENTS

| | | | |
|---|---|---|---|
| CN | 106966955 A | | 7/2017 |
| JP | 2011-256143 A | | 12/2011 |
| JP | 2011256143 A | * | 12/2011 |
| KR | 10-2015-0089263 A | | 8/2015 |
| WO | 2014146752 A1 | | 9/2014 |
| WO | WO 2014/183080 A1 | | 11/2014 |
| WO | 2015175678 A1 | | 11/2015 |
| WO | 2015199303 A1 | | 12/2015 |
| WO | 2016116497 A1 | | 7/2016 |
| WO | 2016116529 A1 | | 7/2016 |
| WO | WO 2016/181846 A1 | | 11/2016 |
| WO | PCT/EP2017/074409 | | 1/2018 |

OTHER PUBLICATIONS

Office action for corresponding CN Patent Application No. 201780086696.6, dated Apr. 2, 2022, 8pp.

* cited by examiner

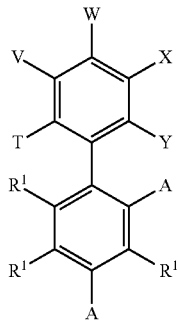

Formula I and
  two second chemical units, which are respectively the same or different in each occurrence, and have a structure according to Formula II,

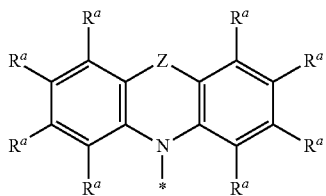

Formula II wherein, in each case, the first chemical unit is connected to the two second chemical units via a single bond.

20 Claims, 7 Drawing Sheets

ORGANIC MOLECULES FOR USE IN ORGANIC OPTOELECTRONIC DEVICES

CROSS-REFERENCE TO RELATED APPLICATIONS

This application claims priority under 35 U.S.C. § 371 to International Application No. PCT/EP2017/074409, filed Sep. 26, 2017, which claims priority to German Patent Application No. 10 2017 103 542.7 filed Feb. 21, 2017, the disclosures of which are incorporated by reference herein in their entireties.

FIELD OF INVENTION

The invention relates to purely organic molecules and the use thereof in organic light-emitting diodes (OLEDs) and in other organic optoelectronic devices.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Figure 1:
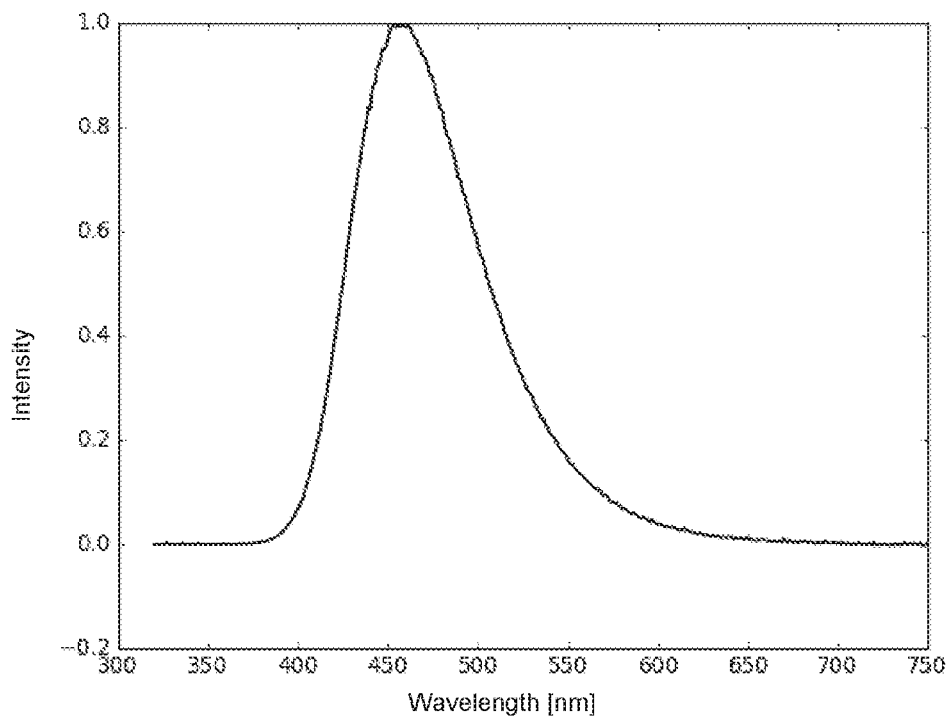
FIG. 1 is an emission spectrum of Example 1 (10% in PMMA).

Exemplary embodiments of the invention will now be discussed in further detail. This invention may, however, be embodied in many different forms and should not be construed as limited to the embodiments set forth herein.

The underlying object of the present invention was to provide molecules which are suitable for use in optoelectronic devices.

This object is achieved through the invention to provide a new class of organic molecules.

The organic molecules according to the invention are purely organic molecules; i.e. they do not have any metal ions, and thus differ from the metal complex compounds known for use in organic optoelectronic devices.

The organic molecules according to the invention are characterized by emissions in the blue, sky blue, or green spectral range. The photoluminescence quantum yields of the organic molecules according to the invention are, in particular, 20% and more. The molecules according to the invention in particular exhibit thermally activated delayed fluorescence (TADF). The use of the molecules according to the invention in an optoelectronic device, for example an organic light-emitting diode (OLED), results in higher efficiencies of the device. Corresponding OLEDs have a higher stability than OLEDs having known emitter materials and comparable color.

The blue spectral range here is understood to be the visible range from 420 nm to 470 nm. The sky blue spectral range is understood here to be the range between 470 nm and 499 nm. The green spectral range is understood here to be the range between 500 nm and 599 nm. The emission maximum is in the respective range.

The organic molecules contain a first chemical unit comprising a structure according to Formula I or consisting of a structure according to Formula I,

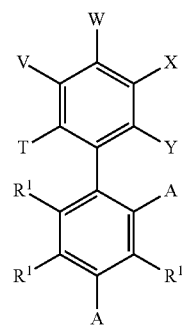

Formula I and
two second chemical units D, which are respectively the same or different in each occurrence, comprising or consisting of a structure according to Formula II,

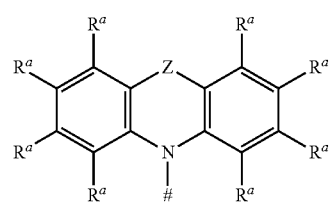

Formula II

The first chemical unit is thereby respectively connected to the two second chemical units D via a single bond.

T is the point of attachment of the single bond between the chemical unit as per Formula I and a chemical unit or is H.

V is the point of attachment of the single bond between the chemical unit as per Formula I and a chemical unit D or is H.

W is the point of attachment of the single bond between the chemical unit as per Formula I and a chemical unit D or is selected from the group consisting of H, CN and $CF_3$.

X is the point of attachment of the single bond between the chemical unit as per Formula I and a chemical unit or is selected from the group consisting of H, CN and $CF_3$.

Y is the point of attachment of the single bond between the chemical unit as per Formula I and a chemical unit D or is selected from the group consisting of H, CN and $CF_3$;

\#is the point of attachment of the single bond between the respective second chemical unit D and the chemical unit as per Formula I.

Z is the same or different in each occurrence as a direct bond or is selected from the group consisting of $CR^3R^4$, $C=CR^3R^4$, $C=O$, $C=NR^3$, $NR^3$, $O$, $SiR^3R^4$, $S$, $S(O)$ and $S(O)_2$.

In each occurrence, A is selected from the group consisting of CN and $CF_3$, wherein one of the two As is $CF_3$ and the other A is CN. It is therefore not possible for A to be CN in both cases, or to be $CF_3$ in both cases.

In each occurrence $R^1$ is the same or different and is H, deuterium, a linear alkyl group having 1 to 5 C atoms, wherein in each case one or more H atoms can be replaced by deuterium; a linear alkenyl or alkynyl group having 2 to 8 C atoms, wherein in each case one or more H atoms can be replaced by deuterium; a branched or cyclic alkyl, alkenyl or alkynyl group having 3 to 10 C atoms, wherein in each case one or more H atoms can be replaced by deuterium, or an aromatic or heteroaromatic ring system having 5 to 15 aromatic ring atoms, which can in each case be substituted with one or more radicals $R^6$.

In each occurrence, $R^a$, $R^3$ and $R^4$ is the same or different and is H, deuterium, $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 C atoms, which can in each case be substituted with one or more radicals $R^5$, wherein one or more non-adjacent $CH_2$ groups can be replaced by $R^5C=CR^5$; $C≡C$, $Si(R^5)_2$, $Ge(R^5)_2$; $Sn(R^5)_2$, $C=O$, $C=S$, $C=Se$, $C=NR^5$, $P(=O)(R^5)$; SO, $SO_2$, $NR^5$, O, S or $CONR^5$ and wherein one or more H atoms can be replaced by deuterium, CN, $CF_3$ or $NO_2$;

or a linear alkenyl or alkynyl group having 2 to 40 C atoms, which can in each case be substituted with one or more radicals $R^5$, wherein one or more non-adjacent $CH_2$ groups can be replaced by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;

or a branched or cyclic alkyl, alkenyl, alkynyl, alkoxy or thioalkoxy group having 3 to 40 C atoms, which can in each case be substituted with one or more radicals $R^5$, wherein one or more non-adjacent $CH_2$ groups can be replaced by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;

or an aromatic or heteroaromatic ring system having 5 to 60 aromatic ring atoms, which can in each case be substituted with one or more radicals $R^5$;

or an aryloxy or heteroaryloxy group having 5 to 60 aromatic ring atoms, which can be substituted with one or more radicals $R^5$;

or a diarylamino group, diheteroarylamino group or arylheteroarylamino group having 10 to 40 aromatic ring atoms, which can be substituted with one or more radicals $R^5$.

In each occurrence, $R^5$ is the same or different and is H, Deuterium, $N(R^6)_2$, OH, $Si(R^6)_3$, $B(OR^6)_2$, $OSO_2R^6$, $CF_3$, CN, F, Br, I, a linear alkyl, alkoxy or thioalkoxy group having 1 to 40 C atoms, which can in each case be substituted with one or more radicals $R^6$, wherein one or more non-adjacent $CH_2$ groups can be replaced by $R^6C=CR^6$, $C≡C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$ and wherein one or more H atoms can be replaced by deuterium, CN, $CF_3$ or $NO_2$ and wherein one or more H atoms can be replaced by deuterium, CN, $CF_3$ or $NO_2$;

or a linear alkenyl or alkynyl group having 2 to 40 C atoms, which can in each case be substituted with one or more radicals $R^6$, wherein one or more non-adjacent $CH_2$ groups can be replaced by $R^6C=CR^6$, $C≡C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$ and wherein one or more H atoms can be replaced by deuterium, CN, $CF_3$ or $NO_2$ and wherein one or more H atoms can be replaced by deuterium, CN, $CF_3$ or $NO_2$ or a branched or cyclic alkyl, alkenyl, alkynyl, alkoxy or thioalkoxy group having 3 to 40 C atoms, which can in each case be substituted with one or more radicals $R^6$, wherein one or more non-adjacent $CH_2$ groups can be replaced by $R^6C=CR^6$, $C≡C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$ and wherein one or more H atoms can be replaced by deuterium, CN, $CF_3$ or $NO_2$;

or an aromatic or heteroaromatic ring system having 5 to 60 aromatic ring atoms, which can in each case be substituted with one or more radicals $R^6$;

or an aryloxy or heteroaryloxy group having 5 to 60 aromatic ring atoms, which can be substituted with one or more radicals $R^6$;

or a diarylamino group, diheteroarylamino group or arylheteroarylamino group having 10 to 40 aromatic ring atoms, which can be substituted with one or more radicals $R^6$.

In each occurrence, $R^6$ is the same or different and is H, Deuterium, OH, $CF_3$, CN, F, a linear alkyl, alkoxy or thioalkoxy group having 1 to 5 C atoms, wherein one or more H atoms can respectively be replaced by deuterium, CN, $CF_3$ or $NO_2$;

or a linear alkenyl or alkynyl group having 2 to 5 C atoms, wherein one or more H atoms can respectively be replaced by deuterium, CN, $CF_3$ or $NO_2$;

or a branched or cyclic alkyl, alkenyl, alkynyl, alkoxy or thioalkoxy group having 3 to 5 C atoms, wherein one or more H atoms can respectively be replaced by deuterium, CN, $CF_3$ or $NO_2$;

or an aromatic or heteroaromatic ring system having 5 to 60 aromatic ring atoms:

or an aryloxy or heteroaryloxy group having 5 to 60 aromatic ring atoms;

or a diarylamino group, diheteroarylamino group or arylheteroarylamino group having 10 to 40 aromatic ring atoms.

According to the invention, each of the radicals $R^a$, $R^3$, $R^4$ or $R^5$ can also form a mono- or polycyclic, aliphatic, aromatic and/or benzoannelated ring system with one or more further radicals $R^a$, $R^3$, $R^4$ or $R^5$.

According to the invention, exactly one radical selected from W, X and Y is CN or $CF_3$ and exactly two radicals selected from the group consisting of T, V, W, X and Y are a point of attachment of a single bond between the chemical unit as per Formula I and a chemical unit D.

In a further embodiment, the organic molecules according to the invention have a structure of Formula Ia or consist of a structure of Formula Ia:

Formula Ia

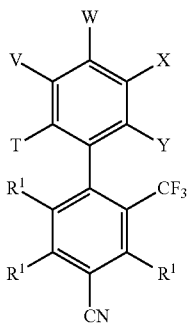

wherein the definitions stated for Formula I and II apply for R¹, T, V, W, X, and Y.

In one embodiment, R¹ is the same or different in each occurrence and is H, methyl or phenyl.

In one embodiment, W is CN.

In a further embodiment of the organic molecules, in each occurrence the second chemical group D is the same or different comprising a structure of Formula IIa or consisting of a structure of Formula IIa:

Formula IIa

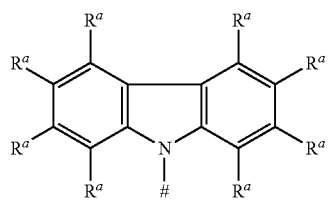

wherein the definitions stated for Formula I and II apply for # and $R^a$.

In a further embodiment of the organic molecules according to the invention, in each occurrence the second chemical unit D is the same or different comprising a structure of Formula IIb, Formula IIb-2, Formula IIb-3 or Formula IIb-4 or consisting thereof:

Formula IIb

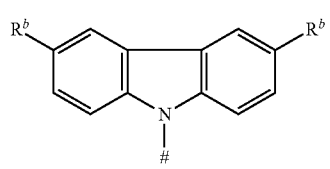

Formula IIb-2

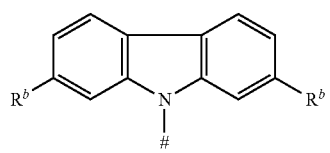

Formula IIb-3

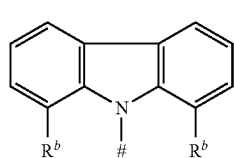

Formula IIb-4

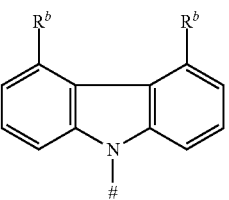

wherein the following applies

In each occurrence, $R^b$ is the same or different and is $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 C atoms, which can in each case be substituted with one or more radicals $R^5$, wherein one or more non-adjacent $CH_2$ groups can be replaced by $R^5C=CR^5$, C≡C, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;

or a linear alkenyl or alkynyl group having 2 to 40 C atoms, which can in each case be substituted with one or more radicals $R^5$, wherein one or more non-adjacent $CH_2$ groups can be replaced by $R^5C=CR^5$, C≡C, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;

or a branched or cyclic alkyl, alkenyl, alkynyl, alkoxy or thioalkoxy group having 3 to 40 C atoms, which can in each case be substituted with one or more radicals $R^5$, wherein one or more non-adjacent $CH_2$ groups can be replaced by $R^5C=CR^5$, C≡C, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;

or an aromatic or heteroaromatic ring system having 5 to 60 aromatic ring atoms, which can in each case be substituted with one or more radicals $R^5$;

or an aryloxy or heteroaryloxy group having 5 to 60 aromatic ring atoms, which can be substituted with one or more radicals $R^5$;

or a diarylamino group, diheteroarylamino group or aryl-heteroarylamino group having 10 to 40 aromatic ring atoms, which can be substituted with one or more radicals $R^5$. Otherwise, the above-mentioned definitions apply.

In a further embodiment of the organic molecules according to the invention, in each occurrence the second chemical unit D is the same or different comprising a structure of Formula IIc, Formula IIc-2, Formula IIc-3 or Formula IIc-4 or consisting thereof:

Formula IIc

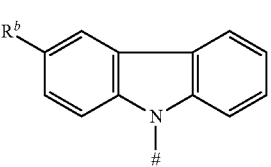

-continued

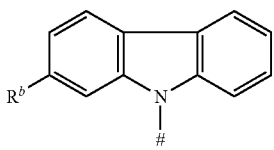

Formula IIc-2

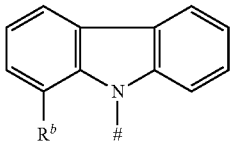

Formula IIc-3

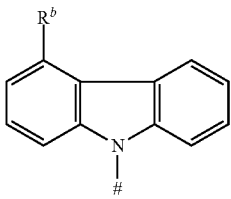

Formula IIc-4 wherein the abovementioned definitions apply.

In a further embodiment of the organic molecules according to the invention, in each occurrence $R^b$ is independently selected from the group consisting of Me, $^i$Pr, $^t$Bu, CN, CF$_3$, Ph, which can in each case be substituted with one or more radicals selected from Me, $^i$Pr, $^t$Bu, CN, CF$_3$ or Ph, pyridinyl, which can in each case be substituted with one or more radicals selected from Me, $^i$Pr, $^t$Bu, CN, CF$_3$ or Ph, pyrimidinyl, which can in each case be substituted with one or more radicals selected from Me, $^i$Pr, $^t$Bu, CN, CF$_3$ or Ph, carbazolyl, which can in each case be substituted with one or more radicals selected from Me, $^i$Pr, $^t$Bu, CN, CF$_3$ or Ph, triazinyl, which can in each case be substituted with one or more radicals selected from Me, $^i$Pr, $^t$Bu, CN, CF$_3$ or Ph, and N(Ph)$_2$.

Embodiments of chemical Group D are shown in the following as examples:

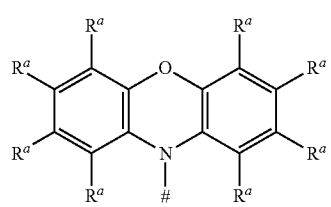

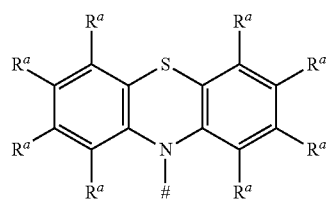

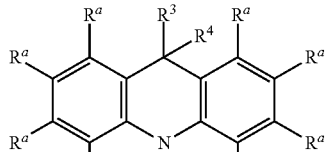

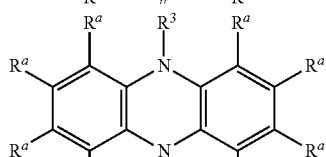

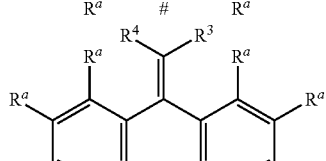

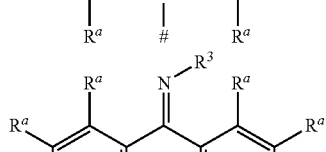

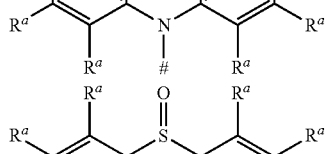

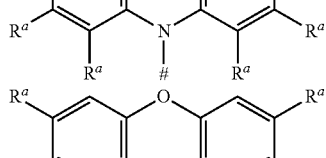

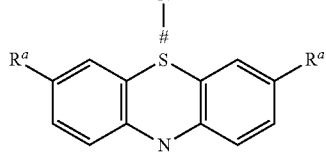

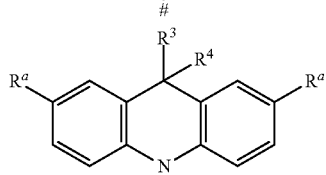

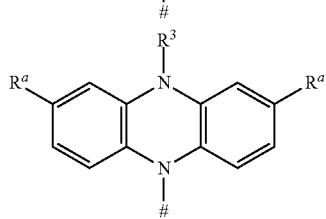

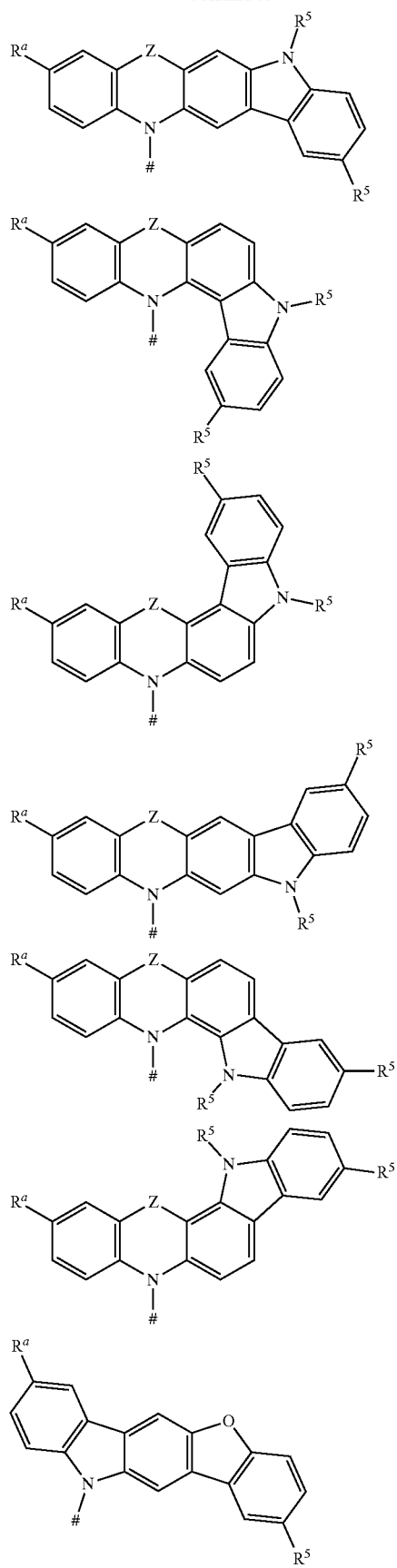
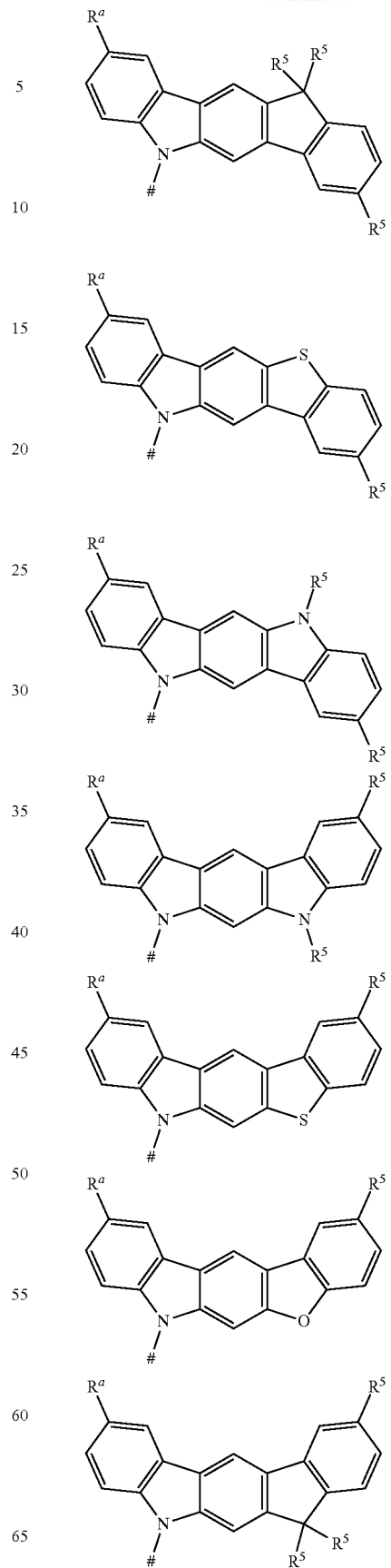

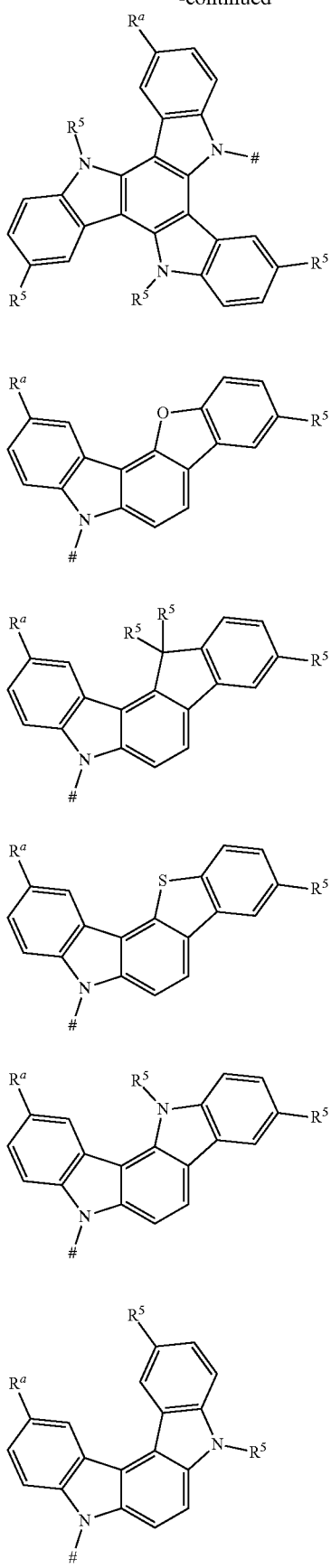
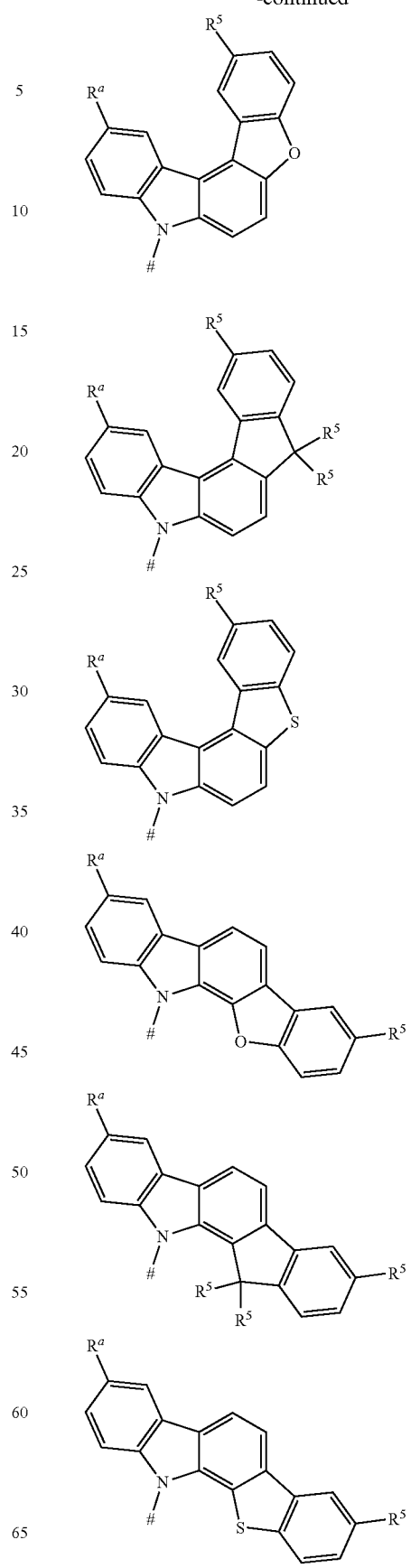

-continued

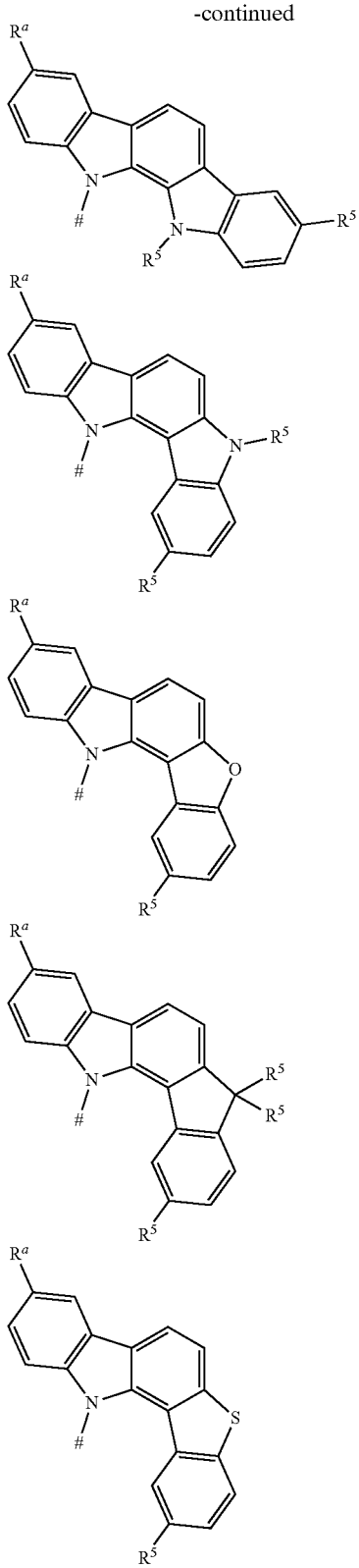

wherein the abovementioned definitions apply for #, Z, $R^a$, $R^3$, $R^4$ and $R^5$. In one embodiment, in each occurrence, the radical $R^5$ is the same or different and is selected from the group consisting of H, methyl, ethyl, phenyl and mesityl. In one embodiment, in each occurrence, the radical $R^a$ is the same or different and is selected from the group consisting of H, methyl (Me), i-propyl ($CH(CH_3)_2$) ($^iPr$), t-butyl ($^tBu$), phenyl (Ph), CN, $CF_3$ and diphenylamine ($NPh_2$).

In one embodiment, the organic molecules according to the invention have a structure of Formula III-1 or Formula III-2:

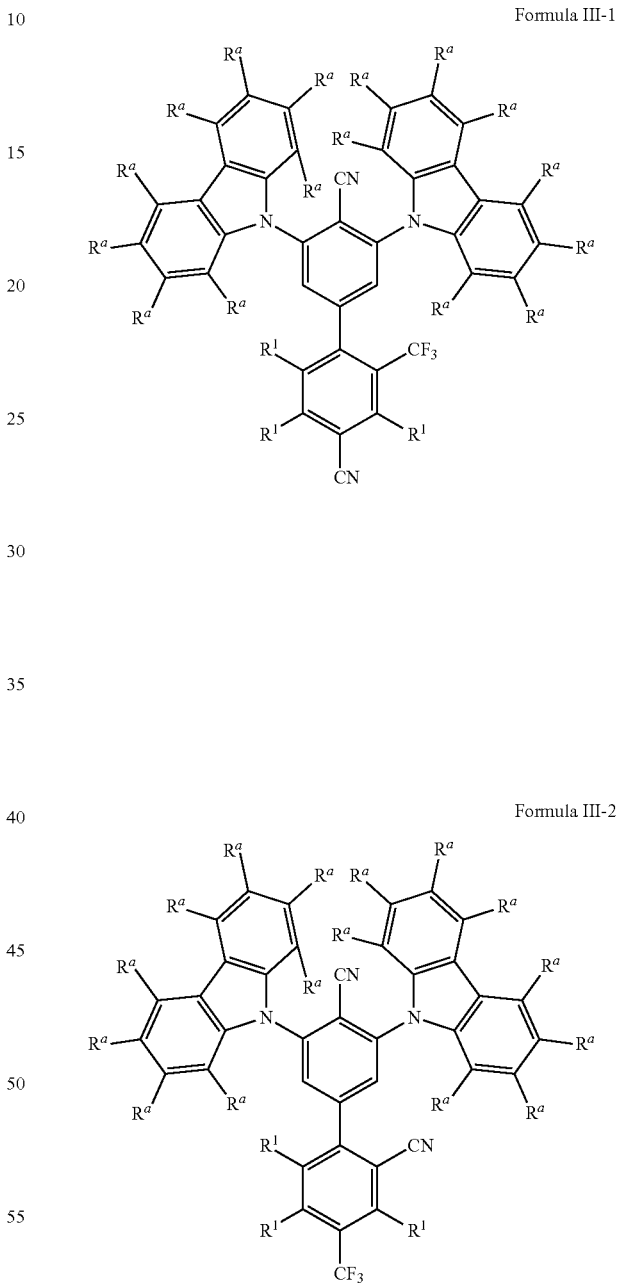

wherein the abovementioned definitions apply.

In a further embodiment, the organic molecules according to the invention have a structure of Formula III-1, wherein the definitions stated for Formulas III-1 to III-2 apply.

In a further embodiment, the organic molecules according to the invention have a structure of Formula IIIa-1 or Formula IIIa-2:

Formula IIIa-1

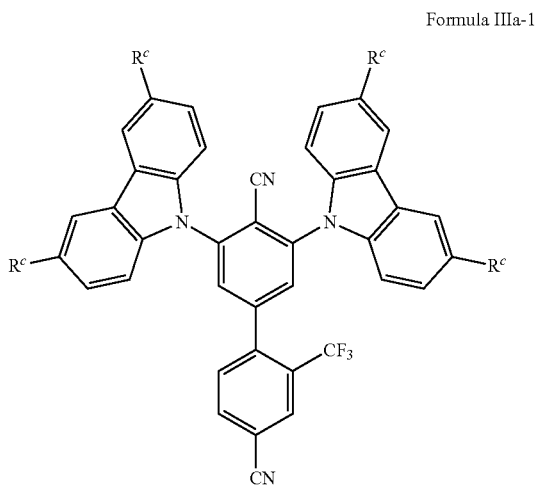

Formula IIIb-1

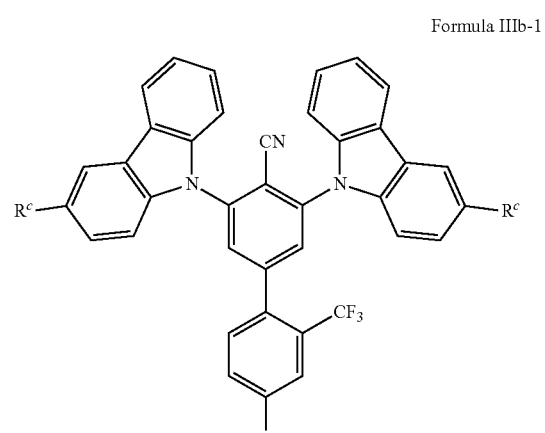

Formula IIIa-2

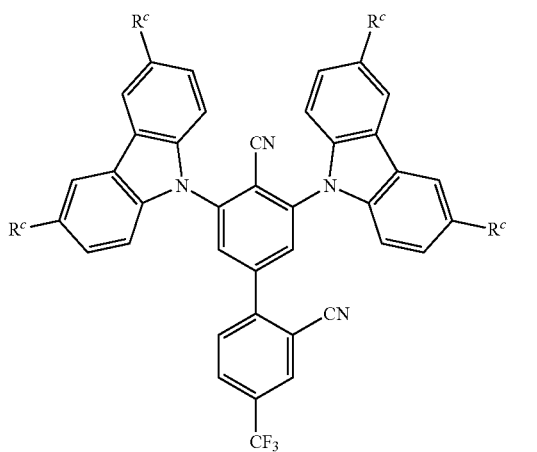

Formula IIIb-2

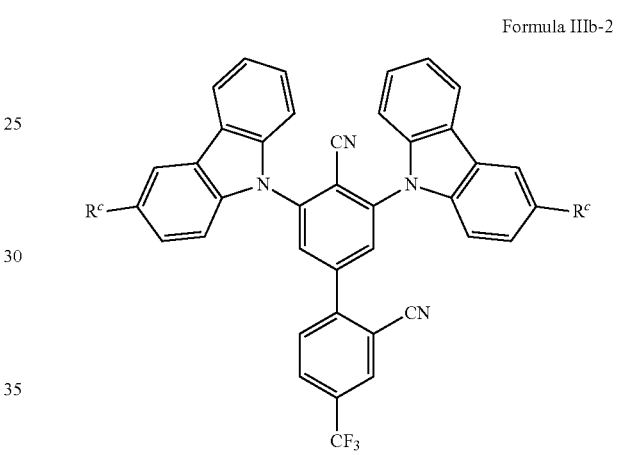

wherein the abovementioned definitions apply.

In a further embodiment, the organic molecules according to the invention have a structure of Formula IIIb-1, wherein the abovementioned definitions apply.

In a further embodiment, the organic molecules according to the invention have a structure of Formula IIIc-1 or Formula IIIc-2:

wherein in each occurrence, $R^c$ is independently selected from the group consisting of Me, $^i$Pr, $^t$Bu, CN, $CF_3$, Ph, which can in each case be substituted with one or more radicals selected from Me, $^i$Pr, $^t$Bu, CN, $CF_3$ or Ph, pyridinyl, which can in each case be substituted with one or more radicals selected from Me, $^i$Pr, $^t$Bu, CN, $CF_3$ or Ph, pyrimidinyl, which can in each case be substituted with one or more radicals selected from Me, $^i$Pr, $^t$Bu, CN, $CF_3$ or Ph, carbazolyl, which can in each case be substituted with one or more radicals selected from Me, $^i$Pr, $^t$Bu, CN, $CF_3$ or Ph, triazinyl, which can in each case be substituted with one or more radicals selected from Me, $^i$Pr, $^t$Bu, CN, $CF_3$ or Ph, and is $N(Ph)_2$.

In a further embodiment, the organic molecules according to the invention have a structure of Formula IIIa-1, wherein the abovementioned definitions apply.

In a further embodiment, the organic molecules according to the invention have a structure of Formula IIIb-1 or Formula IIIb-2:

Formula IIIc-1

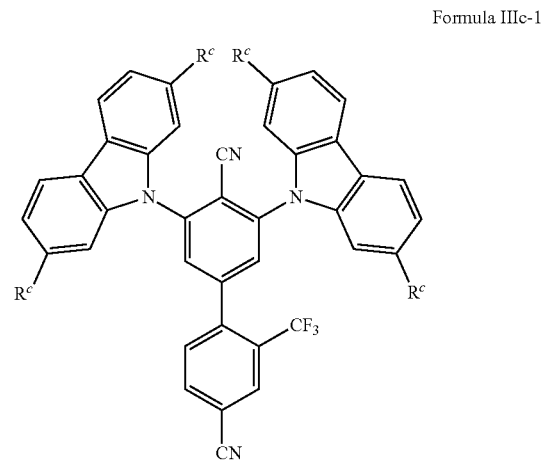

-continued

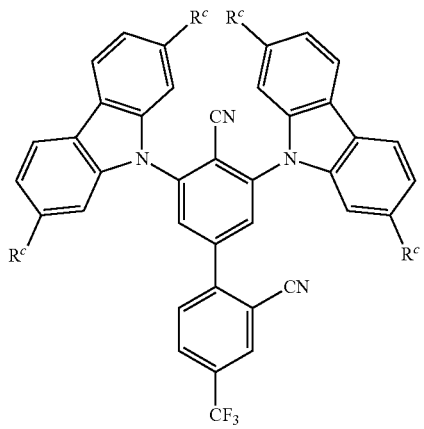

Formula IIIc-2 wherein the abovementioned definitions apply.

In a further embodiment, the organic molecules according to the invention have a structure of Formula IIIc-1, wherein the abovementioned definitions apply.

In a further embodiment, the organic molecules according to the invention have a structure of Formula IIId-1 or Formula IIId-2:

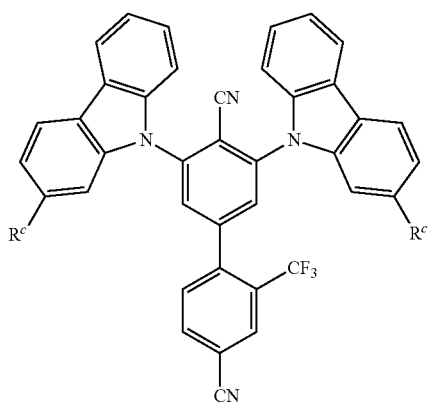

Formula IIId-1

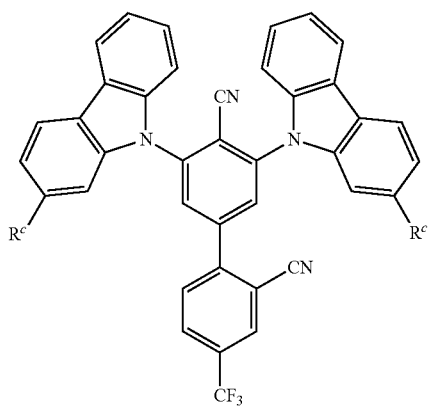

Formula IIId-2 wherein the abovementioned definitions apply.

In a further embodiment, the organic molecules according to the invention have a structure of Formula IIId-1, wherein the abovementioned definitions apply.

In a further embodiment, the organic molecules according to the invention have a structure of Formula IIIe-1 or Formula IIIe-2:

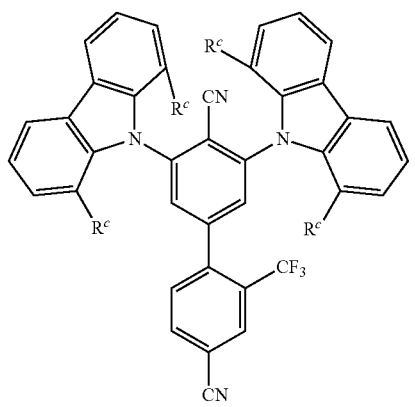

Formula IIIe-1

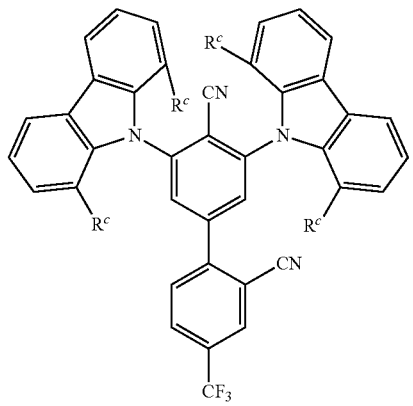

Formula IIIe-2 wherein the abovementioned definitions apply.

In a further embodiment, the organic molecules according to the invention have a structure of Formula IIIe-1, wherein the abovementioned definitions apply.

In a further embodiment, the organic molecules according to the invention have a structure of Formula IIIf-1 or Formula IIIf-2:

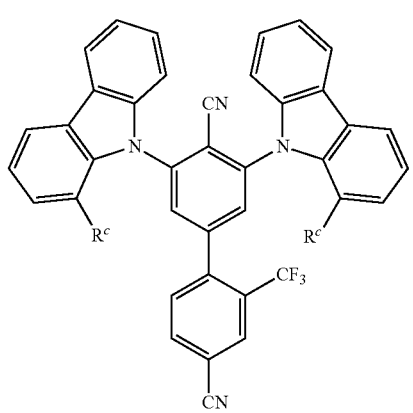

Formula IIIf-1

Formula IIIf-2

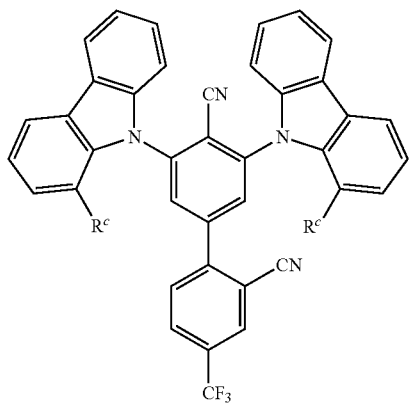

wherein the abovementioned definitions apply.

In a further embodiment, the organic molecules according to the invention have a structure of Formula IIIf-1, wherein the abovementioned definitions apply.

In a further embodiment, the organic molecules according to the invention have a structure of Formula IIIg-1 or Formula IIIg-2:

Formula IIIg-1

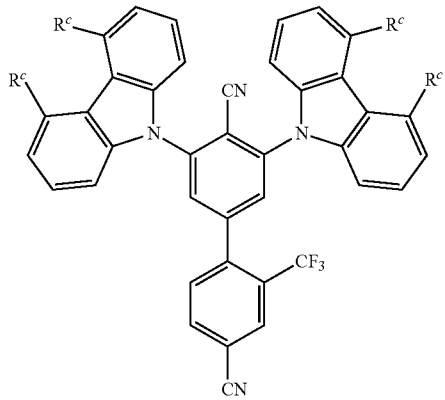

Formula IIIg-2

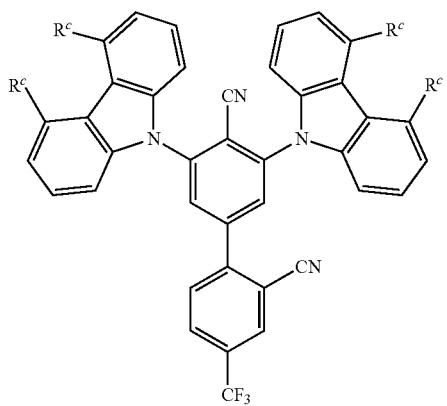

wherein the abovementioned definitions apply.

In a further embodiment, the organic molecules according to the invention have a structure of Formula IIIg-1, wherein the abovementioned definitions apply.

In a further embodiment, the organic molecules according to the invention have a structure of Formula IIIh-1 or Formula IIIh-2:

Formula IIIh-1

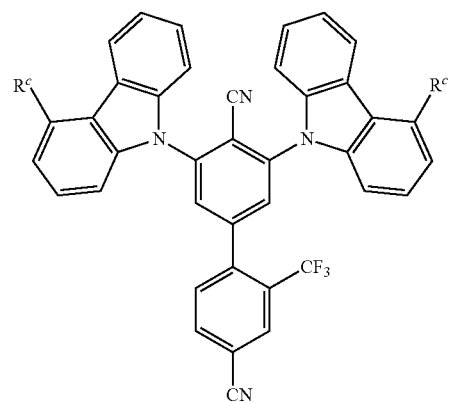

Formula IIIh-2

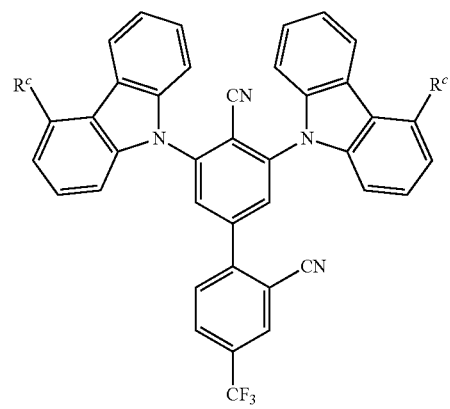

wherein the abovementioned definitions apply.

In a further embodiment, the organic molecules according to the invention have a structure of Formula IIIh-1, wherein the abovementioned definitions apply.

In one embodiment, the organic molecules according to the invention have a structure of Formula IV-1 or Formula IV-2:

Formula IV-1

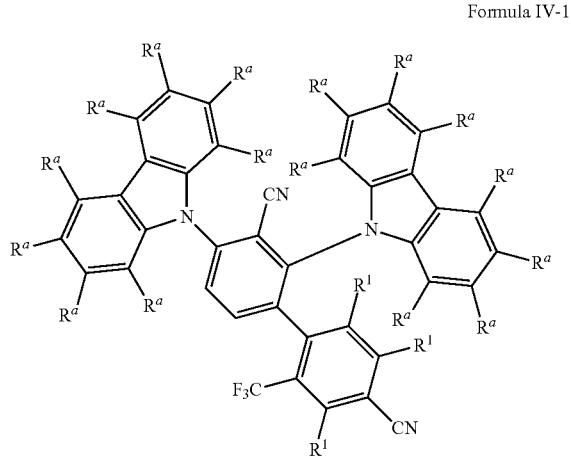

-continued

Formula IV-2

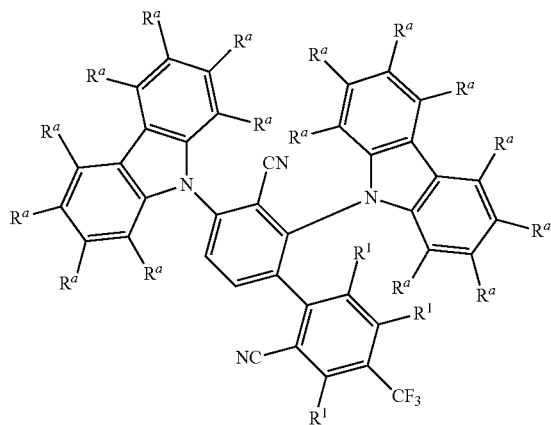

wherein the abovementioned definitions apply.

In one embodiment, the organic molecules according to the invention have a structure of Formula IV-1, wherein the abovementioned definitions apply.

In a further embodiment, the organic molecules according to the invention have a structure of Formula IVa-1 or Formula IVa-2:

Formula IVa-1

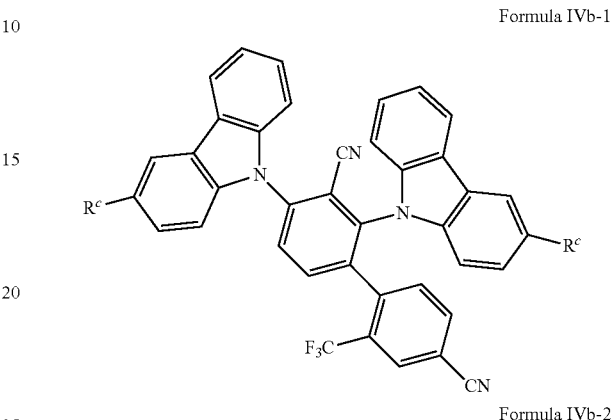

Formula IVa-2 wherein the abovementioned definitions apply.

In a further embodiment, the organic molecules according to the invention have a structure of Formula IVa-1, wherein the abovementioned definitions apply.

In a further embodiment, the organic molecules according to the invention have a structure of Formula IVb-1 or Formula IVb-2:

Formula IVb-1

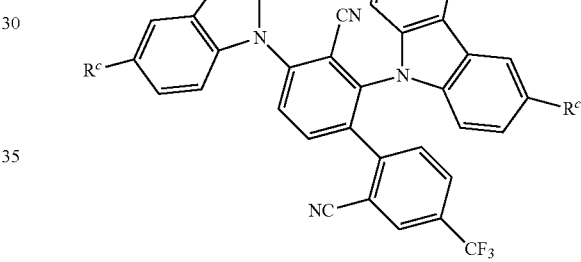

Formula IVb-2 wherein the abovementioned definitions apply.

In a further embodiment, the organic molecules according to the invention have a structure of Formula IVb-1, wherein the abovementioned definitions apply.

In a further embodiment, the organic molecules according to the invention have a structure of Formula IVc-1 or Formula IVc-2:

Formula IVc-1

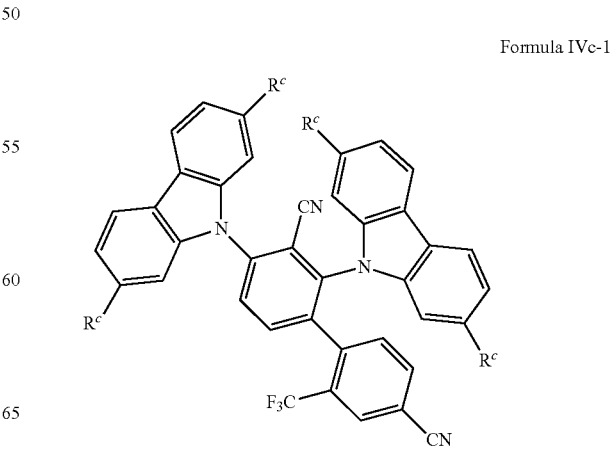

Formula IVc-2

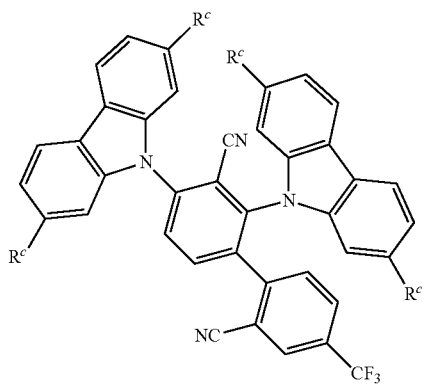

wherein the abovementioned definitions apply.

In a further embodiment, the organic molecules according to the invention have a structure of Formula IVc-1, wherein the abovementioned definitions apply.

In a further embodiment, the organic molecules according to the invention have a structure of Formula IVd-1 or Formula IVd-2:

Formula IVd-1

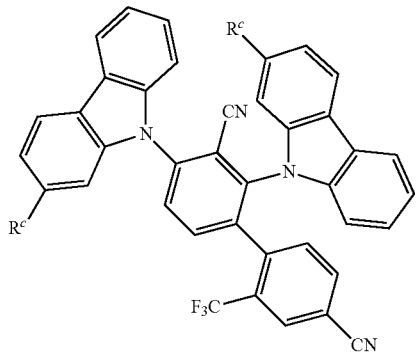

Formula IVd-2

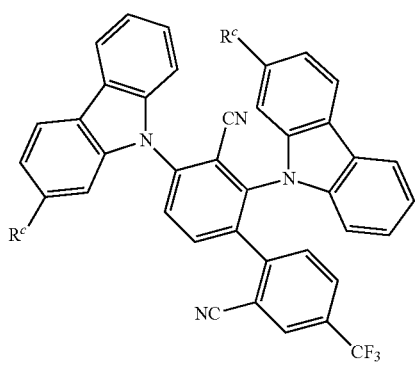

wherein the abovementioned definitions apply.

In a further embodiment, the organic molecules according to the invention have a structure of Formula IVd-1, wherein the abovementioned definitions apply.

In a further embodiment, the organic molecules according to the invention have a structure of Formula IVe-1 or Formula IVe-2:

Formula IVe-1

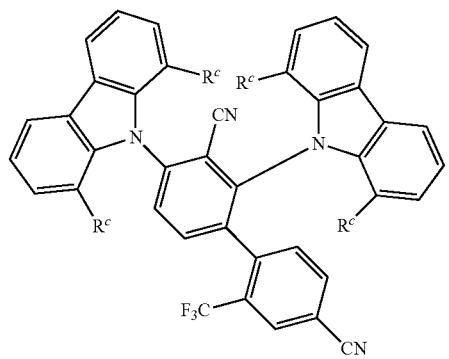

Formula IVe-2

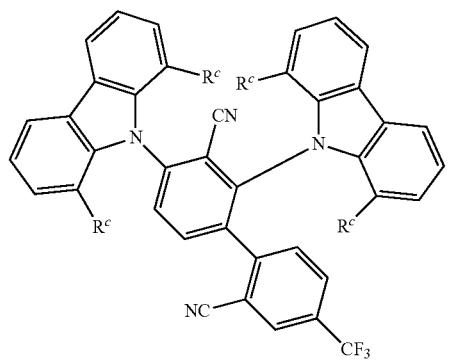

wherein the abovementioned definitions apply.

In a further embodiment, the organic molecules according to the invention have a structure of Formula IVe-1, wherein the abovementioned definitions apply.

In a further embodiment, the organic molecules according to the invention have a structure of Formula IVf-1 or Formula IVf-2:

Formula IVf-1

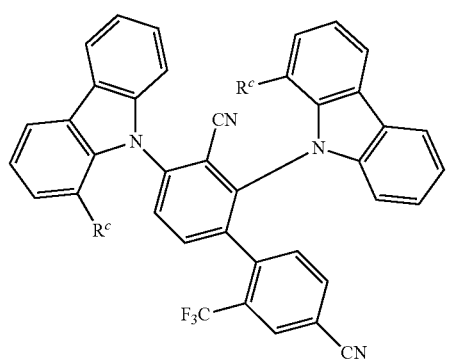

Formula IVf-2

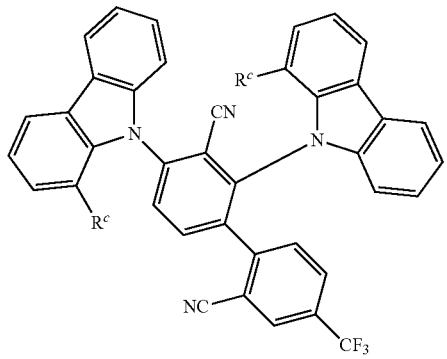

wherein the abovementioned definitions apply.

In a further embodiment, the organic molecules according to the invention have a structure of Formula IVf-1, wherein the abovementioned definitions apply.

In a further embodiment, the organic molecules according to the invention have a structure of Formula IVg-1 or Formula IVg-2:

Formula IVg-1

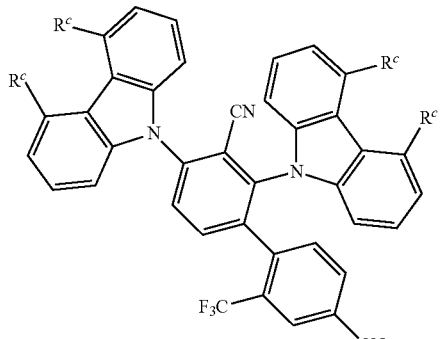

Formula IVg-2

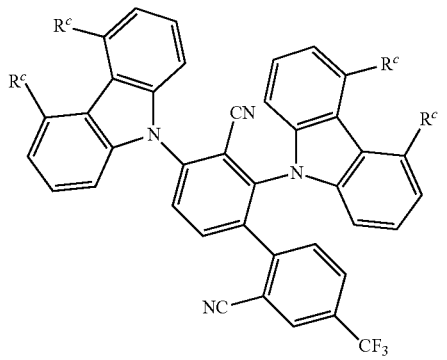

wherein the abovementioned definitions apply.

In a further embodiment, the organic molecules according to the invention have a structure of Formula IVg-1, wherein the abovementioned definitions apply.

In a further embodiment, the organic molecules according to the invention have a structure of Formula IVh-1 or Formula IVh-2:

Formula IVh-1

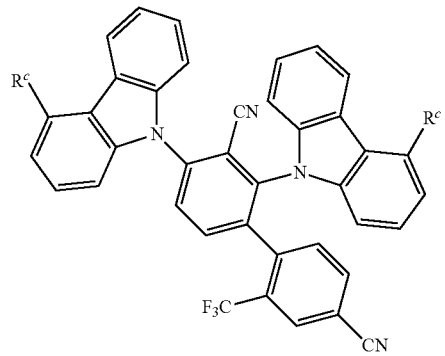

Formula IVh-2

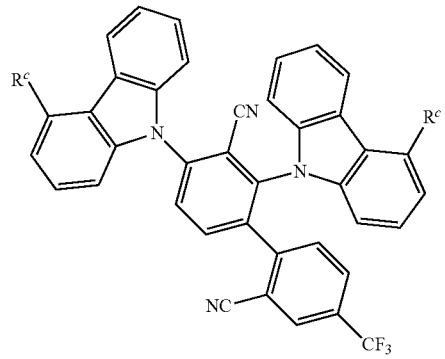

wherein the abovementioned definitions apply.

In a further embodiment, the organic molecules according to the invention have a structure of Formula IVh-1, wherein the abovementioned definitions apply.

In a further embodiment, the organic molecules according to the invention have a structure of Formula V-1 or Formula V-2:

Formula V-1

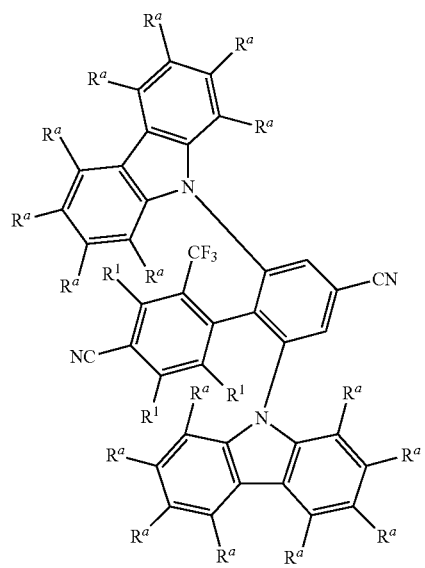

Formula V-2

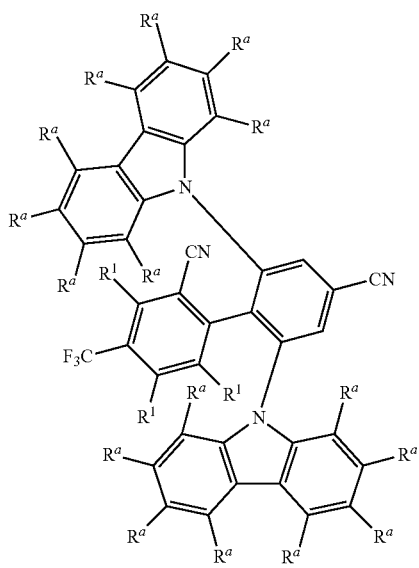

wherein the abovementioned definitions apply.

In a further embodiment, the organic molecules according to the invention have a structure of Formula V-1, wherein the abovementioned definitions apply.

In a further embodiment, the organic molecules according to the invention have a structure of Formula Va-1 or Formula Va-2:

Formula Va-1

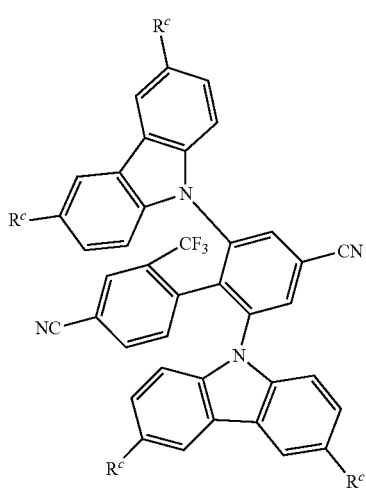

Formula Va-2

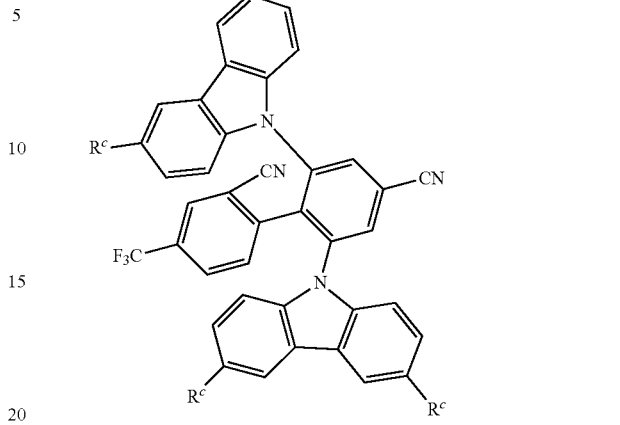

wherein the abovementioned definitions apply.

In a further embodiment, the organic molecules according to the invention have a structure of Formula Va-1, wherein the abovementioned definitions apply.

In a further embodiment, the organic molecules according to the invention have a structure of Formula Vb-1 or Formula Vb-2:

Formula Vb-1

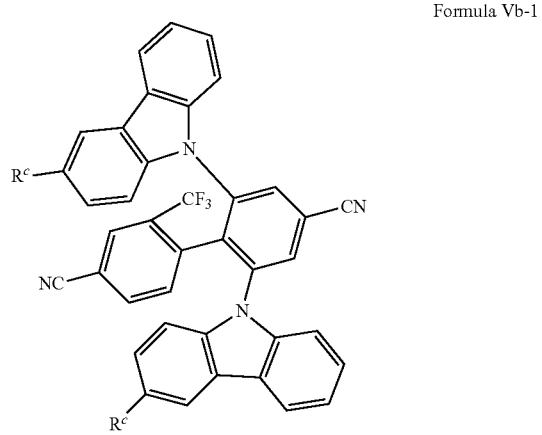

Formula Vb-2

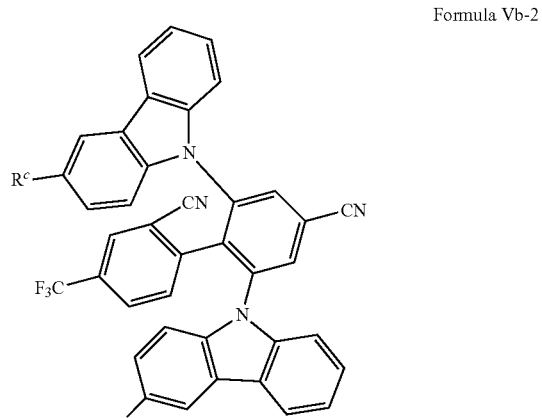

wherein the abovementioned definitions apply.

In a further embodiment, the organic molecules according to the invention have a structure of Formula Vb-1, wherein the abovementioned definitions apply.

In a further embodiment, the organic molecules according to the invention have a structure of Formula Vc-1 or Formula Vc-2:

Formula Vc-1

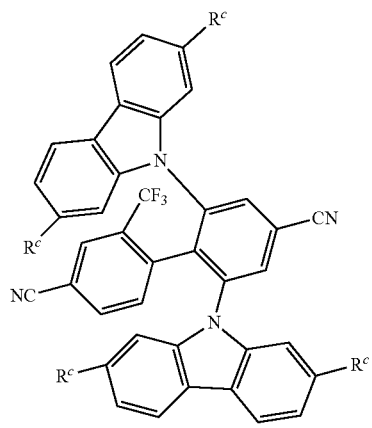

Formula Vc-2

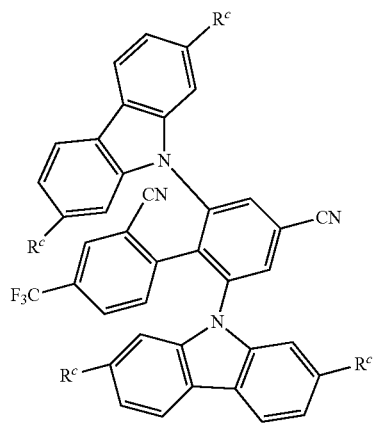

wherein the abovementioned definitions apply.

In a further embodiment, the organic molecules according to the invention have a structure of Formula Vc-1, wherein the abovementioned definitions apply.

In a further embodiment, the organic molecules according to the invention have a structure of Formula Vd-1 or Formula Vd-2:

Formula Vd-1

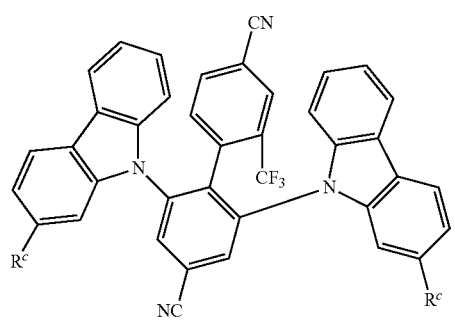

Formula Vd-2

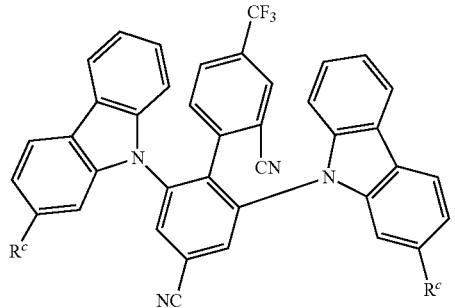

wherein the abovementioned definitions apply.

In a further embodiment, the organic molecules according to the invention have a structure of Formula Vd-1, wherein the abovementioned definitions apply.

In a further embodiment, the organic molecules according to the invention have a structure of Formula Ve-1 or Formula Ve-2:

Formula Ve-1

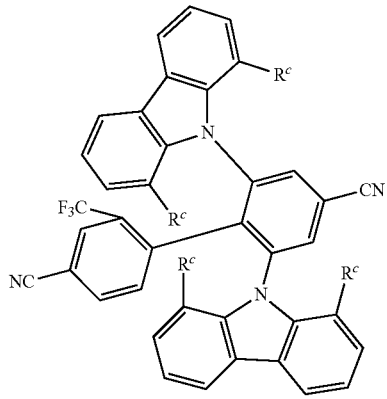

Formula Ve-2

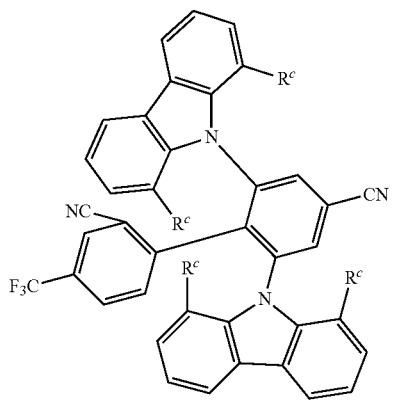

wherein the abovementioned definitions apply.

In a further embodiment, the organic molecules according to the invention have a structure of Formula Ve-1, wherein the abovementioned definitions apply.

In a further embodiment, the organic molecules according to the invention have a structure of Formula Vf-1 or Formula Vf-2:

Formula Vf-1

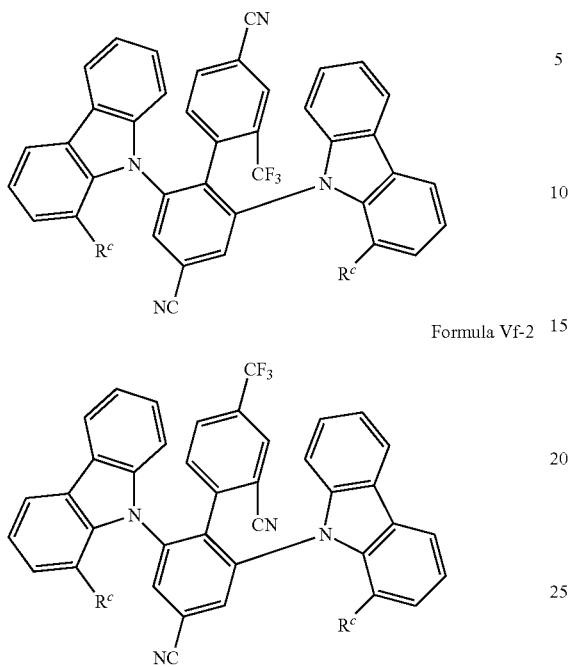

Formula Vf-2 wherein the abovementioned definitions apply.

In a further embodiment, the organic molecules according to the invention have a structure of Formula Vf-1, wherein the abovementioned definitions apply.

In a further embodiment, the organic molecules according to the invention have a structure of Formula Vg-1 or Formula Vg-2:

Formula Vg-1

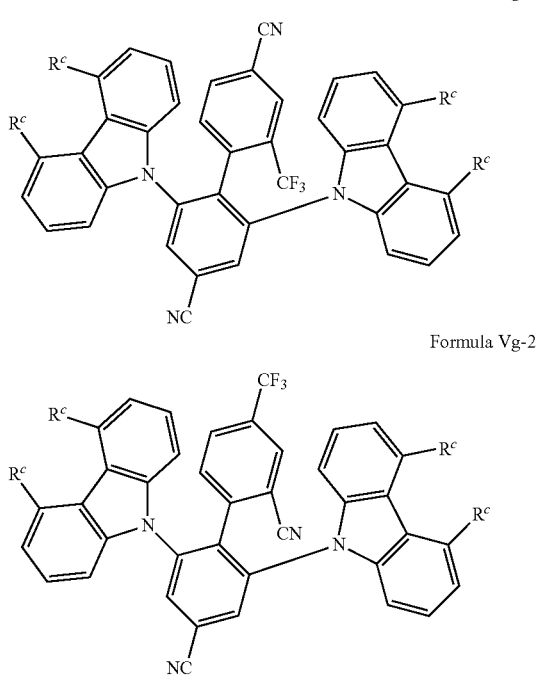

Formula Vg-2 wherein the abovementioned definitions apply.

In a further embodiment, the organic molecules according to the invention have a structure of Formula Vg-1, wherein the abovementioned definitions apply.

In a further embodiment, the organic molecules according to the invention have a structure of Formula Vh-1 or Formula Vh-2:

Formula Vh-1

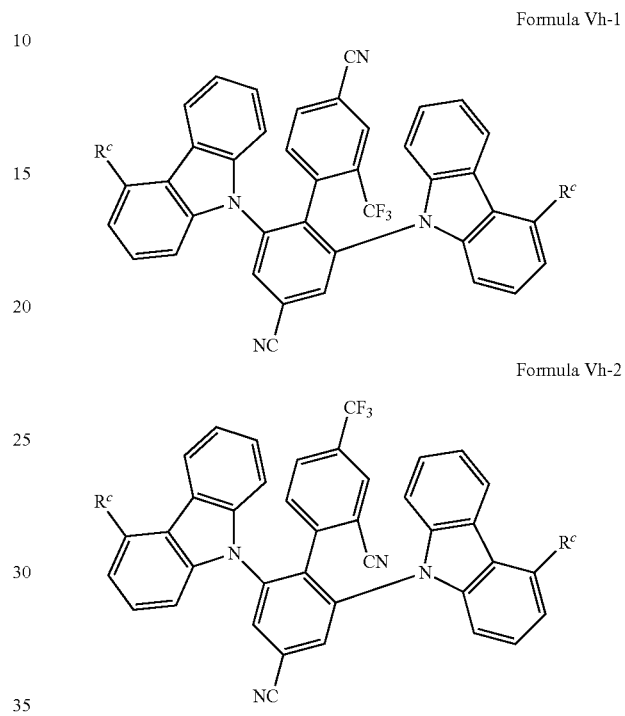

Formula Vh-2 wherein the abovementioned definitions apply.

In a further embodiment, the organic molecules according to the invention have a structure of Formula Vh-1, wherein the abovementioned definitions apply.

In one embodiment, the organic molecules according to the invention have a structure of Formula VI-1 or Formula VI-2:

Formula VI-1

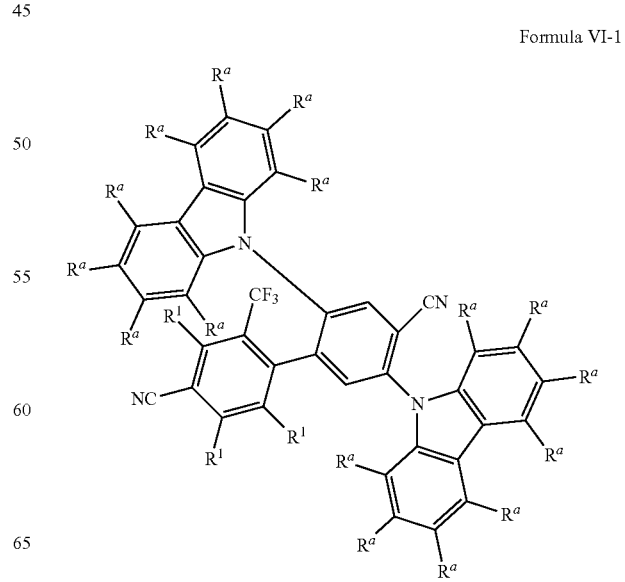

Formula VI-2

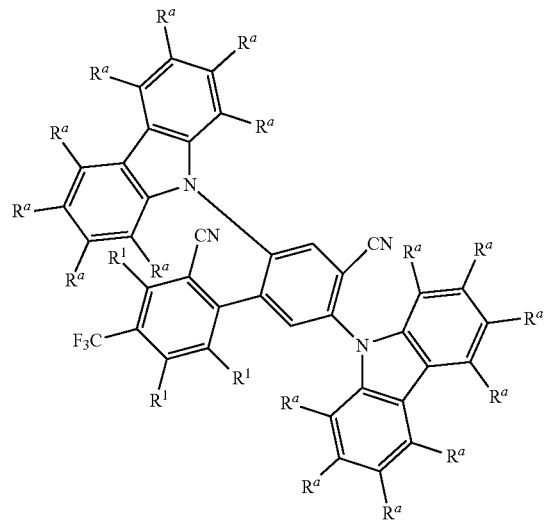

wherein the abovementioned definitions apply.

In one embodiment, the organic molecules according to the invention have a structure of Formula VI-1, wherein the abovementioned definitions apply.

In a further embodiment, the organic molecules according to the invention have a structure of Formula VIa-1 or Formula VIa-2:

Formula VIa-1

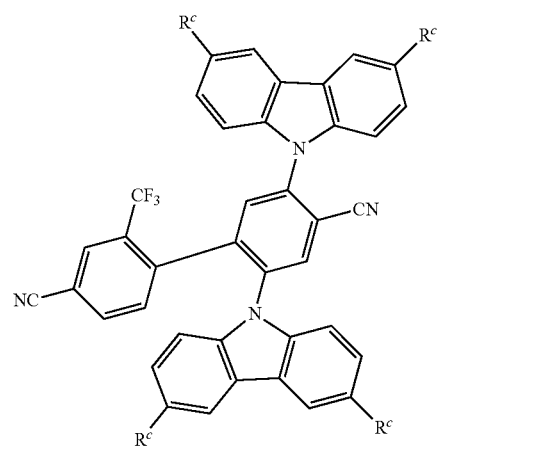

Formula VIa-2

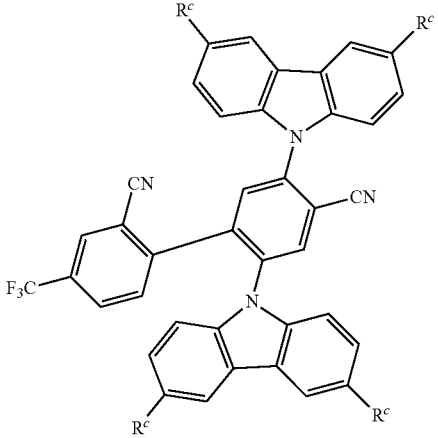

wherein the abovementioned definitions apply.

In a further embodiment, the organic molecules according to the invention have a structure of Formula VIa-1, wherein the abovementioned definitions apply.

In a further embodiment, the organic molecules according to the invention have a structure of Formula VIb-1 or Formula VIb-2:

Formula VIb-1

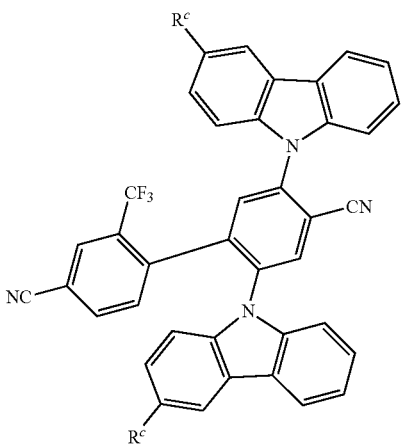

Formula VIb-2

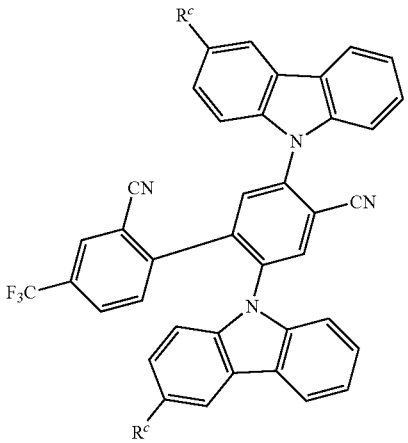

wherein the abovementioned definitions apply.

In a further embodiment, the organic molecules according to the invention have a structure of Formula VIb-1, wherein the abovementioned definitions apply.

In a further embodiment, the organic molecules according to the invention have a structure of Formula VIc-1 or Formula VIc-2:

Formula VIc-1

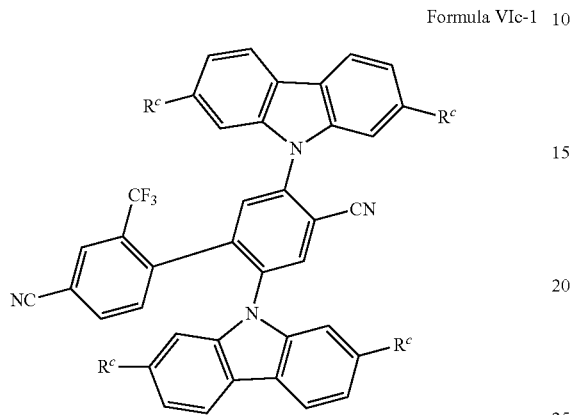

Formula VIc-2 wherein the abovementioned definitions apply.

In a further embodiment, the organic molecules according to the invention have a structure of Formula VIc-1, wherein the abovementioned definitions apply.

In a further embodiment, the organic molecules according to the invention have a structure of Formula VId-1 or Formula VId-2:

Formula VId-1

Formula VId-2 wherein the abovementioned definitions apply.

In a further embodiment, the organic molecules according to the invention have a structure of Formula VId-1, wherein the abovementioned definitions apply.

In a further embodiment, the organic molecules according to the invention have a structure of Formula VIe-1 or Formula VIe-2:

Formula VIe-1

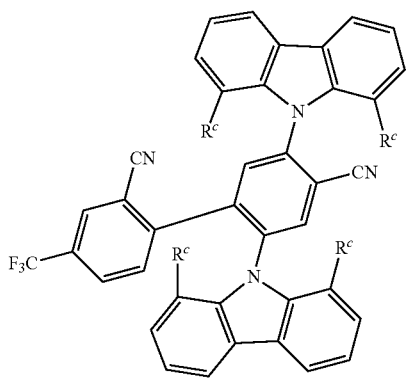

Formula VIe-2 wherein the abovementioned definitions apply.

In a further embodiment, the organic molecules according to the invention have a structure of Formula VIe-1, wherein the abovementioned definitions apply.

In a further embodiment, the organic molecules according to the invention have a structure of Formula VIf-1 or Formula VIf-2:

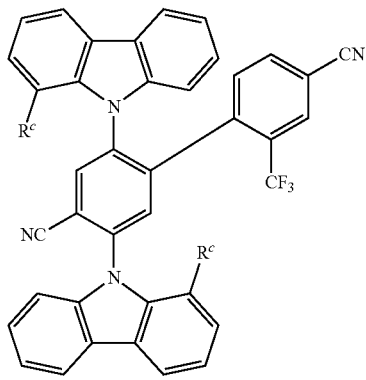

Formula VIf-1

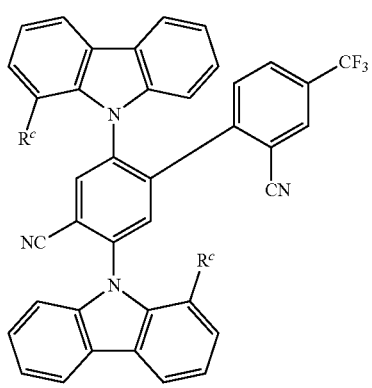

Formula VIf-2 wherein the abovementioned definitions apply.

In a further embodiment, the organic molecules according to the invention have a structure of Formula VIf-1, wherein the abovementioned definitions apply.

In a further embodiment, the organic molecules according to the invention have a structure of Formula VIg-1 or Formula VIg-2:

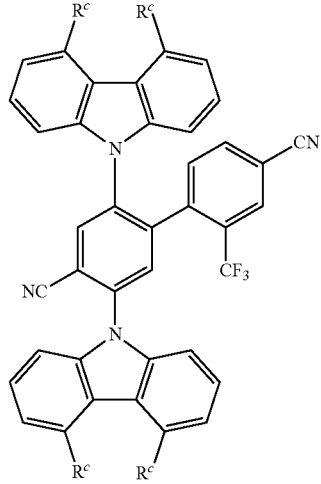

Formula VIg-1

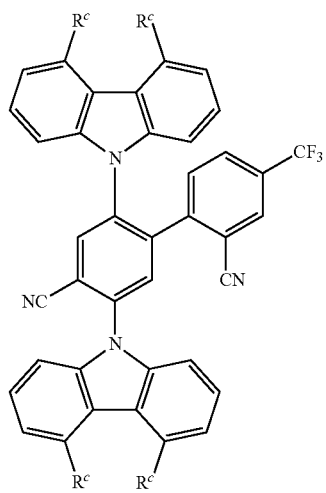

Formula VIg-2 wherein the abovementioned definitions apply.

In a further embodiment, the organic molecules according to the invention have a structure of Formula VIg-1, wherein the abovementioned definitions apply.

In a further embodiment, the organic molecules according to the invention have a structure of Formula VIh-1 or Formula VIh-2:

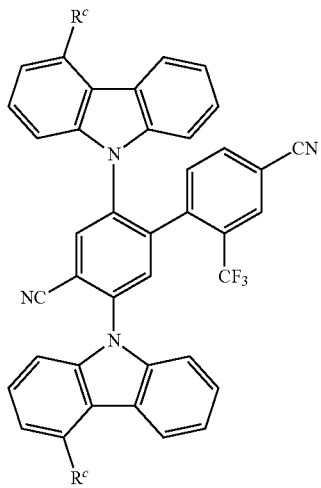

Formula VIh-1

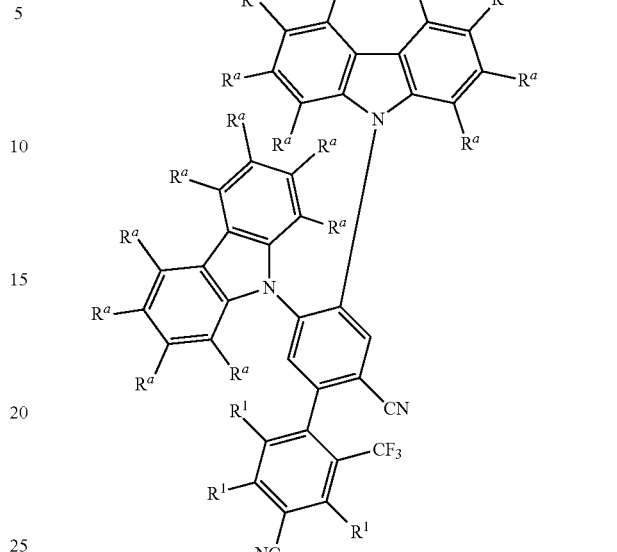

Formula VII-1

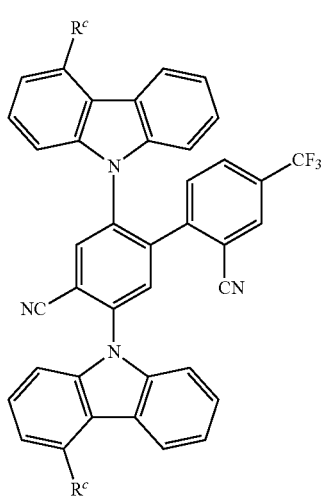

Formula VIh-2

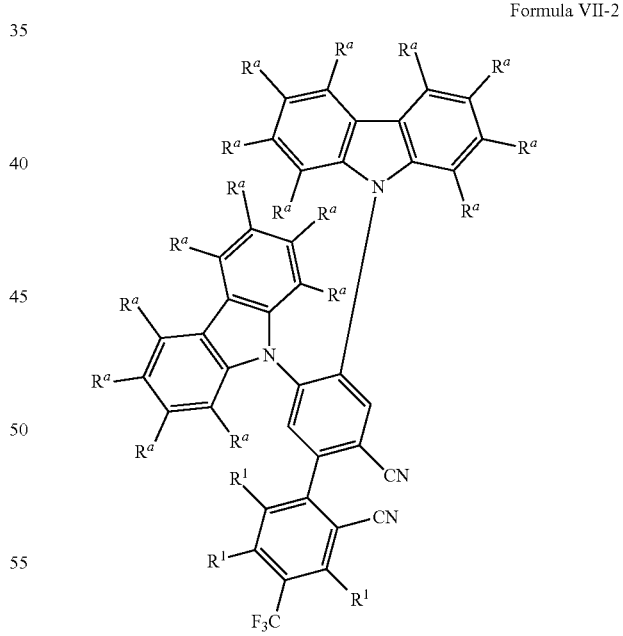

Formula VII-2 wherein the abovementioned definitions apply.

In a further embodiment, the organic molecules according to the invention have a structure of Formula VIh-1, wherein the abovementioned definitions apply.

In one embodiment, the organic molecules according to the invention have a structure of Formula VII-1 or Formula VII-2:

wherein the abovementioned definitions apply.

In one embodiment, the organic molecules according to the invention have a structure of Formula VII-1, wherein the abovementioned definitions apply.

In a further embodiment, the organic molecules according to the invention have a structure of Formula VIIa-1 or Formula VIIa-2:

Formula VIIa-1

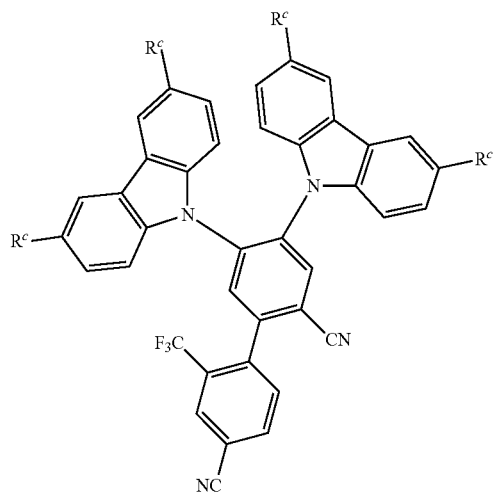

Formula VIIb-1

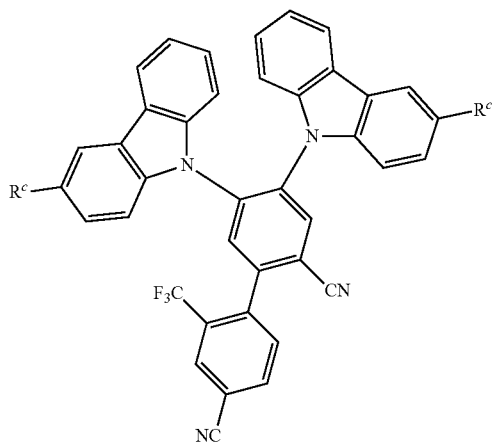

Formula VIIa-2

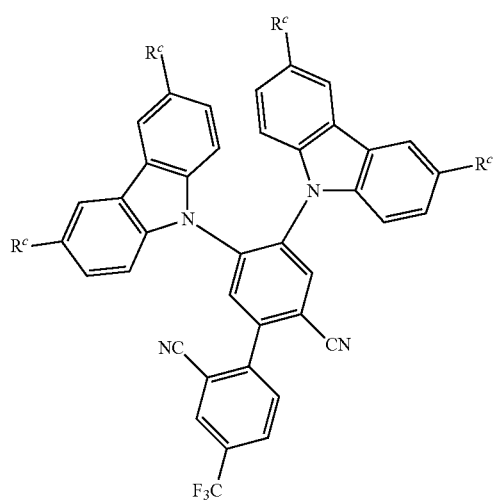

Formula VIIb-2

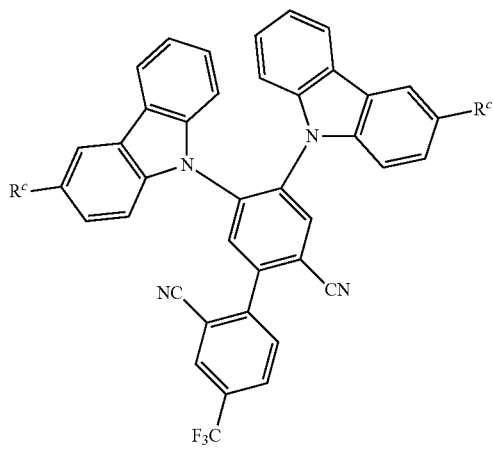

wherein the abovementioned definitions apply.

In a further embodiment, the organic molecules according to the invention have a structure of Formula VIIa-1, wherein the abovementioned definitions apply.

In a further embodiment, the organic molecules according to the invention have a structure of Formula VIIb-1 or Formula VIIb-2:

wherein the abovementioned definitions apply.

In a further embodiment, the organic molecules according to the invention have a structure of Formula VIIb-1, wherein the abovementioned definitions apply.

In a further embodiment, the organic molecules according to the invention have a structure of Formula VIIc-1 or Formula VIIc-2:

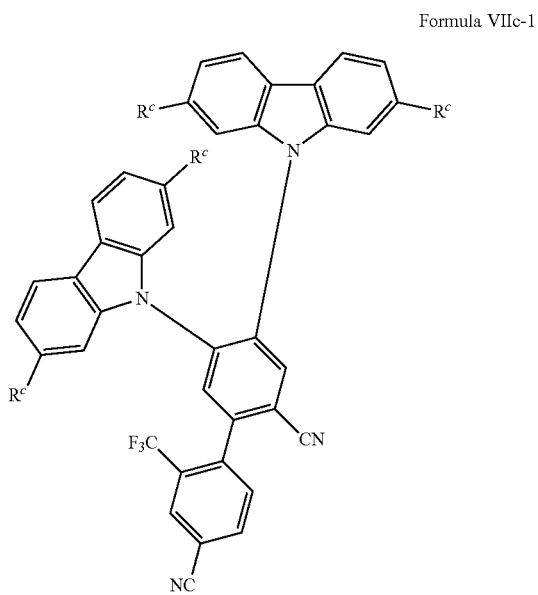

Formula VIIc-1

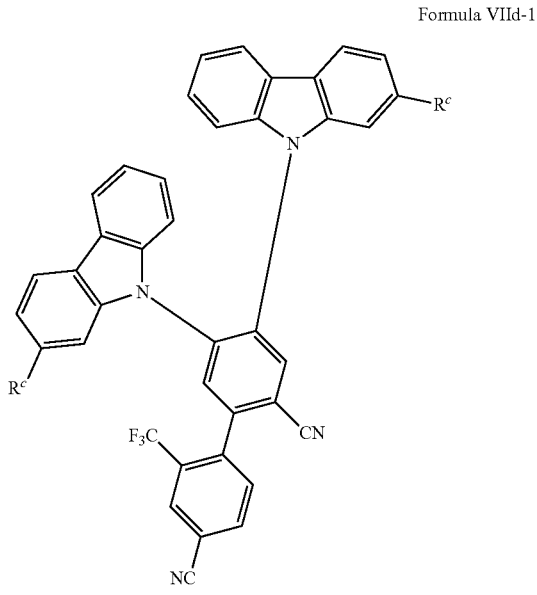

Formula VIId-1

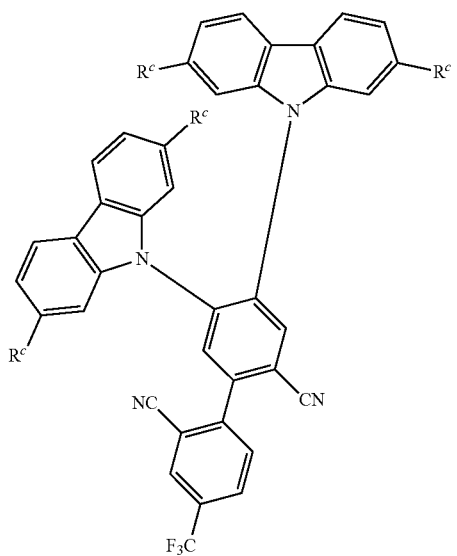

Formula VIIc-2

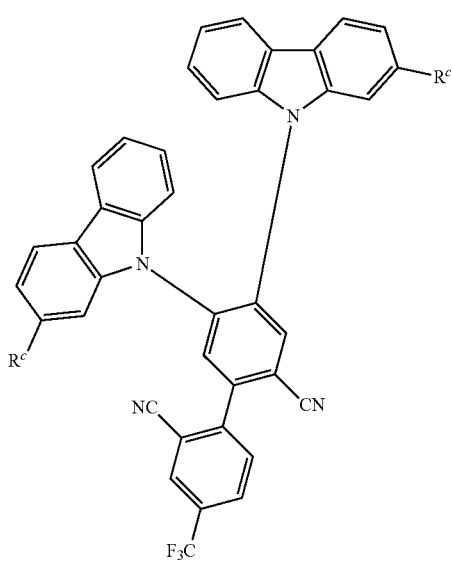

Formula VIId-2 wherein the abovementioned definitions apply.

In a further embodiment, the organic molecules according to the invention have a structure of Formula VIIc-1, wherein the abovementioned definitions apply.

In a further embodiment, the organic molecules according to the invention have a structure of Formula VIId-1 or Formula VIId-2:

wherein the abovementioned definitions apply.

In a further embodiment, the organic molecules according to the invention have a structure of Formula VIId-1, wherein the abovementioned definitions apply.

In a further embodiment, the organic molecules according to the invention have a structure of Formula VIIe-1 or Formula VIIe-2:

Formula VIIe-1

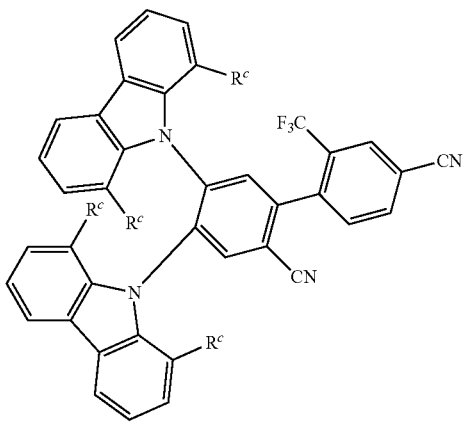

Formula VIIe-2

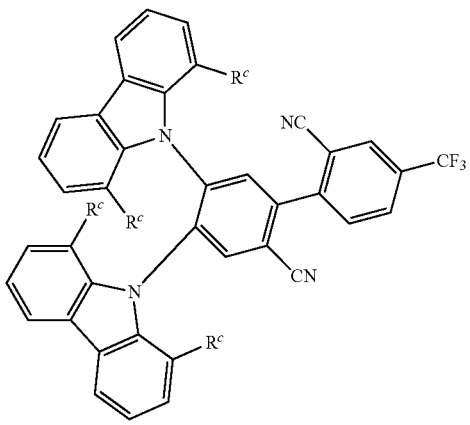

wherein the abovementioned definitions apply.

In a further embodiment, the organic molecules according to the invention have a structure of Formula VIIe-1, wherein the abovementioned definitions apply.

In a further embodiment, the organic molecules according to the invention have a structure of Formula VIIf-1 or Formula VIIf-2:

Formula VIIf-1

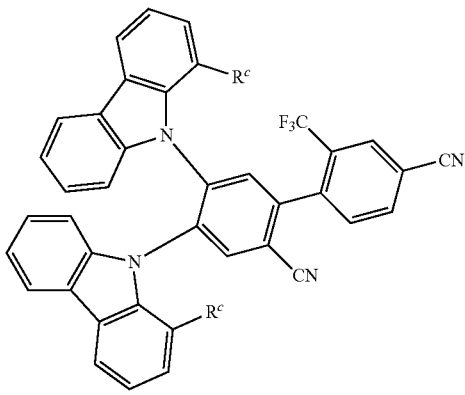

Formula VIIf-2

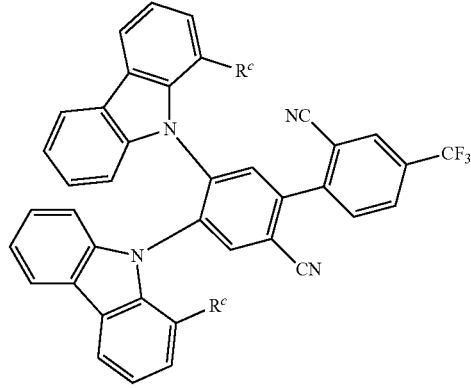

wherein the abovementioned definitions apply.

In a further embodiment, the organic molecules according to the invention have a structure of Formula VIIf-1, wherein the abovementioned definitions apply.

In a further embodiment, the organic molecules according to the invention have a structure of Formula VIIg-1 or Formula VIIg-2:

Formula VIIg-1

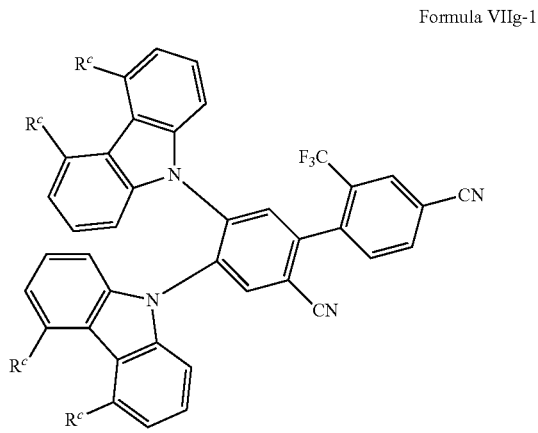

Formula VIIg-2

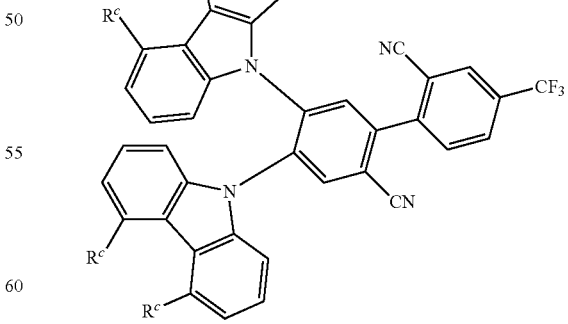

wherein the abovementioned definitions apply.

In a further embodiment, the organic molecules according to the invention have a structure of Formula VIIg-1, wherein the abovementioned definitions apply.

In a further embodiment, the organic molecules according to the invention have a structure of Formula VIIh-1 or Formula VIIh-2:

Formula VIIh-1

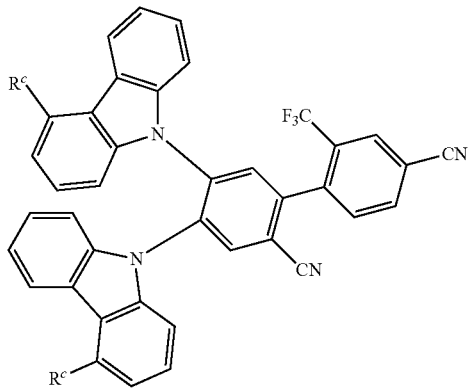

Formula VIIh-2

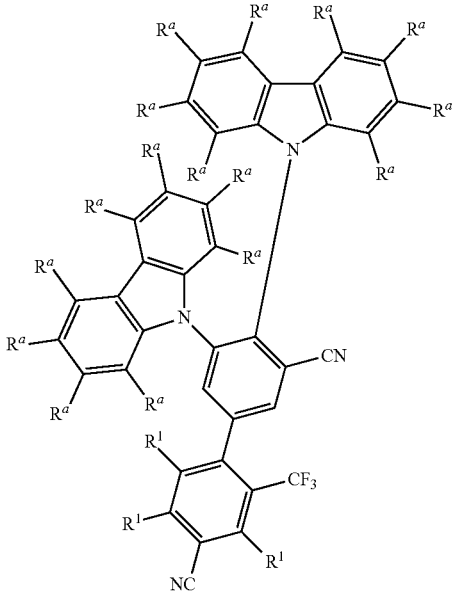

wherein the abovementioned definitions apply.

In a further embodiment, the organic molecules according to the invention have a structure of Formula VIIh-1, wherein the abovementioned definitions apply.

In a further embodiment, the organic molecules according to the invention have a structure of Formula VIII-1 or Formula VIII-2:

Formula VIII-1

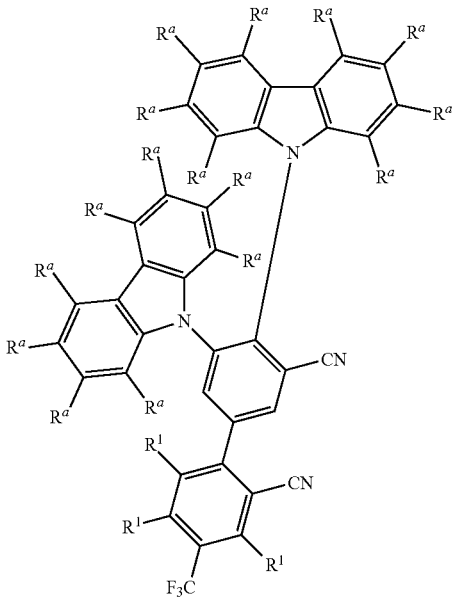

Formula VIII-2 wherein the abovementioned definitions apply.

In a further embodiment, the organic molecules according to the invention have a structure of Formula VIII-1, wherein the abovementioned definitions apply.

In one embodiment, in each occurrence $R^c$ is independently selected from the group consisting of Me, $^i$Pr, $^t$Bu, Ph, which can in each case be substituted with one or more radicals selected from Me, $^i$Pr, $^t$Bu, CN, $CF_3$ or Ph, and carbazolyl, which can in each case be substituted with one or more radicals selected from Me, $^i$Pr, $^t$Bu, or Ph, triazinyl, which can in each case be substituted with one or more radicals selected from Me, $^i$Pr, $^t$Bu, CN, $CF_3$ or Ph, and is $N(Ph)_2$.

In the context of this invention, an aryl group contains 6 to 60 aromatic ring atoms; a heteroaryl group contains 5 to 60 aromatic ring atoms, at least one of which represents a heteroatom. The heteroatoms are, in particular, N, O and/or S. In the event that other definitions, which differ from the stated definitions, for example with respect to the number of aromatic ring atoms or the contained heteroatoms, are specified in the description of specific embodiments of the invention, then these definitions apply.

An aryl group or heteroaryl group is understood to be a simple aromatic ring, i.e. benzene, or a simple heteroaromatic ring, for example pyridine, pyrimidine or thiophene, or a heteroaromatic polycyclic compound, for example phenanthrene, quinoline or carbazole. In the context of the present application, a condensed (annelated) aromatic or heteroaromatic polycyclic compound consists of two or more simple aromatic or heteroaromatic rings which are condensed with one another.

An aryl or heteroaryl group, which can be respectively substituted with the abovementioned radicals and which can be linked to the aromatic or heteroaromatic group via any desired positions, are in particular understood to be groups which are derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, isoquinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, napthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,5-triazine, 1,2,3,4-tetrazine, purine, pteridine, indolizine and benzothiadiazole or combinations of said groups.

A cyclic alkyl, alkoxy or thioalkoxy group is understood here to be a monocyclic, a bicyclic or a polycyclic group.

Within the scope of the present invention, a $C_1$ to $C_{40}$ alkyl group, in which individual H atoms or $CH_2$ groups can also be substituted with the abovementioned groups or replaced by the abovementioned groups, is understood to be, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]-octyl, 2-(2,6-dimethyl)octyl, 3-(3,7-dimethyl)octyl, adamantyl, trifluoromethyl, pentafluorethyl, 2,2,2-trifluorethyl, 1,1-dimethyl-n-hex-1-yl-, 1,1-dimethyl-n-hept-1-yl-, 1,1-dimethyl-n-oct-1-yl-, 1,1-dimethyl-n-dec-1-yl-, 1,1-dimethyl-n-dodec-1-yl-, 1,1-dimethyl-n-tetradec-1-yl-, 1,1-dimethyl-n-hexadec-1-yl-, 1,1-dimethyl-n-octadec-1-yl-, 1,1-diethyl-n-hex-1-yl-, 1,1-diethyl-n-hept-1-yl-, 1,1-diethyl-n-oct-1-yl-, 1,1-diethyl-n-dec-1-yl-, 1,1-diethyl-n-dodec-1-yl-, 1,1-diethyl-n-tetradec-1-yl-, 1,1-diethyln-hexadec-1-yl-, 1,1-diethyl-n-octadec-1-yl-, 1-(n-propyl)-cyclohex-1-yl-, 1-(n-butyl)-cyclohex-1-yl-, 1-(n-hexyl)-cyclohex-1-yl-, 1-(n-octyl)-cyclohex-1-yl- and 1-(n-decyl)-cyclohex-1-yl. An alkenyl group is understood to be ethenyl, propenyl, butenyl, pentenyl, cyclopentenyl, hexenyl, cyclohexenyl, heptenyl, cycloheptenyl, octenyl, cyclooctenyl or cyclooctadienyl, for example. An alkynyl group is understood to be ethinyl, propinyl, butinyl, pentinyl, hexinyl, heptinyl or octinyl, for example. A $C_1$ to $C_{40}$ alkoxy group is understood to be methoxy, trifluoromethoxy, ethoxy, n-propoxy, i-propoxy, n-butoxy, i-butoxy, s-butoxy, t-butoxy or 2-methylbutoxy, for example.

One embodiment of the invention relates to organic molecules, which have an $\Delta E(S_1-T_1)$ value between the lowest excited singlet $(S_1)$ state and the triplet $(T_1)$ state below it that is no higher than 5000 cm$^{-1}$, in particular no higher than 3000 cm$^{-1}$, or no higher than 1500 cm$^{-1}$ or 1000 cm$^{-1}$ and/or an emission lifetime of at most 150 μs, in particular at most 100 μs, at most 50 μs, or at most 10 μs and/or a main emission band having a full width at half maximum of less than 0.55 eV, in particular less than 0.50 eV, less than 0.48 eV, or less than 0.45 eV.

The organic molecules in particular display an emission maximum between 420 and 500 nm, between 430 and 480 nm, in particular between 450 and 470 nm.

The molecules in particular have a "blue material index" (BMI), the quotient of the PLQY (in %) and their CIE$_y$ color coordinate of the light emitted by the molecule according to the invention, that is greater than 150, in particular greater than 200, greater than 250 or greater than 300.

In a further aspect, the invention relates to a method for producing an organic molecule according to the invention of the type described here (with a possible subsequent reaction), wherein a in 2, 5, 6 position $R^1$-substituted 4-bromo-3-(trifluoromethyl)benzonitrile or a in 3, 4, 6 position $R^1$-substituted 2-bromo-5-(trifluoromethyl)benzonitrile is used as the educt,

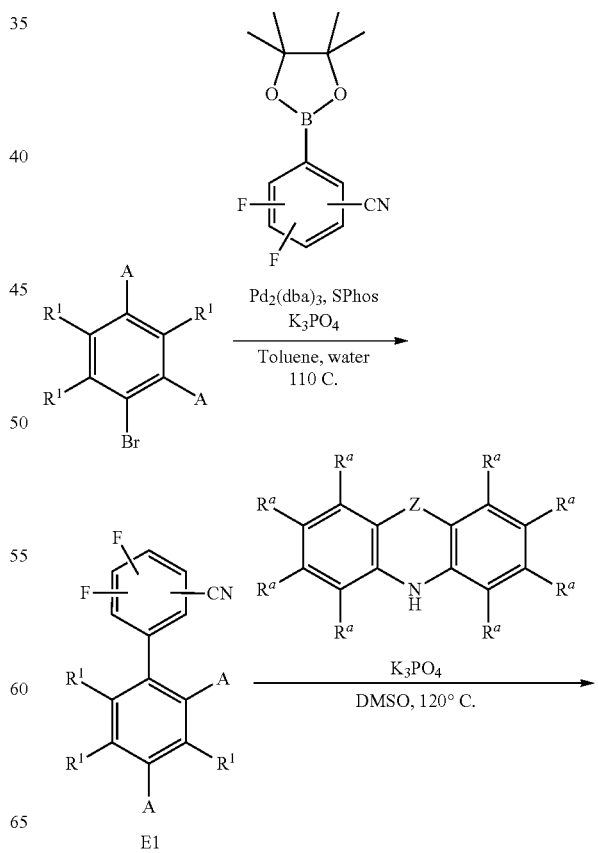

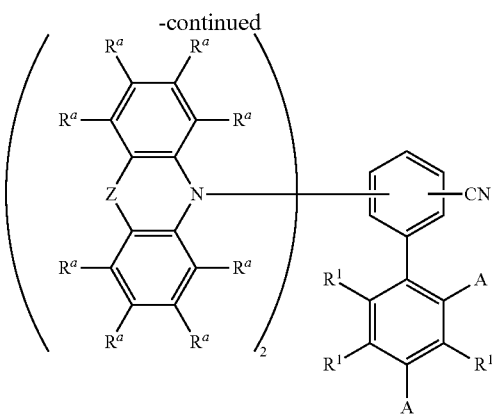

In the above schematic diagram, one of the two As is $CF_3$ and the other A is CN. In one embodiment of the above schema, the chemical group CN of the cyano-difluorophenylboronic acid ester is replaced by $CF_3$.

According to the invention, a boronic acid ester can be used instead of a boronic acid.

In one embodiment, an in 2, 5, 6 position $R^1$-substituted 4-bromo-3-(trifluoromethyl)benzonitrile as the educt is reacted with a cyano-difluorophenylboronic acid ester or a corresponding cyano-difluorophenylboronic acid in a palladium-catalyzed cross-coupling reaction. According to the invention, 4-cyano-2,6-difluorophenylboronic acid ester, 4-cyano-2,5-difluorophenylboronic acid ester, 4-cyano-3,5-difluorophenylboronic acid ester, 3-cyano-2,4-difluorophenylboronic acid ester, 3-cyano-4,5-difluorophenylboronic acid ester and 2-cyano-4,5-difluorophenylboronic acid ester or 4-cyano-2,6-difluorophenylboronic acid, 4-cyano-2,5-difluorophenylboronic acid, 4-cyano-3,5-difluorophenylboronic acid, 3-cyano-2,4-difluorophenylboronic acid, 3-cyano-4,5-difluorophenylboronic acid and 2-cyano-4,5-difluorophenylboronic acid, for example, can be used. The product is obtained by deprotonation of the corresponding amine and subsequent nucleophilic substitution of the two fluorine groups. To do this, a nitrogen heterocyclic compound is reacted with an educt E1 in the context of a nucleophilic aromatic substitution. Typical conditions include the use of a base, such as potassium phosphate tribasic or sodium hydride, in an aprotic polar solvent, such as dimethyl sulfoxide (DMSO) or N,N-dimethyl formamide (DMF).

According to the invention, instead of using a in 2,5,6-position $R^1$-substituted 4-bromo-3-(trifluoromethyl)benzonitrile as the educt, a in 3, 4, 6 position $R^1$-substituted 2-bromo-5-(trifluoromethyl)benzonitrile can be used as the educt.

In a further aspect, the invention relates to the use of the organic molecules as luminescent emitters or as host material in an organic optoelectronic device, in particular wherein the organic optoelectronic device is selected from the group consisting of:
organic light-emitting diodes (OLEDs),
light-emitting electrochemical cells,
OLED sensors, in particular in gas and vapor sensors which are not hermetically shielded to the outside,
organic diodes,
organic solar cells,
organic transistors,
organic field-effect transistors,
organic lasers and
down-conversion elements.

In a further aspect, the invention relates to a composition having or consisting of:
(a) at least one organic molecule according to the invention, in particular as an emitter and/or host, and
(b) at least one, i.e. one or more emitter and/or host materials, that is or are different from the organic molecule according to the invention, and
(c) optionally one or more dyes and/or one or more organic solvents.

In one embodiment, the composition according to the invention consists of an organic molecule according to the invention and one or more host materials. The host material or the host materials in particular have first excited triplet ($T_1$) energy levels, which are energetically higher than the first excited triplet ($T_1$) energy levels of the organic molecule according to the invention, and have first excited singlet ($S_1$) energy levels, which are energetically higher than the singlet ($S_1$) energy levels of the organic molecule according to the invention.

The orbital energies and the energies of the excited states can be determined via experimental methods or by the use of quantum chemical methods, in particular density functional theory calculations. The energy of the highest occupied orbital $E^{HOMO}$ is determined by means of cyclic voltammetry, as is known to the person skilled in the art, with an accuracy of 0.1 eV. The energy of the lowest unoccupied orbital $E^{LUMO}$ is calculated via the sum of $E^{HOMO}$ and $E^{gap}$, whereby $E^{gap}$ is determined as follows: Unless stated otherwise, the energy used for $E^{gap}$ for a host molecule is the energy at which emission sets in for a film having 10% host (percent by mass) in polymethyl methacrylate (PMMA). For an emitter molecule, $E^{gap}$ is determined as the energy, at which the excitation and emission spectra of a film having 10% emitter (percent by mass) in PMMA intersect.

The energy of the first excited triplet state $T_1$ is determined via the energy, at which emission sets in at low temperature, typically 77 K. For a host molecule, for which the energy difference between the first excited singlet state and the first excited triplet state differs by more than 0.4 eV, the phosphorescence is typically visible in the steady-state spectrum in 2-Me-THF. The triplet energy can therefore be determined as the energy at which the phosphorescence spectrum sets in. For TADF emitter molecules, the energy of the first excited triplet state $T_1$ is determined via the energy at which the delayed emission spectrum sets in at 77 K, which, unless stated otherwise, is measured in a film having 10% emitter molecule (percent by mass) in PMMA. For host and emitter molecules, the energy of the first excited singlet state $S_1$ is determined with the energy, at which the emission spectrum sets in, which, unless stated otherwise, is measured in a film having 10% host molecule or emitter molecule (percent by mass) in PMMA.

In one embodiment, in addition to the organic molecule according to the invention, the composition has an electron-dominant and a hole-dominant host material. The highest occupied orbital (HOMO) of the hole-dominant host material is in particular energetically higher than the HOMO of the electron-dominant host material and the lowest unoccupied orbital (LUMO) of the hole-dominant host material is in particular energetically higher than the LUMO of the electron-dominant host material. In a further embodiment, the HOMO of the hole-dominant host material is energetically above the HOMO of the organic molecule according to the invention, while the LUMO of the electron-dominant host material is energetically below the LUMO of the organic molecule according to the invention. In order to prevent exciplex formation between the emitter and the host material or between host materials, the materials should be selected such that the energy gaps between the LUMO of the electron-dominant host material and the LUMO of the organic molecule according to the invention are in particular less than 0.5 eV, preferably less than 0.3 eV, more preferably less than 0.2 eV. The energy gap between the HOMO of the hole-dominant host material and the HOMO of the organic molecule according to the invention is in particular less than 0.5 eV, preferably less than 0.3 eV, and even more preferably less than 0.2 eV.

In a further embodiment, in addition to the organic molecule according to the invention, the composition has an electron-dominant host material. The energy difference between the highest occupied orbital (HOMO) of the organic molecule according to the invention and the HOMO of the electron-dominant host material is between −0.5 eV and 0.5 eV, preferably −0.3 eV and 0.3 eV, more preferably −0.2 eV and 0.2 eV, or even between −0.1 eV and 0.1 eV.

In a further embodiment, in addition to the organic molecule according to the invention, the composition has an electron-dominant host material. The energy difference between the lowest unoccupied orbital (LUMO) of the organic molecule according to the invention and the LUMO of the electron-dominant host material is between −0.5 eV and 0.5 eV, preferably between −0.5 eV and 0.5 eV, preferably between −0.3 eV and 0.3 eV, more preferably between −0.2 eV and 0.2 eV, or even between −0.1 eV and 0.1 eV-0.3 eV and 0.3 eV, more preferably between −0.2 eV and 0.2 eV, or even between −0.1 eV and 0.1 eV.

In a further embodiment, in addition to the organic molecule according to the invention, the composition has a hole-dominant host material. The energy difference between the highest occupied orbital (HOMO) of the organic molecule according to the invention and the HOMO of the hole-dominant host material is between −0.5 eV and 0.5 eV, preferably between −0.3 eV and 0.3 eV, more preferably between −0.2 eV and 0.2 eV, or even between −0.1 eV and 0.1 eV.

In a further embodiment, in addition to the organic molecule according to the invention, the composition has a hole-dominant host material. The energy difference between the lowest unoccupied orbital (LUMO) of the organic molecule according to the invention and the LUMO of the hole-dominant host material is between −0.5 eV and 0.5 eV, preferably between −0.3 eV and 0.3 eV, more preferably between −0.2 eV and 0.2 eV, or even between −0.1 eV and 0.1 eV.

In one embodiment, in addition to the organic molecule according to the invention, the composition has an electron-dominant and a hole-dominant host material. The energy difference between the highest occupation orbital (HOMO) of the organic molecule according to the invention and the HOMO of the electron-dominant host material is between −0.5 eV and 0.5 eV, preferably between −0.3 eV and 0.3 eV, more preferably between −0.2 eV and 0.2 eV, or even between −0.1 eV and 0.1 eV and the energy difference between the lowest unoccupied orbital (LUMO) of the organic molecule according to the invention and the LUMO of the electron-dominant host material is between −0.5 eV and 0.5 eV, preferably between −0.3 eV and 0.3 eV, more preferably between −0.2 eV and 0.2 eV, or even between −0.1 eV and 0.1 eV. Accordingly, the energy difference between the highest occupation orbital (HOMO) of the organic molecule according to the invention and the HOMO of the hole-dominant host material is between −0.5 eV and 0.5 eV, preferably between −0.3 eV and 0.3 eV, more preferably between −0.2 eV and 0.2 eV, or even between −0.1 eV and 0.1 eV and the energy difference between the lowest unoccupied orbital (LUMO) of the organic molecule according to the invention and the LUMO of the hole-dominant host material is between −0.5 eV and 0.5 eV, preferably between −0.3 eV and 0.3 eV, more preferably between −0.2 eV and 0.2 eV, or even between −0.1 eV and 0.1 eV.

In a further aspect, the invention relates to an organic optoelectronic device which has an organic molecule according to the invention or a composition according to the invention. The organic optoelectronic device is, in particular, formed as a device selected from the group consisting of organic light-emitting diode (OLED); light-emitting electrochemical cell; OLED sensor, in particular gas and vapor sensors which are not hermetically shielded to the outside; organic diode; organic solar cell; organic transistor; organic field-effect transistor; organic laser and down-conversion element.

An organic optoelectronic device having
  a substrate,
  an anode and
  a cathode, wherein the anode or the cathode are disposed on the substrate, and
  at least one light-emitting layer, which is disposed between the anode and the cathode and which has an organic molecule according to the invention, represents a further embodiment of the invention.

In one embodiment, the optoelectronic device is an OLED. A typical OLED, for example, has the following layer structure:
  1. Substrate (supporting material)
  2. Anode
  3. Hole injection layer (HIL)
  4. Hole transport layer (HTL)
  5. Electron blocking layer (EBL)
  6. Emitting layer (EML)
  7. Hole blocking layer (HBL)
  8. Electron transport layer (ETL)
  9. Electron injection layer (EIL)
  10. Cathode.

The presence of specific layers is merely optional. Several of these layers can also coincide. Specific layers can also be present more than once in the component.

According to one embodiment, at least one electrode of the organic component is designed to be translucent. In this case, "translucent" describes a layer that is transmissive to visible light. The translucent layer can be clearly translucent, i.e. transparent, or at least partially light-absorbing and/or partially light-diffusing, so that the translucent layer can, for example, also be diffusely or milkily translucent. A layer referred to here as translucent is, in particular, designed to be as transparent as possible, so that, in particular, the absorption of light is as low as possible.

According to a further embodiment, the organic component, in particular an OLED, has an inverted structure. The inverted structure is characterized in that the cathode is located on the substrate and the other layers are disposed in a correspondingly inverted manner:
  1. Substrate (supporting material)
  2. Cathode
  3. Electron injection layer (EIL)
  4. Electron transport layer (ETL)
  5. Hole blocking layer (HBL)
  6. Emission layer or emitting layer (EML)
  7. Electron blocking layer (EBL)
  8. Hole transport layer (HTL)
  9. Hole injection layer (HIL)
  10. Anode The presence of specific layers is merely optional. Several of these layers can also coincide. Specific layers can also be present more than once in the component.

In one embodiment, in the inverted OLED, the anode layer of the typical structure e.g. an ITO layer (indium tin oxide), is connected as the cathode.

According to a further embodiment, the organic component, in particular an OLED, has a stacked structure. In this case, the individual OLEDs are arranged one above the other and not next to one another as usual. The production of mixed light can be made possible with the aid of a stacked structure. This structure can be used to produce white light, for example. To produce said white light, the entire visible spectrum is typically imaged by combining the emitted light of blue, green and red emitters. Furthermore, with practically the same efficiency and identical luminance, significantly longer lifetimes can be achieved in comparison to conventional OLEDs. A so-called charge generation layer (CGL) between two OLEDs is optionally used for the stacked structure. Said layer consists of an n-doped and a p-doped layer, wherein the n-doped layer is typically disposed closer to the anode.

In one embodiment—a so-called tandem OLED—two or more emission layers occur between the anode and the cathode. In one embodiment, three emission layers are arranged one above the other, wherein one emission layer emits red light, one emission layer emits green light and one emission layer emits blue light, and additional charge generation, blocking or transport layers are optionally disposed between the individual emission layers. In a further embodiment, the respective emission layers are disposed directly adjacent to one another. In another embodiment, one respective charge generation layer is situated between the emission layers. Emission layers that are directly adjacent to one another and emission layers that are separated by charge generation layers can furthermore be combined in an OLED.

An encapsulation arrangement can furthermore be disposed above the electrodes and the organic layers as well. The encapsulation arrangement can, for example, be designed in the form of a glass cover or in the form of a thin-film encapsulation arrangement.

The supporting material of the optoelectronic device can, for example, be glass, quartz, plastic, metal, a silicon wafer or any other suitable solid or flexible, optionally transparent material. The supporting material can, for example, have one or more materials in the form of a layer, a film, a plate or a laminate.

Transparent conductive metal oxides such as, for example, ITO (indium tin oxide), zinc oxide, tin oxide, cadmium oxide, titanium oxide, indium oxide or aluminum zinc oxide (AZO), $Zn_2SnO_4$, $OdSnO_3$, $ZnSnO_3$, $MgIn_2O_4$, $GaInO_3$, $Zn_2In_2O_5$ or $In_4Sn_3O_{12}$ or mixtures of different transparent conductive oxides, for example, can be used as the anode of the optoelectronic device.

PEDOT:PSS (poly-3,4-ethylenedioxythiophene: polystyrene sulfonic acid), PEDOT (poly-3,4-ethylenedioxythiophene), m-MTDATA (4,4',4"-tris[phenyl(m-tolyl)amino]triphenylamine), Spiro-TAD (2,2',7,7'-tetrakis(N,N-diphenylamino)-9,9-spirobifluorene), DNTPD (4,4'-bis[N-4-{N,N-bis(3-methyl-phenyl)amino}phenyl]-N-phenylamino]biphenyl), NPB (N,N'-bis-(1-naphthalenyl)-N,N'-bis-phenyl-(1,1'-biphenyl)-4,4'-diamine), NPNPB (N,N'-diphenyl-N,N'-di-[4-(N,N-diphenyl-amino)phenyl]benzene), MeO-TPD (N,N,N',N'-tetrakis(4-methoxyphenyl)benzene), HAT-CN (1,4,5,8,9,11-hexaazatriphenylene-hexacarbonitrile) or Spiro-NPD (N,N'-diphenyl-N,N'-bis-(1-naphthyl)-9,9'-spirobifluorene-2,7-diamine), for example, are suitable materials for an HIL. The layer thickness is 10-80 nm, for example. Small molecules (e.g. copper phthalocyanine (CuPc e.g. 10 nm thick)) or metal oxides, such as $MoO_3$, $V_2O_5$, can also be used.

Tertiary amines, carbazole derivatives, polyethylenedioxythiophene doped with polystyrene sulfonic acid, polyaniline poly-TPD (poly(4-butylphenyl-diphenyl-amine)) doped with camphor sulfonic acid, [alpha]-NPD (poly(4-butylphenyl-diphenyl-amine)), TAPC (4,4'-cyclohexylidene-bis[N,N-bis(4-methylphenyl)benzenamine]), TCTA (tris(4-carbazoyl-9-ylphenyl)amine), 2-TNATA (4,4',4"-tris[2-naphthyl(phenyl)amino]triphenylamine), Spiro-TAD, DNTPD, NPB, NPNPB, MeO-TPD, HAT-CN or TrisPcz (9,9'-diphenyl-6-(9-phenyl-9H-carbazole-3-yl)-9H,9'H-3,3'-bicarbazole) can be used as materials for an HTL. The layer thickness is 10 nm to 100 nm, for example.

The HTL can have a p-doped layer which has an inorganic or organic dopant in an organic hole transporting matrix. Transition metal oxides such as vanadium oxide, molybdenum oxide or tungsten oxide, for example, can be used as the inorganic dopant. Tetrafluorotetracyanoquinodimethane (F4-TCNQ), copper pentafluorobenzoate (Cu(I)pFBz) or transition metal complexes can, for example, be used as the organic dopants. The layer thickness is 10 nm to 100 nm, for example.

MCP (1,3-bis(carbazole-9-yl)benzene), TCTA, 2-TNATA, mCBP (3,3-Di(9H-carbazole-9-yl)biphenyl), tris-Pcz (9,9'-diphenyl-6-(9-phenyl-9H-carbazole-3-yl)-9H,9'H-3,3'-bicarbazole), CzSi (9-(4-tert-butylphenyl)-3,6-bis(triphenylsilyl)-9H-carbazole) or DCB (N,N'-dicarbazolyl-1,4-dimethylbenzene) can, for example, be used as the materials of an electron blocking layer. The layer thickness is 10 nm to 50 nm, for example.

The emitter layer EML or emission layer consists of or contains emitter material or a mixture having at least two emitter materials and optionally one or more host materials. Suitable host materials are, for example, mCP, TCTA, 2-TNATA, mCBP, CBP (4,4'-bis-(N-carbazolyl)-biphenyl), Sif87 (dibenzo[b,d]thiophene-2-yltriphenylsilane), Sif88 (dibenzo[b,d]thiophene-2-yl)diphenylsilane) or DPEPO (bis [2-((oxo)diphenylphosphino)phenyl]ether). The common matrix materials, such as CBP, are suitable for emitter material emitting in the green or in the red range or for a mixture having at least two emitter materials. UHC matrix materials (ultra-high energy gap materials) (see, for example, M. E. Thompson et al., Chem. Mater. 2004, 16, 4743) or other so-called wide-gap matrix materials can be used for emitter material emitting in the blue range or a mixture having at least two emitter materials. The layer thickness is 10 nm to 250 nm, for example.

The hole blocking layer HBL can, for example, have BCP (2,9-dimethyl-4,7-diphenyl-1,10-phenanthroline=bathocuproine), bis-(2-methyl-8-hydroxyquinolinato)-(4-phenylphenolato)-aluminum(III) (BAlq), Nbphen (2,9-bis(naphthalene-2-yl)-4,7-diphenyl-1,10-phenanthroline), Alq3 (aluminum-tris(8-hydroxyquinoline)), TSPO1 (diphenyl-4-triphenylsilyl-phenylphosphine oxide) or TCB/TCP (1,3,5-tris(N-carbazolyl)benzene/1,3,5-tris (carbazole)-9-yl)benzene). The layer thickness is 10 nm to 50 nm, for example.

The electron transport layer ETL can, for example, have materials on the basis of $AlQ_3$, TSPO1, BPyTP2 (2,7-di(2,2'-bipyridine-5-yl)triphenyl)), Sif87, Sif88, BmPyPhB (1,3-bis[3,5-di(pyridine-3-yl)phenyl]benzene) or BTB (4,4'-bis-

[2-(4,6-diphenyl-1,3,5-triazinyl)]-1,1'-biphenyl). The layer thickness is 10 nm to 200 nm, for example.

CsF, LiF, 8-hydroxyquinolinolatolithium (Liq), $Li_2O$, $BaF_2$, MgO or NaF can be used as materials for a thin electron injection layer EIL.

Metals or alloys, for example Al, Al>AlF, Ag, Pt, Au, Mg, Ag:Mg, can be used as materials of the cathode layer. Typical layer thicknesses are 100 nm to 200 nm. In particular, one or more metals are used, which are stable when exposed to air and/or which are self-passivating, for example by forming a thin protective oxide layer.

Aluminum oxide, vanadium oxide, zinc oxide, zirconium oxide, titanium oxide, hafnium oxide, lanthanum oxide, tantalum oxide, for example, are suitable materials for encapsulation.

In one embodiment of the organic optoelectronic device according to the invention, the organic molecule according to the invention is used as the emission material in a light-emitting layer EML, wherein it is used either as a pure layer or in combination with one or more host materials.

One embodiment of the invention relates to organic optoelectronic devices which have an external quantum efficiency (EQE) at 1000 $cd/m^2$ greater than 5%, in particular greater than 8%, in particular greater than 10%, or greater than 13%, or greater than 16% and in particular greater than 20% and/or an emission maximum at a wavelength between 420 nm and 500 nm, in particular between 430 nm and 490 nm, or between 440 nm and 480 nm, and in particular between 450 nm and 470 nm and/or an LT80 value at 500 $cd/m^2$ greater than 30 h, in particular greater than 70 h, or greater than 100 h, or greater than 150 h and in particular greater than 200 h.

In another embodiment, the mass fraction of the organic molecule according to the invention in the emitter layer EML of a light-emitting layer in devices emitting optical light, in particular in OLEDs, is between 1% and 80%. In one embodiment of the organic optoelectronic device according to the invention, the light-emitting layer is disposed on a substrate, wherein an anode and a cathode are preferably disposed on the substrate and the light-emitting layer is disposed between the anode and the cathode.

In one embodiment, the light-emitting layer can have only one organic molecule according to the invention in 100% concentration, wherein the anode and the cathode are disposed on the substrate, and the light-emitting layer is disposed between the anode and the cathode.

In one embodiment of the organic optoelectronic device according to the invention, a hole- and electron-injecting layer is disposed between the anode and the cathode, and a hole- and electron-transporting layer is disposed between the hole- and electron-injecting layer, and the light-emitting layer is disposed between the hole- and electron-transporting layer.

In a further embodiment of the invention, the organic optoelectronic device has: a substrate, an anode, a cathode and at least one respective hole- and electron-injecting layer, and at least one respective hole- and electron-transporting layer, and at least one light-emitting layer comprising the organic molecule according to the invention and one or more host materials, the triplet ($T_1$) energy levels of which are energetically higher than the triplet ($T_1$) energy levels of the organic molecule and the singlet ($S_1$) energy levels of which are energetically higher than the singlet ($S_1$) energy levels of the organic molecule, wherein the anode and the cathode are disposed on the substrate, and the hole- and electron-injecting layer is disposed between the anode and the cathode, and the hole- and electron-transporting layer is disposed between the hole- and electron-injecting layer, and the light-emitting layer is disposed between the hole- and electron-transporting layer.

In a further aspect, the invention relates to a method for producing an optoelectronic component. To do this, an organic molecule according to the invention is used.

In one embodiment, the production method comprises the processing of the organic molecule according to the invention by means of a vacuum evaporation method or from a solution.

The invention also relates to a method for producing an optoelectronic device according to the invention, in which at least one layer of the optoelectronic device is coated using a sublimation process, is coated using an OVPD (organic vapor phase deposition) process, is coated using a carrier-gas sublimation, and/or is produced from solution or using a pressure process.

Known methods are used for the production of the optoelectronic device according to the invention. The layers are generally disposed individually onto a suitable substrate in successive deposition method steps. The common methods, such as thermal evaporation, chemical vapor deposition (CVD), physical vapor deposition (PVD) can be used for the vapor deposition. For active matrix OLED (AMOLED) displays, deposition takes place onto an AMOLED backplane as the substrate.

Layers can alternatively be deposited from solutions or dispersions in suitable solvents. Spin coating, dip coating and jet pressure methods are examples of suitable coating methods. According to the invention, the individual layers can be produced via the same as well as via respective different coating methods.

EXAMPLES

General Synthesis Scheme I

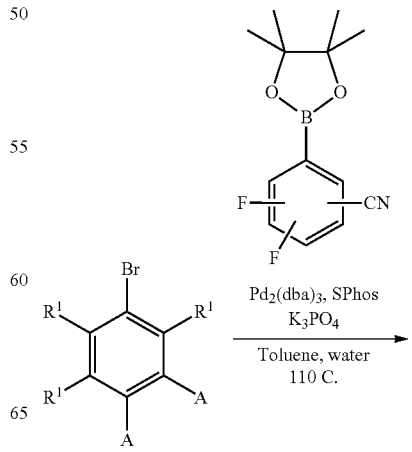

-continued

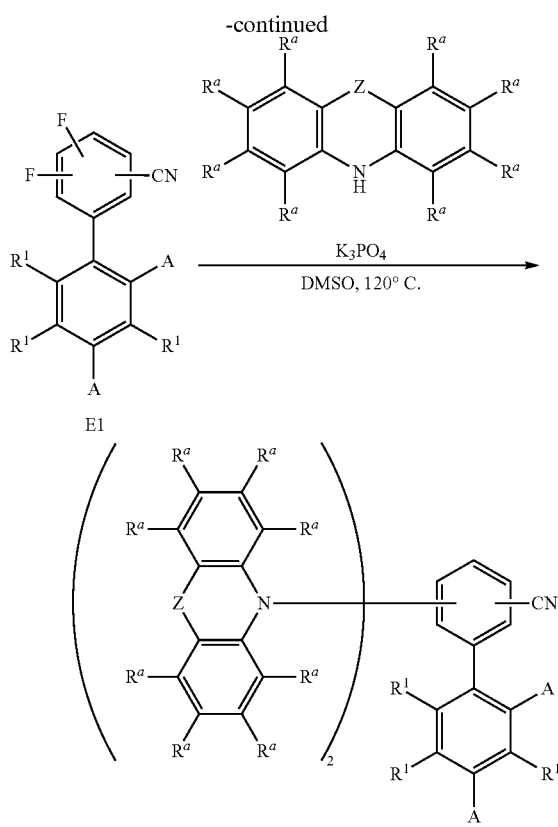

General Synthesis Specification AAV1-1:

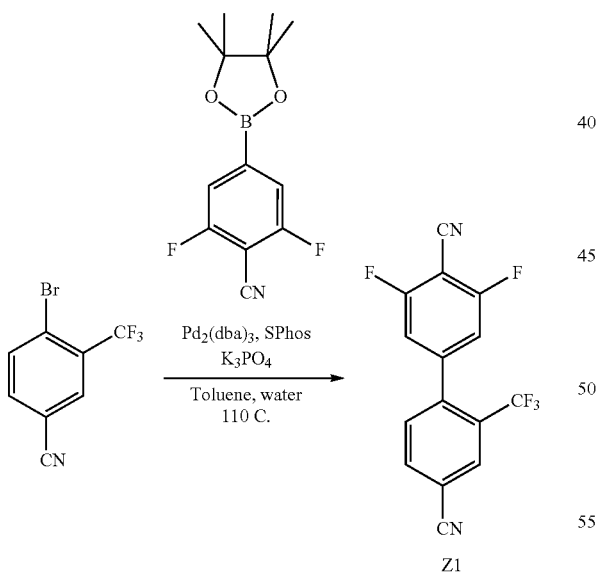

4-bromo-3-(trifluoromethyl)benzonitrile (1.00 equivalent), 4-cyano-3,5-difluorophenylboronic acid ester (1.20 equivalent), Pd$_2$(dba)$_3$ (0.01 equivalent), 2-dicyclohexylphosphino-2',6'-dimethoxybiphenyl and equivalent) 0.04) SPhos)) a in nitrogen under stirred are equivalent) 2.50) sictriba phosphate potassium toluene/water mixture (ratio 10:1) at 110° C. for 17 hours. The product is obtained as a solid by typical purification methods such as extraction or filtration and subsequent removal of the respective solvent.

If necessary, the product can be further purified by recrystallization and/or column chromatography.

According to the invention, a corresponding boronic acid can be used instead of a boronic acid ester. Other suitable solvents such as dioxane, for example, can be used instead of toluene.

General Synthesis Specification AAV2-1:

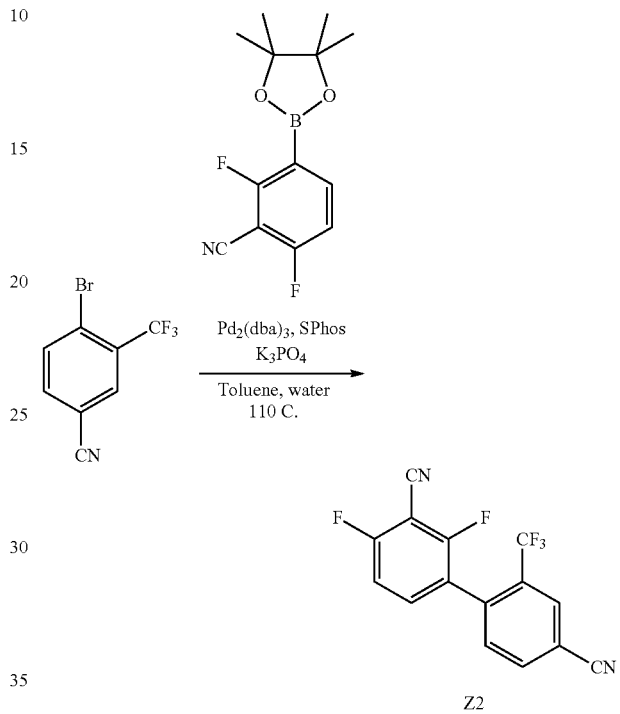

The synthesis of Z2 is analogous to AAV1-1, wherein 4-bromo-3-(trifluoromethyl)benzonitrile is reacted with 3-cyano-2,4-difluorophenylboronic acid ester.

General Synthesis Specification AAV3-1:

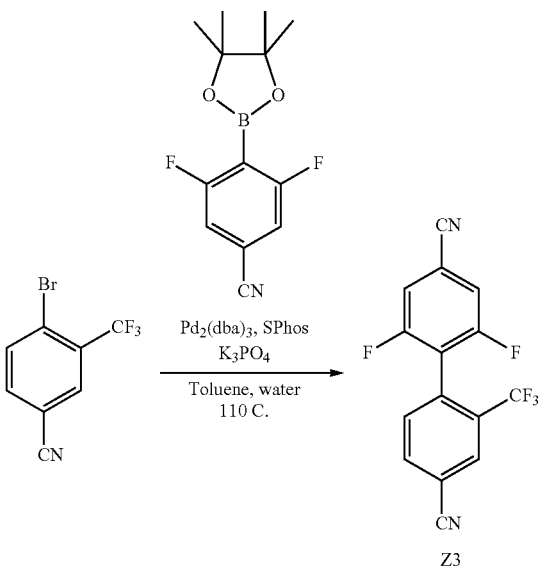 [SMILES: N#Cc1ccc(Br)c(C(F)(F)F)c1 ; CC1(C)OB(c2c(F)cc(C#N)cc2F)OC1(C)C ; N#Cc1cc(F)c(-c2ccc(C#N)cc2C(F)(F)F)c(F)c1]

The synthesis of Z3 is analogous to AAV1-1, wherein 4-bromo-3-(trifluoromethyl)benzonitrile is reacted with 4-cyano-2,6-diflorophenylboronic acid ester.

General Synthesis Specification AAV4-1:

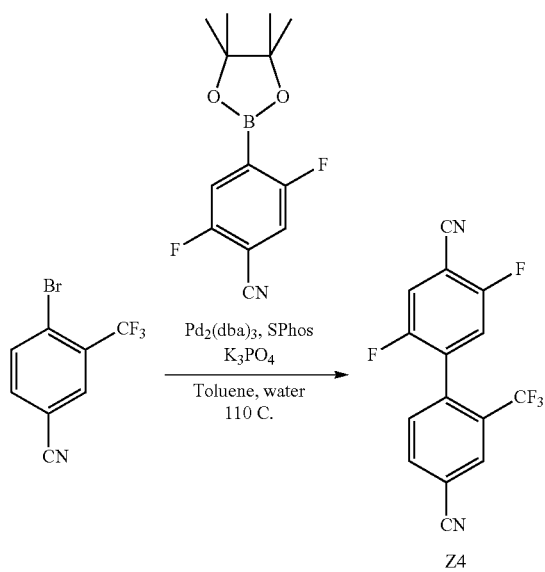 [SMILES: N#Cc1ccc(Br)c(C(F)(F)F)c1 ; CC1(C)OB(c2cc(F)c(C#N)cc2F)OC1(C)C ; N#Cc1ccc(-c2cc(F)c(C#N)cc2F)c(C(F)(F)F)c1]

The synthesis of Z4 is analogous to AAV1-1, wherein 4-bromo-3-(trifluoromethyl)benzonitrile is reacted with 4-cyano-2,5-difluorophenylboronic acid ester.

General Synthesis Specification AAV5-1:

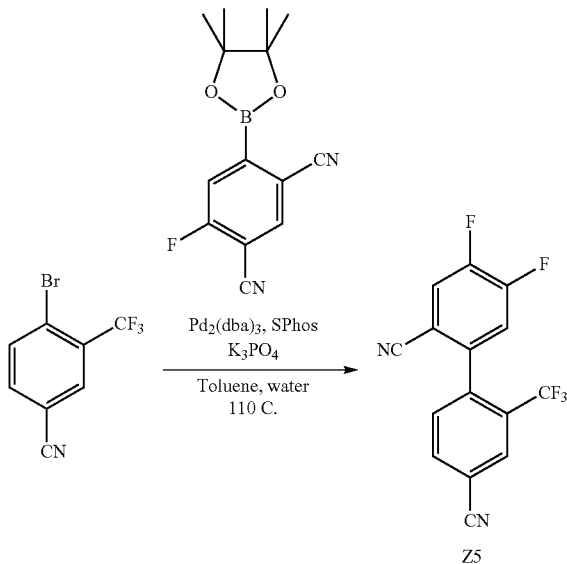 [SMILES: N#Cc1ccc(Br)c(C(F)(F)F)c1 ; CC1(C)OB(c2cc(F)c(C#N)cc2C#N)OC1(C)C ; N#Cc1ccc(-c2cc(F)c(F)cc2C#N)c(C(F)(F)F)c1]

The synthesis of Z5 is analogous to AAV1-1, wherein 4-bromo-3-(trifluoromethyl)benzonitrile is reacted with 2-cyano-4,5-difluorophenylboronic acid ester.

General Synthesis Specification AAV6-1:

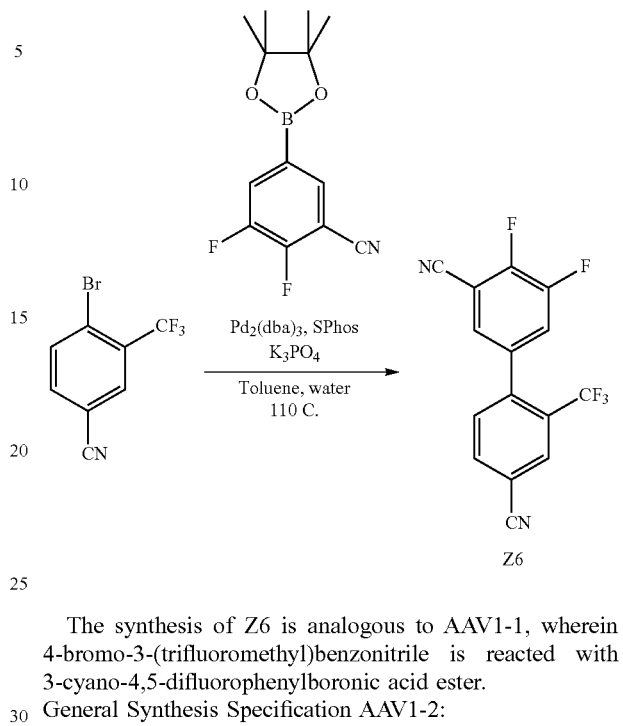

The synthesis of Z6 is analogous to AAV1-1, wherein 4-bromo-3-(trifluoromethyl)benzonitrile is reacted with 3-cyano-4,5-difluorophenylboronic acid ester.

General Synthesis Specification AAV1-2:

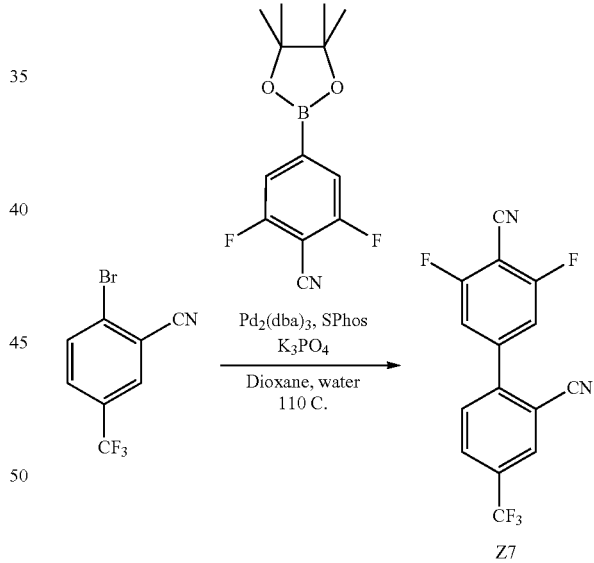

2-bromo-5-(trifluoromethyl)benzonitrile (1.00 equivalent), 4-cyano-3,5-difluorophenylboronic acid ester (1.00 equivalent), Pd$_2$(dba)$_3$ (0.01 equivalent), 2-dicyclohexylphosphino-2',6'-dimethoxybiphenyl potassium equivalent), 0.08) SPhos)) are equivalent) 5.00) tribasic phosphate potassium and equivalent) 2.00) acetate obtaine is product The hours. 17 for C °110 at dioxane in nitrogen under stirredd as a solid by typical purification methods such as extraction, filtration and/or column chromatography and subsequent removal of the respective solvent. If necessary, the product can be further purified by recrystallization and/or sublimation.

According to the invention, a corresponding boronic acid can be used instead of a boronic acid ester. Other suitable solvents, such as toluene, for example, can be used instead of dioxane.

General Synthesis Specification AAV2-2:

General Synthesis Specification AAV4-2:

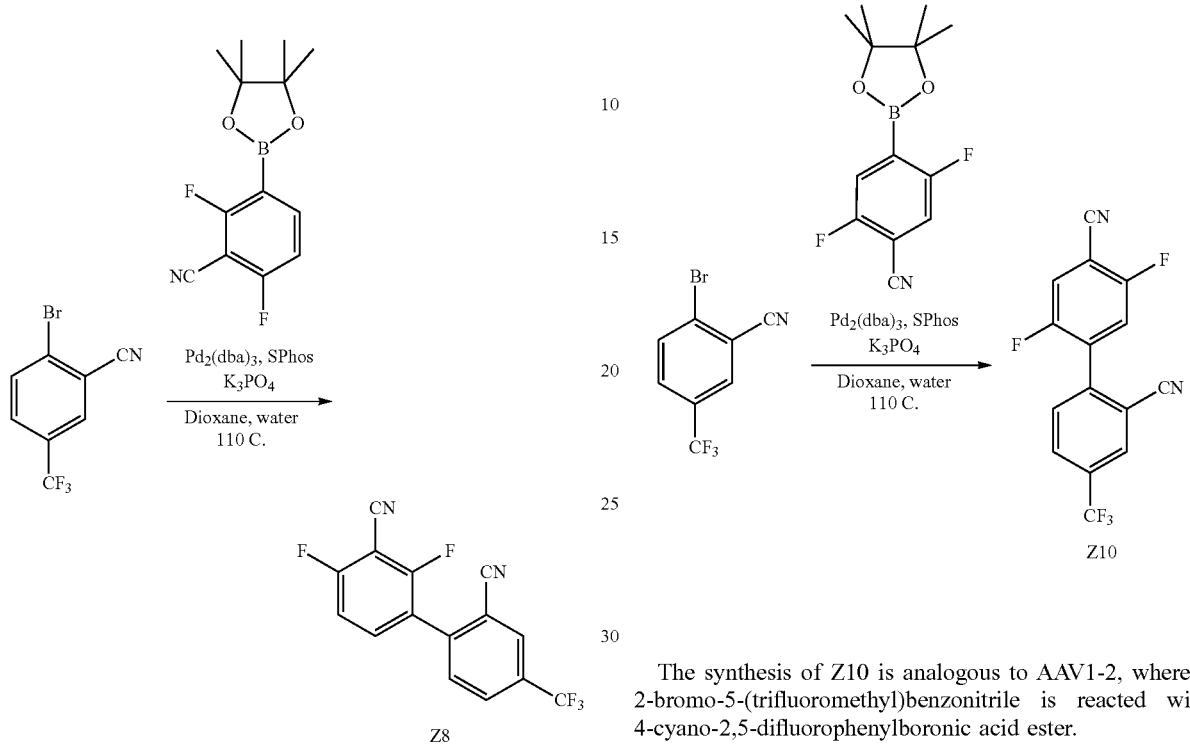

The synthesis of Z8 is analogous to AAV1-2, wherein 2-bromo-5-(trifluoromethyl)benzonitrile is reacted with 3-cyano-2,4-difluorophenylboronic acid ester.

General Synthesis Specification AAV3-2:

The synthesis of Z10 is analogous to AAV1-2, wherein 2-bromo-5-(trifluoromethyl)benzonitrile is reacted with 4-cyano-2,5-difluorophenylboronic acid ester.

General Synthesis Specification AAV5-2:

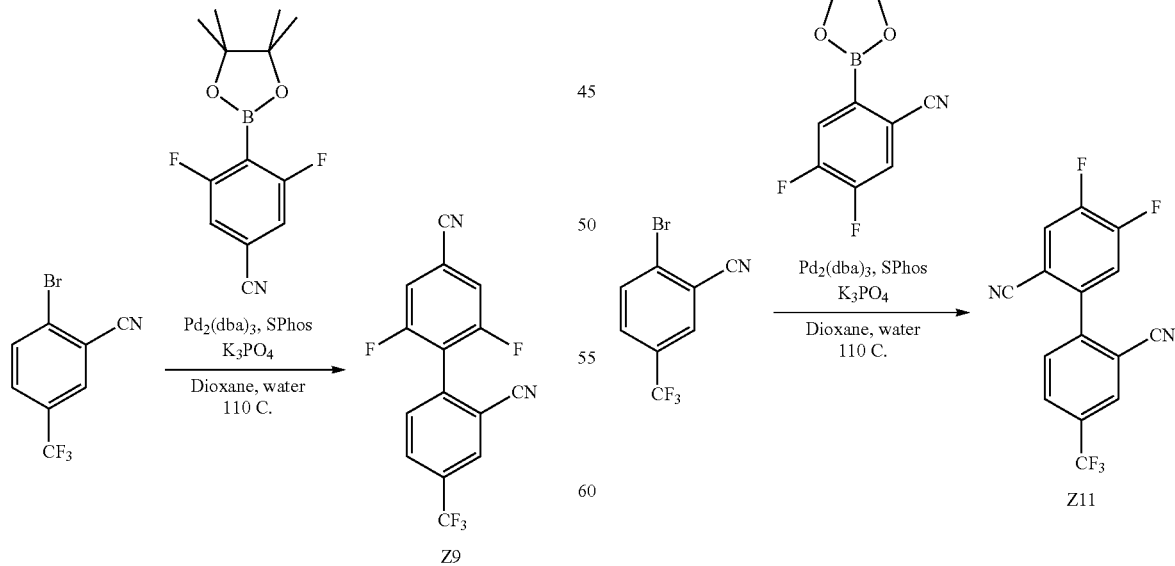

The synthesis of Z9 is analogous to AAV1-2, wherein 2-bromo-5-(trifluoromethyl)benzonitrile is reacted with 4-cyano-2,6-difluorophenylboronic acid ester.

The synthesis of Z11 takes place analogous to AAV1-2, wherein 2-bromo-5-(trifluoromethyl)benzonitrile is reacted with 2-cyano-4,5-difluorophenylboronic acid ester.

General Synthesis Specification AAV6-2:
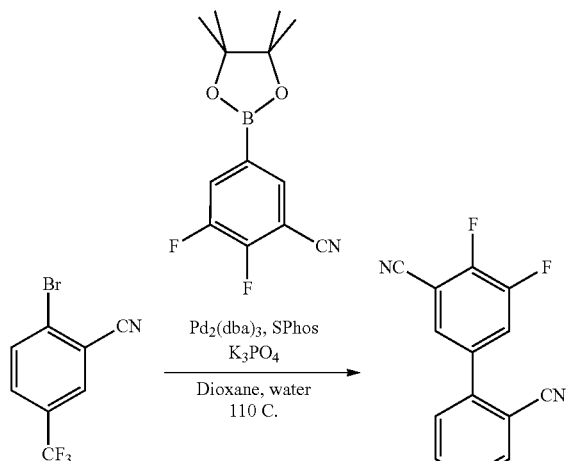
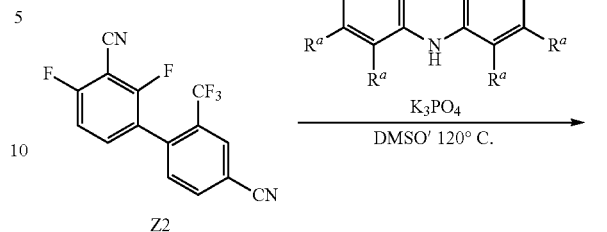
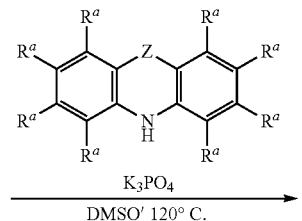
The synthesis of Z12 takes place analogous to AAV1-2, wherein 2-bromo-5-(trifluoromethyl)benzonitrile is reacted with 2-cyano-4,5-difluorophenylboronic acid ester.
General Synthesis Specification AAV7:
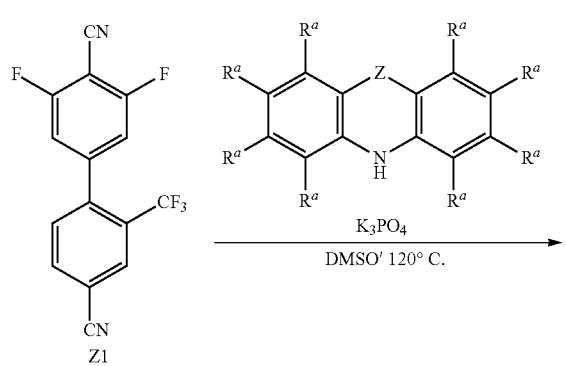
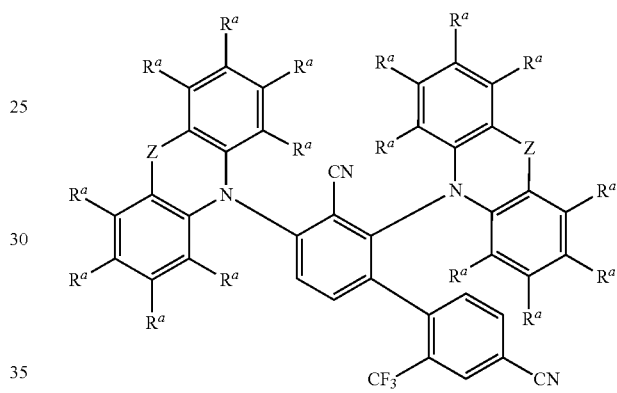
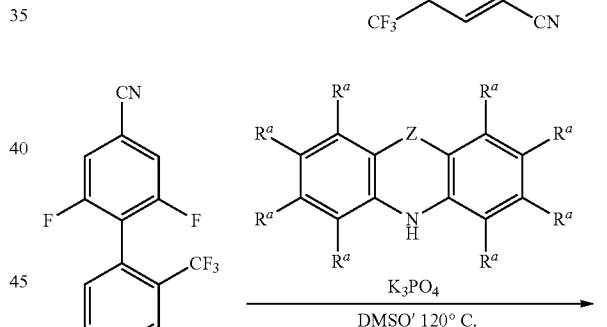
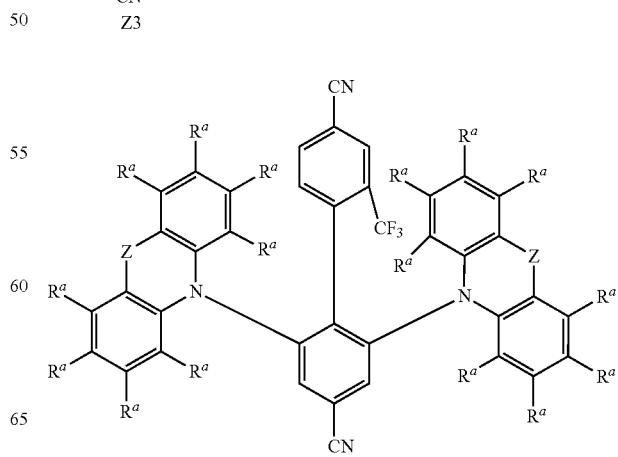

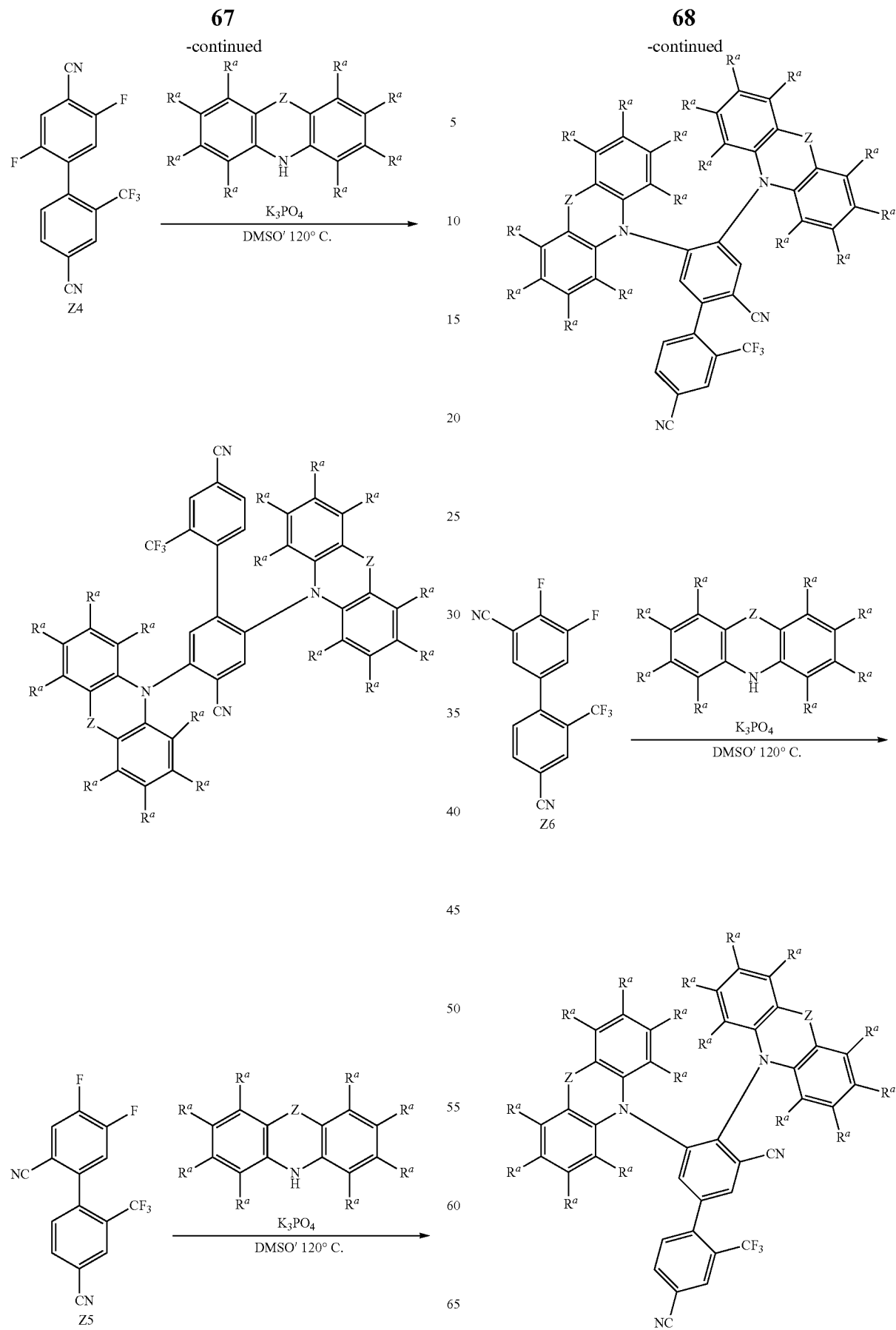

69
-continued
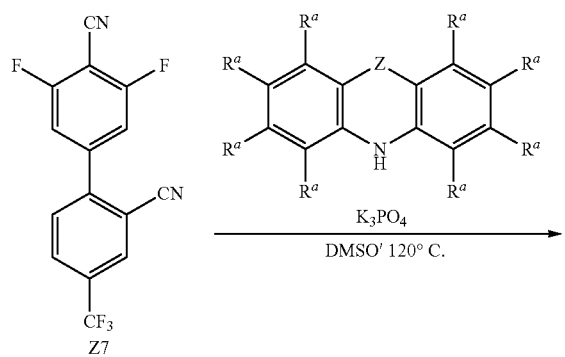
70
-continued
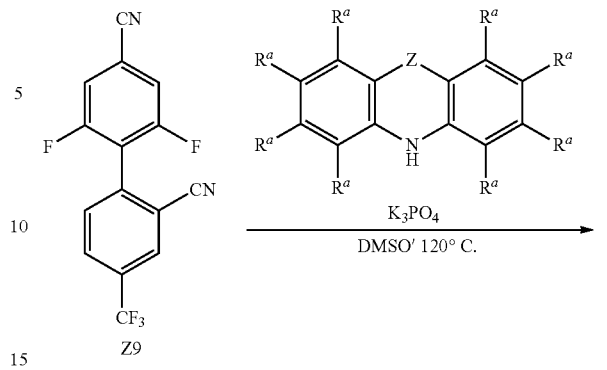
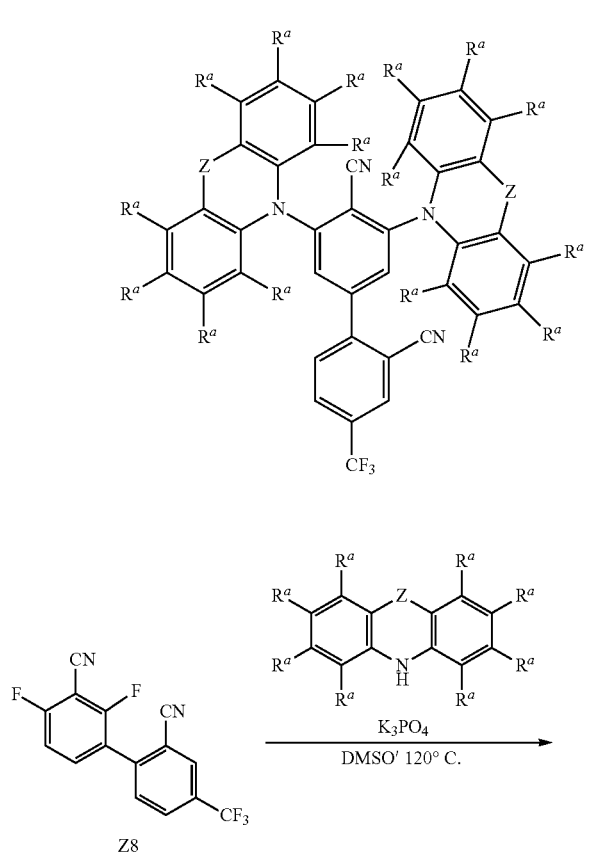
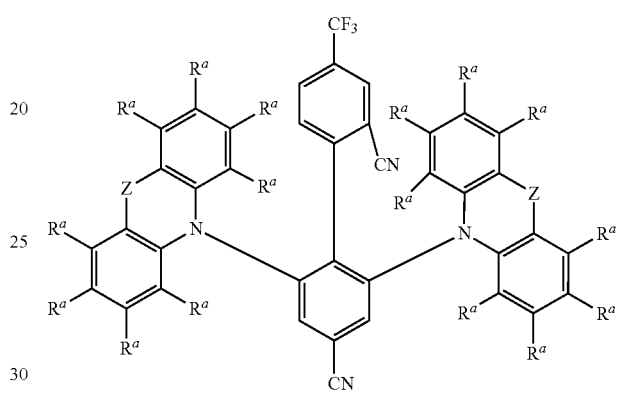
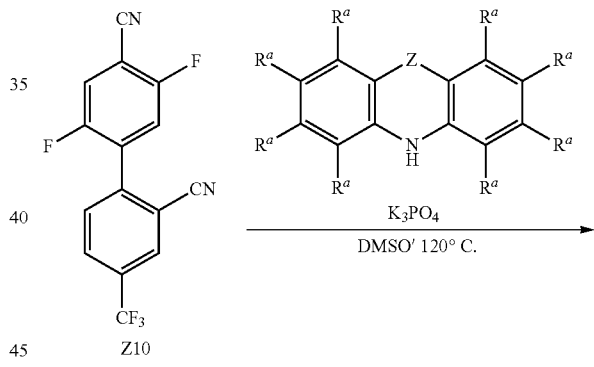
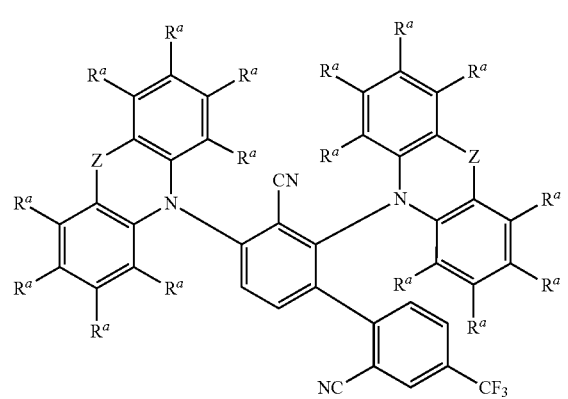
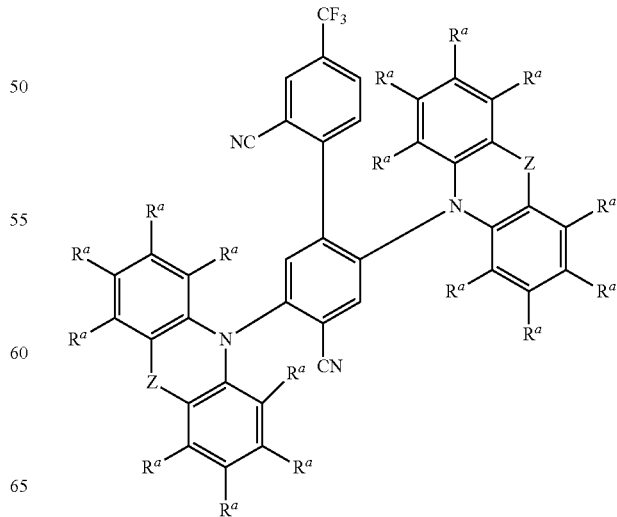

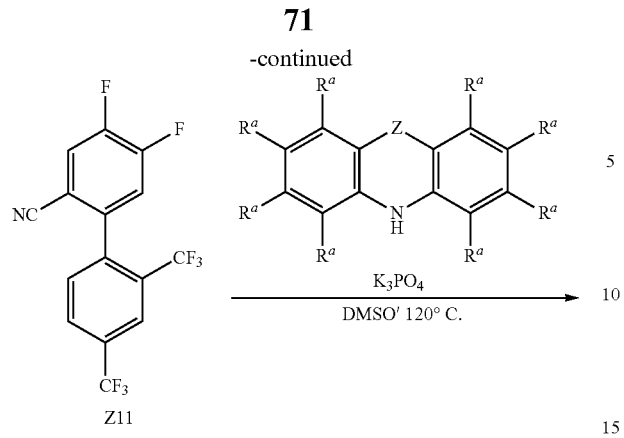
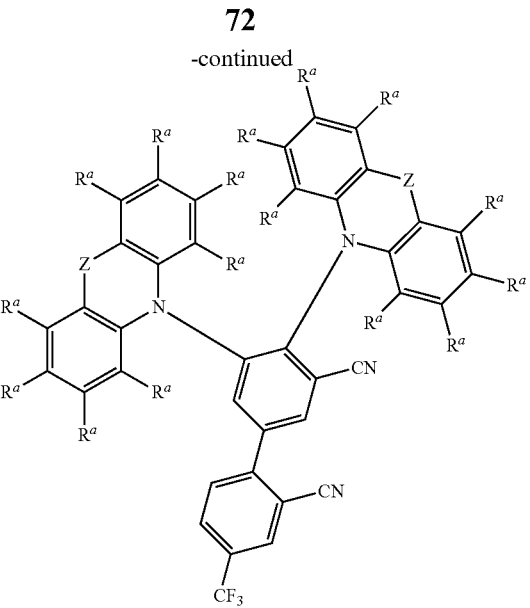
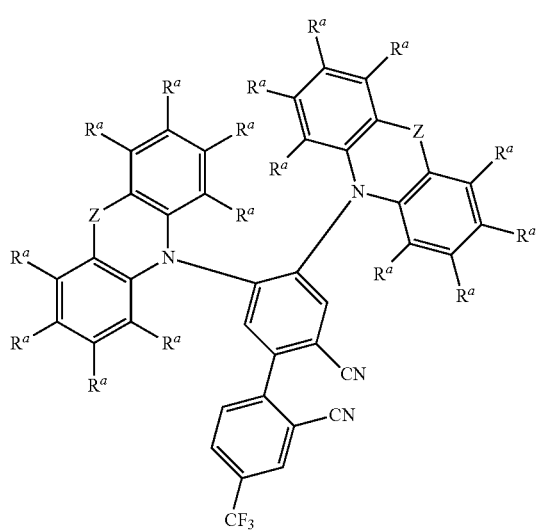
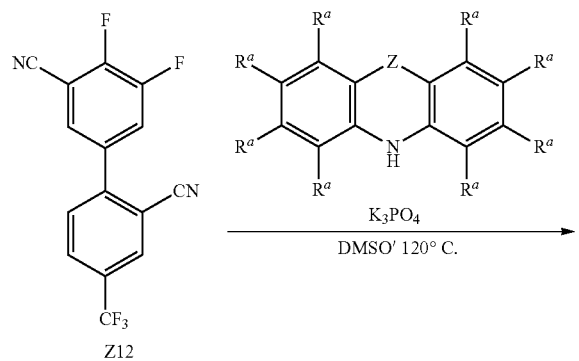

Z1, Z2, Z3, Z4, Z5, Z6, Z7, Z8, Z9, Z10, Z11 or Z12 (respectively 1.00 equivalent), the corresponding donor molecule D-H (2.00 equivalent) and potassium phosphate tribasic (4.00 equivalent) are suspended in DMSO under nitrogen and stirred at 120° C. (16 h). The reaction mixture is then added to water. The precipitated solid is filtered and washed with water. The precipitated solid is dissolved in dichloromethane, dried over sodium sulfate, filtered, and the solvent is subsequently removed. Lastly, the crude product is purified by recrystallization out of ethanol or by flash chromatography. The product is obtained as a solid.

D-H in particular corresponds to a 3,6-substituted carbazole (e.g. 3,6-dimethylcarbazole, 3,6-diphenylcarbazole, 3,6-di-tert-butylcarbazole), a 2,7-substituted carbazole (e.g. 2,7-dimethylcarbazole, 2,7-diphenylcarbazole, 2,7-di-tert-butylcarbazole), an 1,8-substituted carbazole (e.g. 1,8-dimethylcarbazole, 1,8-diphenylcarbazole, 1,8-di-tert-butylcarbazole), a 1-substituted carbazole (e.g. 1-methylcarbazole, 1-phenylcarbazole, 1-tert-butylcarbazole), a 2-substituted carbazole (e.g. 2-methylcarbazole, 2-phenylcarbazole, 2-tert-butylcarbazole) or a 3-substituted carbazole (e.g. 3-methylcarbazole, 3-phenylcarbazole, 3-tert-butylcarbazole).

General Experimental Methods
Cyclic Voltammetry

Cyclic voltammograms of $10^{-3}$ molar solutions of the organic molecules in dichloromethane and tetrabutylammonium hexafluorophosphate (0.1 mol/l) as the supporting electrolyte were recorded with the aid of a Model 600D Series Electrochemical Analyzer with Workstation (CH Instruments) at a scan rate of 100 mV s$^{-1}$. The measurements were carried out at room temperature, under a protective gas atmosphere, with a three electrode arrangement (working electrode and counter electrode: Pt wire. Reference electrode: Pt wire) and calibrated against FeCp$_2$/FeCp$_2^+$ as the internal standard. HOMO and LUMO data were corrected using ferrocene as the internal standard against SCE (saturated calomel electrode) and calculated according to the following formula:

$$E_{CV\text{-}HOMO} = -(1.4 \cdot 0.978 \cdot (Ox/V - \text{ferrocene}/V) + 4.6) \text{eV}.$$

Calculations According to the Density Functional Theory

The molecule structures were optimized by means of the BP86 functional, in which the resolution of identity approximation (RI) was used. Excitation energies for the BP86-optimized structures were calculated with the time-dependent DFT method (TD-DFT) using the B3LYP-functional. def2-SV (P) basis sets and an m4 grid were used for numerical integration in all the calculations. All DFT calculations were carried out using the turbomole program package (Version 6.5) (TURBOMOLE V6.4 2012, a development of University of Karlsruhe and Forschungszentrum Karlsruhe GmbH, 1989-2007, TURBOMOLE GmbH, since 2007; available from http://www.turbomole.com).

Photophysical Measurements

Sample Preparation, Film: Spin Coating

Device: Spin150, SPS Euro.

The sample concentration corresponded to 10 mg/ml, prepared in a suitable solvent. Program: 1) 3 s at 400 rpm; 2) 20 sat 1000 rpm at 1000 rpm/s. 3) 10 s at 4000 rpm at 1000 rpm/s. After coating, the films were dried on a LHG precision heating plate for 1 min at 70° C. in air.

Photoluminescence Spectroscopy and TCSPC

Steady-state emission spectroscopy was carried out using a fluorescence spectrometer of the Horiba Scientific company, Model Fluoromax-4, equipped with a 150 W xenon arc lamp, excitation and emission monochromators and a Hamamatsu R928 photomultiplier tube, as well as a "Time-Correlated Single Photon Counting" (TCSPC) option. The emission and excitation spectra were corrected by means of standard correction curves.

The emission decay times were likewise measured on this system, using the TCSPC method with the FM-2013 accessories and a TCSPC hub of the Horiba Yvon Jobin company.

Excitation sources:
NanoLED 370 (wavelength: 371 nm, pulse duration: 1.1 ns)
NanoLED 290 (wavelength: 294 nm, pulse duration: <1 ns)
SpectraLED 310 (wavelength: 314 nm)
SpectraLED 355 (wavelength: 355 nm).

The analysis (exponential fitting) was performed using the DataStation software package and the DAS6 analysis software. The fit was specified with the aid of the chi square method.

Quantum Efficiency Determination

The measurement of the photoluminescence quantum yield (PLQY) was carried out by means of an Absolute PL Quantum Yield Measurement C9920-03G system of the company Hamamatsu Photonics, Said system consists of a 150 W xenon gas discharge lamp, automatically adjustable Czerny-Turner monochromators (250-950 nm) and an Ulbricht sphere with a high reflectance Spectralon coating (a Teflon derivative), which is connected via a fiber optic cable to a PMA-12 multichannel detector with a BT (back-thinned)-CCD chip having 1024×122 pixels (size 24×24 µm). The analysis of the quantum efficiency and the CIE coordinates was carried out using the software U6039-05 Version 3.6.0.

The emission maximum is measured in nm, the quantum yield Φ is measured in % and the CIE color coordinates are stated as x, y values.

The photoluminescence quantum yield was determined according to the following protocol:
1) Implementation of quality assurance measures: Anthracene in ethanol at a known concentration serves as the reference material.
2) Determination of the excitation wavelength: The absorption maximum of the organic molecule was determined first and excitation was carried out with said wavelength.

3) Implementation of the sample measurement:

The absolute quantum yield of degassed solutions and films was determined under a nitrogen atmosphere.

The calculation was performed within the system according to the following equation:

$$\Phi_{PL} = \frac{n_{photon}, \text{emittiert}}{n_{photon}, \text{absorbiert}} = \frac{\int \frac{\lambda}{hc}[Int_{emittiert}^{Probe}(\lambda) - Int_{absorbiert}^{Probe}(\lambda)]d\lambda}{\int \frac{\lambda}{hc}[Int_{emittiert}^{Referenz}(\lambda) - Int_{absorbiert}^{Referenz}(\lambda)]d\lambda}$$

with the photon number $n_{photon}$ and the intensity Int.

All photophysical measurements were carried out in the respectively specified medium and at room temperature.

Production and Characterization of Organic Electroluminescence Devices from the Gas Phase With the organic molecules according to the invention, OLED devices can be produced by means of vacuum sublimation techniques. If a layer contains multiple components, the ratio of said components is stated in percent by mass.

These not yet optimized OLEDs can be characterized in the usual manner. To do this, the electroluminescence spectra, the external quantum efficiency (measured in %) as a function of the brightness and calculated from the light detected by the photodiode, and the current are recorded. The lifetime of the OLEDs can be determined from the time profile of the electroluminescence spectra. The indicated LT50 value corresponds to the time at which the luminance has fallen to 50% of the starting value. The LT70 value analogously corresponds to the time at which the luminance has fallen to 70% of the starting value.

The indicated values are obtained from the average of the various pixels of an OLED. The spectra depicted in each case show a measurement series of a pixel.

HPLC-MS:

HPLC-MS spectroscopy was measured using an HPLC system of the company Agilent (1100 series) with a connected MS detector (Thermo LTQ XL). An RP column 4.6 mm×150 mm and a Waters' particle size of 5.0 µm was used for the HPLC. This was carried out without a precolumn and at room temperature using the solvents acetonitrile, water and tetrahydrofuran in the following concentrations:

| Solvent A: | H2O (90%) | MeCN (10%) |
| Solvent B: | H2O (10%) | MeCN (90%) |
| Solvent C: | THF (50%) | MeCN (50%) |

An injection volume of 15 µL and a concentration of 0.5 mg/ml were used.

| Flow [ml/min] | Time [min] | A[%] | B[%] | C[%] |
|---|---|---|---|---|
| 3 | 0.00 | 40 | 50 | 10 |
| 3 | 10.00 | 15 | 25 | 60 |
| 3 | 14.00 | 15 | 25 | 60 |
| 3 | 14.01 | 40 | 50 | 10 |
| 3 | 18.00 | 40 | 50 | 10 |
| 3 | 19.00 | 40 | 50 | 10 |

Example 1

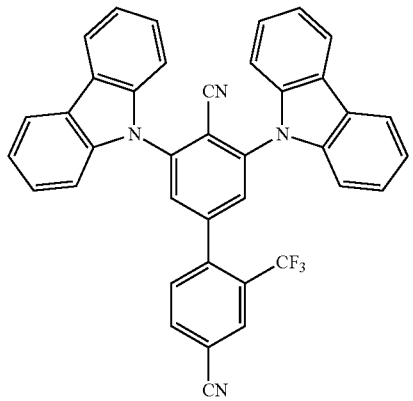 [SMILES: N#Cc1ccc(-c2cc(-n3c4ccccc4c4ccccc43)c(C#N)c(-n3c4ccccc4c4ccccc43)c2)c(C(F)(F)F)c1]

Example 1 was produced in accordance with AAV1-1 (Yield 54%) and AAV7 (Yield 79%).

MS (HPLC-MS), m/z (retention time): 602.18 (6.11 min)

FIG. 1 shows the emission spectrum of Example 1 (10% in PMMA). The emission maximum is at 456 nm. The photoluminescence quantum yield (PLAY) is 88% and the full width at half maximum is 0.47 eV.

Example 2

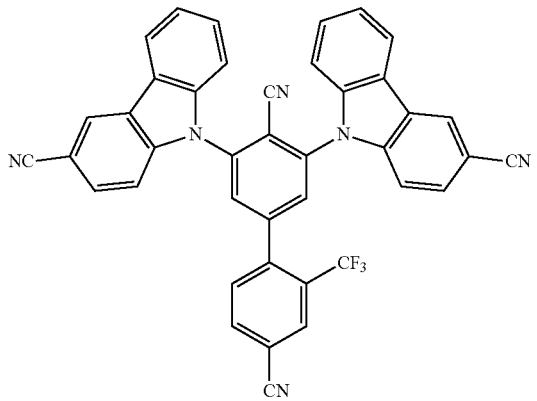 [SMILES: N#Cc1ccc(-c2cc(-n3c4ccccc4c4cc(C#N)ccc43)c(C#N)c(-n3c4ccccc4c4cc(C#N)ccc43)c2)c(C(F)(F)F)c1]

Example 2 was produced in accordance with AAV1-1 (Yield 88%) and AAV7 (Yield 90%).

MS (HPLC-MS), m/z (retention time): 652.2 (4.69 min)

Figure 2:
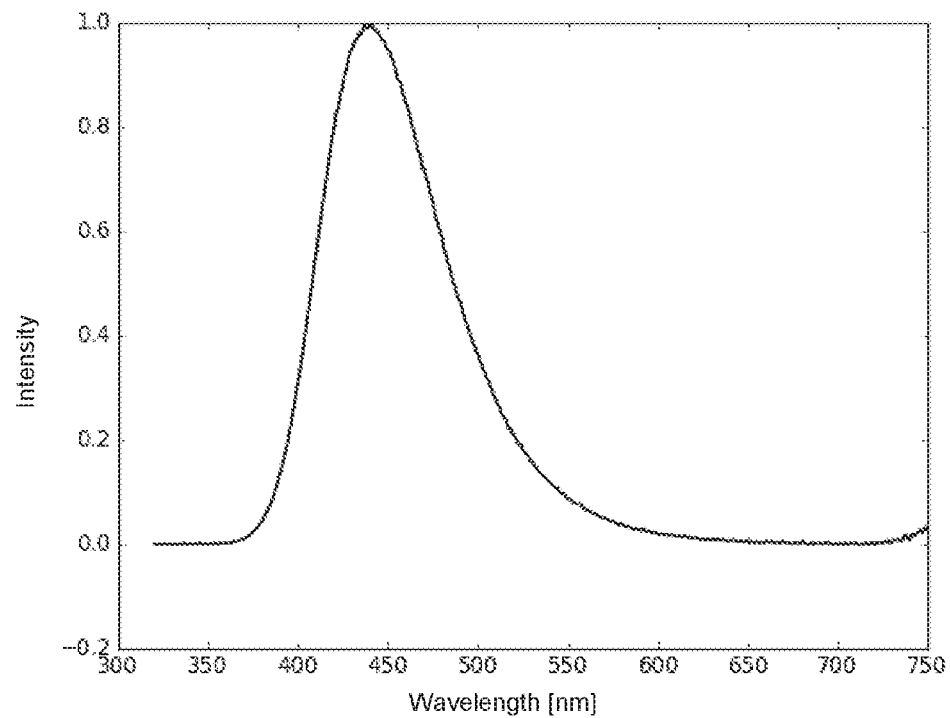
FIG. 2 is an emission spectrum of Example 2 (10% in PMMA).

FIG. 2 shows the emission spectrum of Example 2 (10% in PMMA). The emission maximum is at 437 nm. The photoluminescence quantum yield (PLQY) is 61% and the full width at half maximum is 0.49 eV.

Example 3

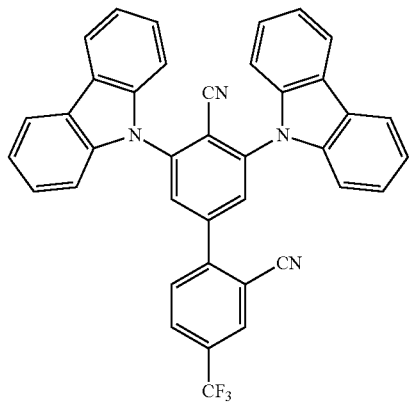 [SMILES: N#Cc1cc(C(F)(F)F)ccc1-c1cc(-n2c3ccccc3c3ccccc32)c(C#N)c(-n2c3ccccc3c3ccccc32)c1]

Example 3 was produced in accordance with AAV1-2 (Yield 54%) and AAV7 (Yield 58%).

MS (HPLC-MS), m/z (retention time): 602.21 (6.23 min)

Figure 3:
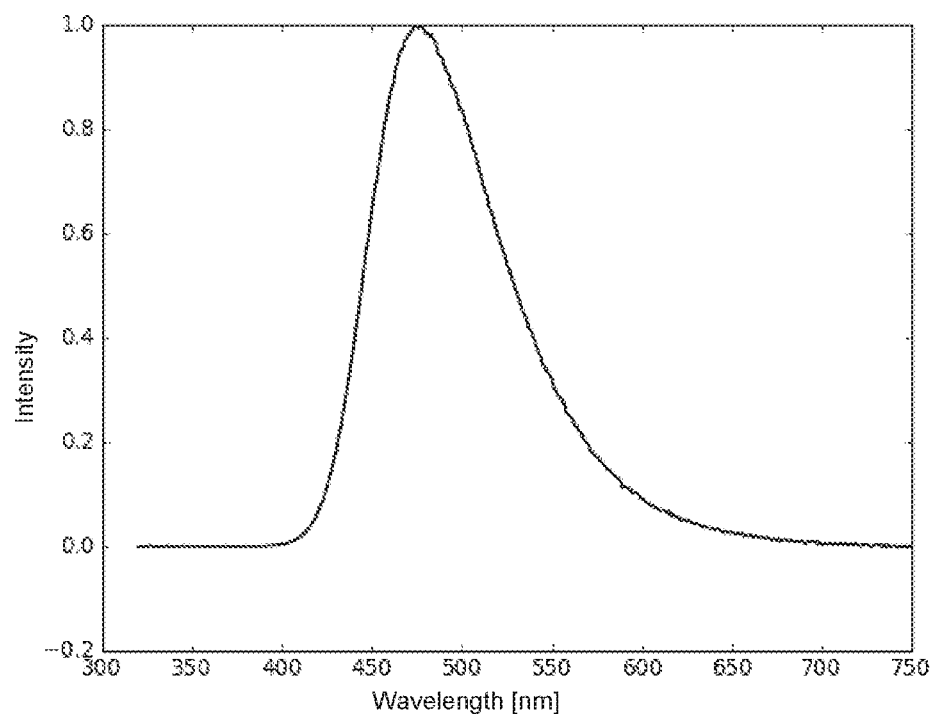
FIG. 3 is an emission spectrum of Example 3 (10% in PMMA).

FIG. 3 shows the emission spectrum of Example 3 (10% in PMMA). The emission maximum is at 474 nm. The photoluminescence quantum yield (PLQY) is 80% and the full width at half maximum is 0.45 eV. The emission decay time is 39 μs.

Example 4

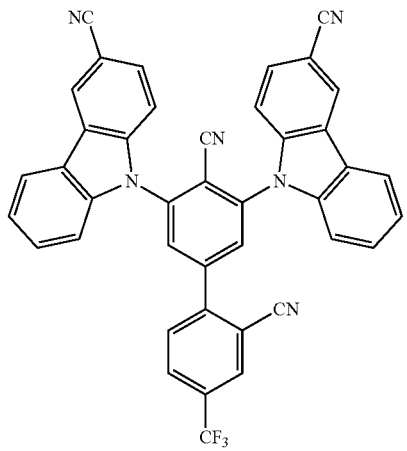 [SMILES: N#Cc1ccc2c(c1)c1ccccc1n2-c1cc(-c2ccc(C(F)(F)F)cc2C#N)cc(-n2c3ccccc3c3cc(C#N)ccc32)c1C#N]

Example 3 was produced in accordance with AAV1-2 (Yield 54%) and AAV7 (Yield 49%).

Figure 4:
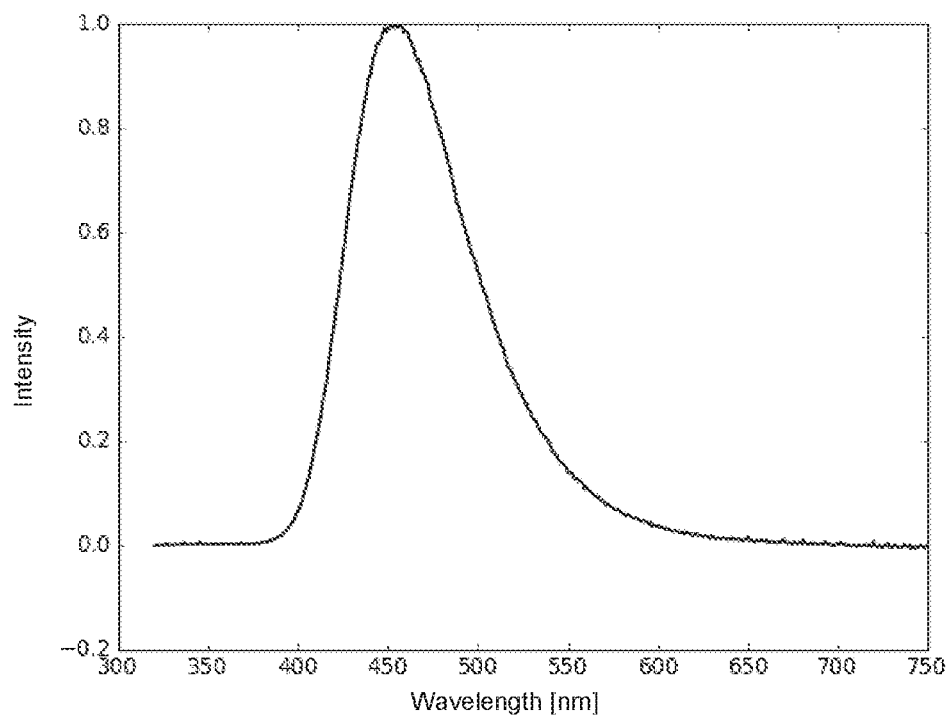
FIG. 4 is an emission spectrum of Example 4 (10% in PMMA).

FIG. 4 shows the emission spectrum of Example 4 (10% in PMMA). The emission maximum is at 452 nm. The photoluminescence quantum yield (PLQY) is 69% and the full width at half maximum is 0.46 eV.

Example 5

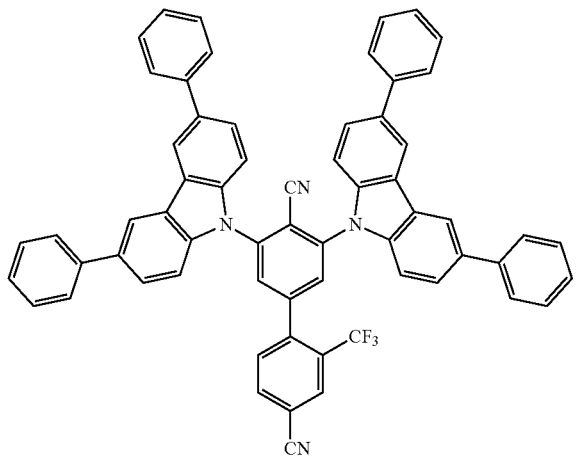 [SMILES: N#Cc1ccc(-c2cc(-n3c4ccc(-c5ccccc5)cc4c4cc(-c5ccccc5)ccc43)c(C#N)c(-n3c4ccc(-c5ccccc5)cc4c4cc(-c5ccccc5)ccc43)c2)c(C(F)(F)F)c1]

Example 5 was produced in accordance with AAV1-1 (Yield 88%) and AAV7 (Yield 16%).

Figure 5:
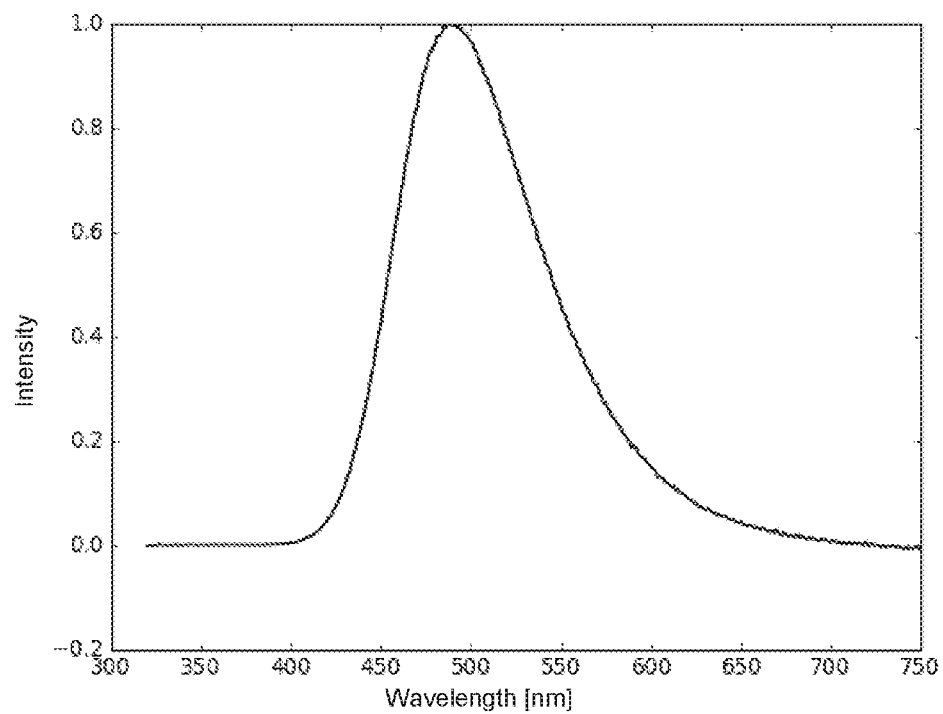
FIG. 5 is an emission spectrum of Example 5 (10% in PMMA).

FIG. 5 shows the emission spectrum of Example 5 (10% in PMMA). The emission maximum is at 489 nm. The photoluminescence quantum yield (PLQY) is 80% and the full width at half maximum is 0.46 eV, The emission decay time is 11 μs.

Example 6

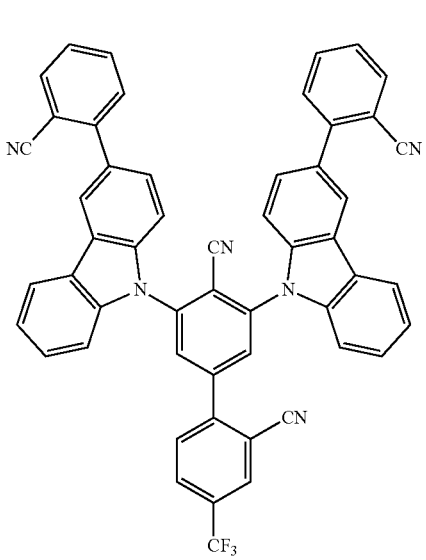 [SMILES: N#Cc1ccccc1-c1ccc2c(c1)c1ccccc1n2-c1cc(-c2ccc(C(F)(F)F)cc2C#N)cc(-n2c3ccccc3c3cc(-c4ccccc4C#N)ccc32)c1C#N]

Example 6 was produced in accordance with AAV1-2 (Yield 54%) and AAV7 (Yield 45%).

Figure 6:
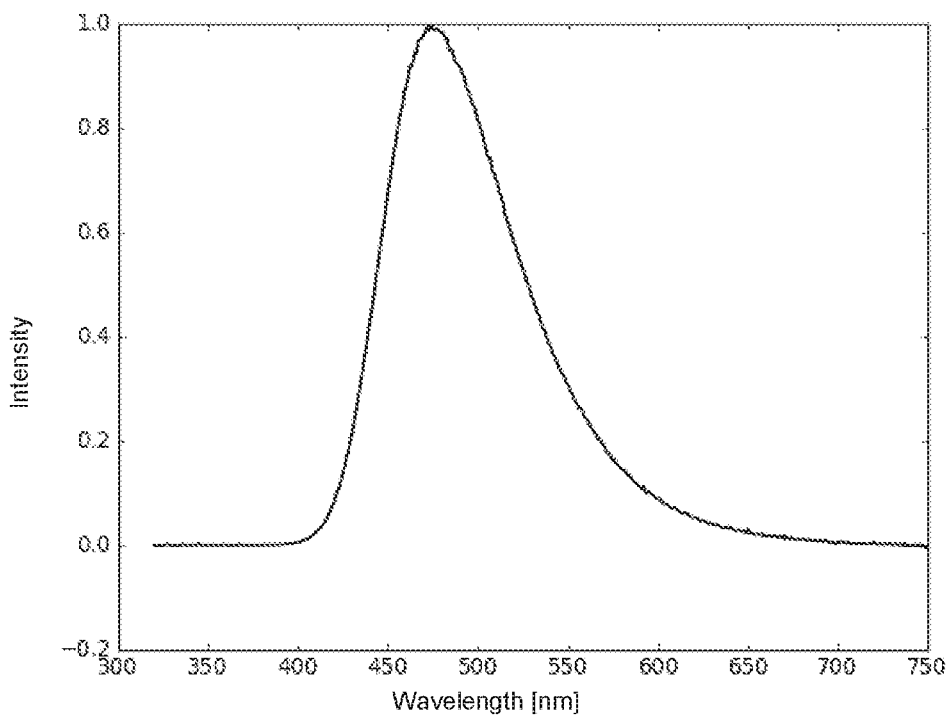
FIG. 6 is an emission spectrum of Example 6 (10% in PMMA).

FIG. 6 shows the emission spectrum of Example 6 (10% in PMMA), The emission maximum is at 474 nm. The photoluminescence quantum yield (PLQY) is 66% and the full width at half maximum is 0.45 eV. The emission decay time is 87 μs.

Example 7

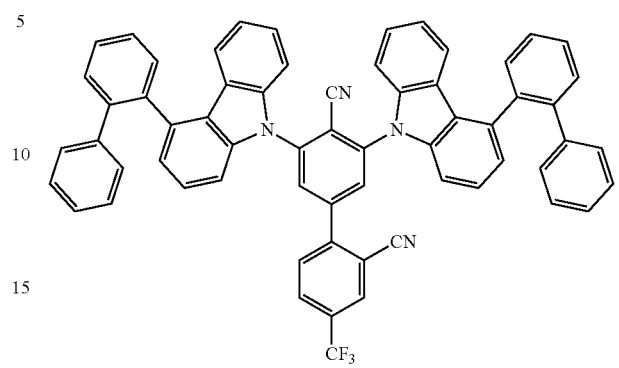

Example 7 was produced in accordance with AAV1-2 (Yield 54%) and AAV7 (Yield 57%).

Figure 7:
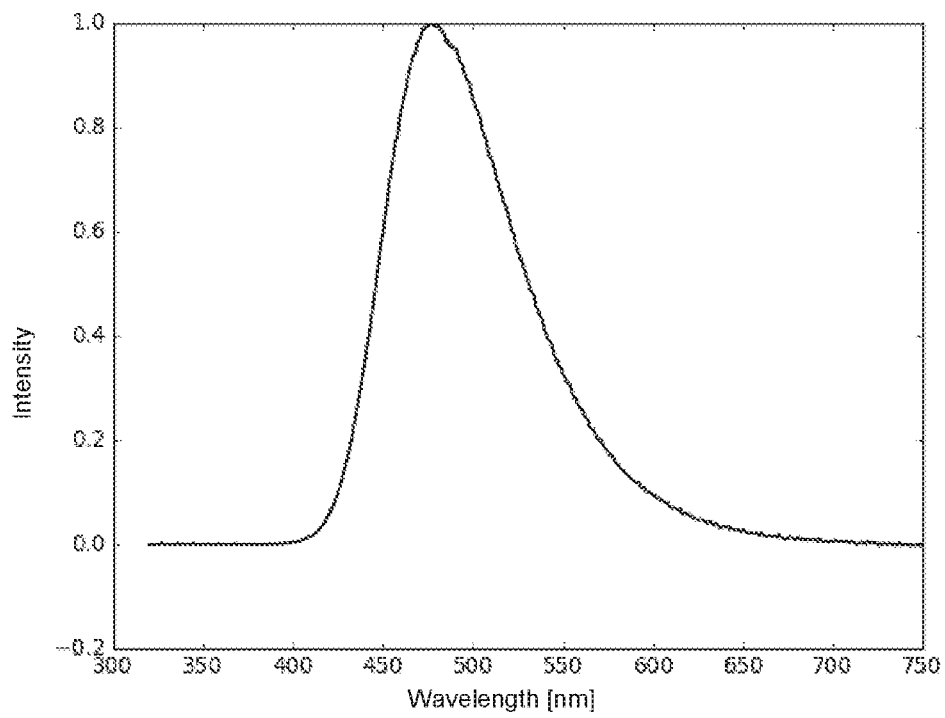
FIG. 7 is an emission spectrum of Example 7 (10% in PMMA).

FIG. 7 shows the emission spectrum of Example 7 (10% in PMMA), The emission maximum is at 477 nm. The photoluminescence quantum yield (PLQY) is 84% and the full width at half maximum is 0.44 eV. The emission decay time is 55 μs.

Example 8

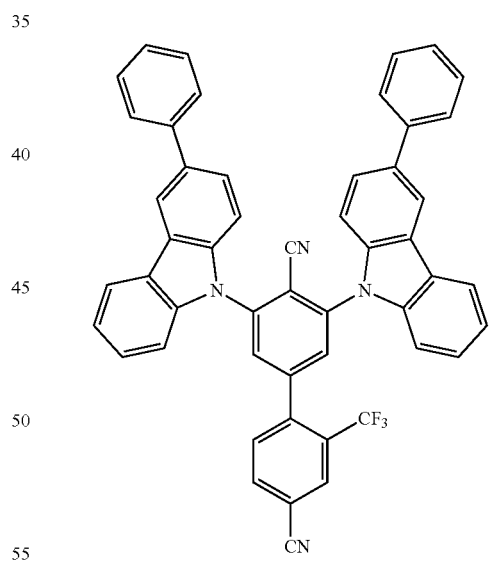

Example 8 was produced in accordance with AAV1-1 (Yield 88%) and AAV7 (Yield 51%).

Figure 8:
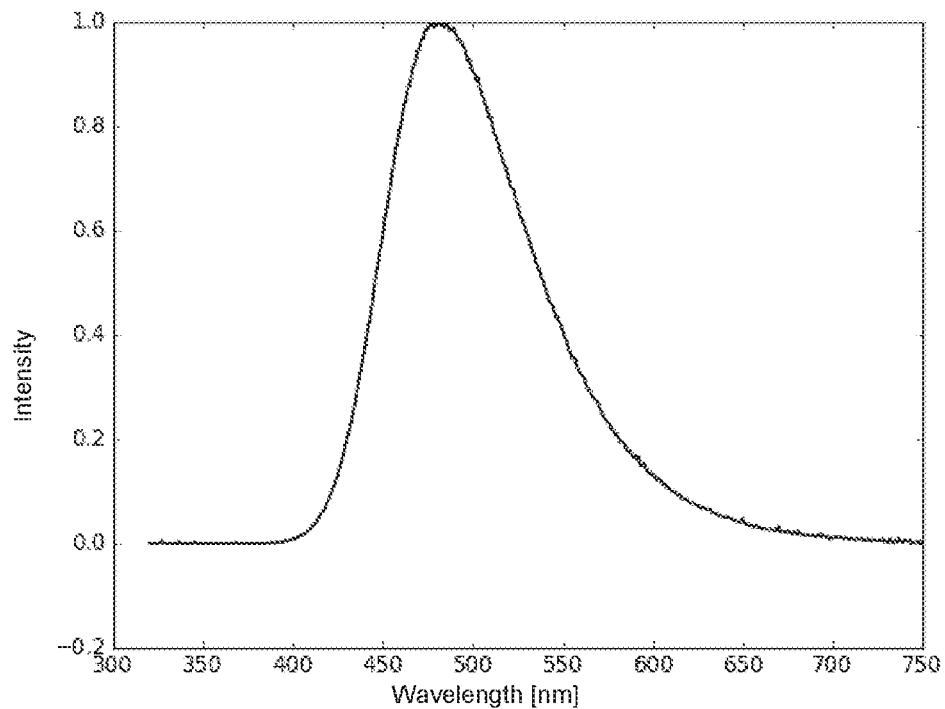
FIG. 8 is an emission spectrum of Example 8 (10% in PMMA).

FIG. 8 shows the emission spectrum of Example 8 (10% in PMMA). The emission maximum is at 481 nm. The photoluminescence quantum yield (PLQY) is 75% and the full width at half maximum is 0.48 eV. The emission decay time is 13 μs.

Example 9

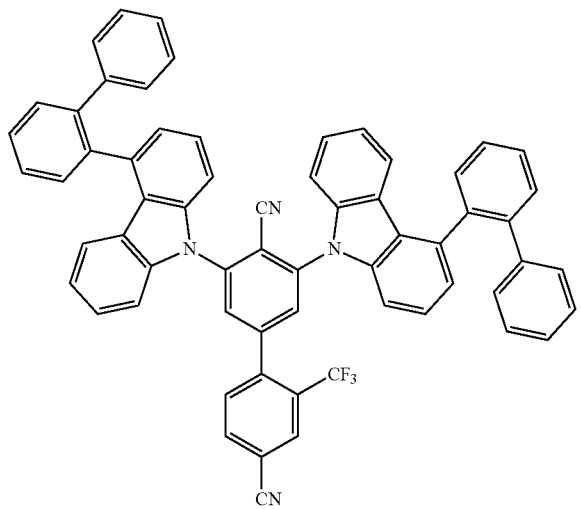 [SMILES: N#Cc1ccc(-c2cc(-n3c4ccccc4c4c(-c5ccccc5-c5ccccc5)cccc43)c(C#N)c(-n3c4ccccc4c4c(-c5ccccc5-c5ccccc5)cccc43)c2)c(C(F)(F)F)c1]

Example 9 was produced in accordance with AAV1-1 (Yield 88%) and AAV7 (Yield 58%).

Figure 9:
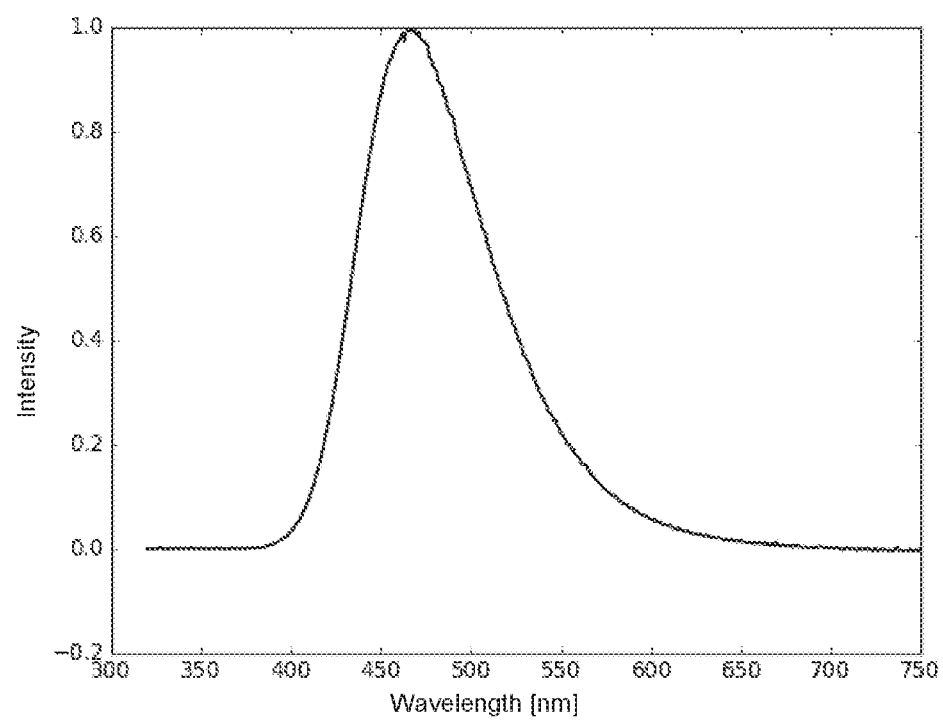
FIG. 9 is an emission spectrum of Example 9 (10% in PMMA).

FIG. 9 shows the emission spectrum of Example 9 (10% in PMMA). The emission maximum is at 466 nm. The photoluminescence quantum yield (PLQY) is 66% and the full width at half maximum is 0.47 eV.

Example 10

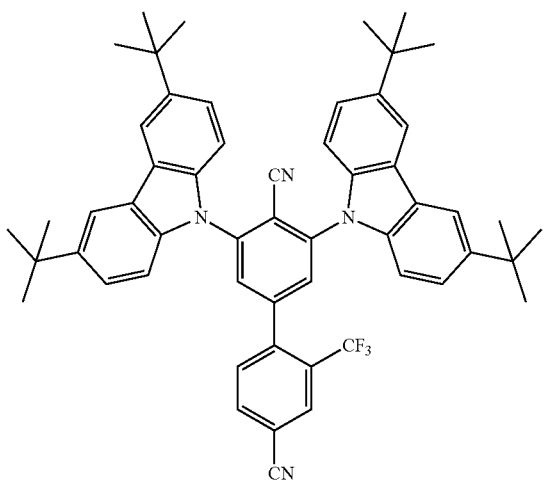 [SMILES: CC(C)(C)c1ccc2c(c1)c1cc(C(C)(C)C)ccc1n2-c1cc(-c2ccc(C#N)cc2C(F)(F)F)cc(-n2c3ccc(C(C)(C)C)cc3c3cc(C(C)(C)C)ccc32)c1C#N]

Example 10 was produced in accordance with AAV1-1 (Yield 88%) and AAV7 (Yield 71%).

Figure 10:
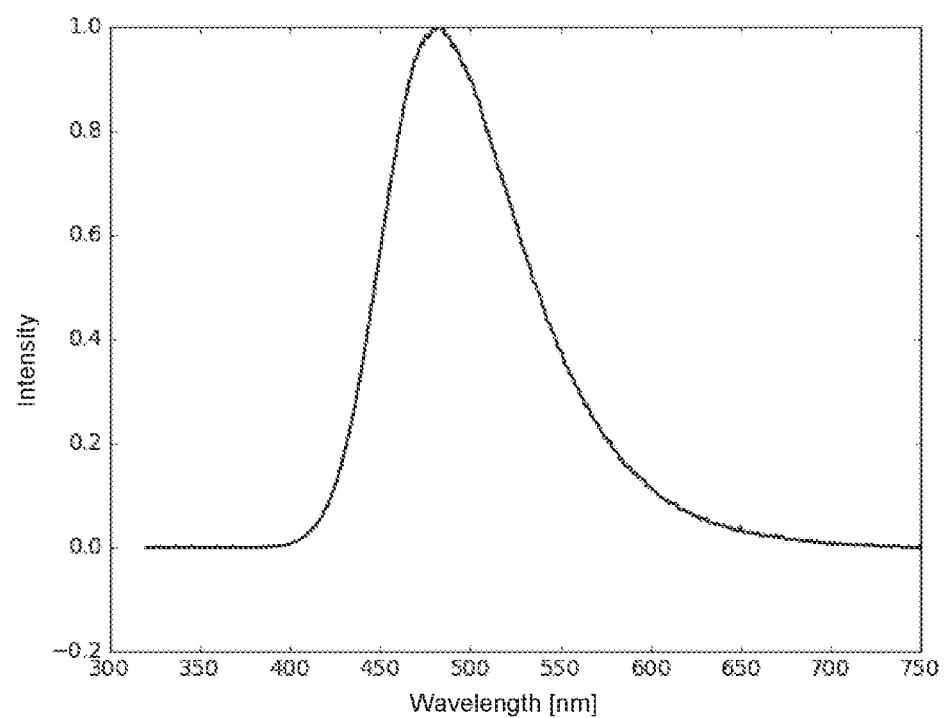
FIG. 10 is an emission spectrum of Example 10 (10% in PMMA).

FIG. 10 shows the emission spectrum of Example 10 (10% in PMMA). The emission maximum is at 480 nm. The photoluminescence quantum yield (PLQY) is 81% and the full width at half maximum is 0.47 eV. The emission decay time is 7 μs.

Example 11

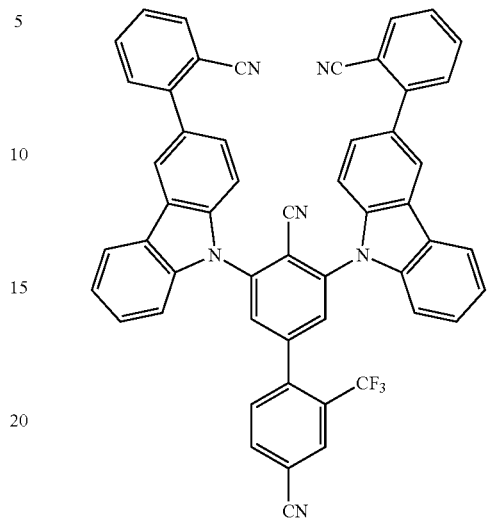

Example 11 was produced in accordance with AAV1-1 (Yield 88%) and AAV7 (Yield 25%).

Figure 11:
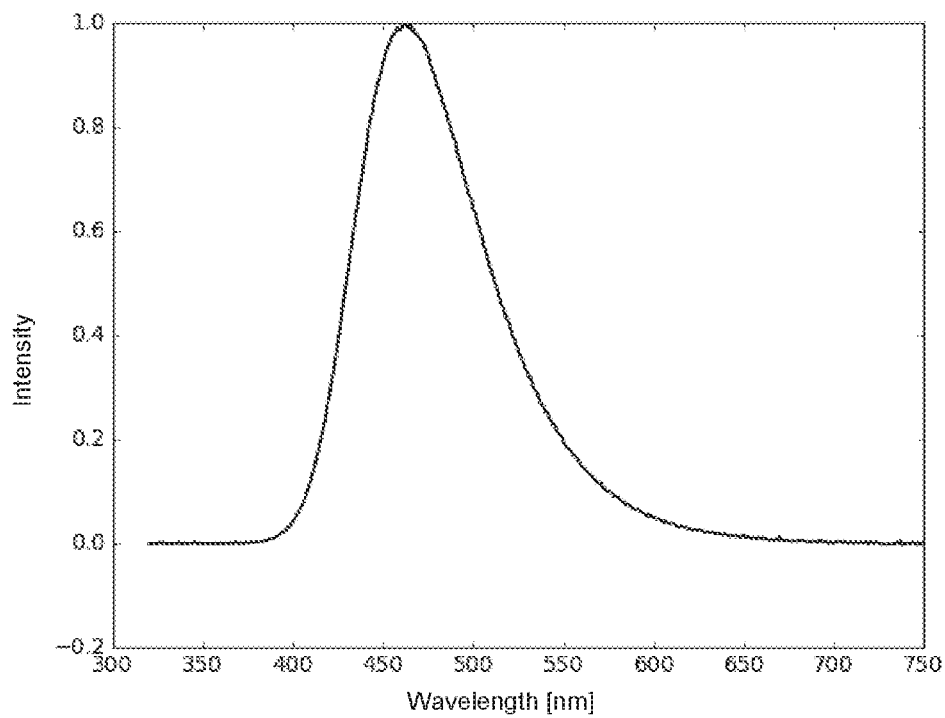
FIG. 11 is an emission spectrum of Example 11 (10% in PMMA).

FIG. 11 shows the emission spectrum of Example 11 (10% in PMMA). The emission maximum is at 462 nm. The photoluminescence quantum yield (PLQY) is 79% and the full width at half maximum is 0.47 eV.

Example 12

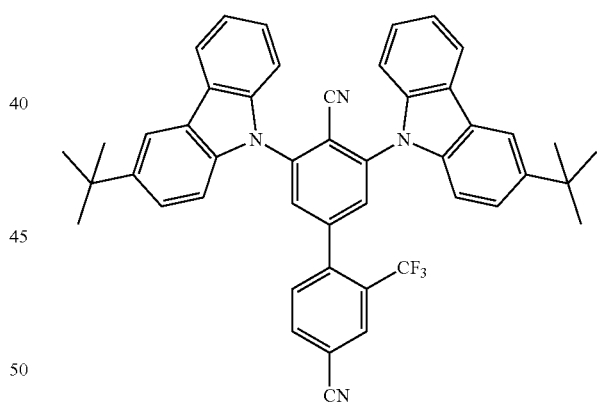

Example 12 was produced in accordance with AAV1-1 (Yield 88%) and AAV7 (Yield 59%).

Figure 12:
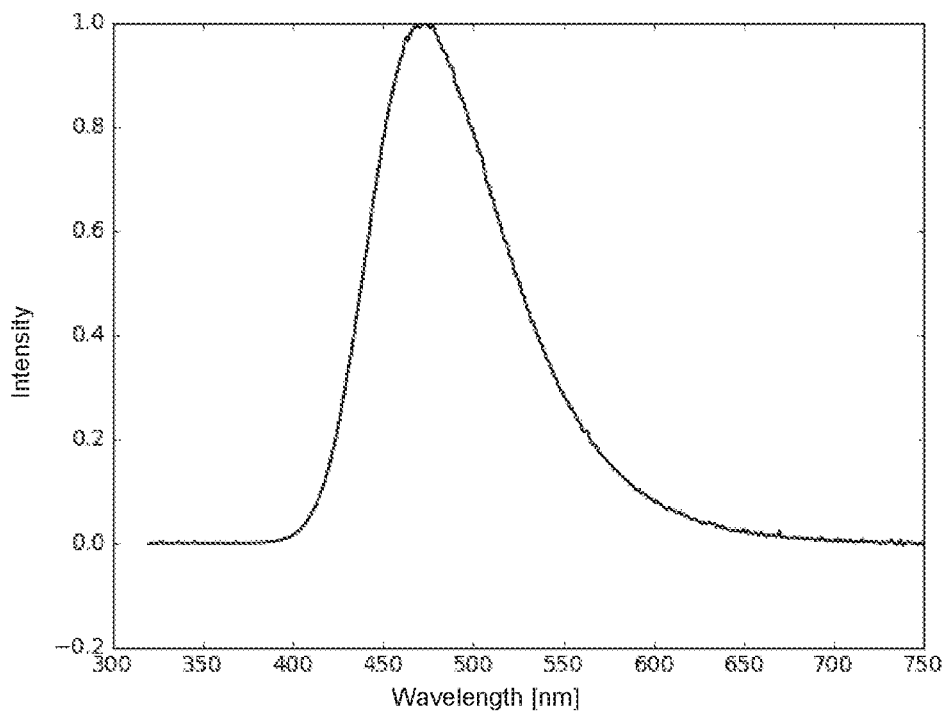
FIG. 12 is an emission spectrum of Example 12 (10% in PMMA).

FIG. 12 shows the emission spectrum of Example 12 (10% in PMMA). The emission maximum is at 473 nm. The photoluminescence quantum yield (PLQY) is 89% and the full width at half maximum is 0.47 eV. The emission decay time is 14 μs.

Example D1

Example 1 was tested in the OLED component D1 with the following structure (the fraction of the molecule according to the invention and the host molecule in the emission layer is respectively stated in percent by mass):

| Layer | Thickness | Material |
|---|---|---|
| 10 | 100 nm | Al |
| 9 | 2 nm | Liq |
| 8 | 30 nm | TPBi |
| 7 | 10 nm | DPEPO |
| 6 | 20 nm | Example 1 (10%):DPEPO(90%) |
| 5 | 10 nm | CzSi |
| 4 | 20 nm | TCTA |
| 3 | 70 nm | NPB |
| 2 | 20 nm | m-MTDATA |
| 1 | 130 nm | ITO |
| Substrate | | Glass |

The emission maximum is at 468 nm, CIEx was determined with 0.17 and the CIEy with 0.24 at 6 V. The EQE at 1000 cd/m² is 7.9±0.2%.

Example D2

The OLED component D2 was produced analogously to the OLED component D1, except that Example 1 was replaced by Example 3 in the emission layer. The emission maximum is at 475 nm, CIEx was determined with 0.19 and the CIEy with 0.31 at 6 V. The EQE at 1000 cd/m² is 8.0±0.3%.

Example D3

Example 3 was tested in the OLED component D3 with the following structure (the fraction of the molecule according to the invention and the host molecule in the emission layer is respectively stated in percent by mass):

| Layer | Thickness | Material |
|---|---|---|
| 8 | 100 nm | Al |
| 7 | 2 nm | Liq |
| 6 | 30 nm | NBPhen |
| 5 | 10 nm | T2T |
| 4 | 20 nm | Example 3 (20%):mCBP (65%):T2T (15%) |
| 3 | 10 nm | TCTA |
| 2 | 80 nm | NPB |
| 1 | 130 nm | ITO |
| Substrate | | Glass |

The emission maximum is at 475 nm, CIEx was determined with 0.19 and the CIEy with 0.34 at 6 V. The EQE at 1000 cd/m² is 11.2±0.1%.

Example D4

Example 7 was tested in the OLED component D4 with the following structure:

| Layer | Thickness | Material |
|---|---|---|
| 9 | 100 nm | Al |
| 8 | 2 nm | Liq |
| 7 | 30 nm | NBPhen |
| 6 | 10 nm | T2T |
| 5 | 30 nm | Example 7 (20%):mCBP (60%):T2T (20%) |
| 4 | 8 nm | mCBP |
| 3 | 10 nm | TCTA |
| 2 | 62 nm | NPB |
| 1 | 130 nm | ITO |
| Substrate | | Glass |

The emission maximum is at 480 nm, CIEx was determined with 0.18 and the CIEy with 0.35 at 6 V. The EQE at 1000 cd/m² is 16.9±0.1%.

Example D5

The OLED component D5 was produced analogously to OLED component D4, with the difference that Layer 5 was constructed as follows: Example 8 (20%): mCBP (70%): T2T (10%).

The emission maximum is at 475 nm, CIEx was determined with 0.20 and the CIEy with 0.30 at 6 V. The EQE at 1000 cd/m² is 11.4±0.1%.

Example D6

The OLED component D6 was produced analogously to the OLED component D4, with the difference that Example 7 was replaced by Example 12.

The emission maximum is at 475 nm, CIEx was determined with 0.19 and the CIEy with 0.29 at 6 V. The EQE at 1000 cd/m² is 8.6±0.2%.

Other Examples of Organic Molecules According to the Invention

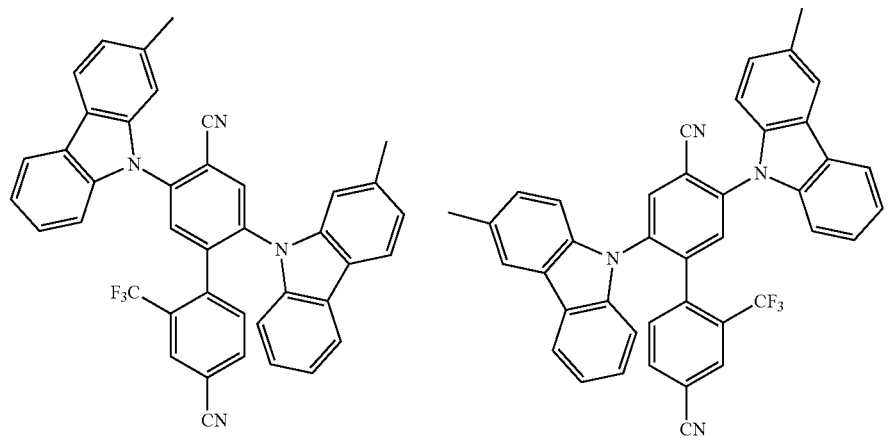

-continued
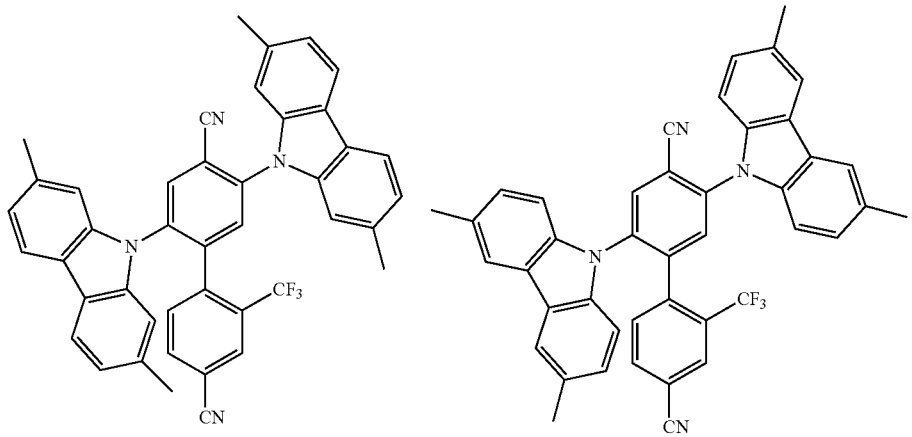
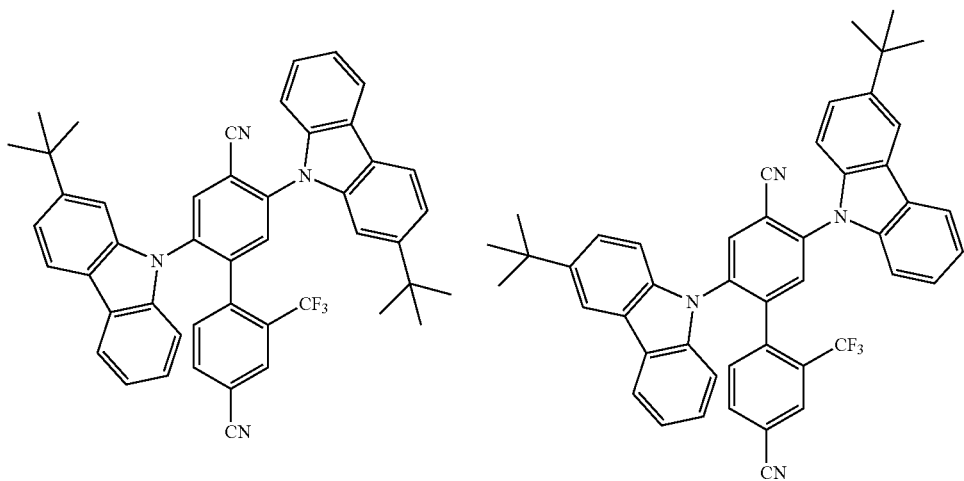
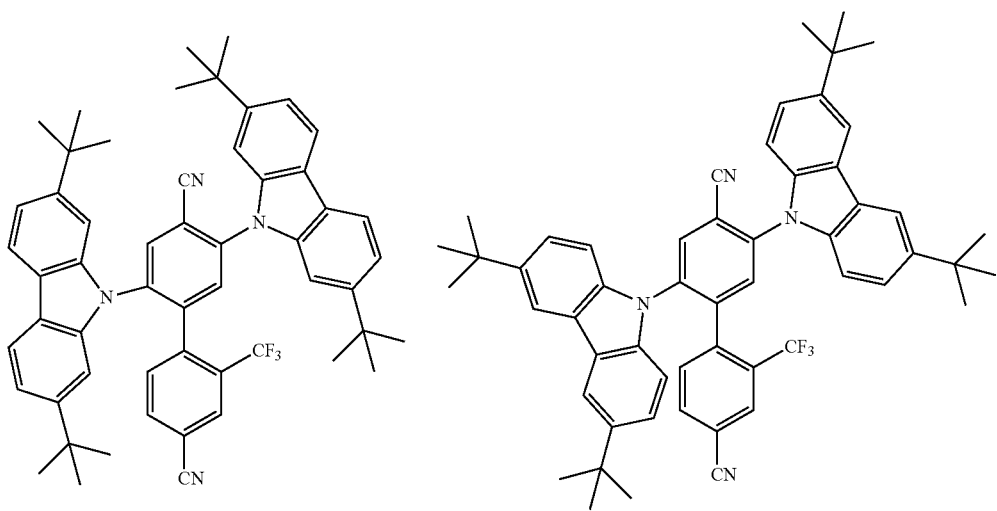

-continued
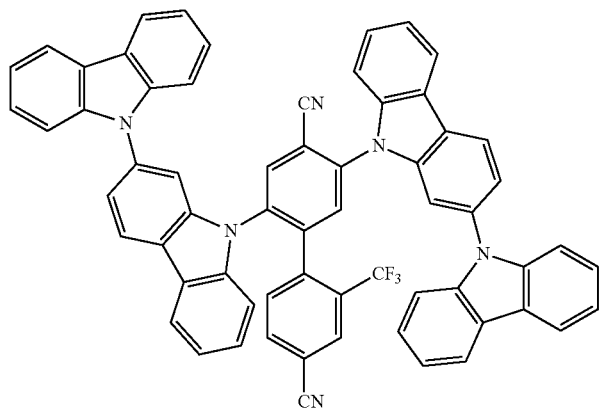
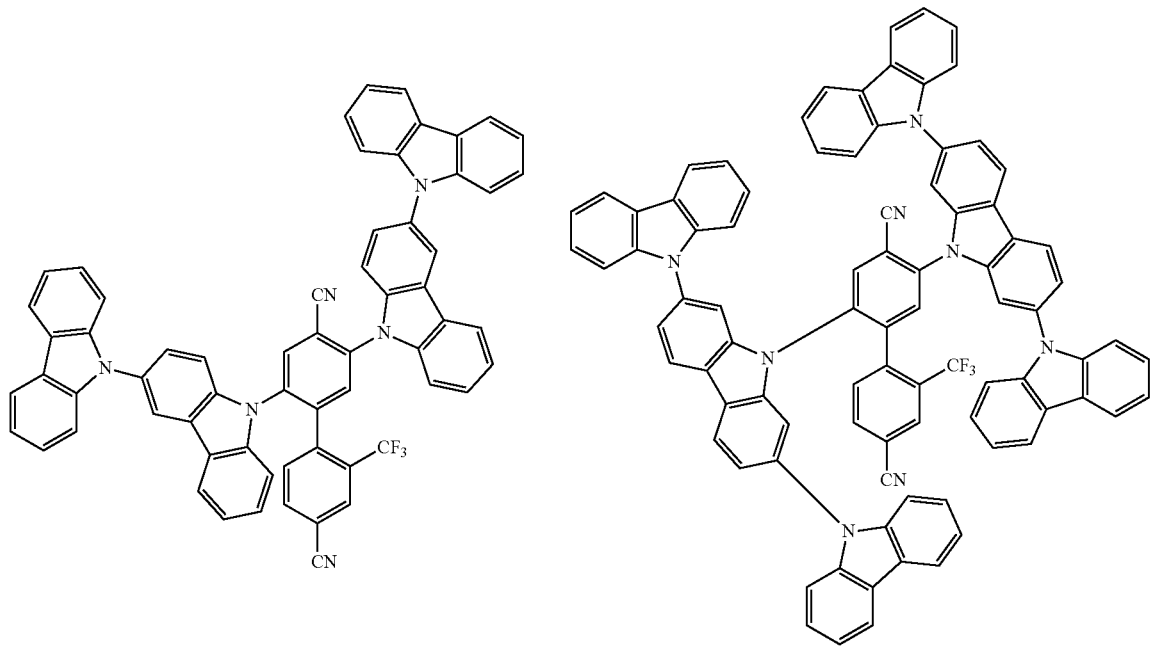
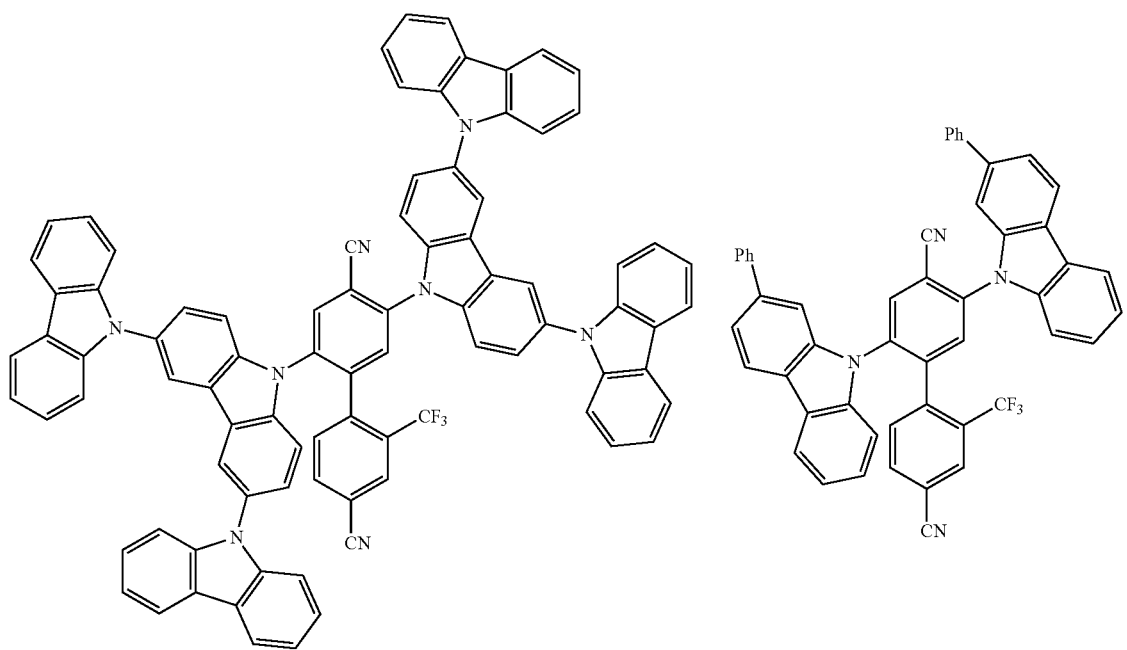

-continued
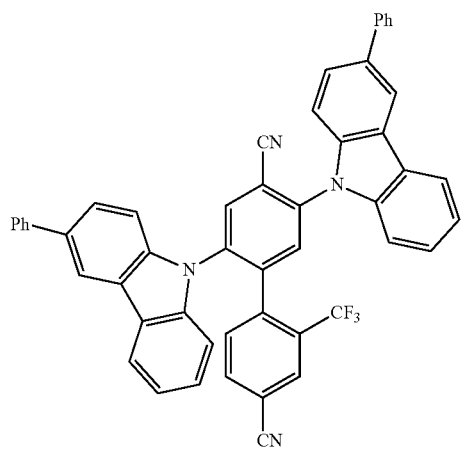
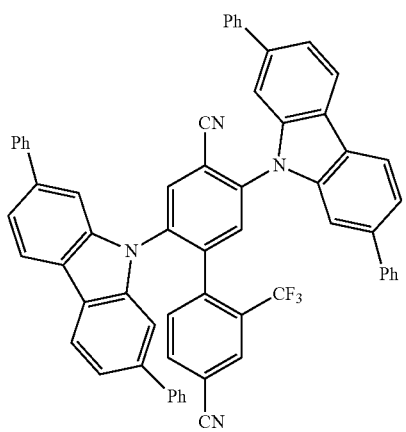
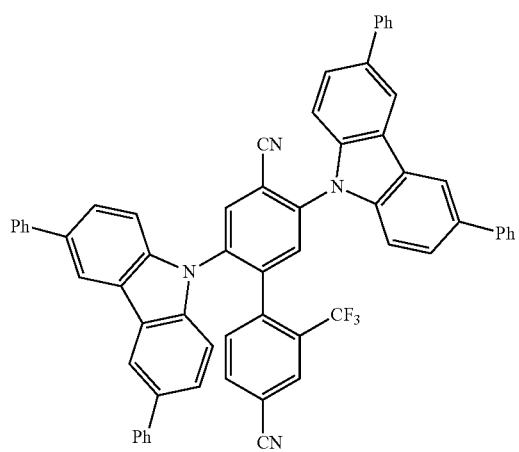
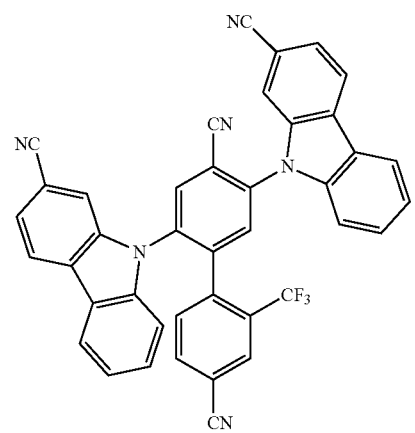
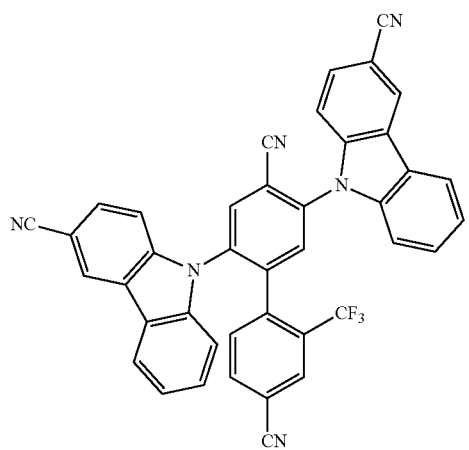
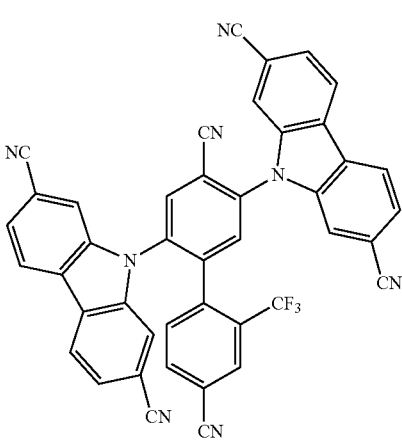

-continued
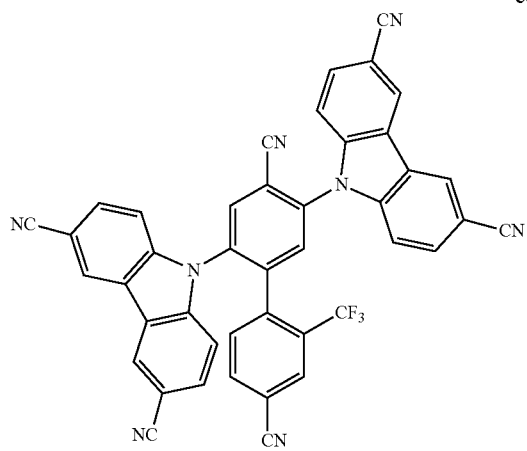
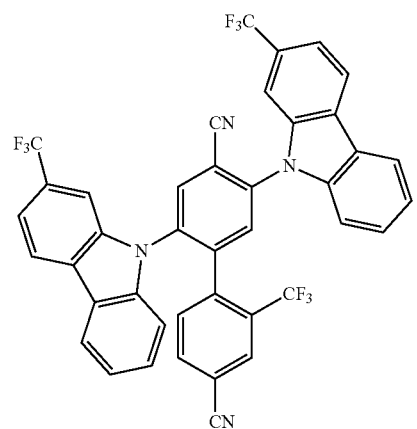
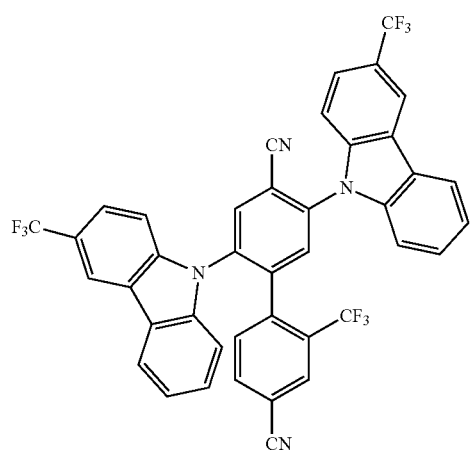
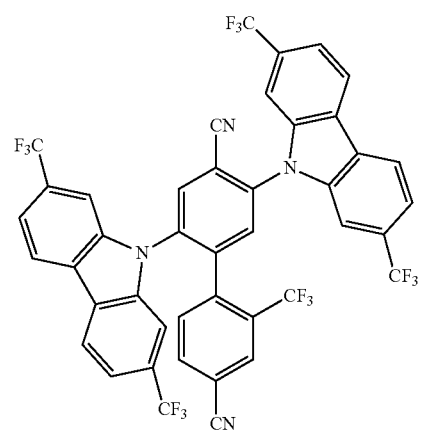
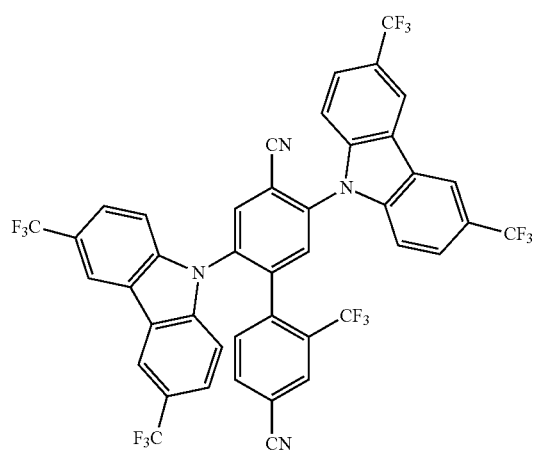
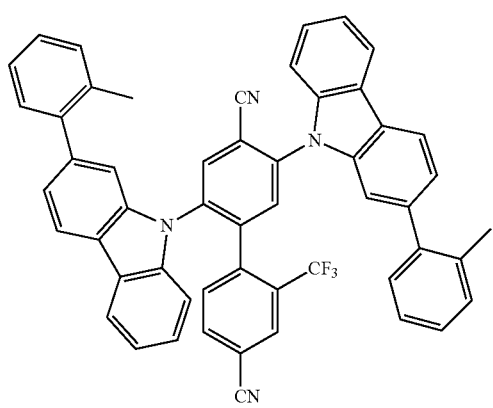

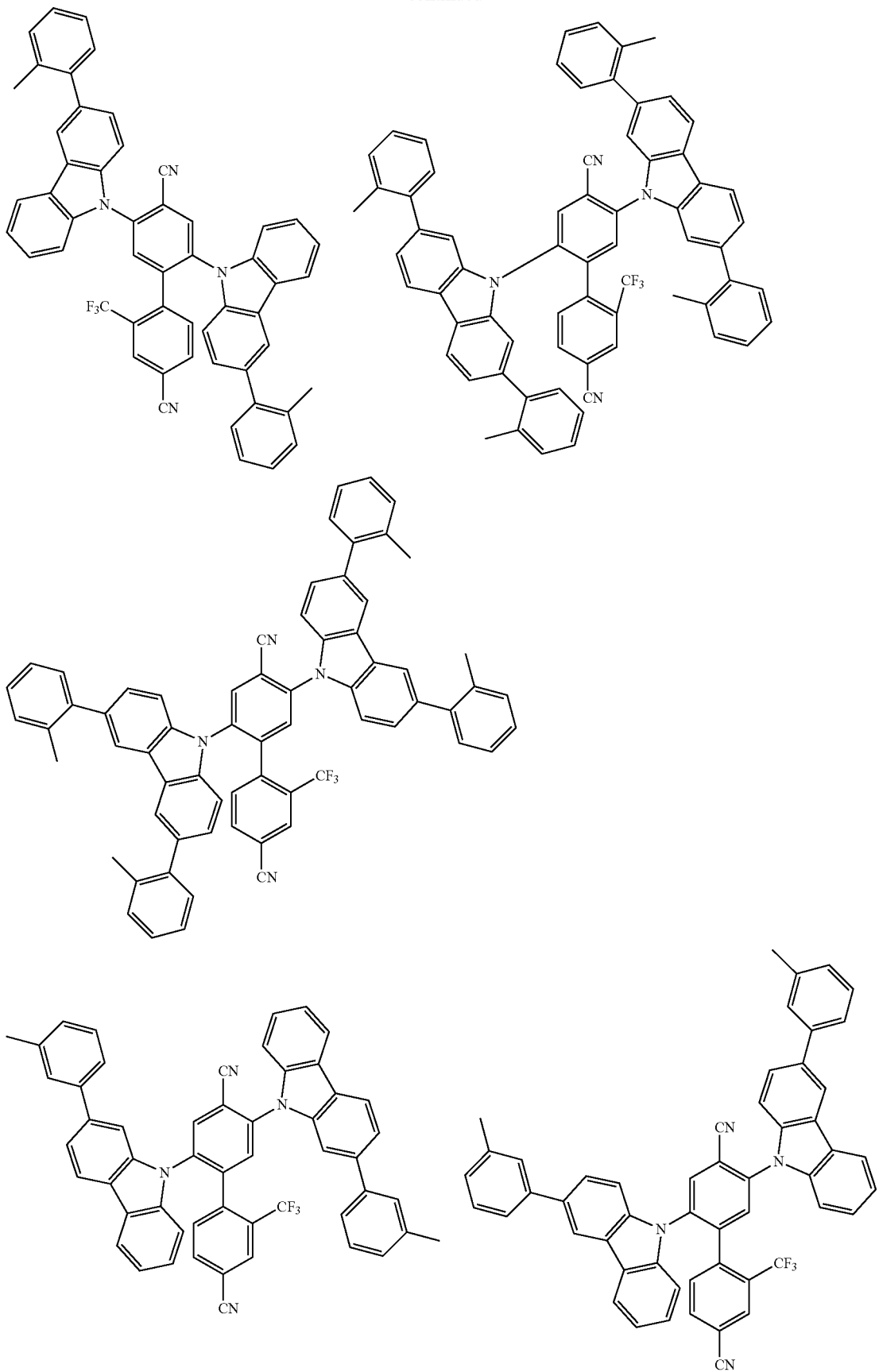

93 94
-continued
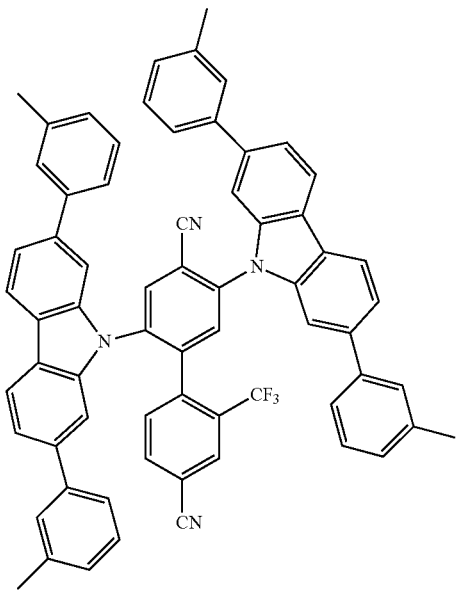
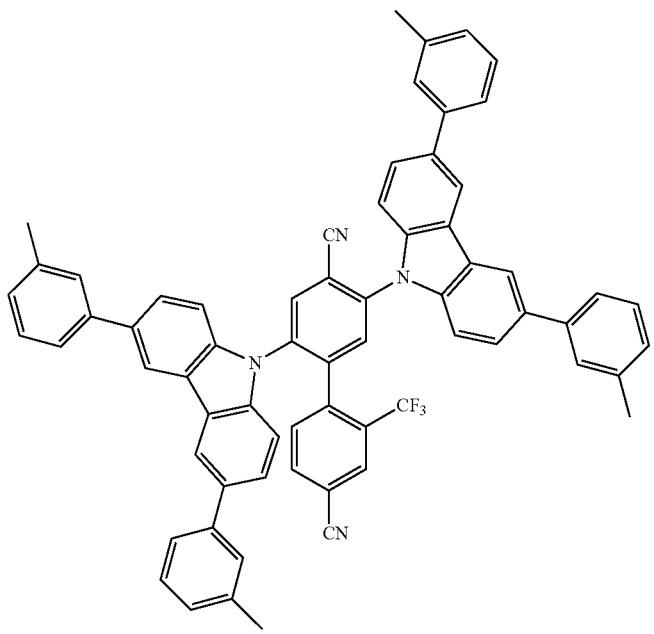
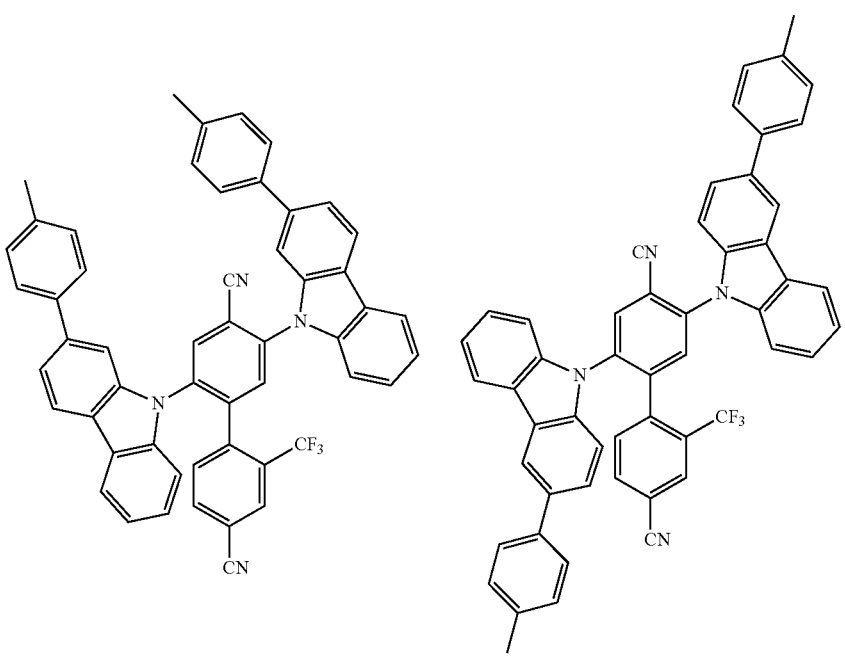
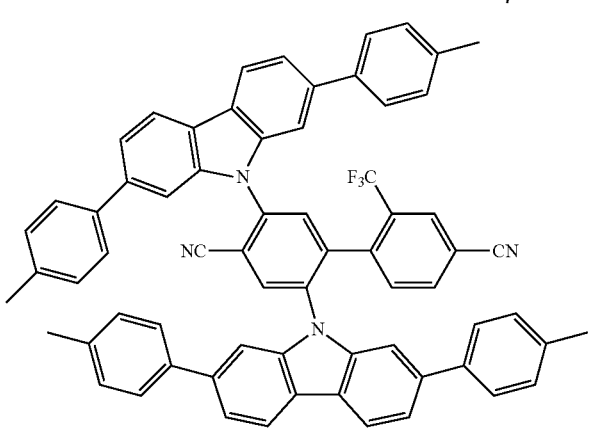

95 96
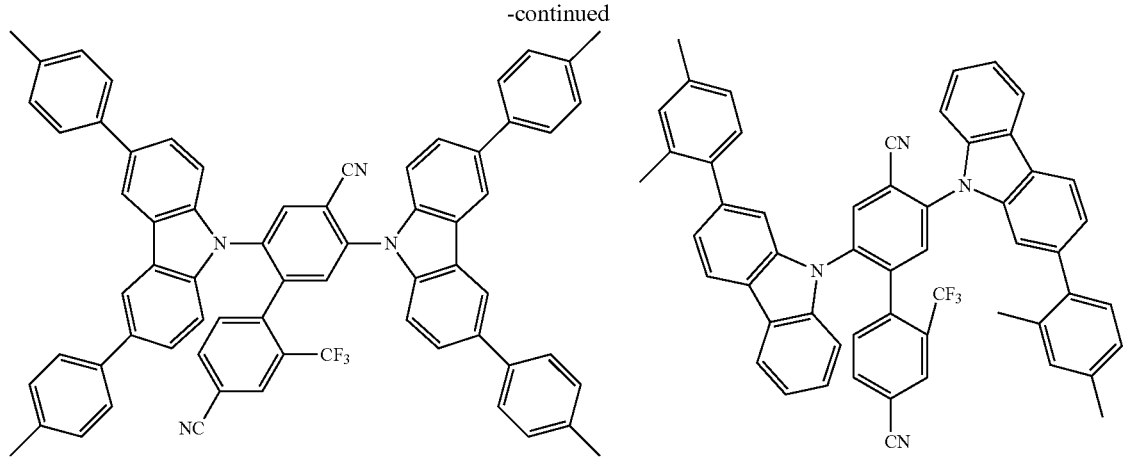
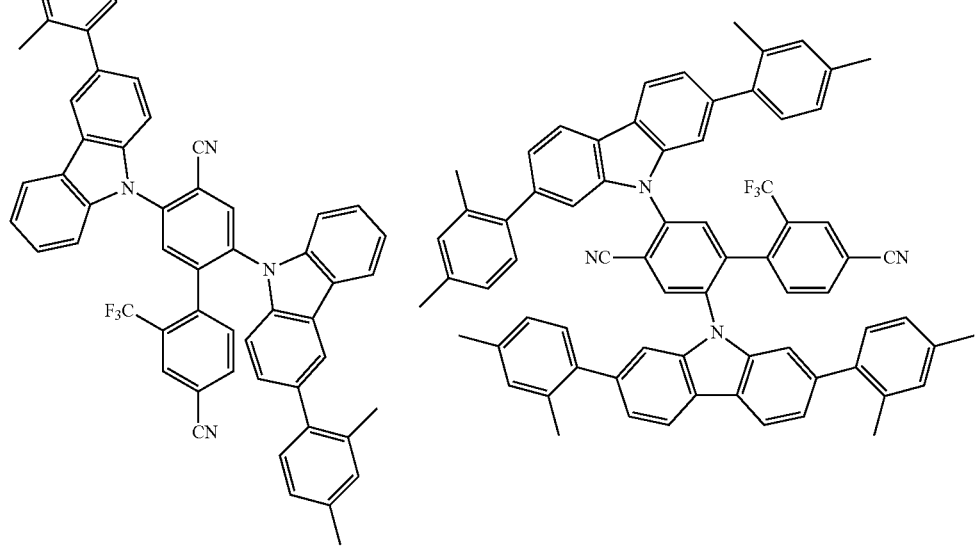
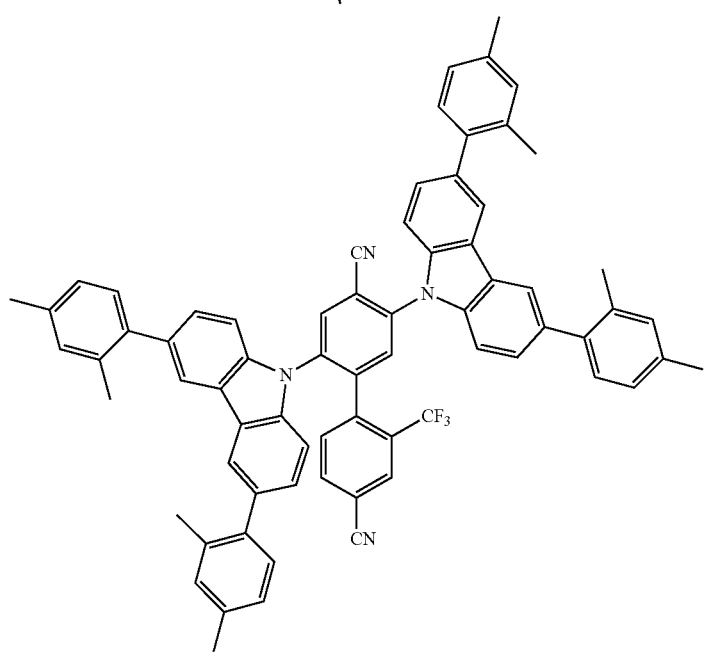

-continued
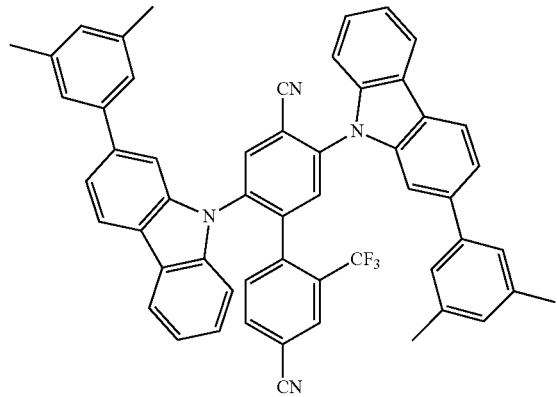
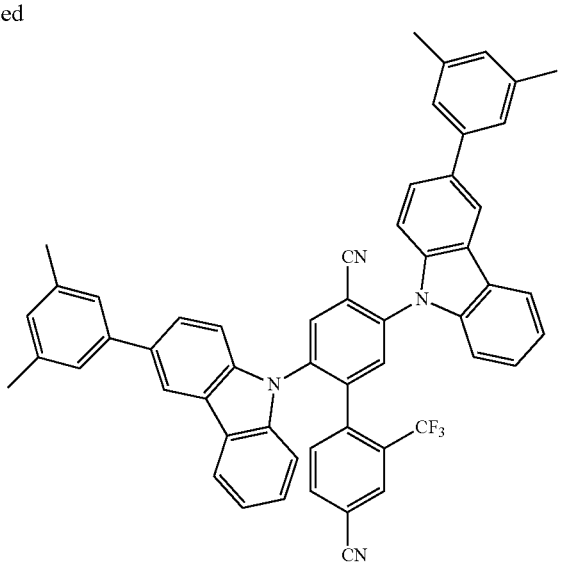
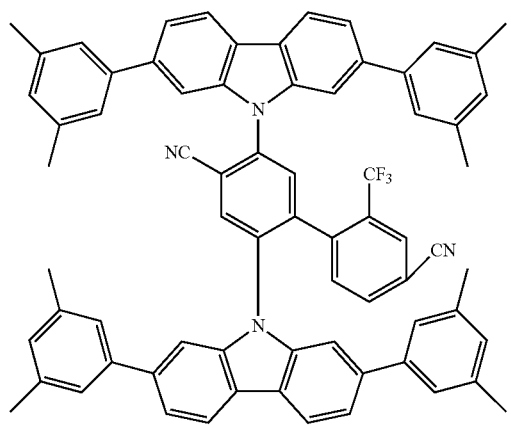
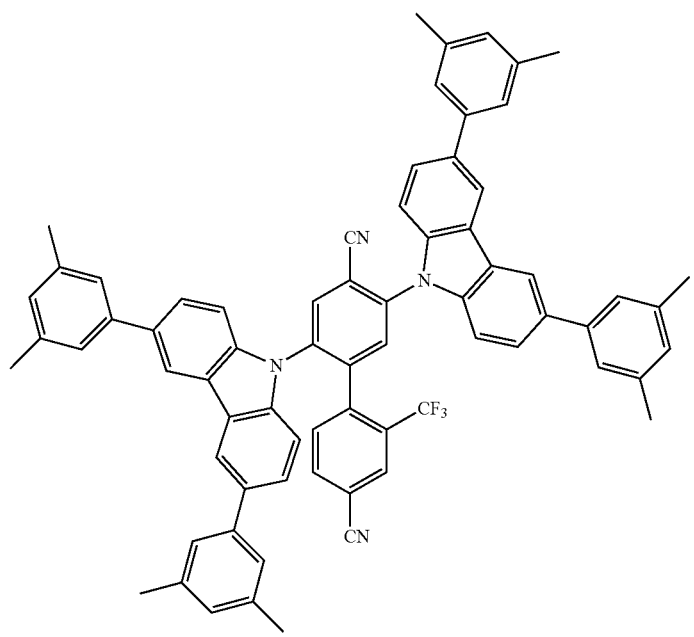

-continued
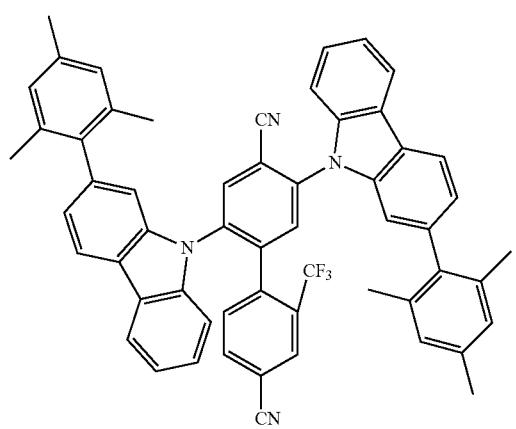
99
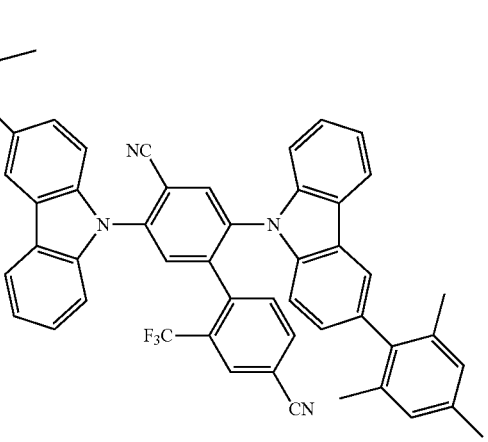
100
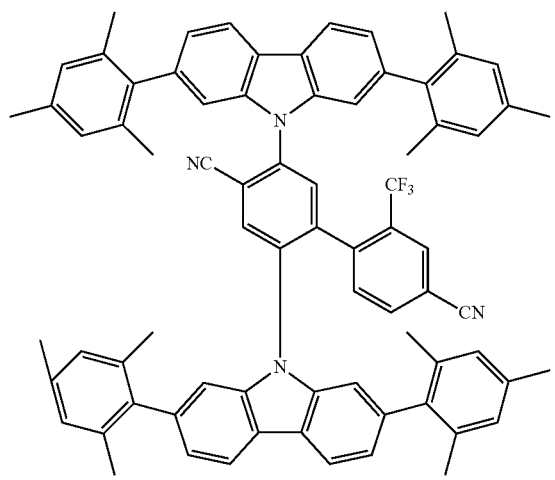
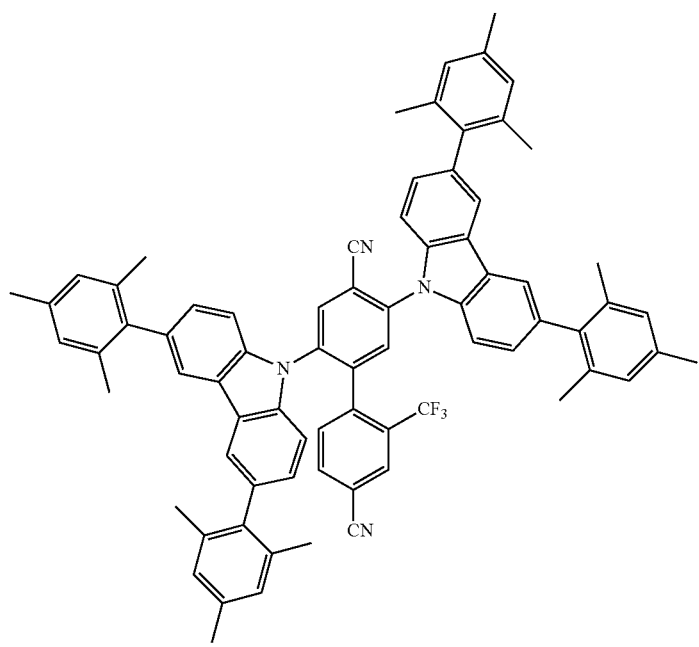

-continued
101
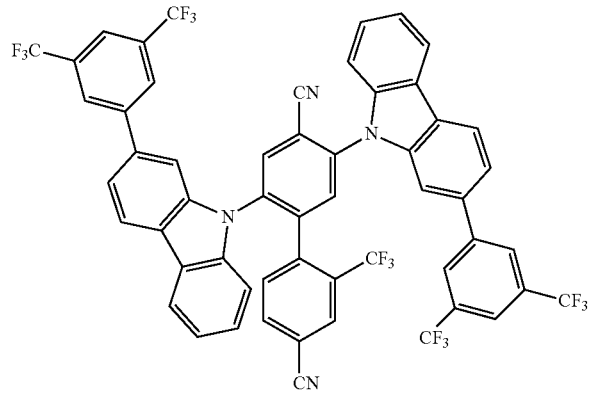
102
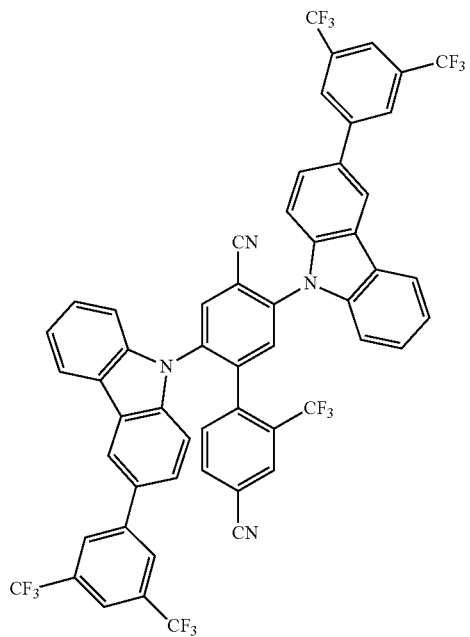
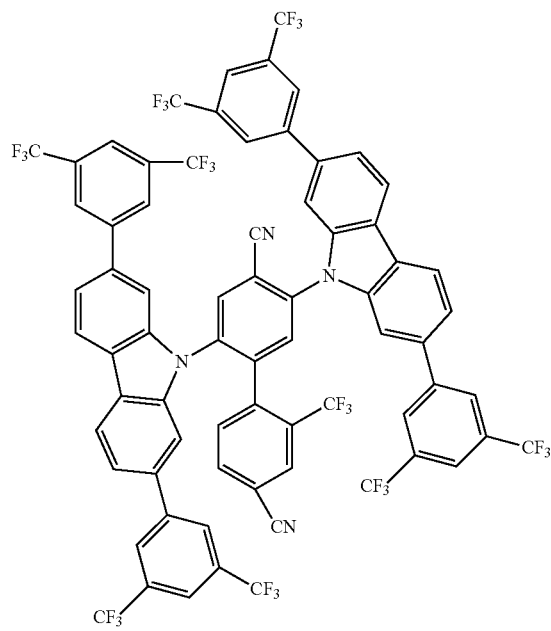
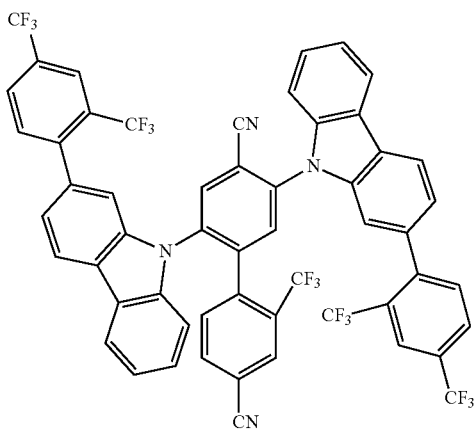

-continued
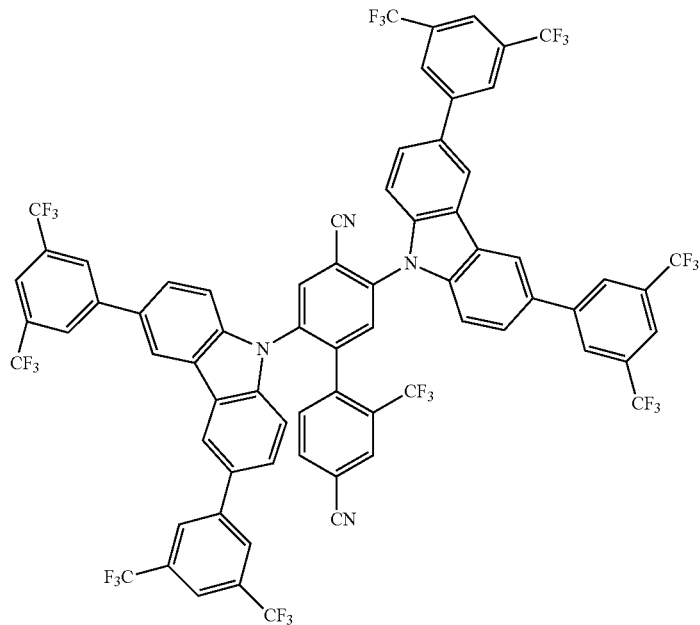
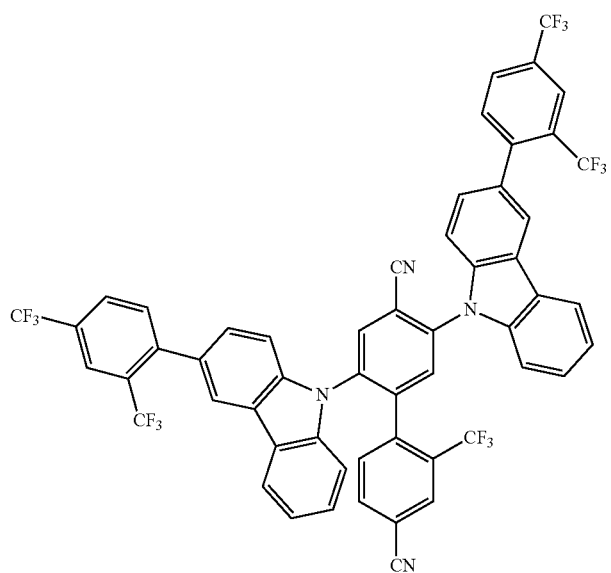
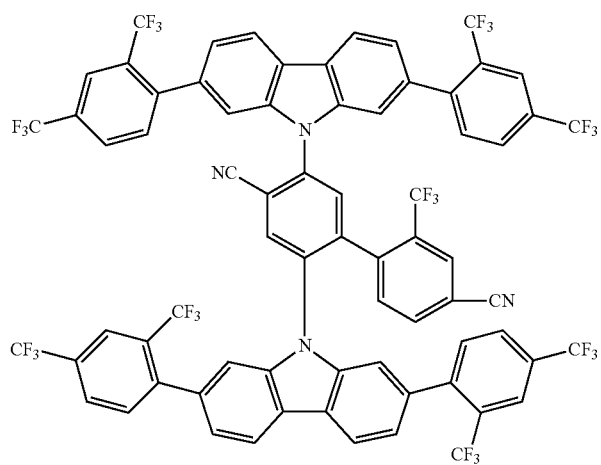

-continued
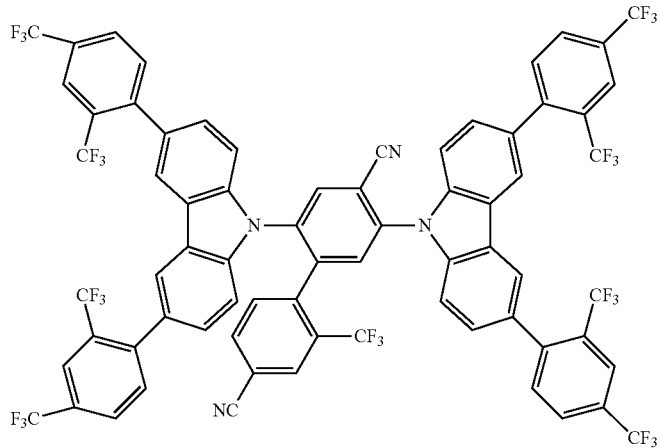
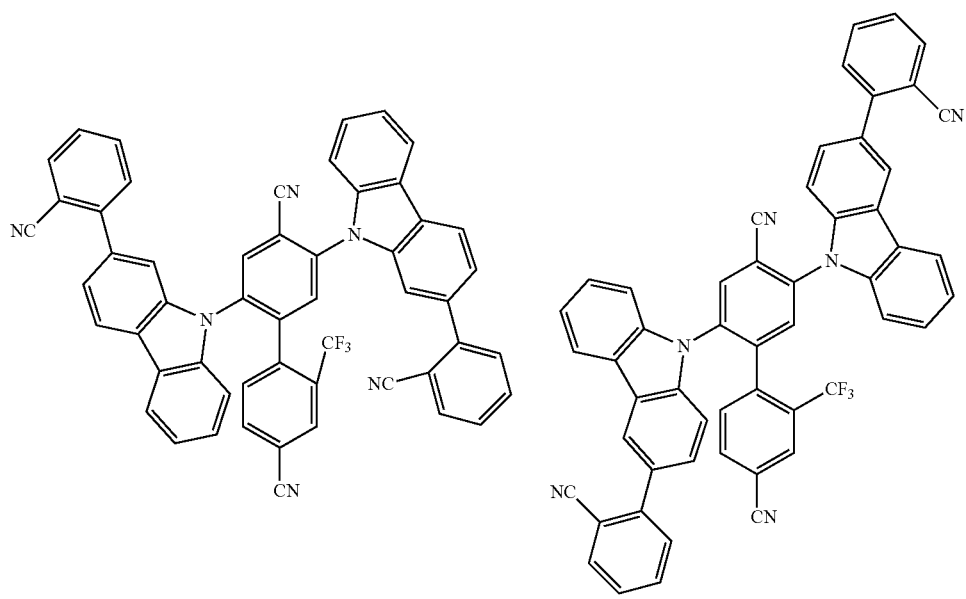
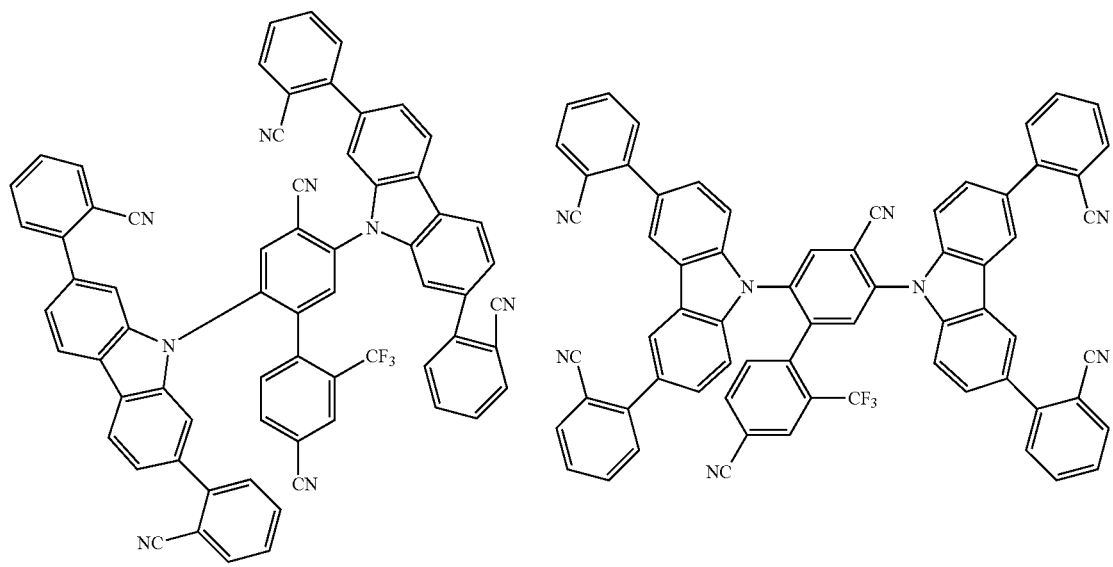

107
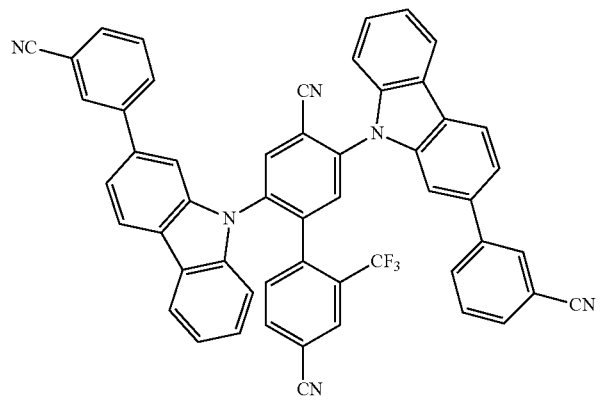
108
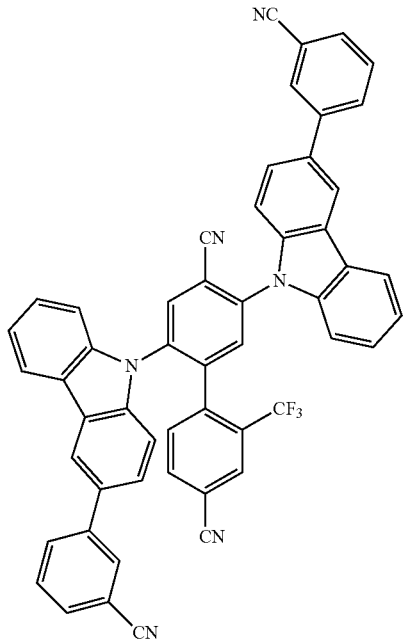
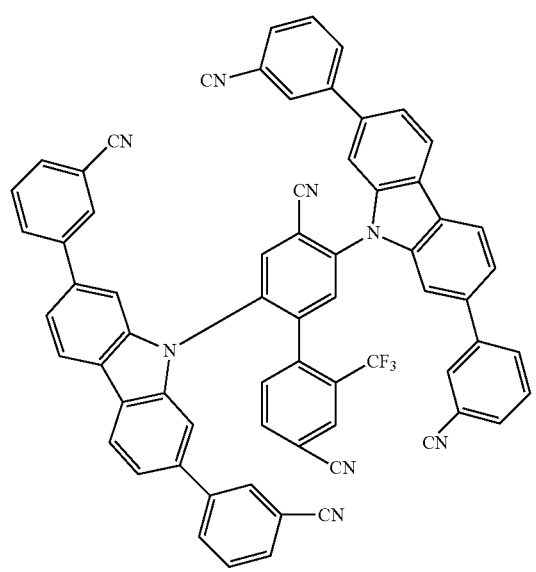
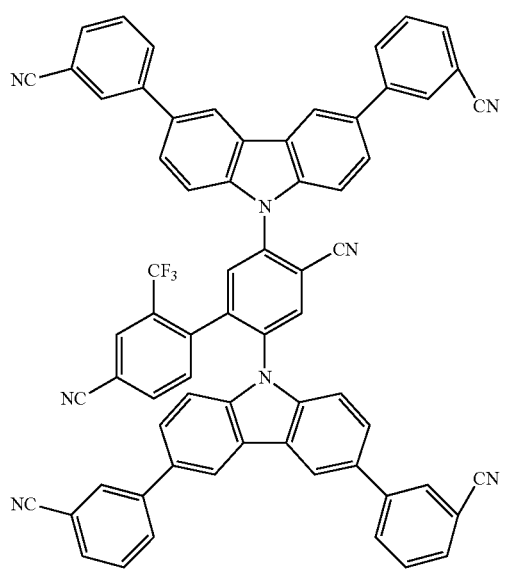

-continued
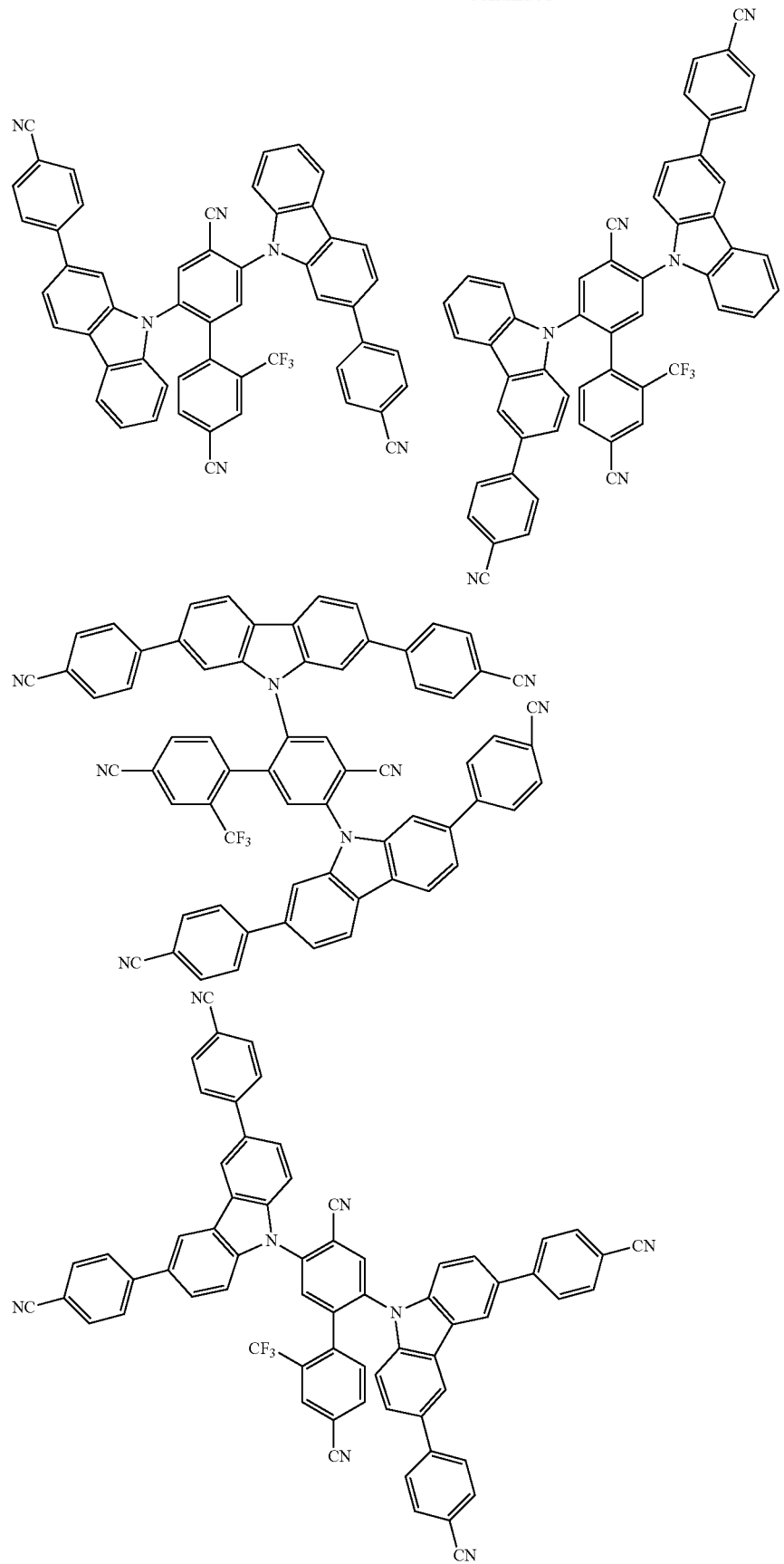

111
112
-continued
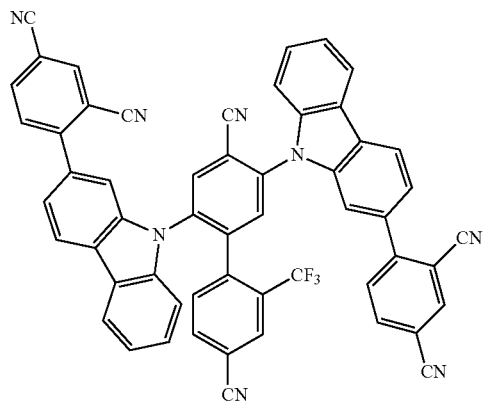
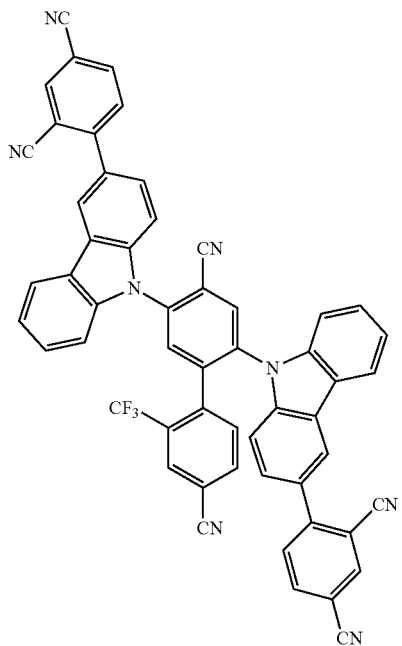
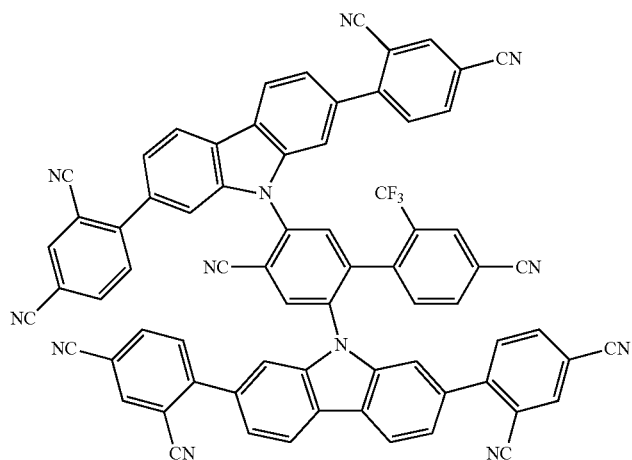
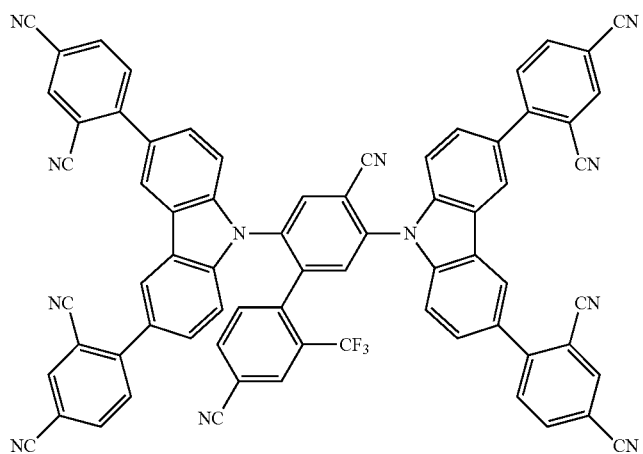

113 114
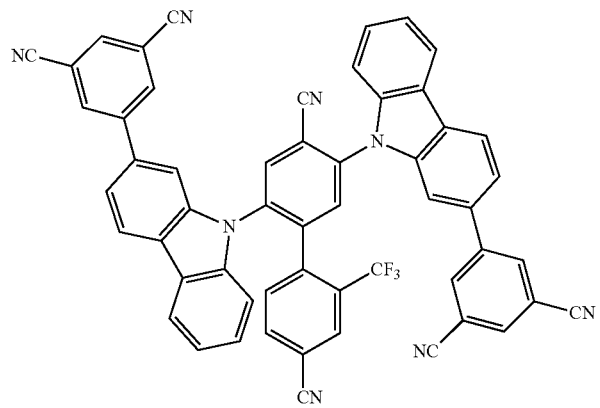 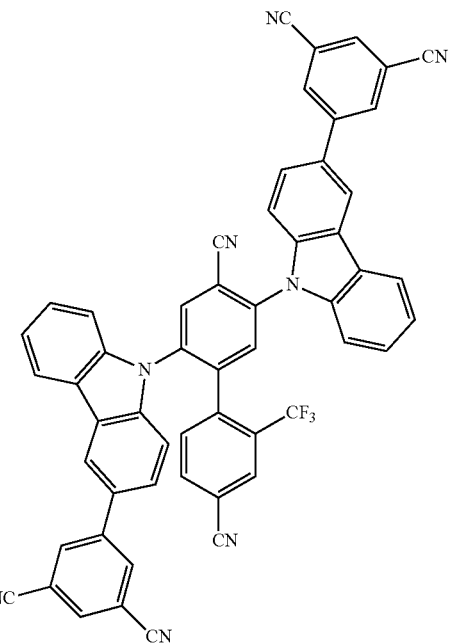
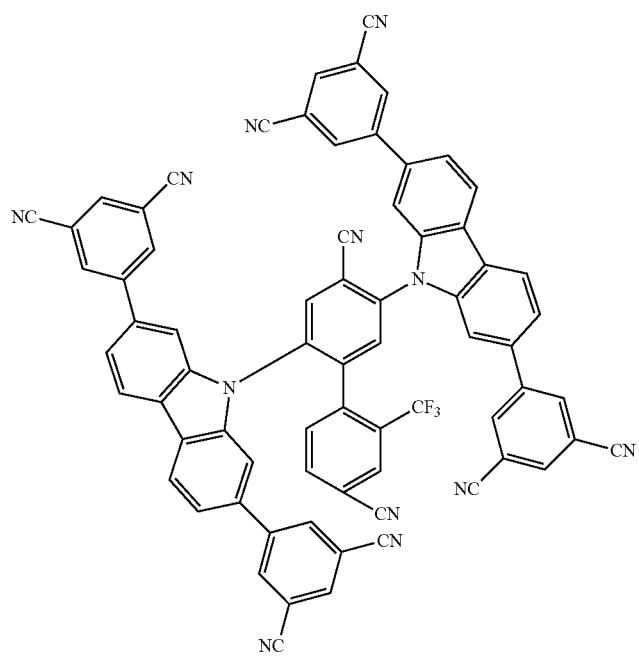

115
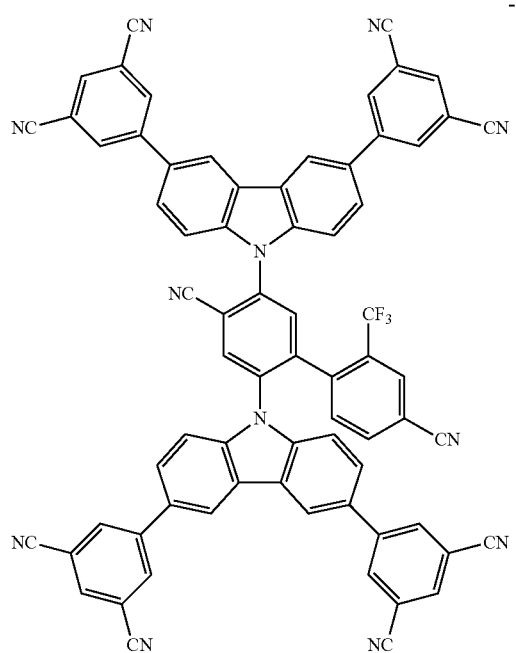
116
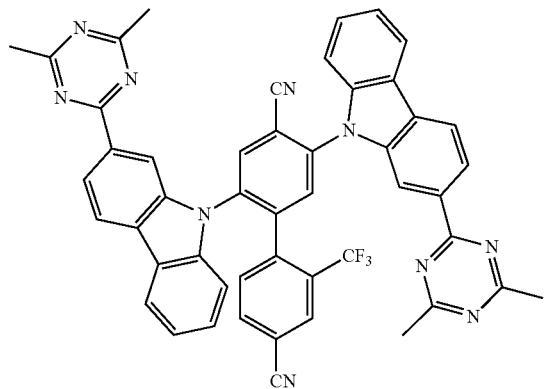
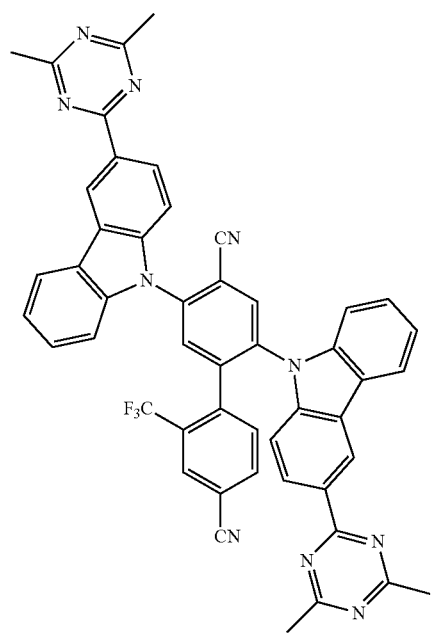
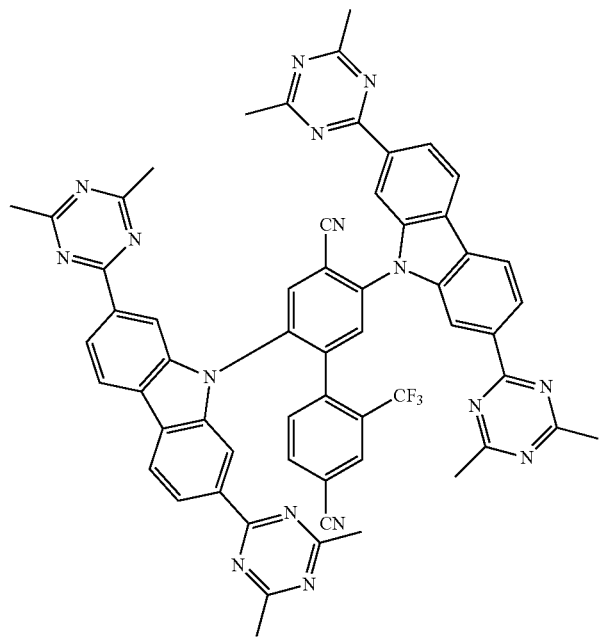

117                                                                    118
-continued
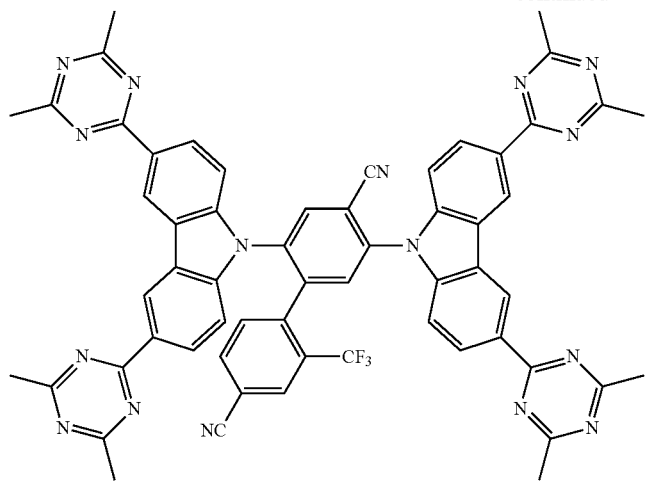
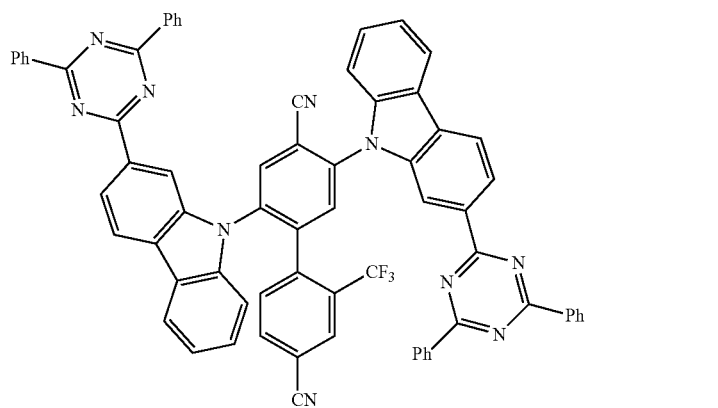
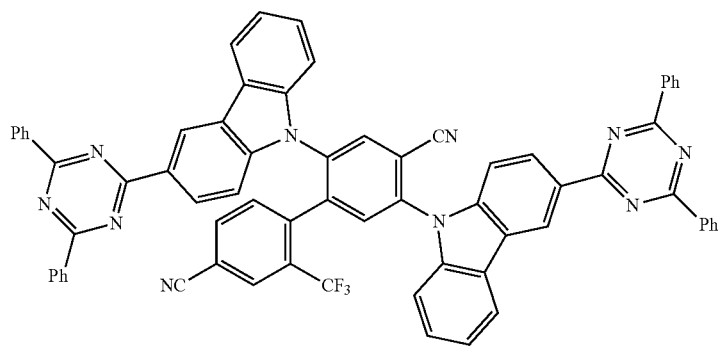
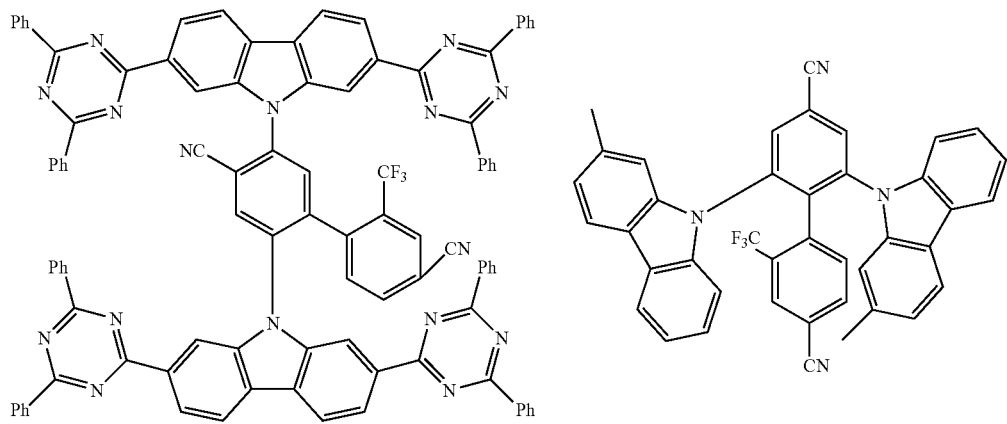

-continued
119         120
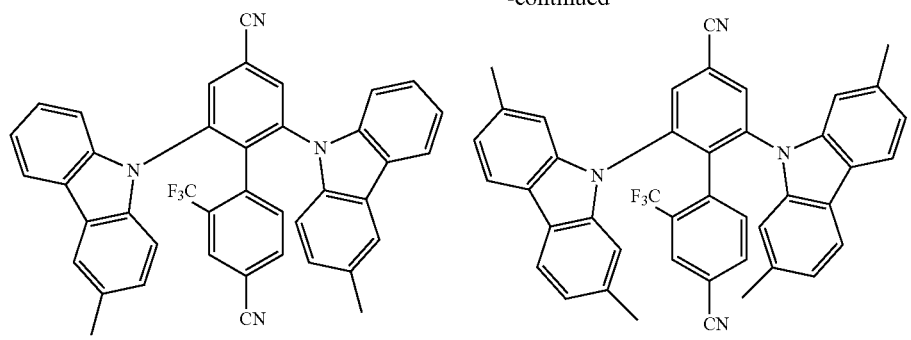
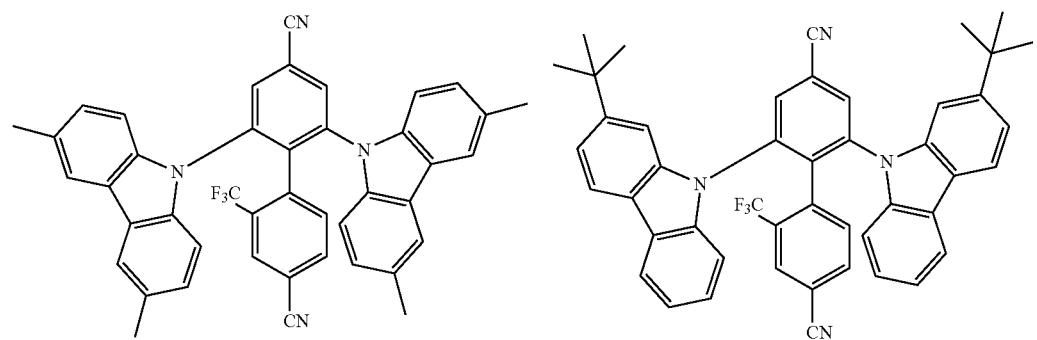
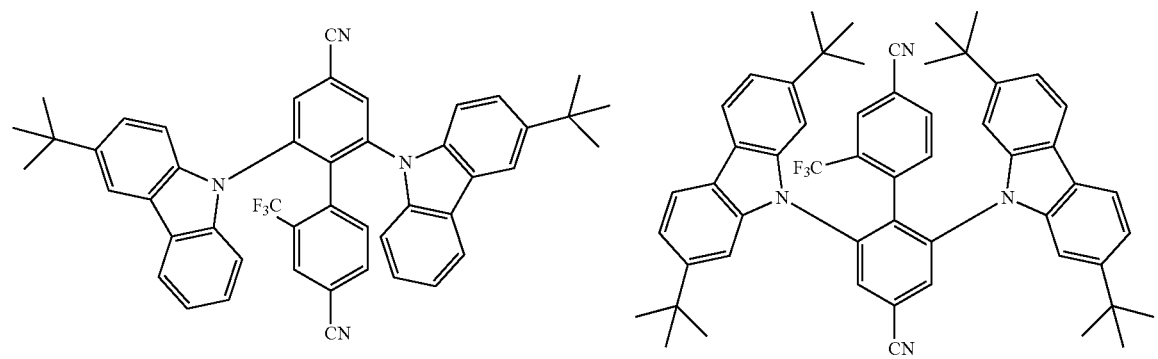
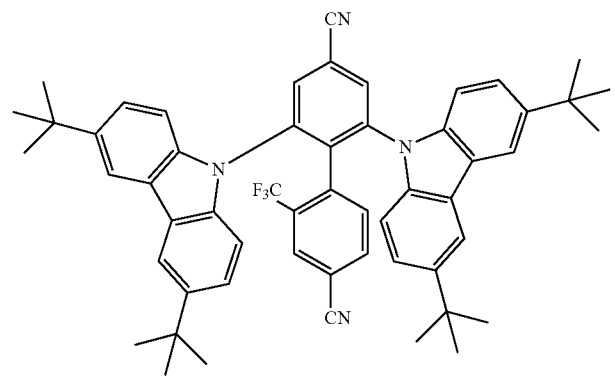

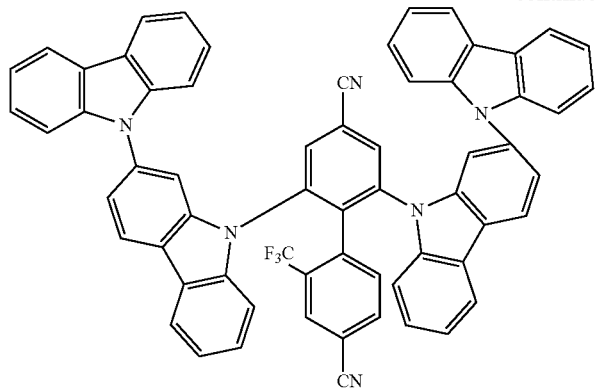
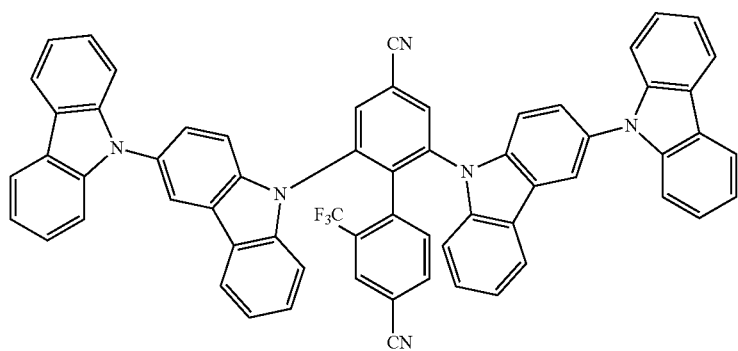
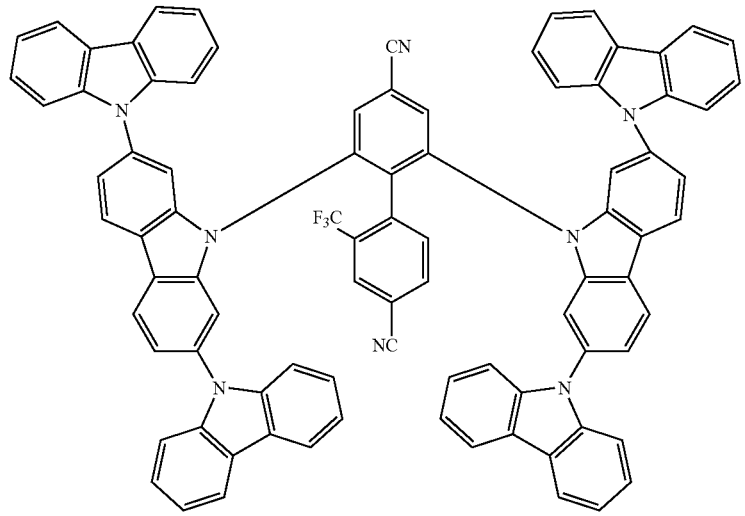
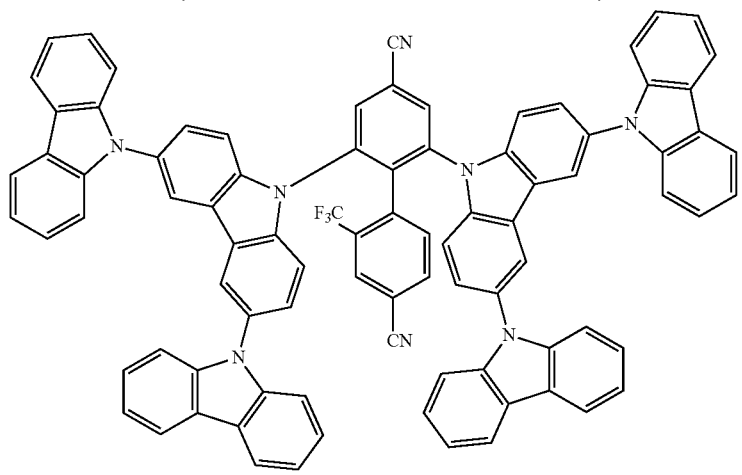

-continued
123
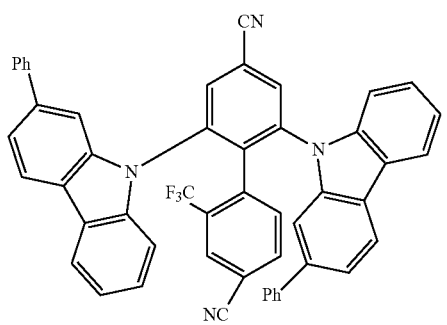
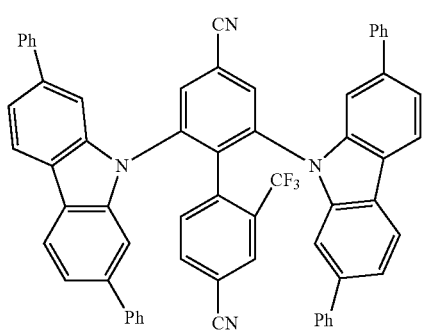
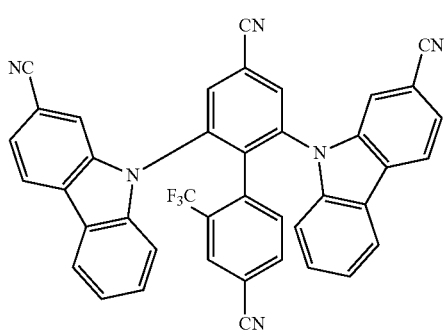
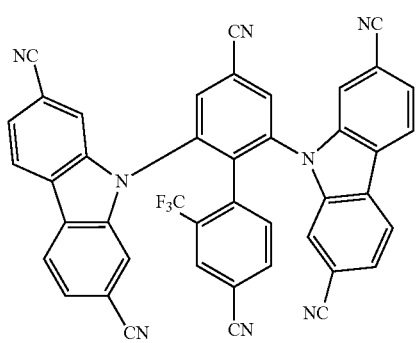
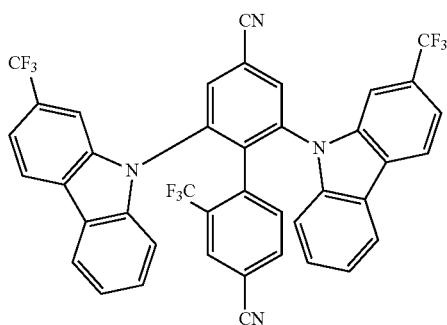
124
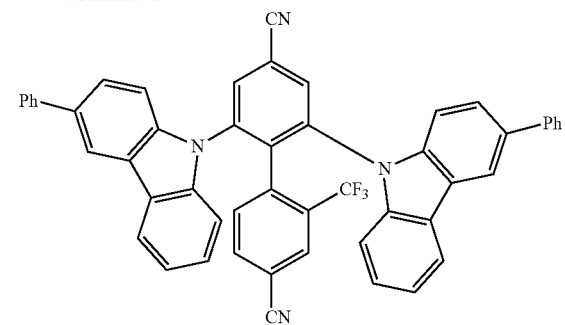
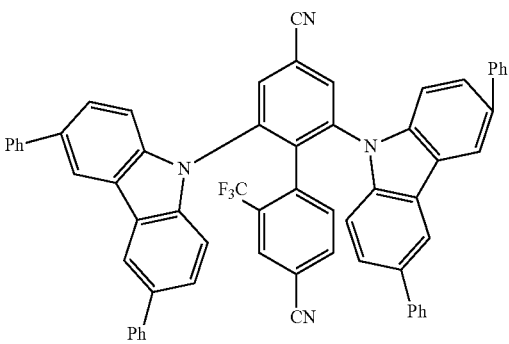
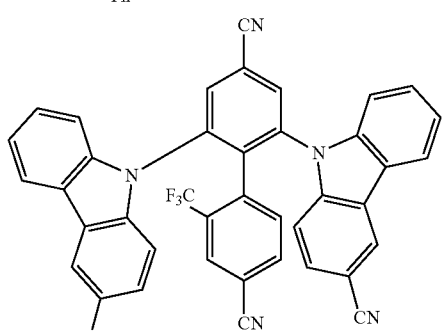
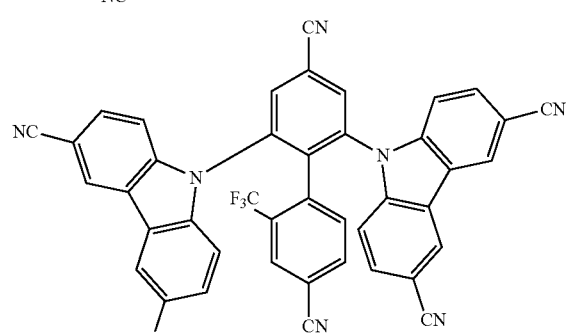
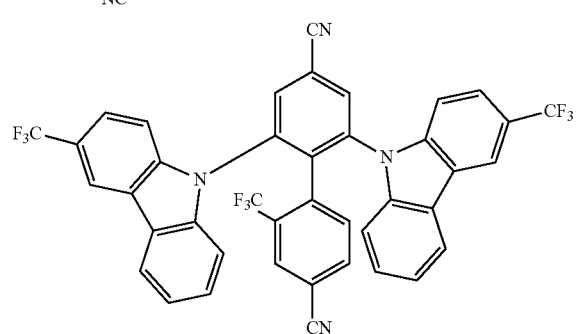

-continued
125 126
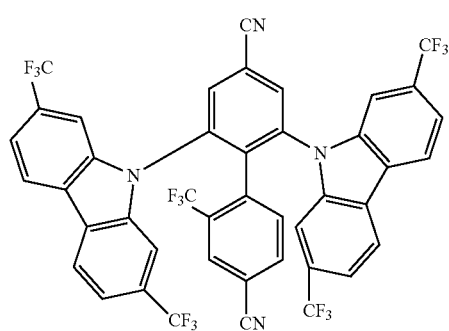
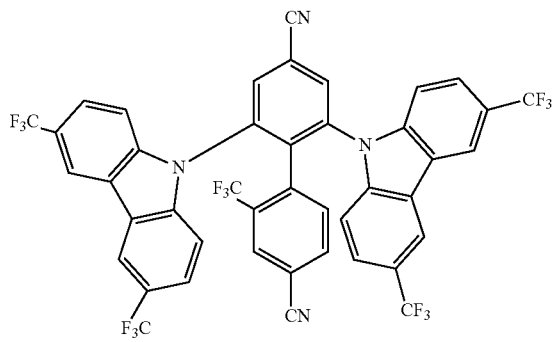
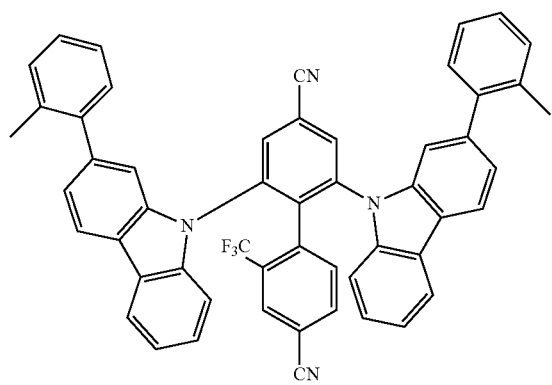
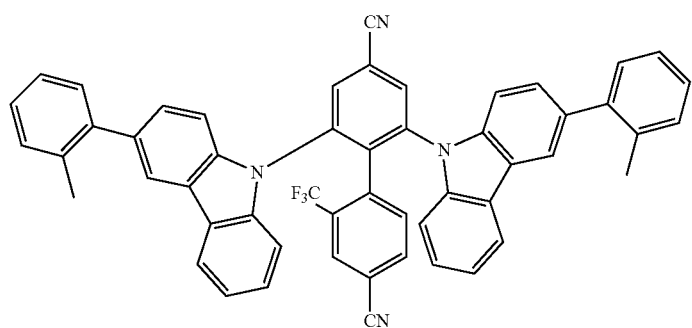
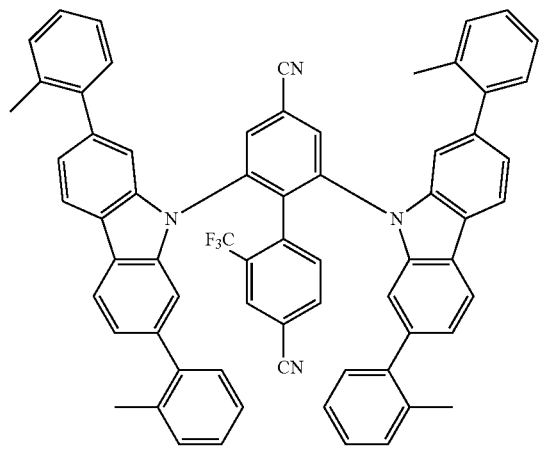

-continued
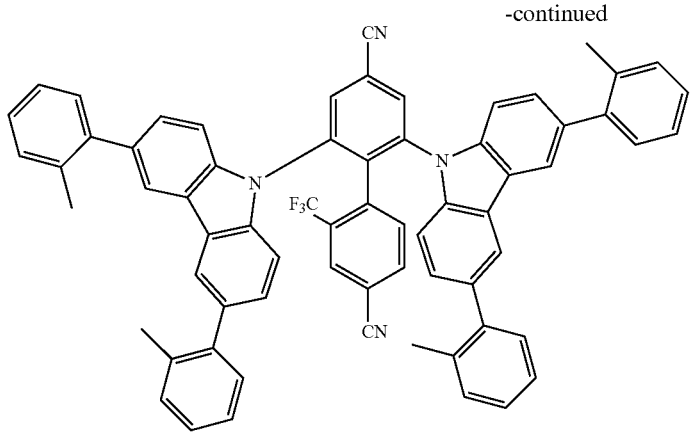
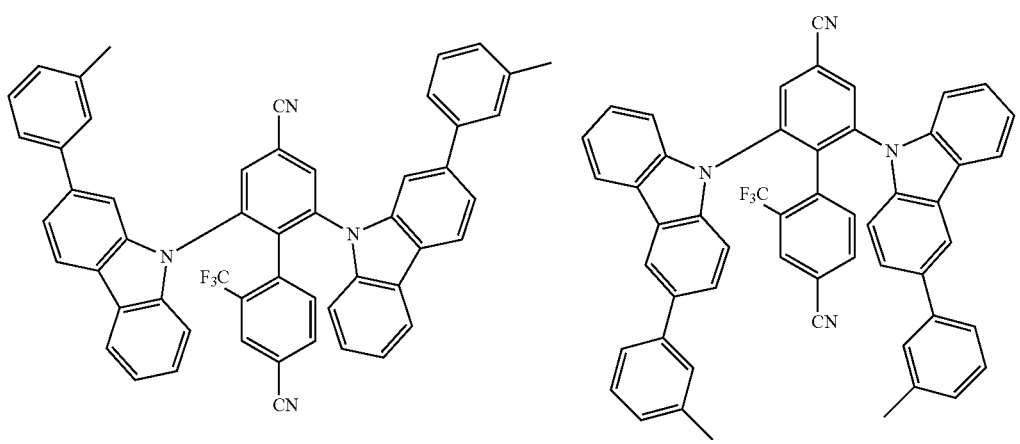
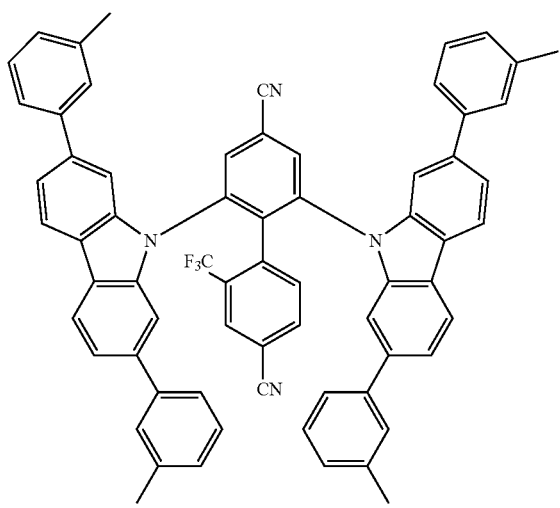

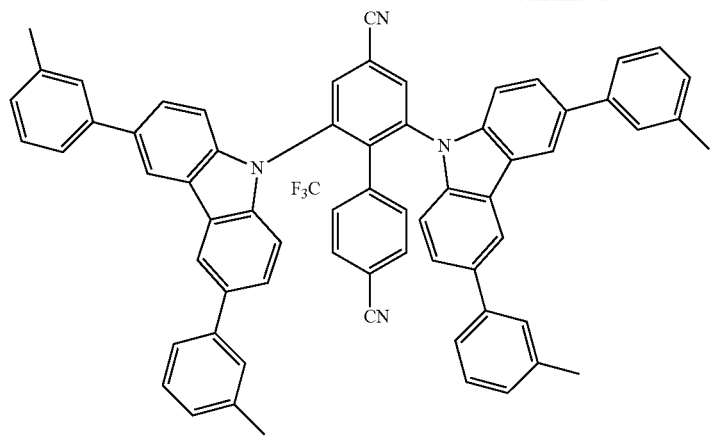
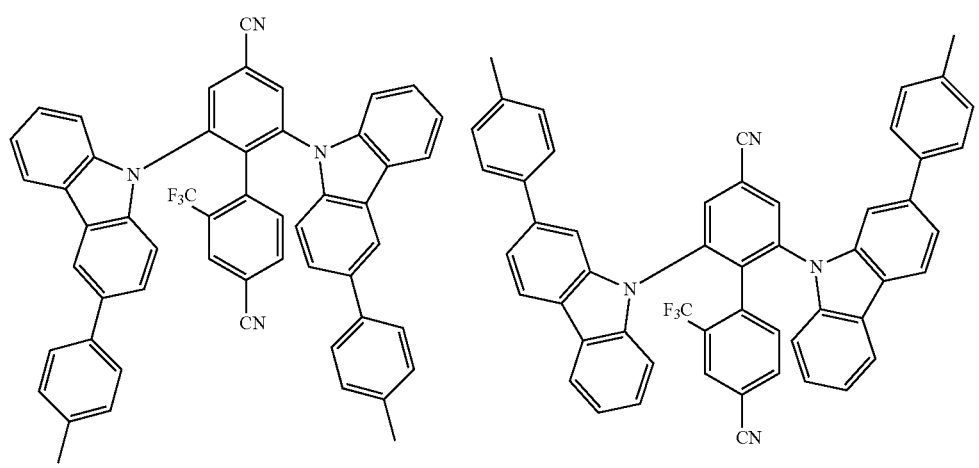
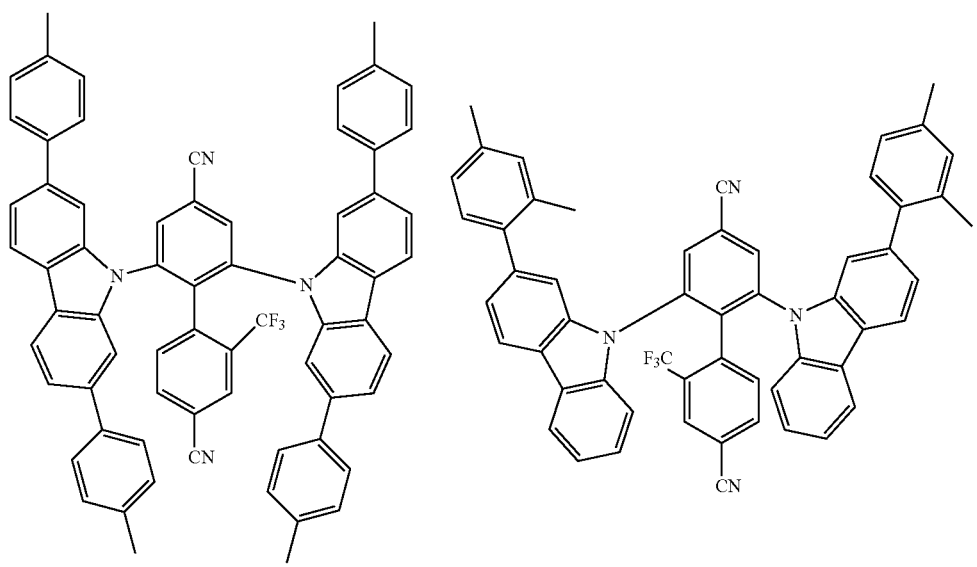

-continued
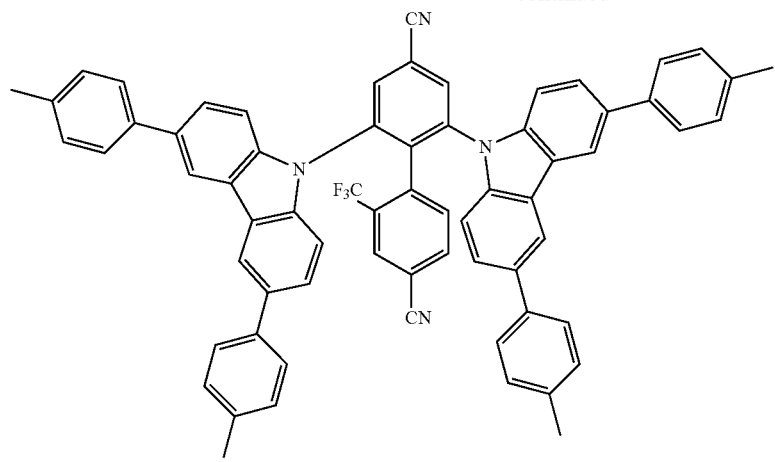
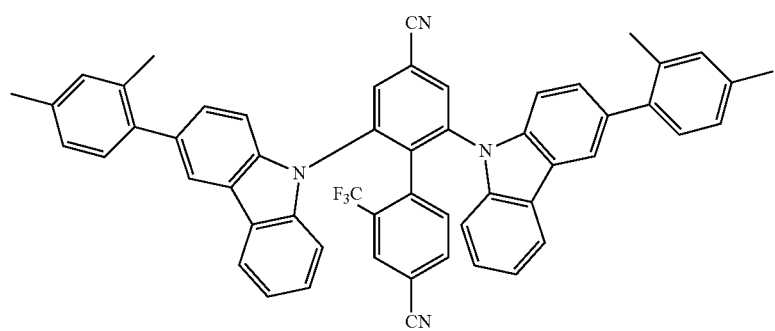
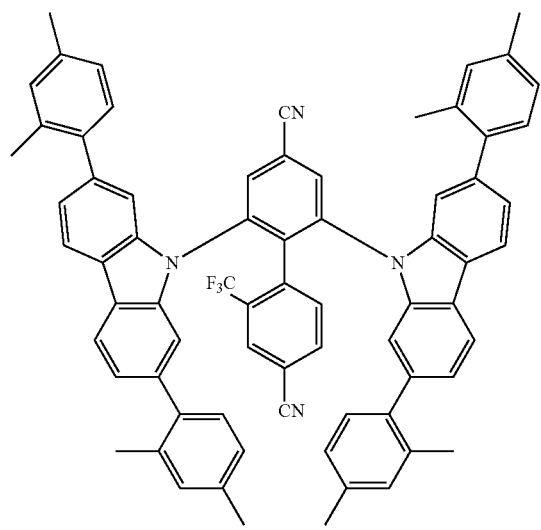

-continued
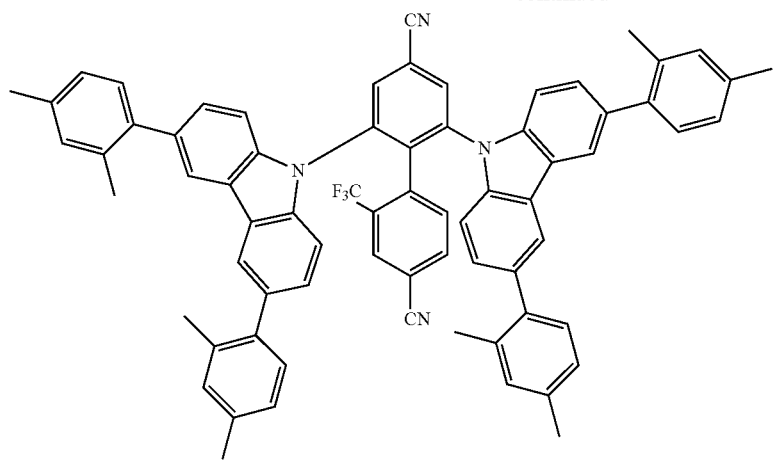
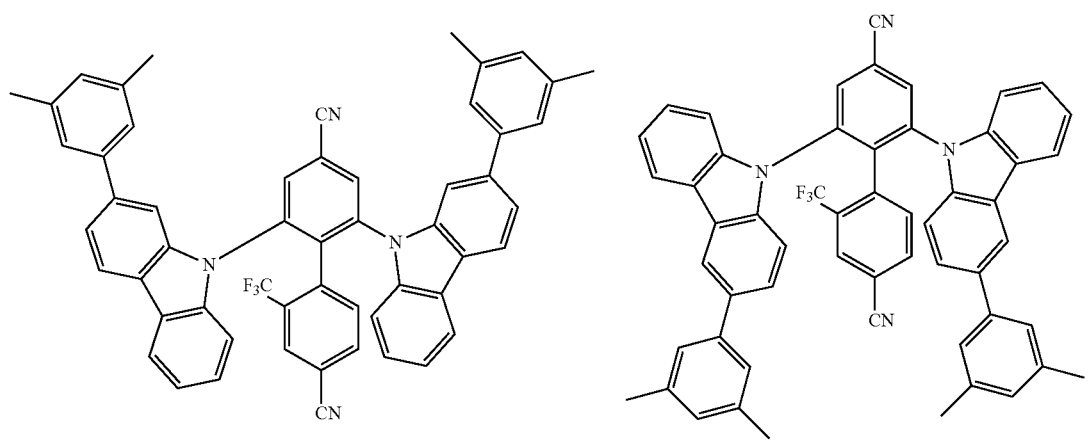
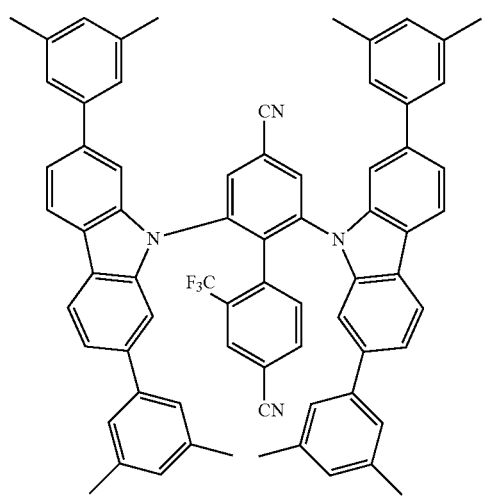

-continued
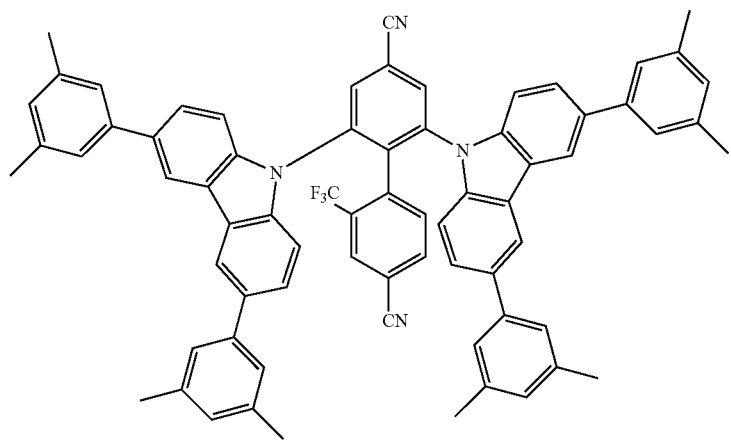
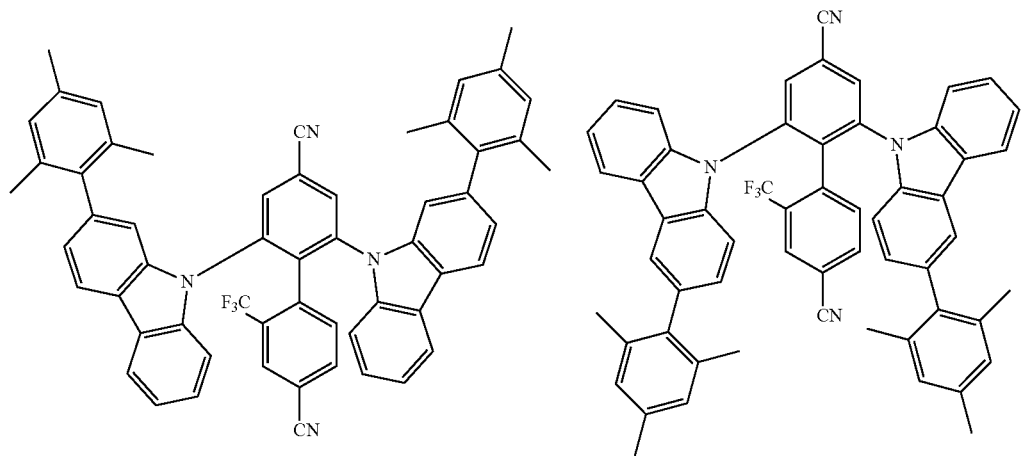
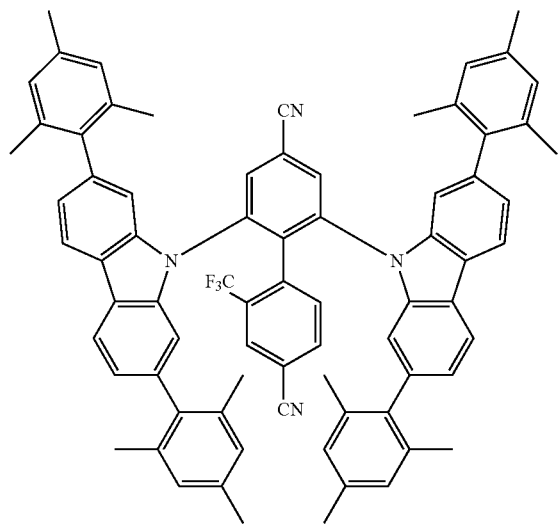

-continued
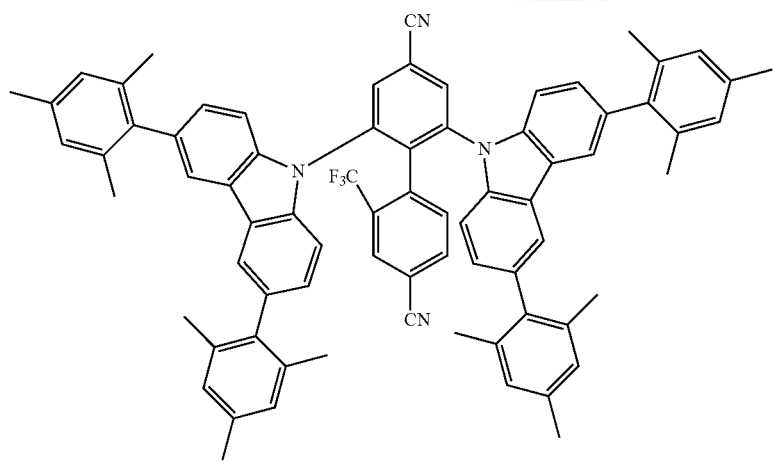
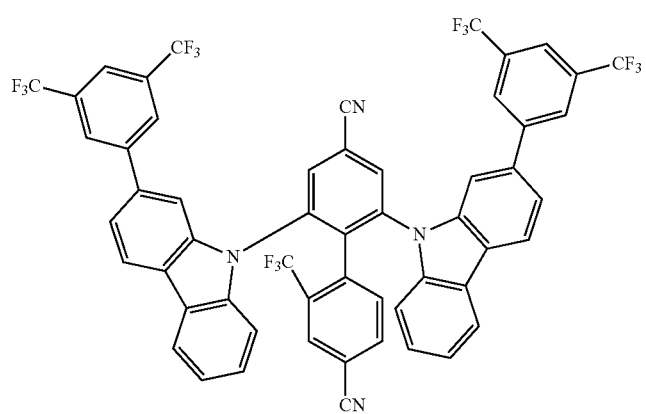
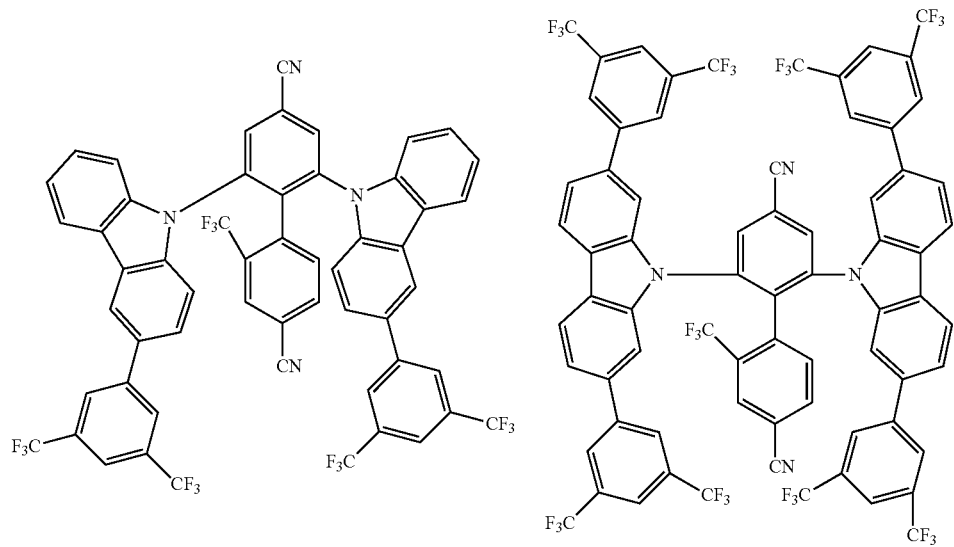

-continued
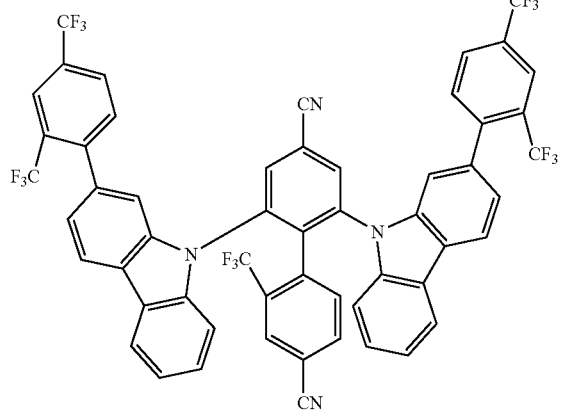
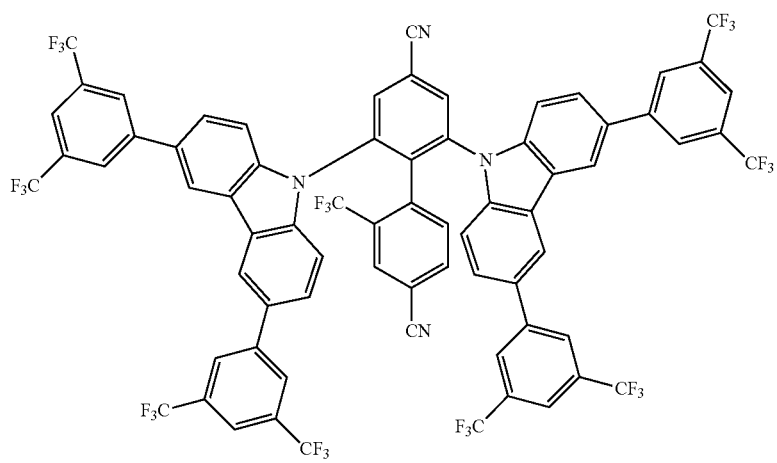
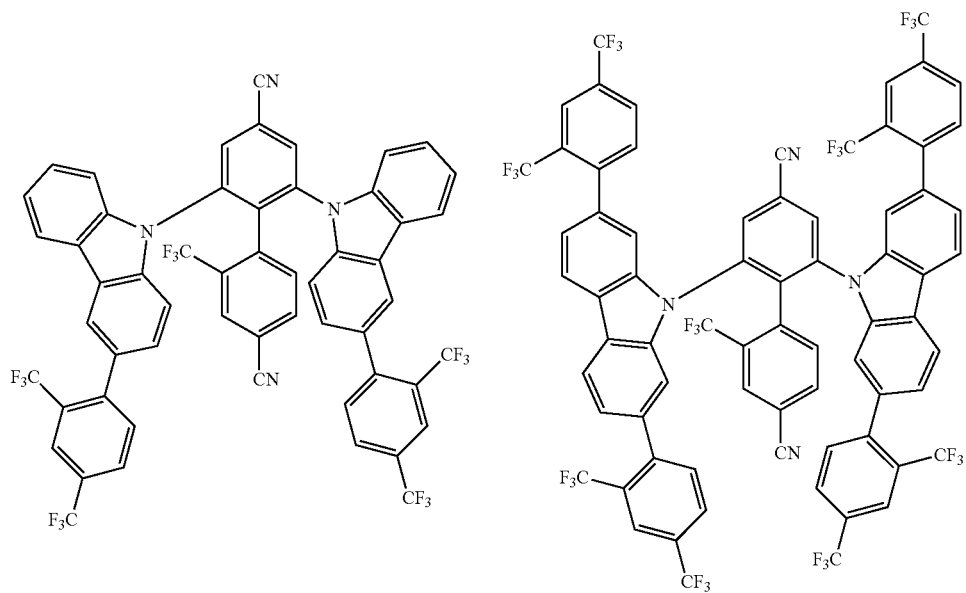

-continued
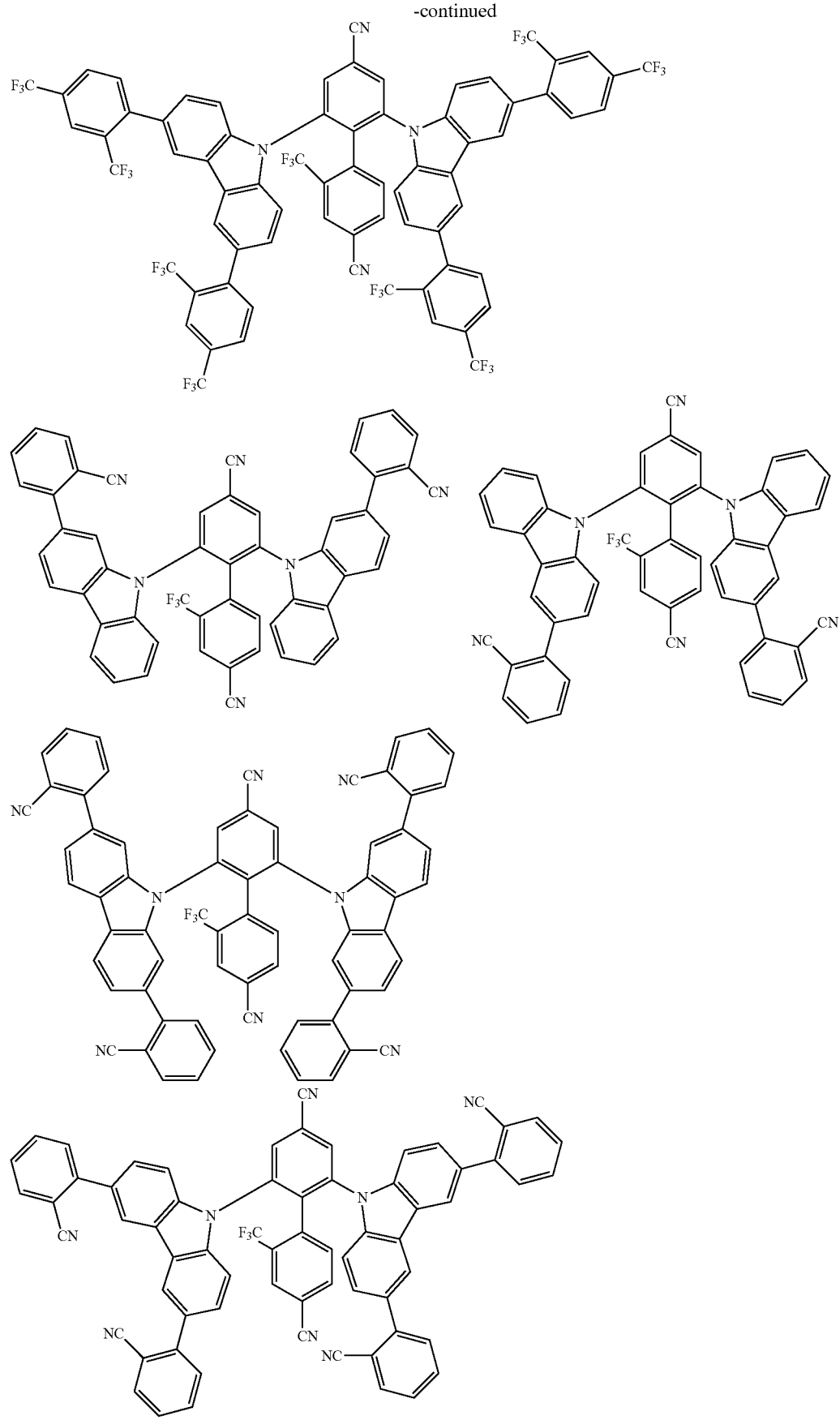

-continued
143 144
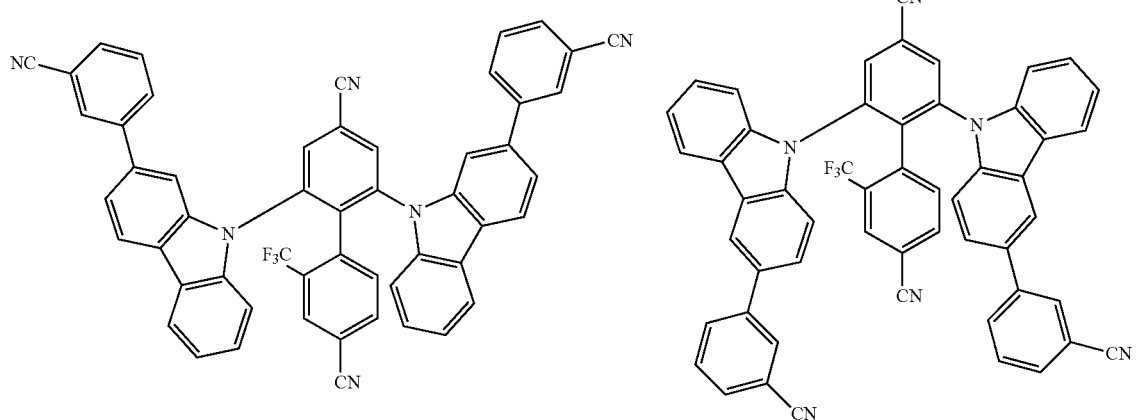
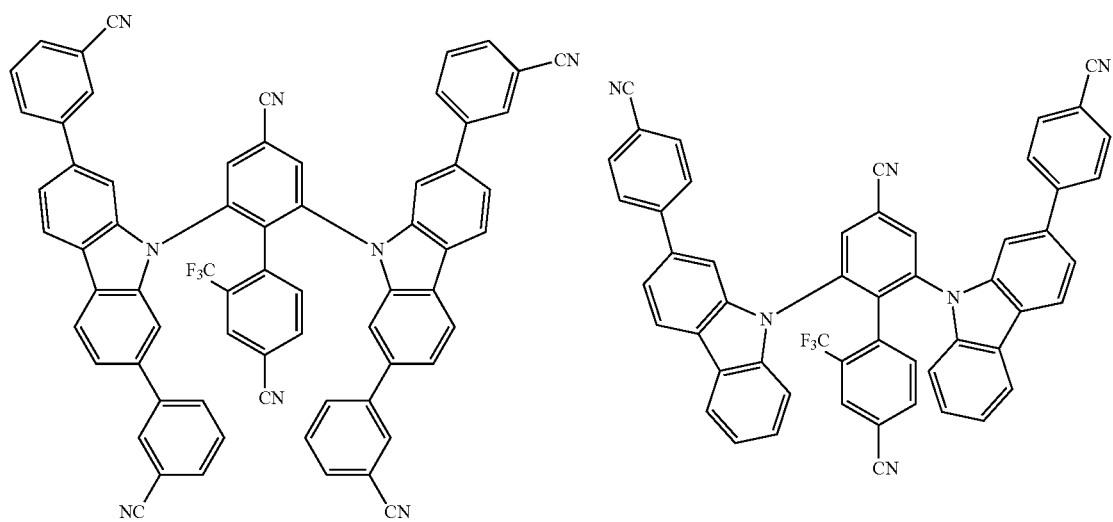
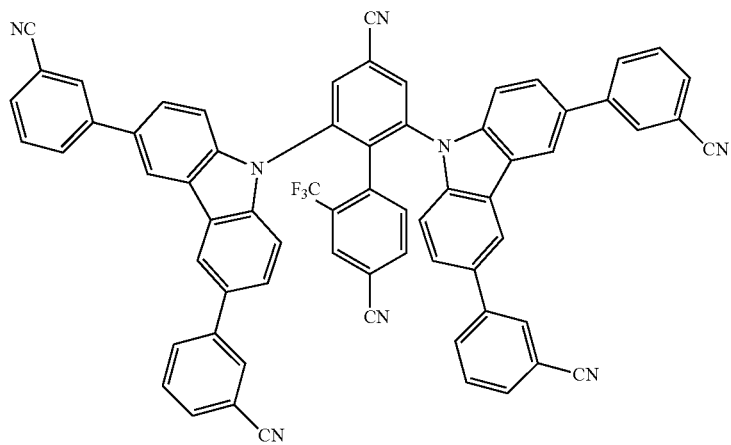

-continued
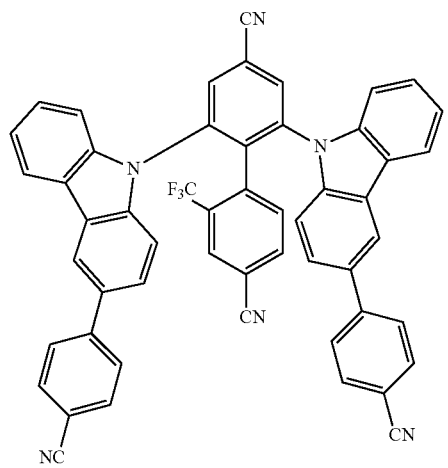
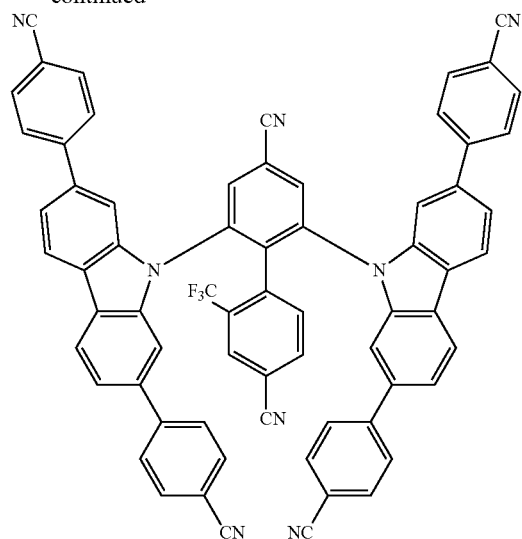
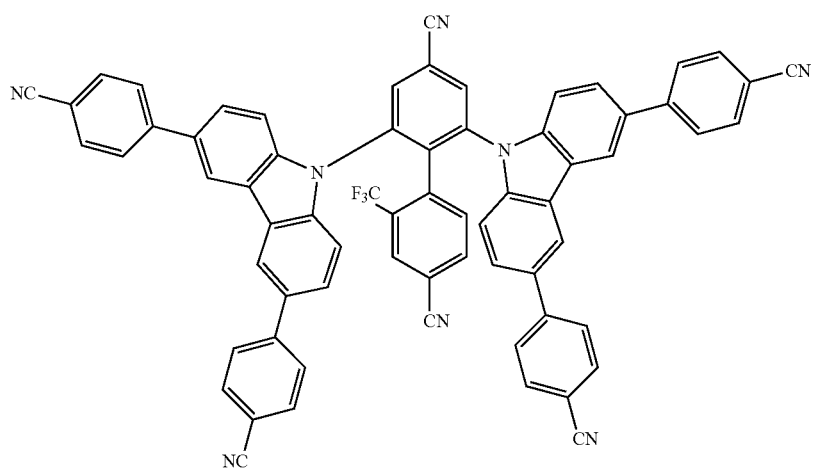
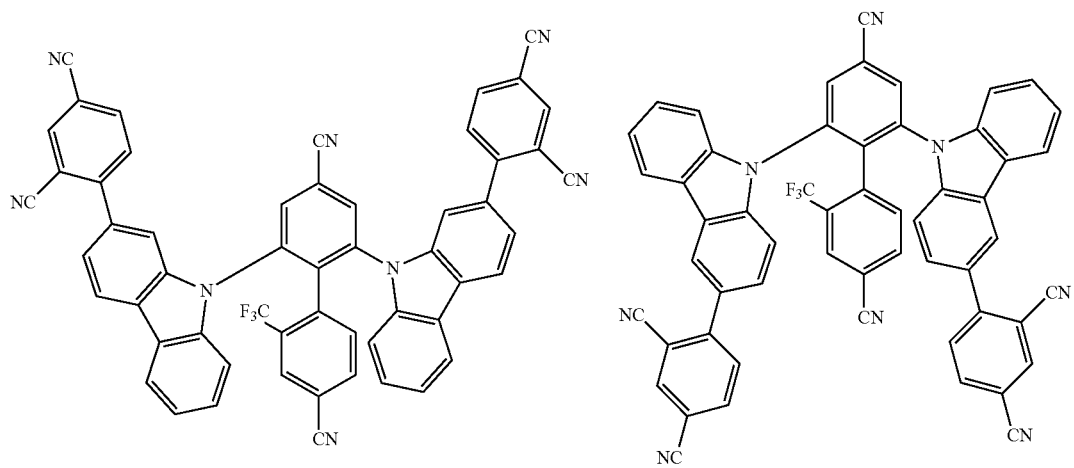

-continued
147
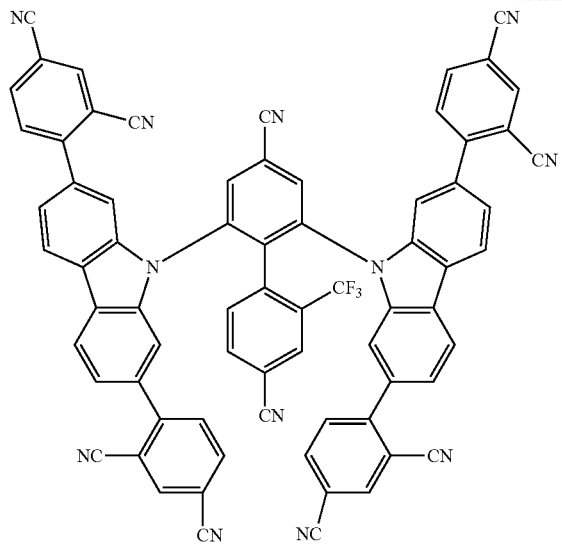
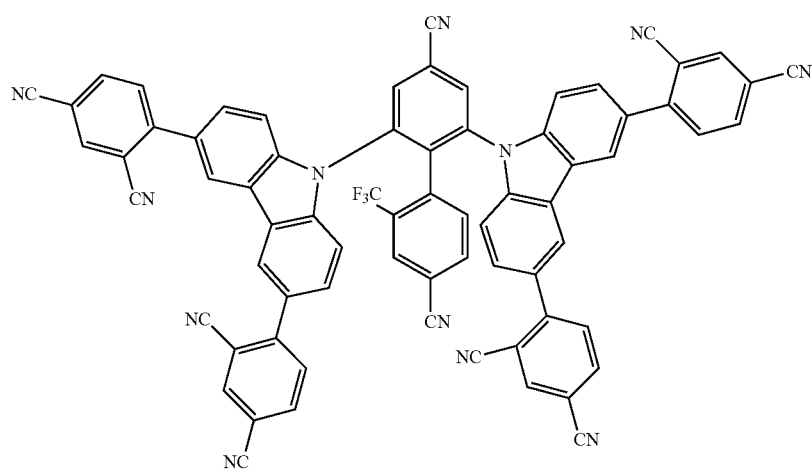
148
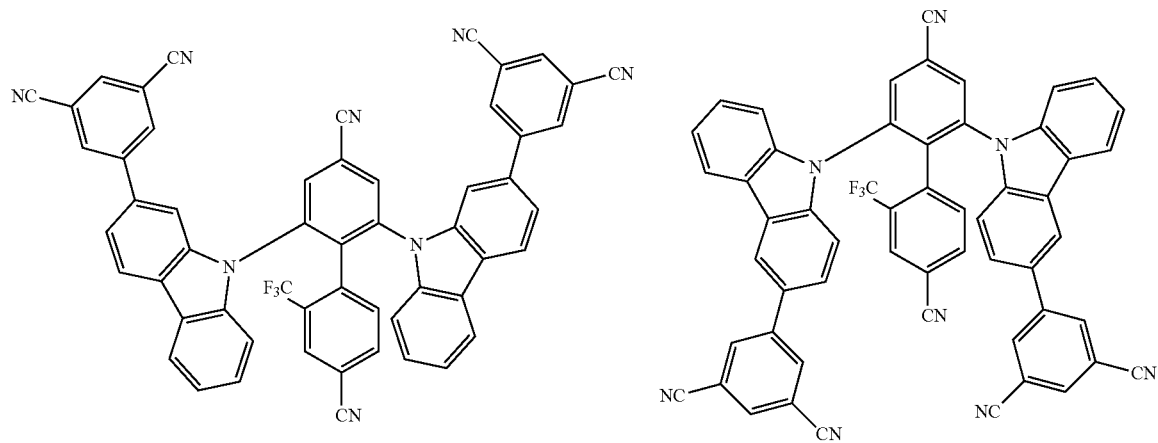

149
-continued
150
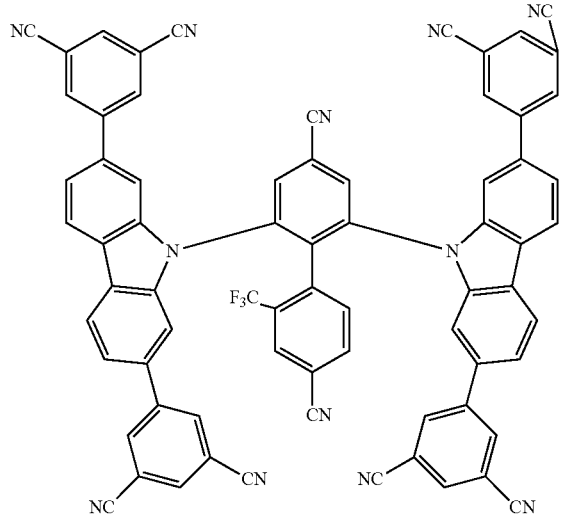
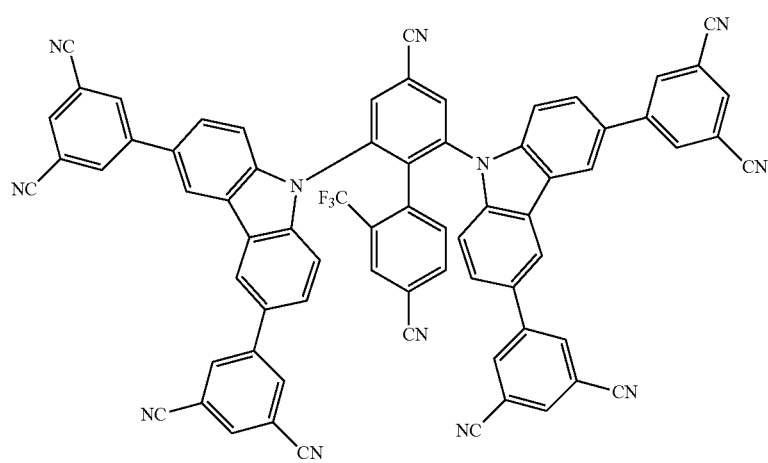
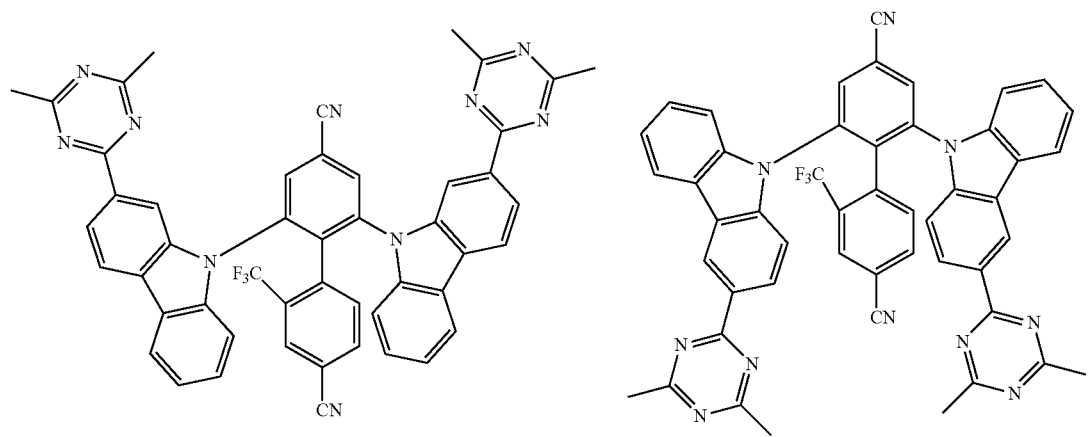

151 152
-continued
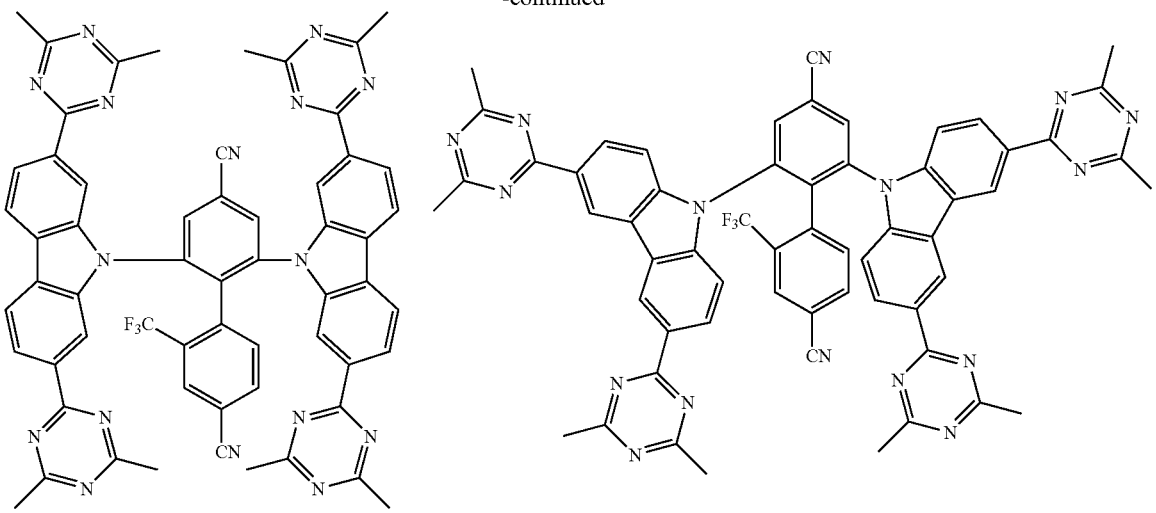
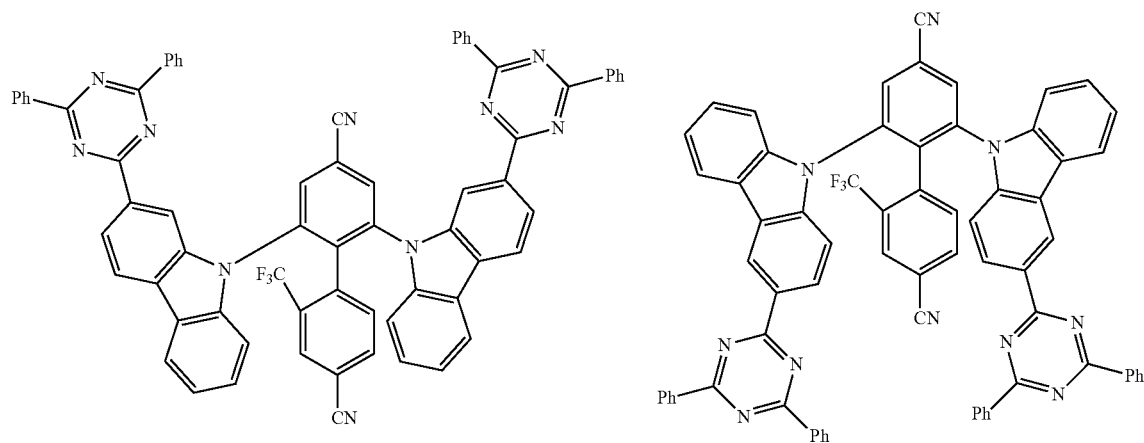
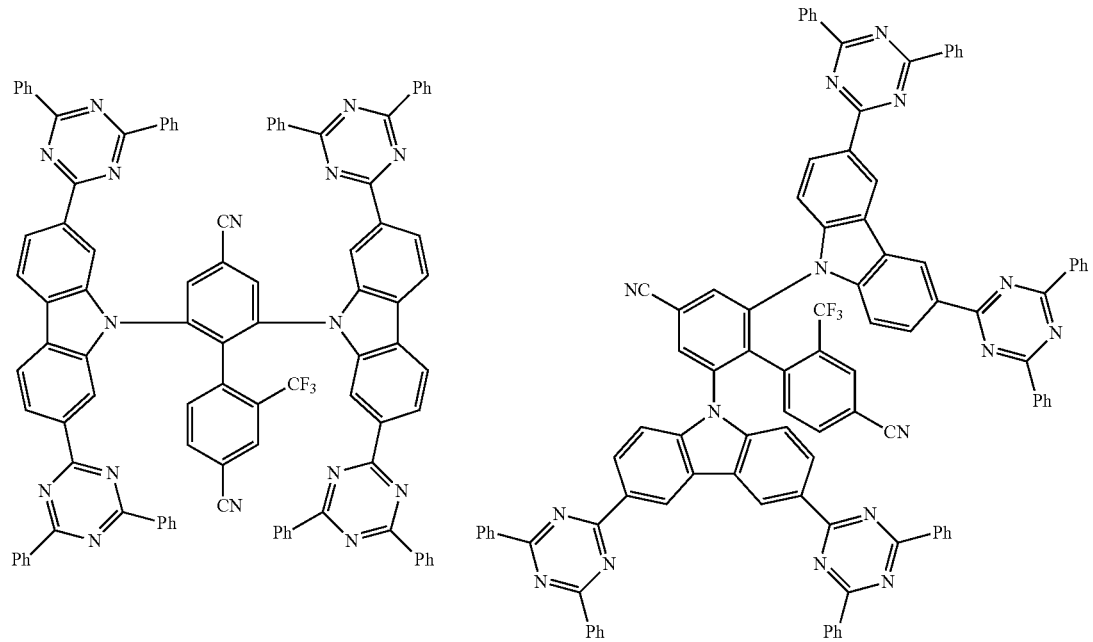

-continued
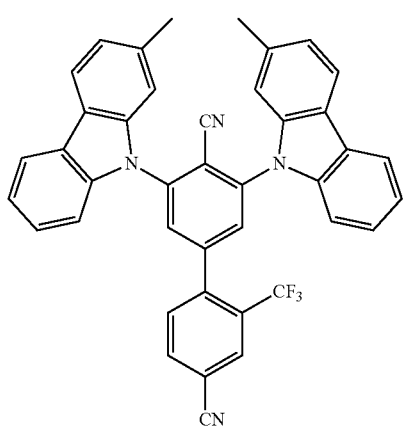
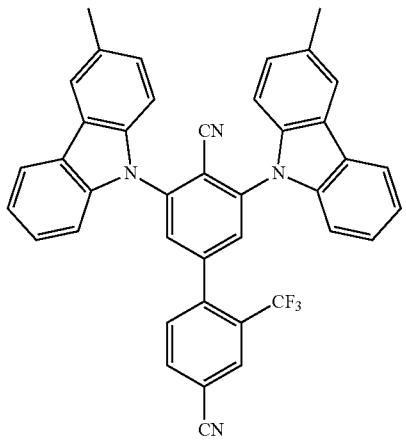
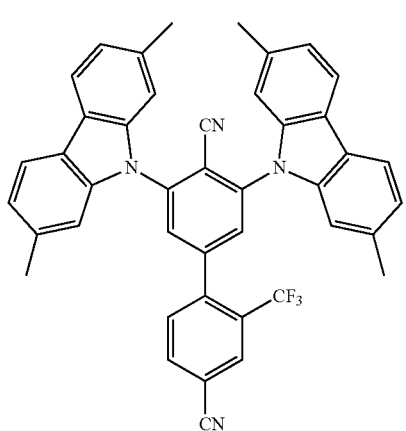
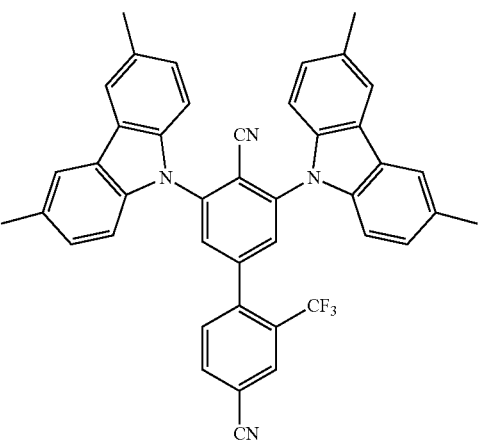
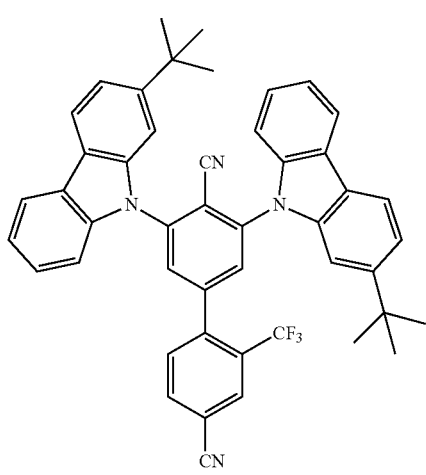
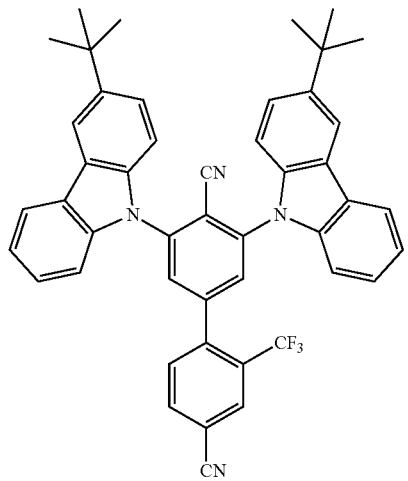

155 156
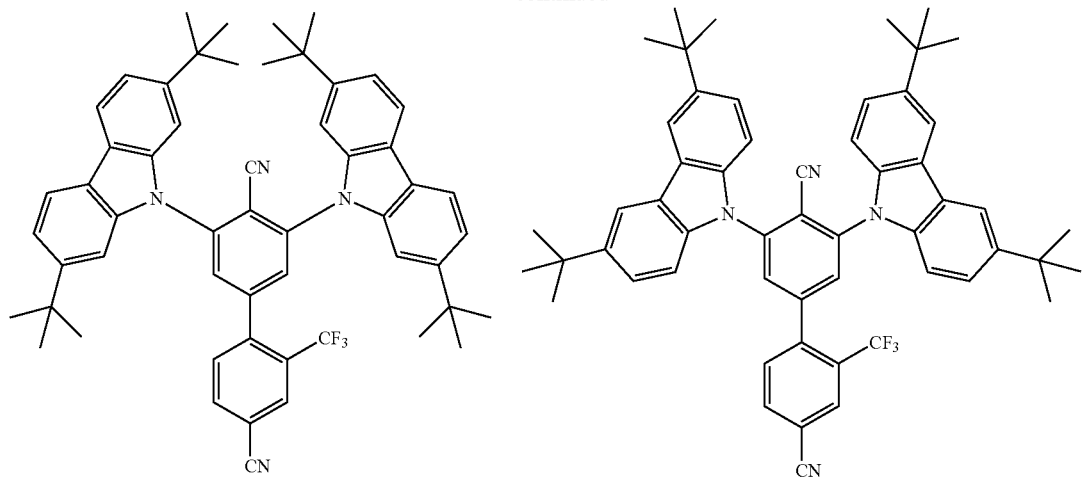
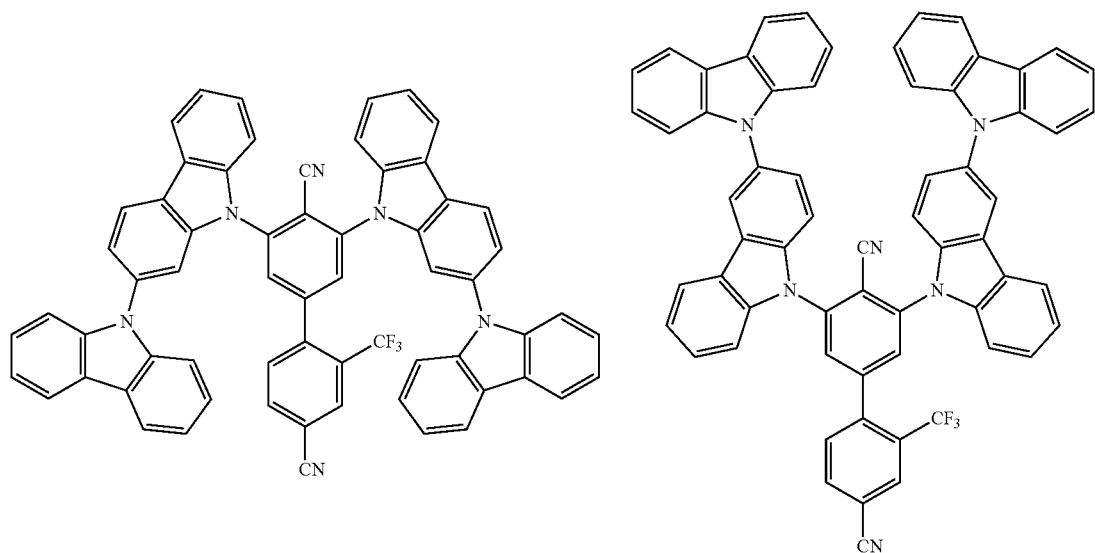
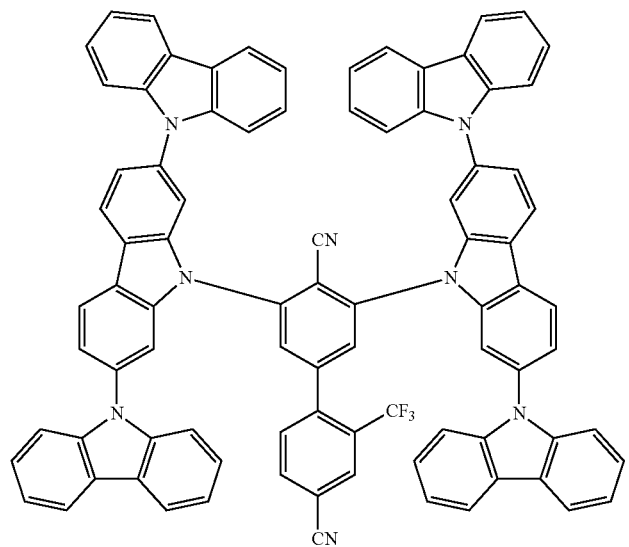

157 158
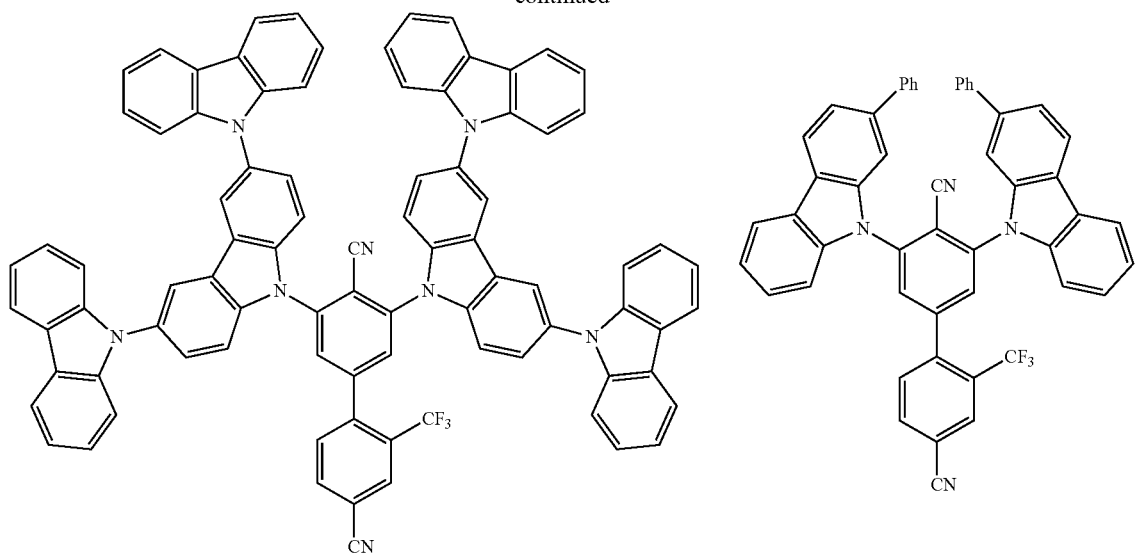
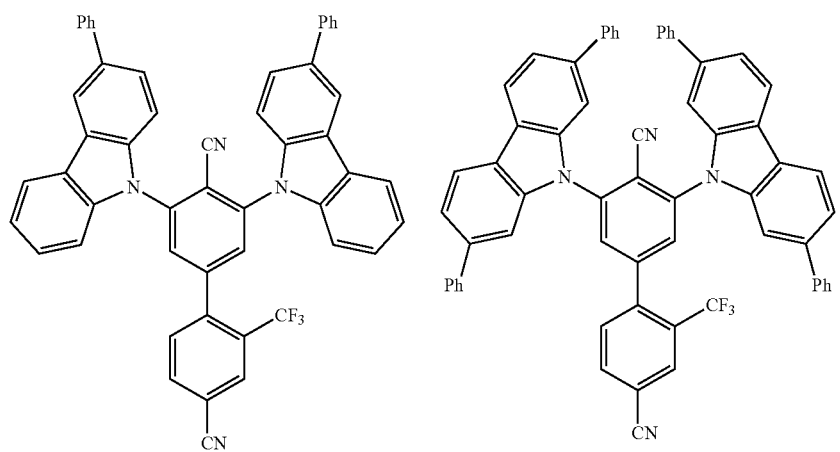
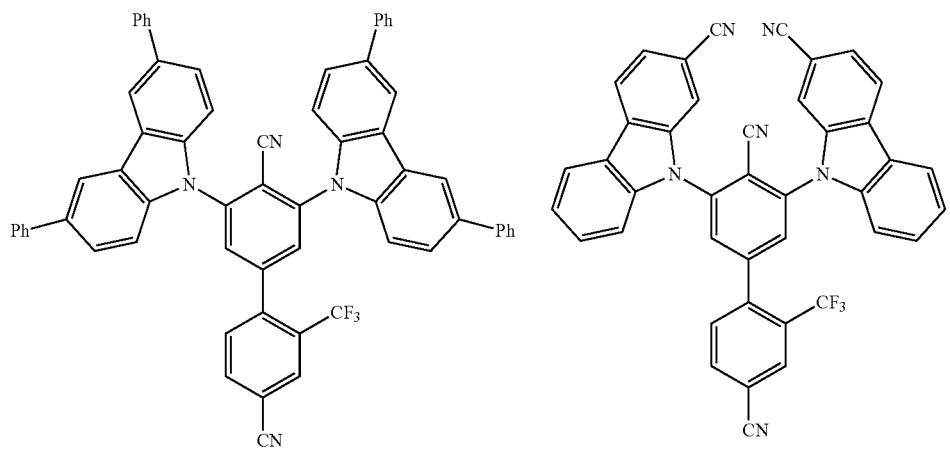

-continued
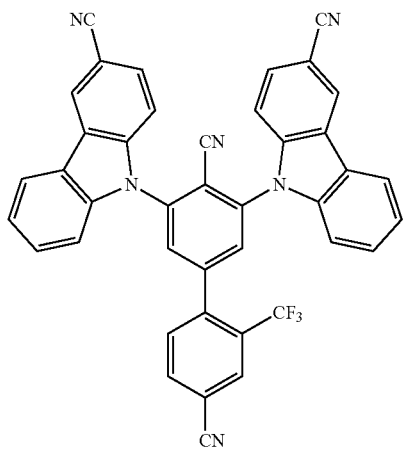
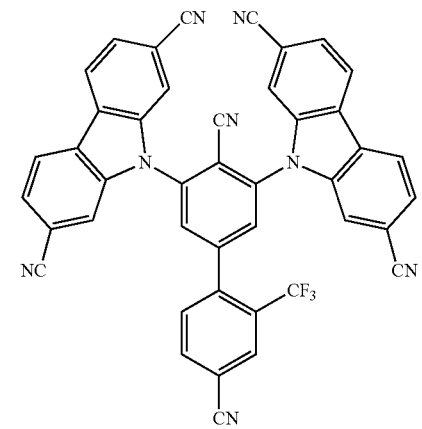
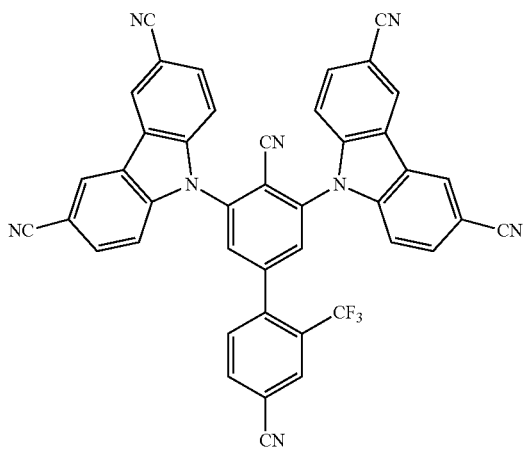
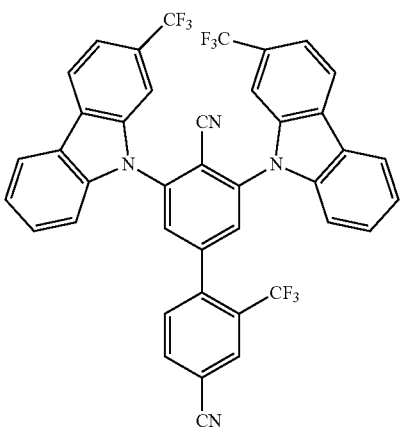
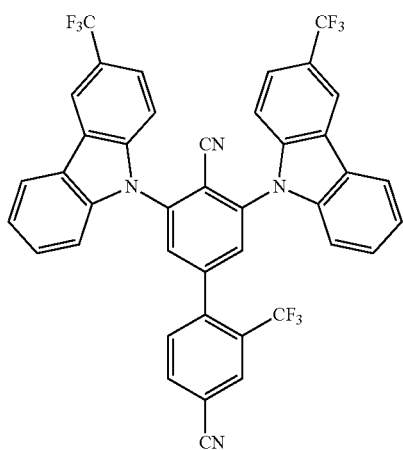
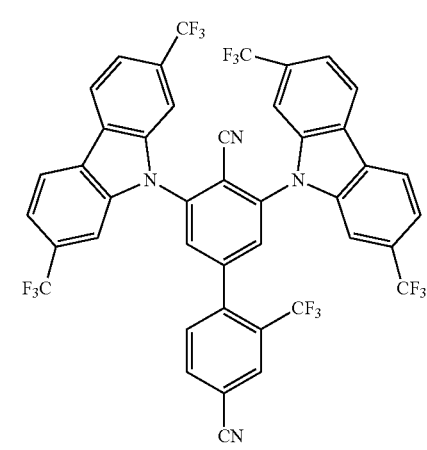

-continued
161
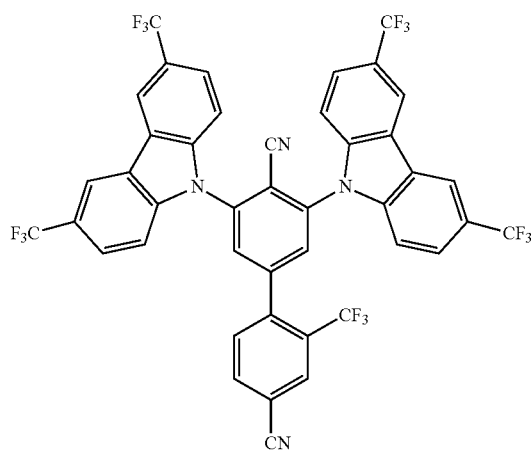
162
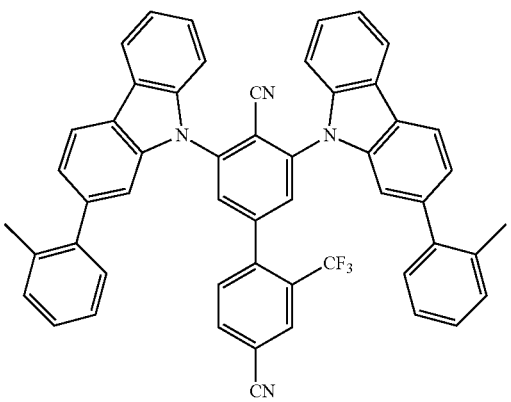
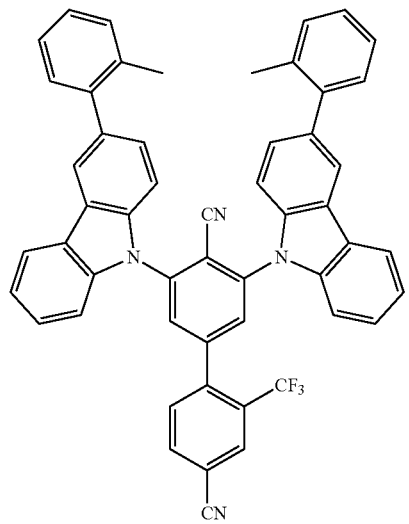
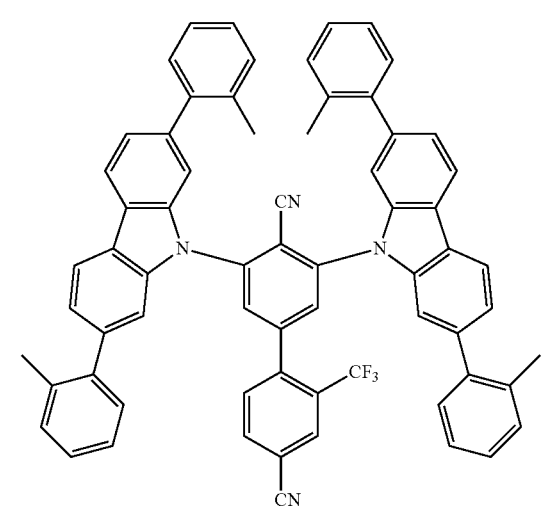
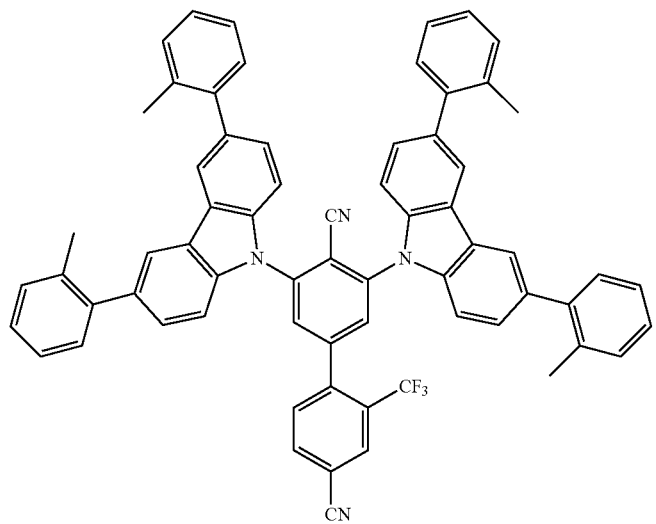
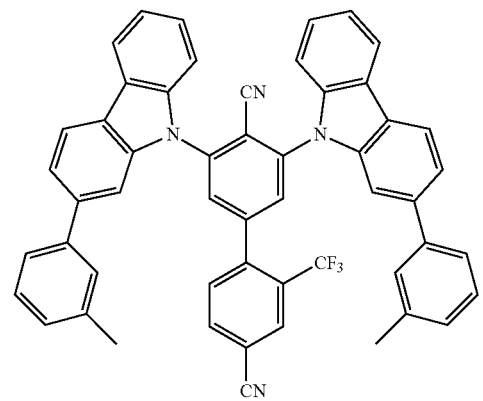

-continued
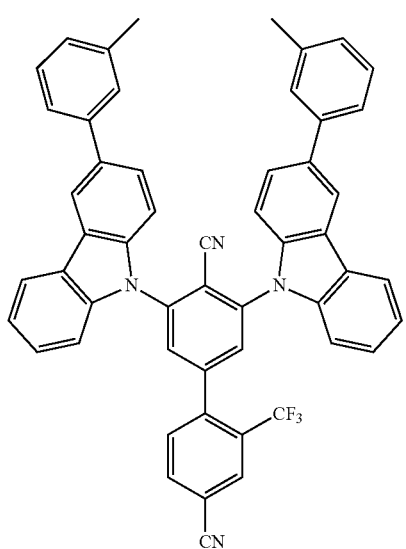
163
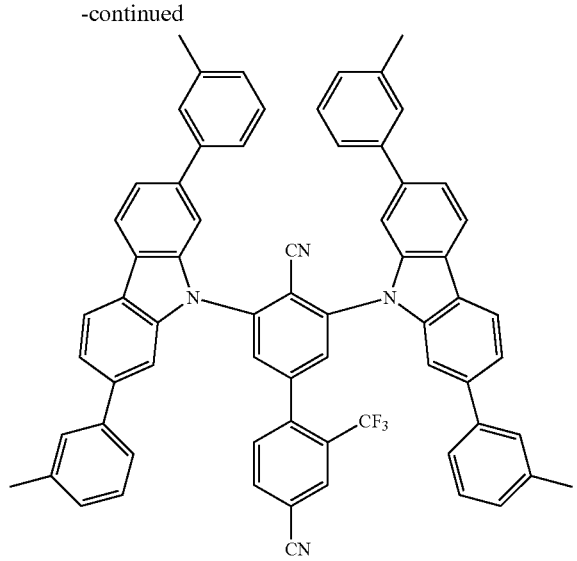
164
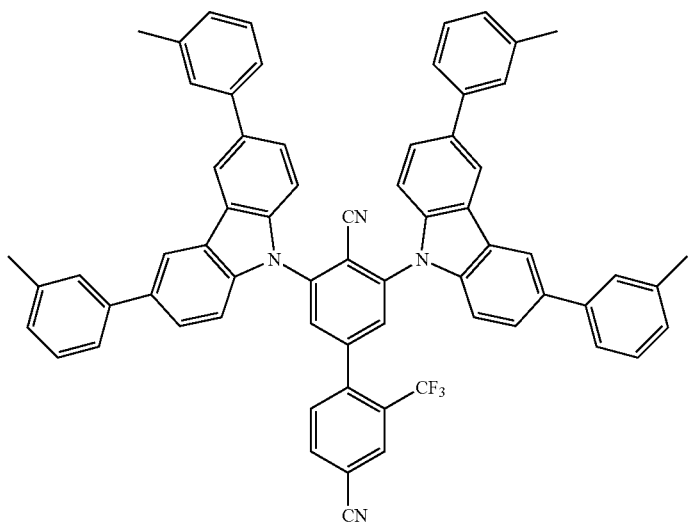
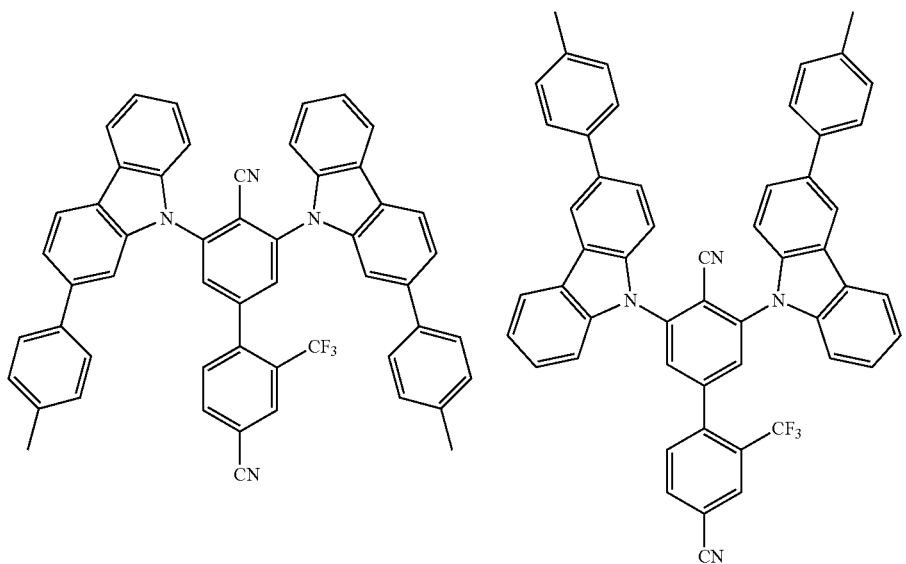

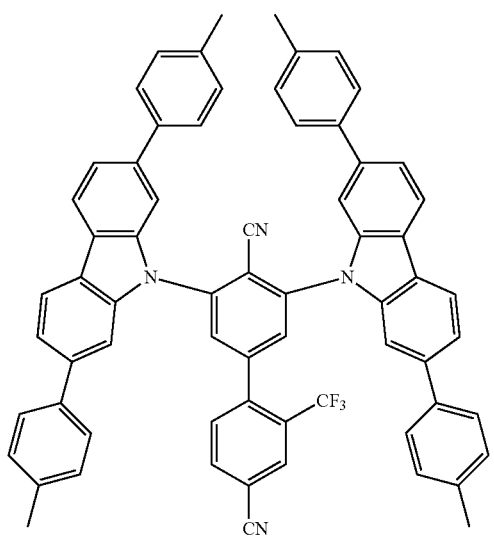
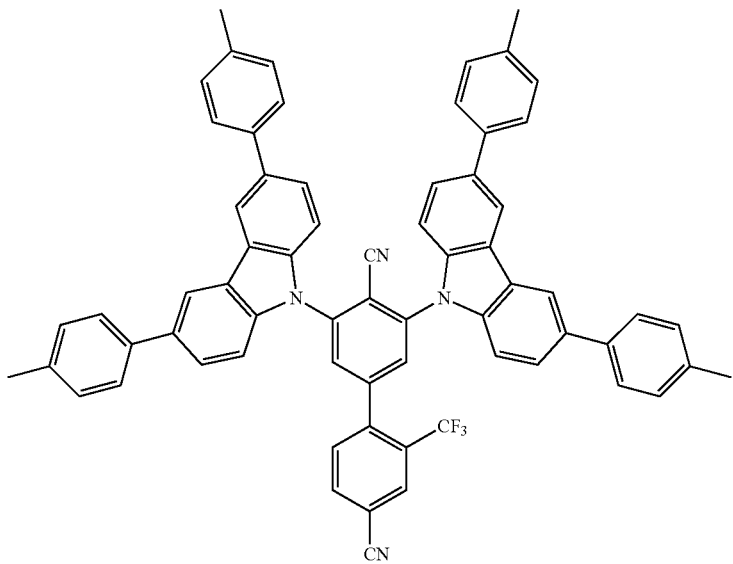
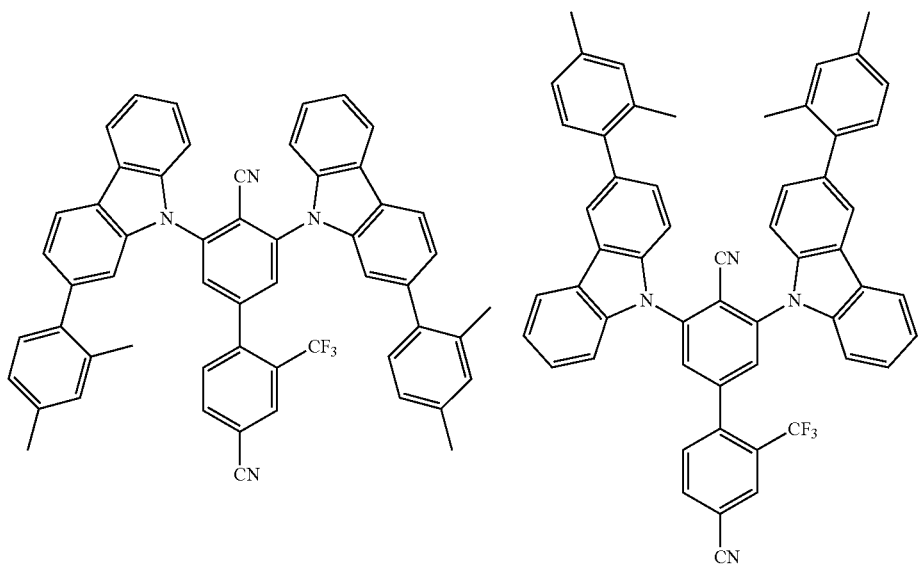

-continued
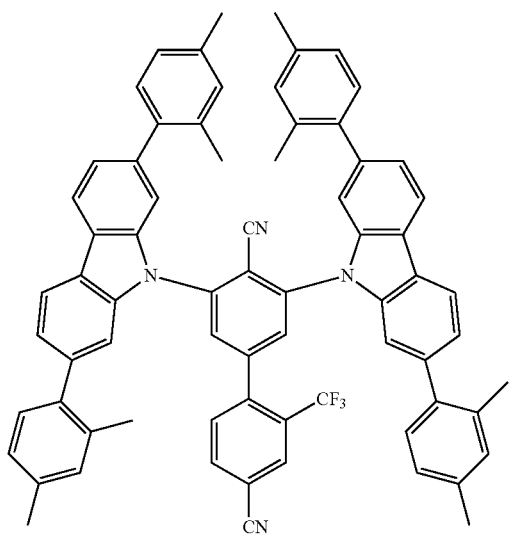
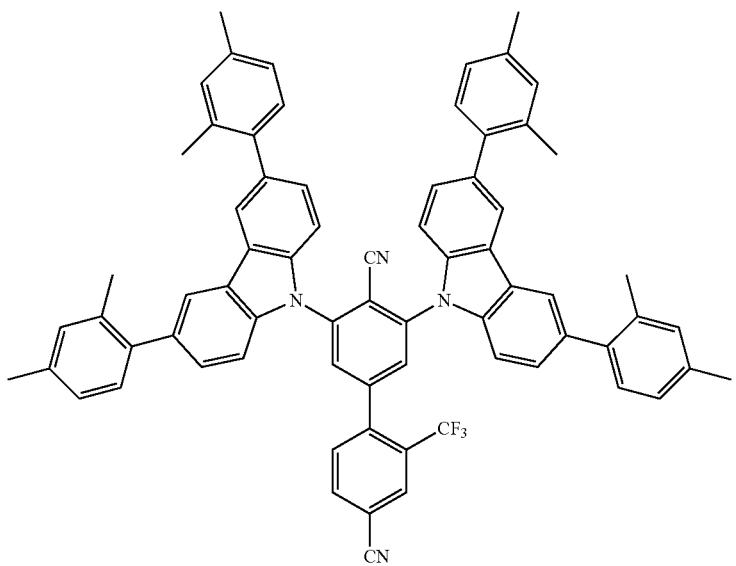
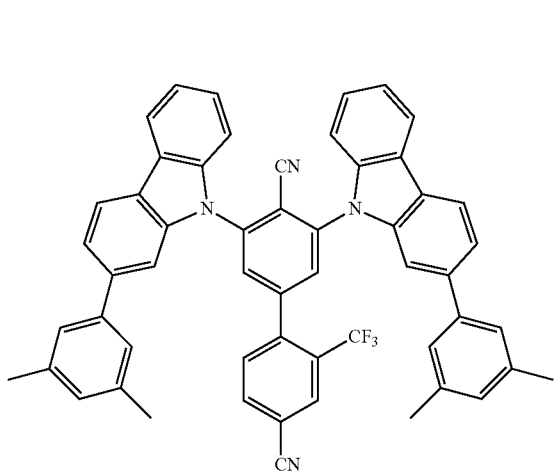
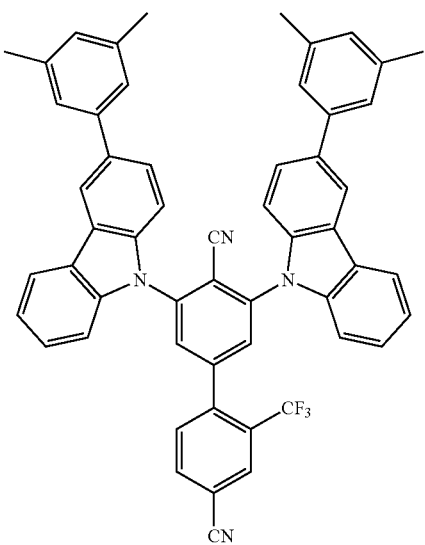

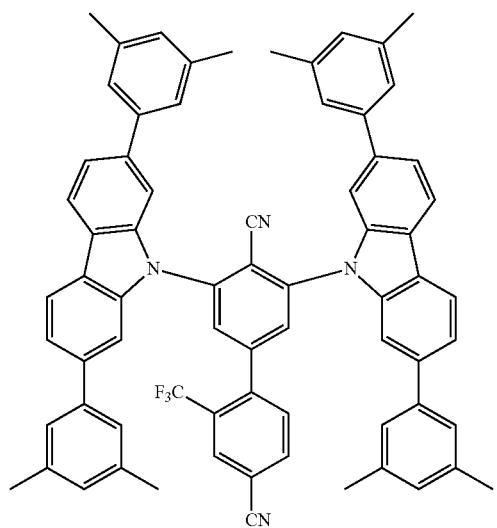
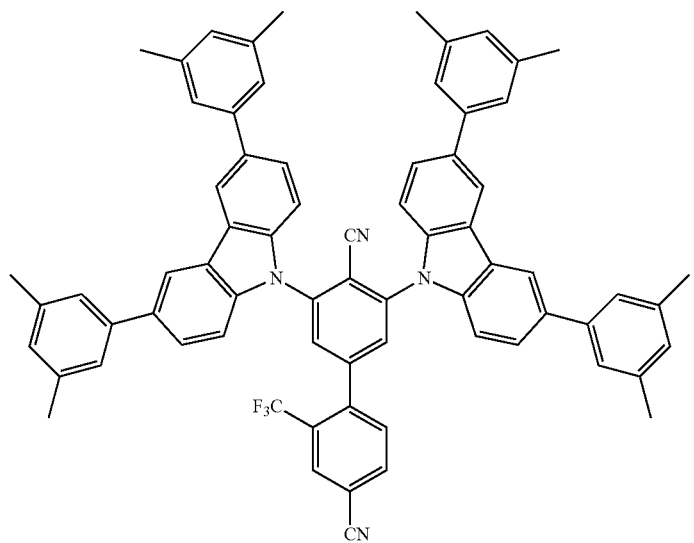
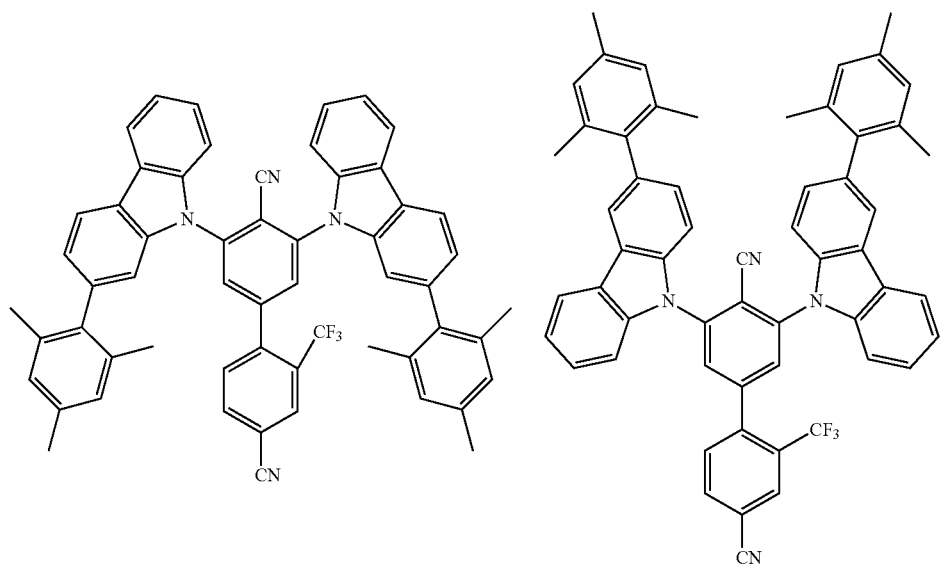

171
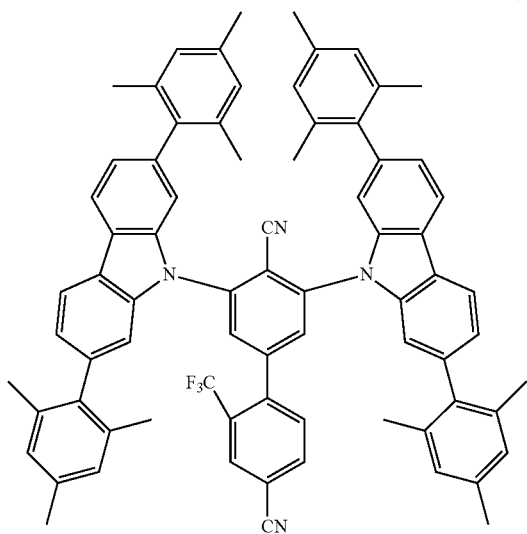
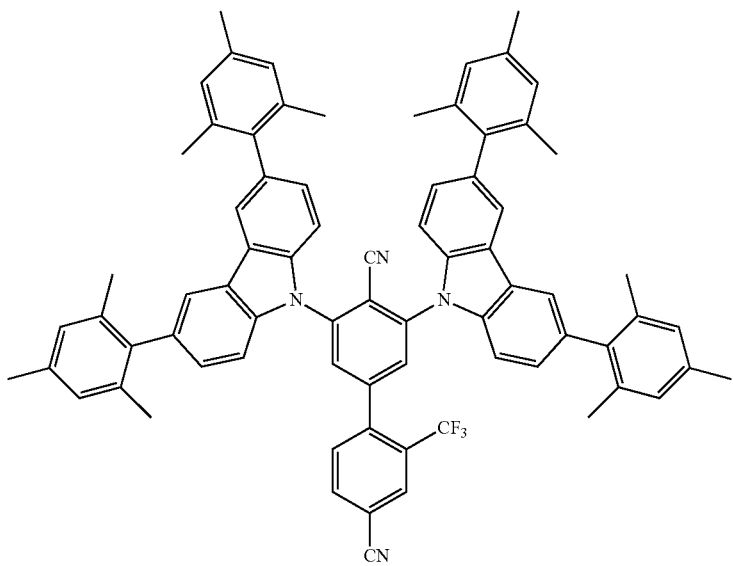
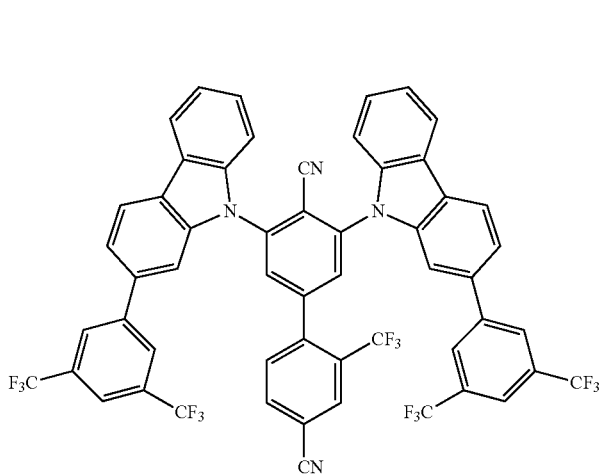
172
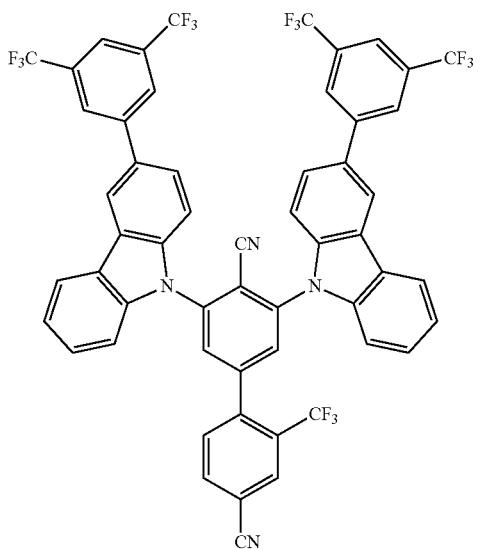

173 174
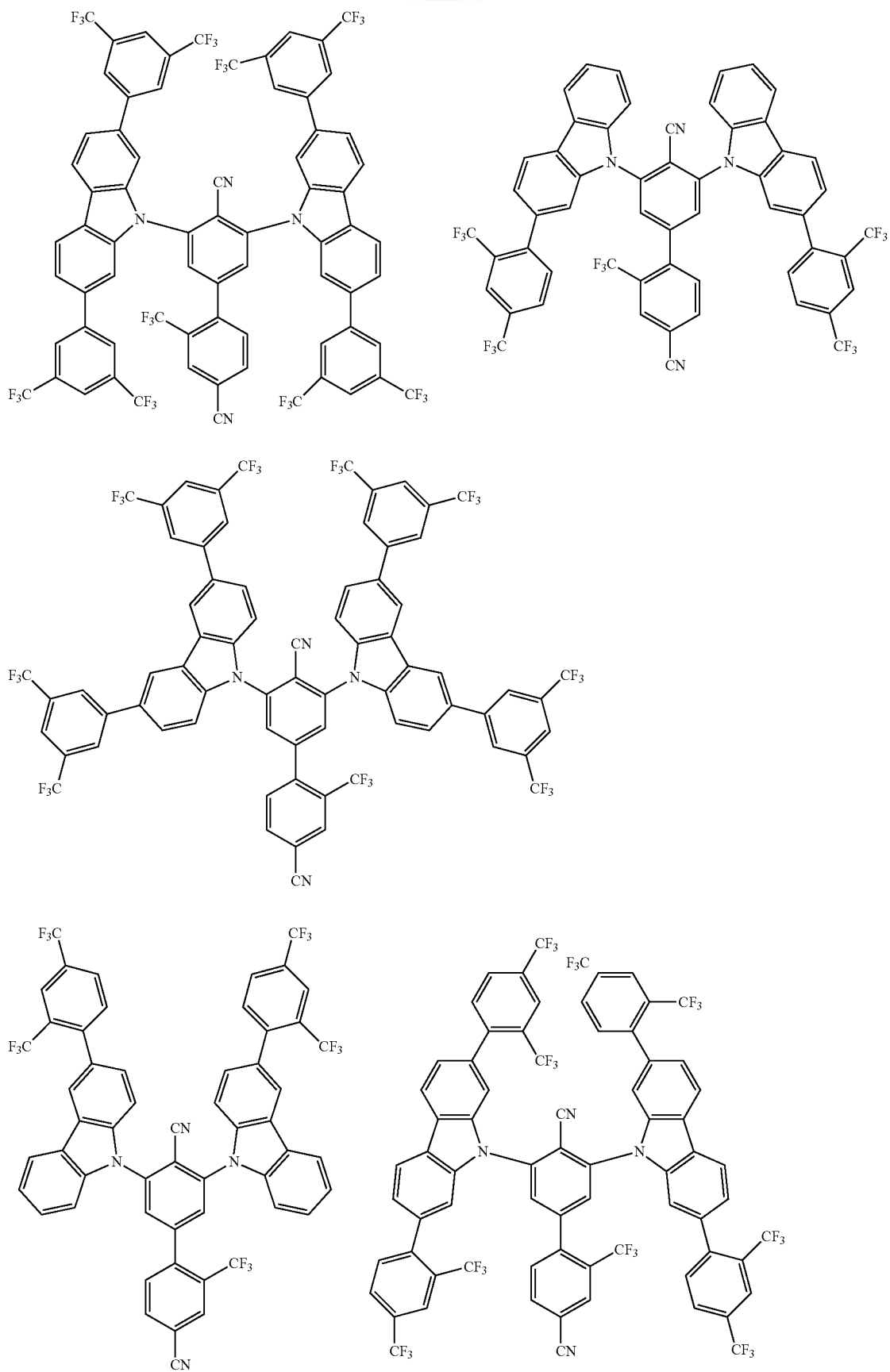

-continued
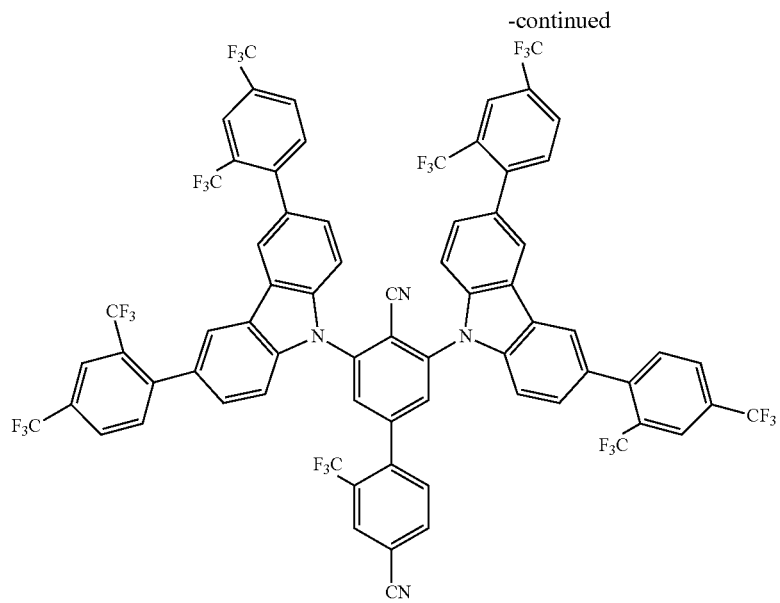
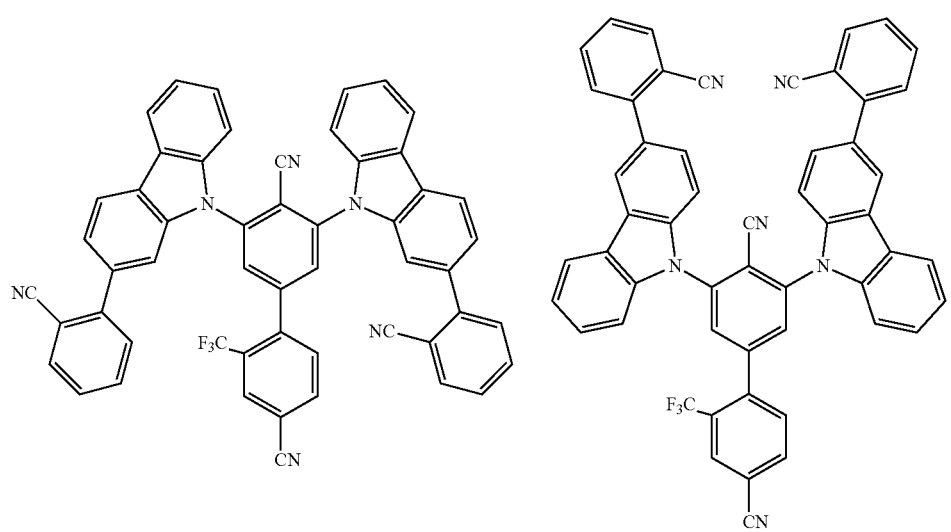
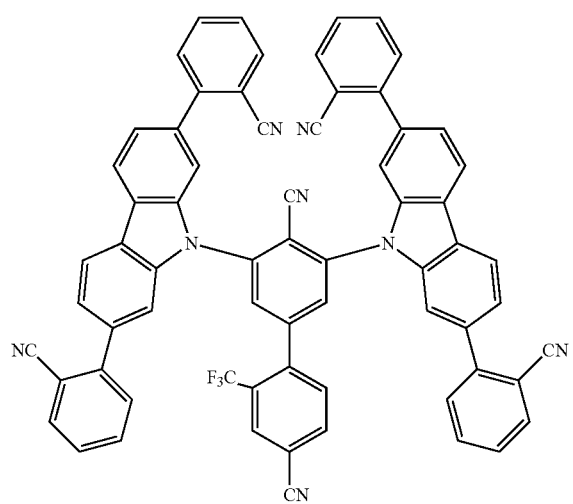

177 178
-continued
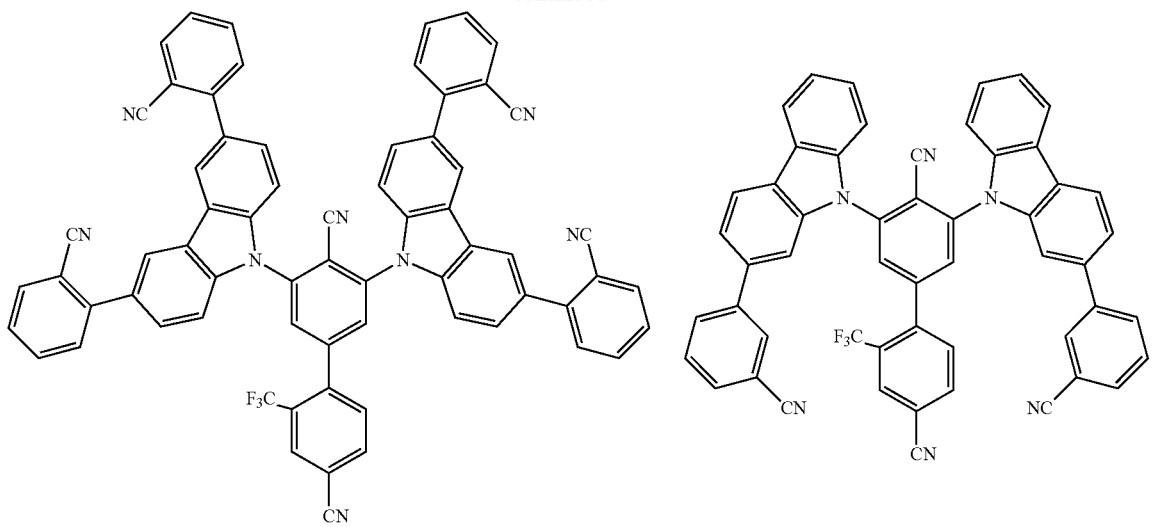
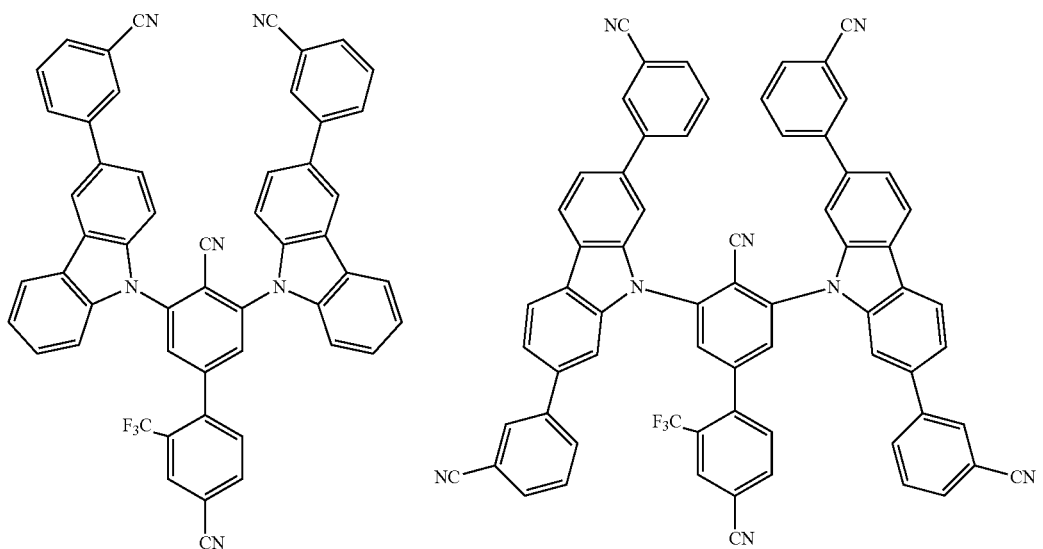
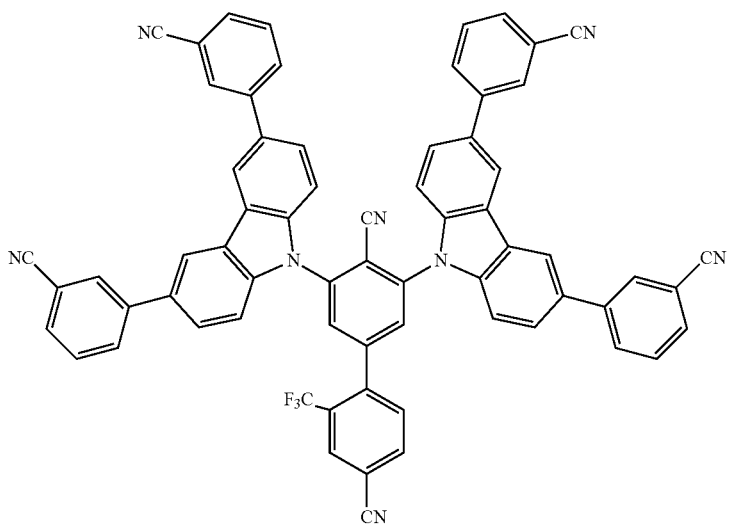

-continued
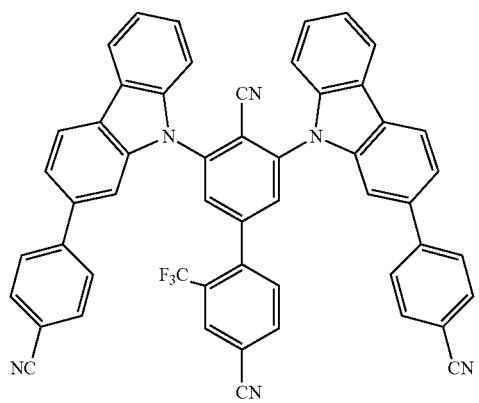
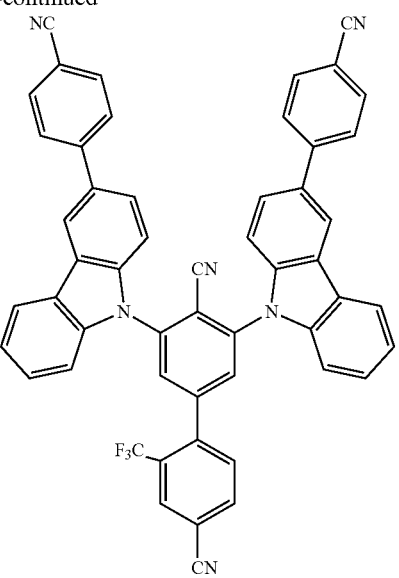
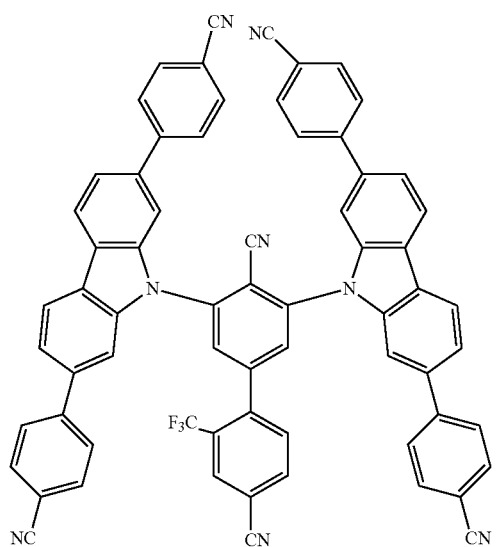
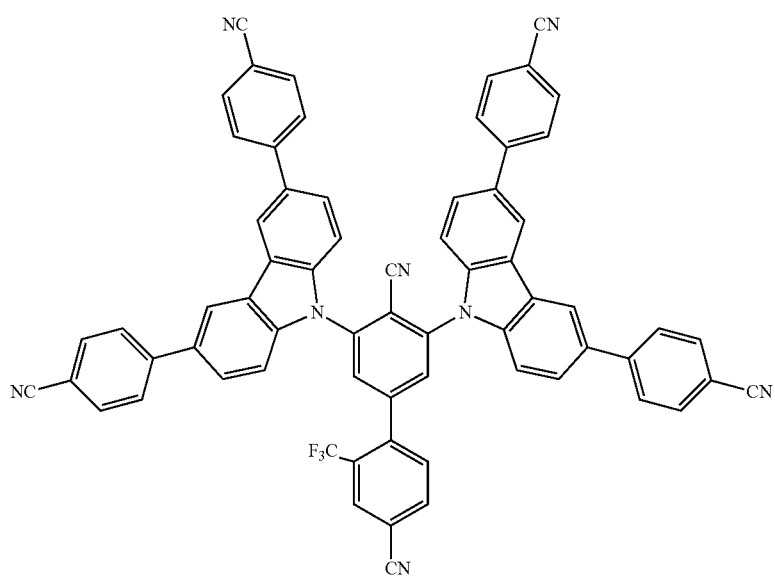

-continued
181
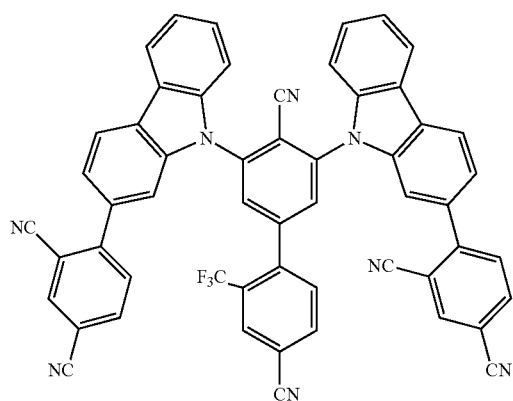
182
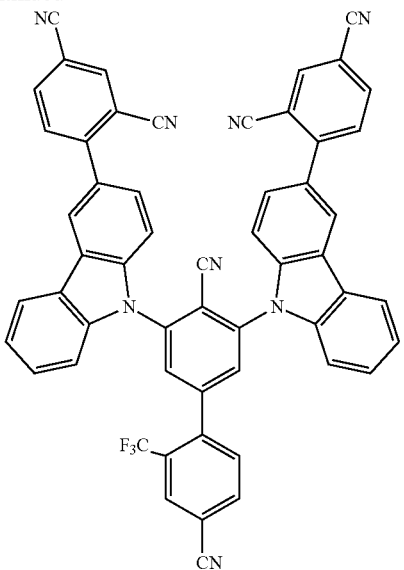
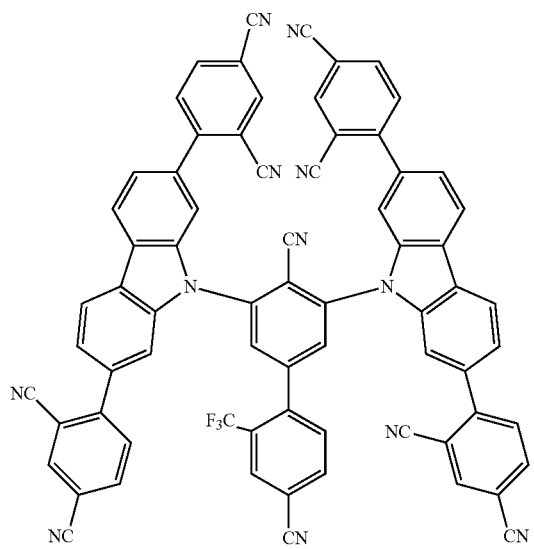
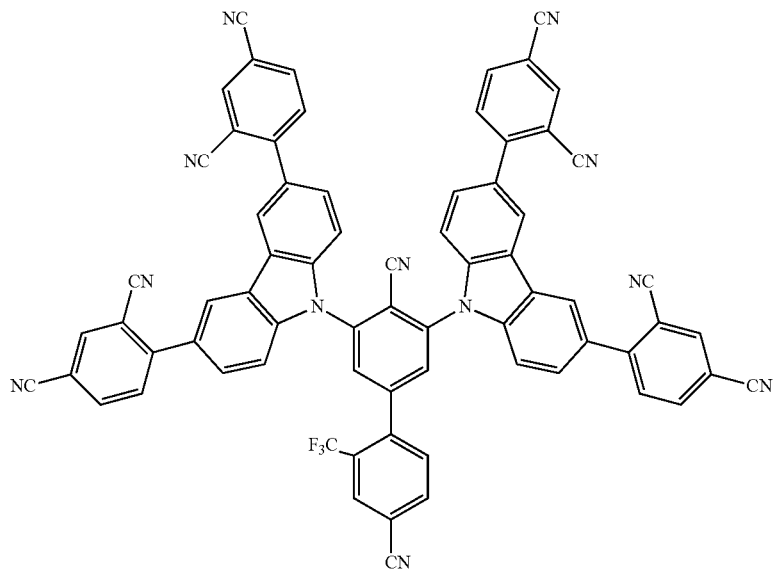

-continued
183
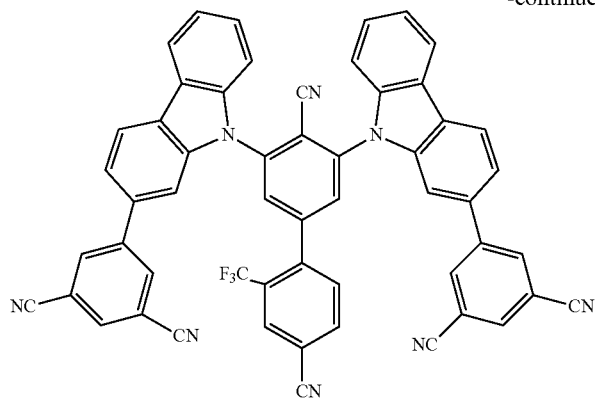
184
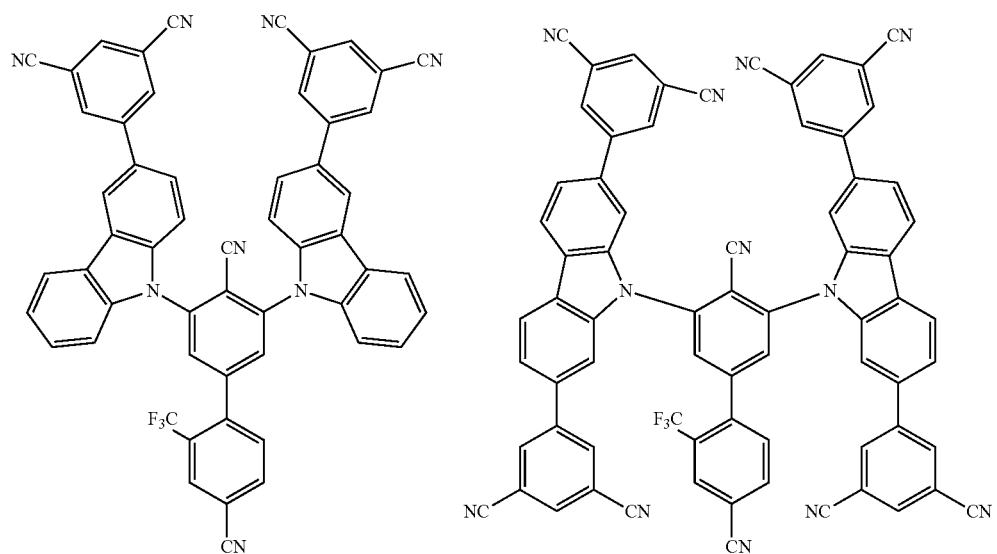
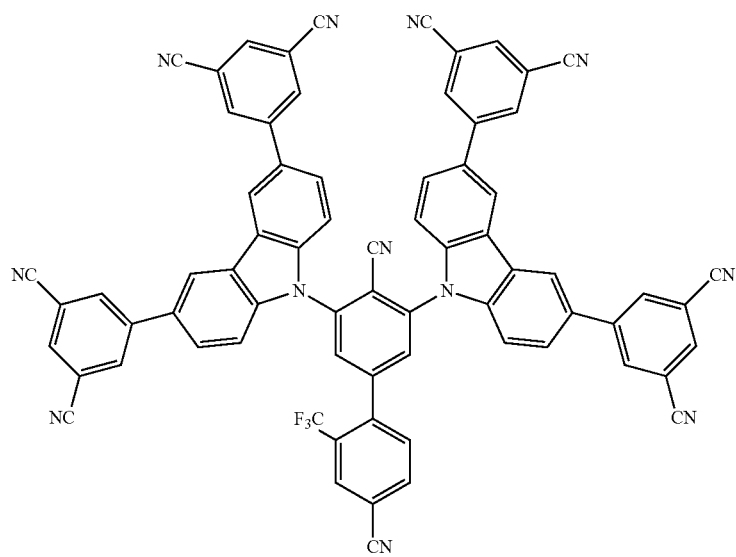

185 186
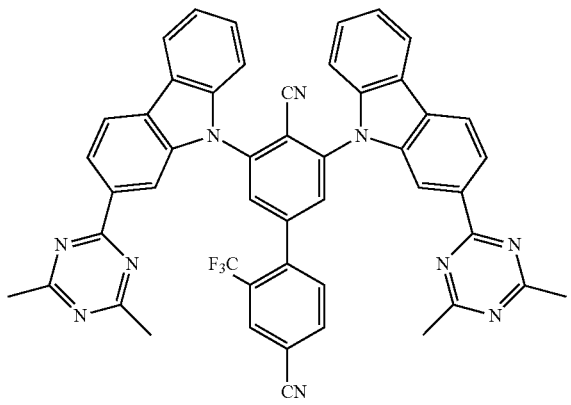
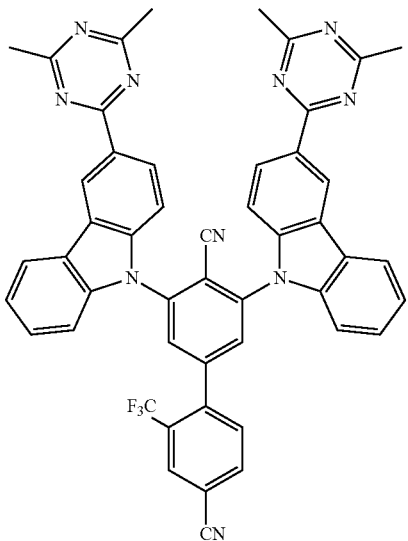
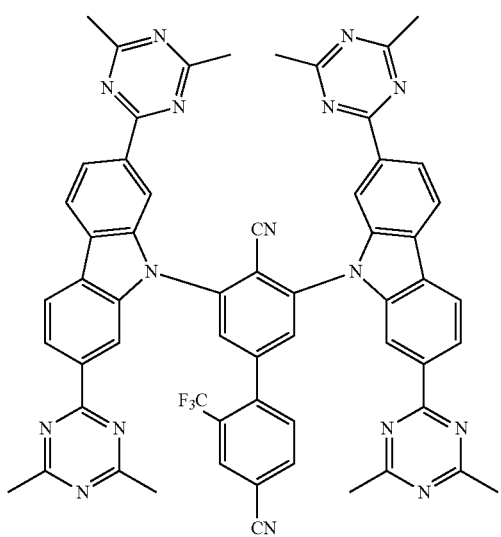
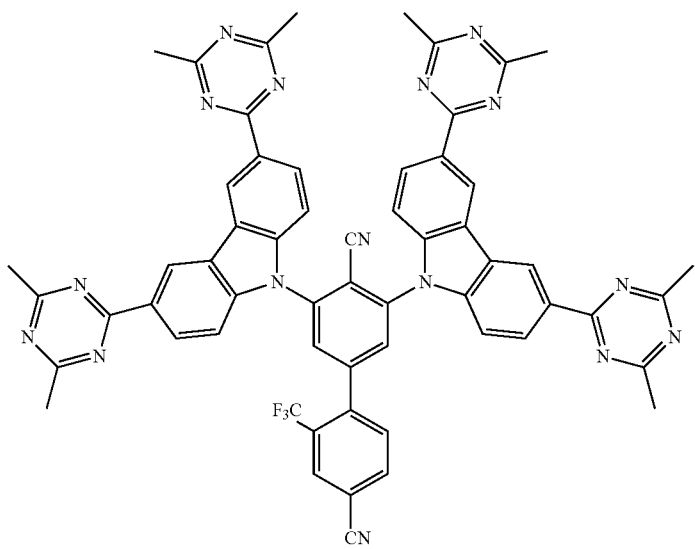

187
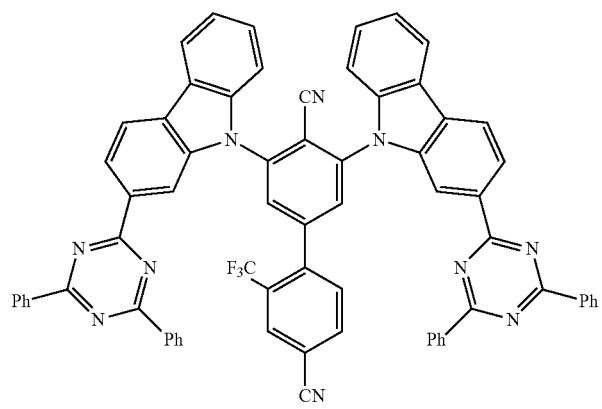
188
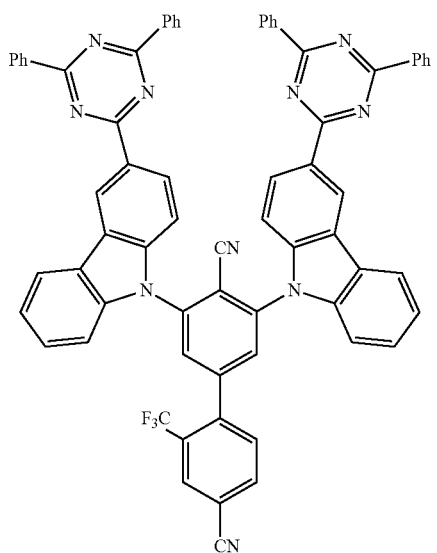
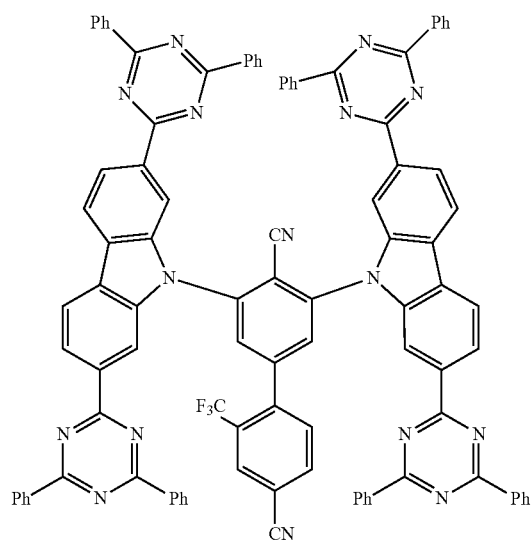
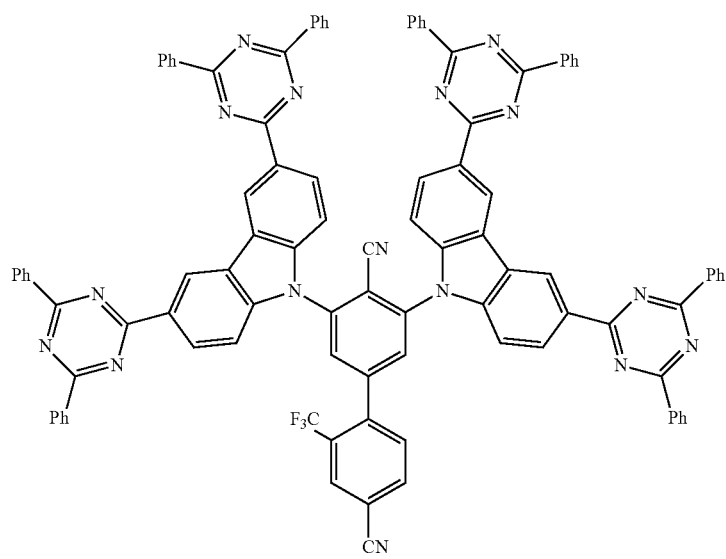
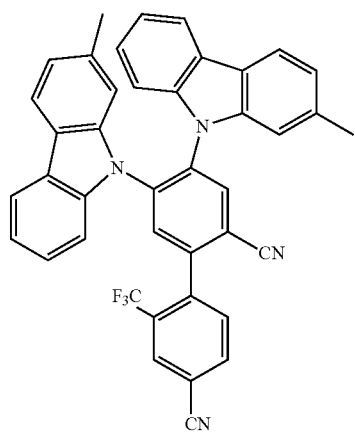

189 190
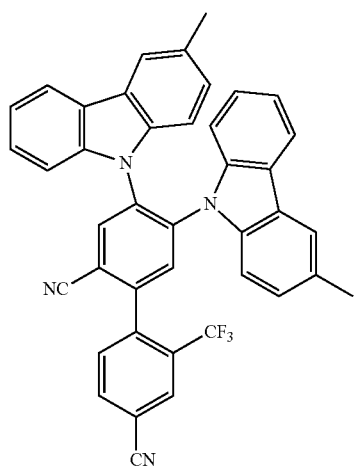 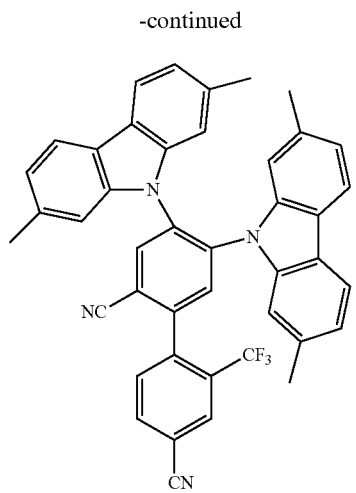 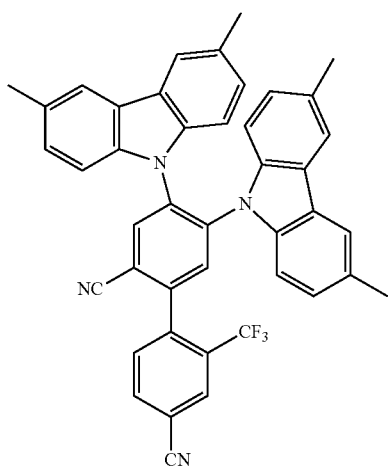
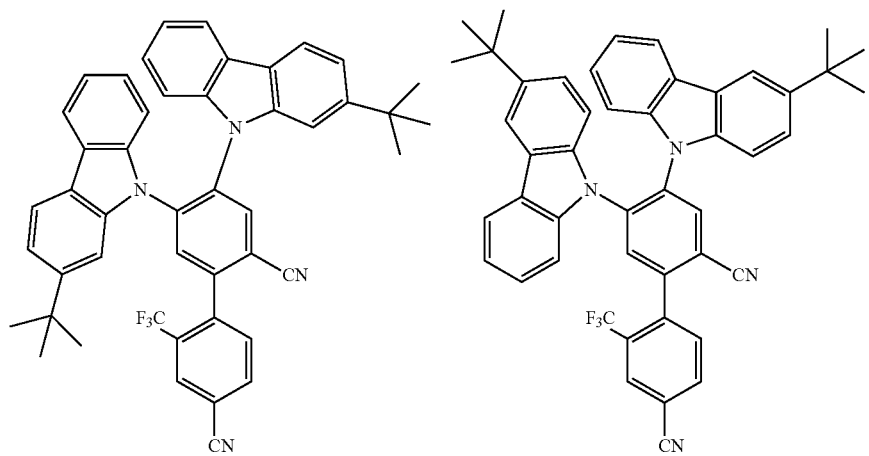
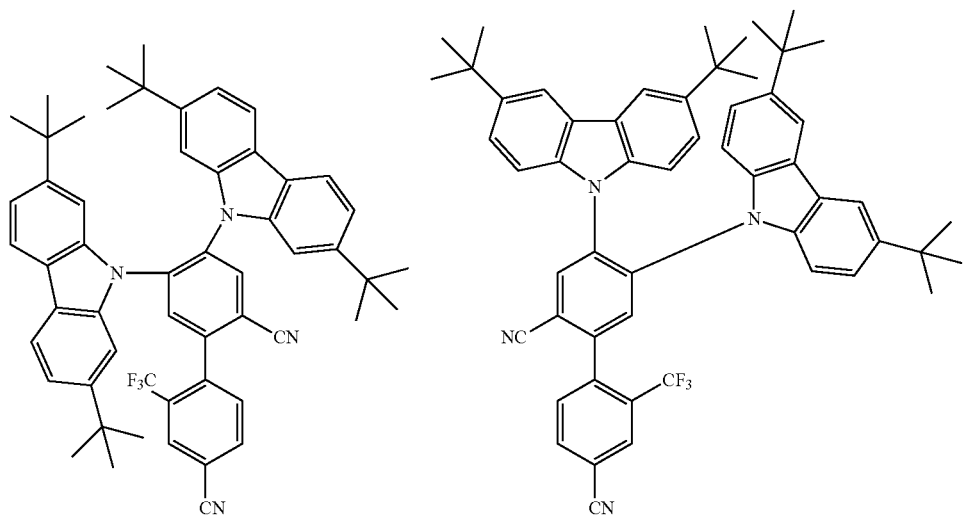

191
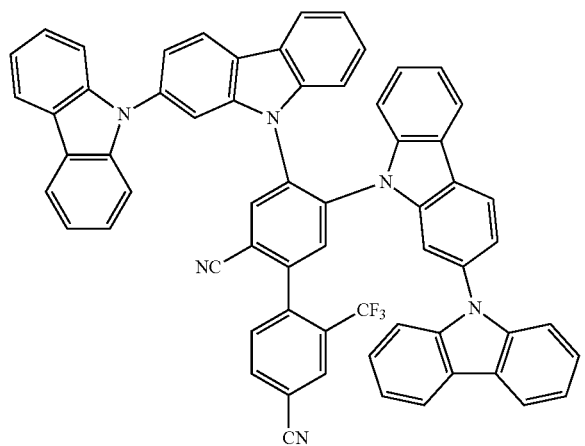
192
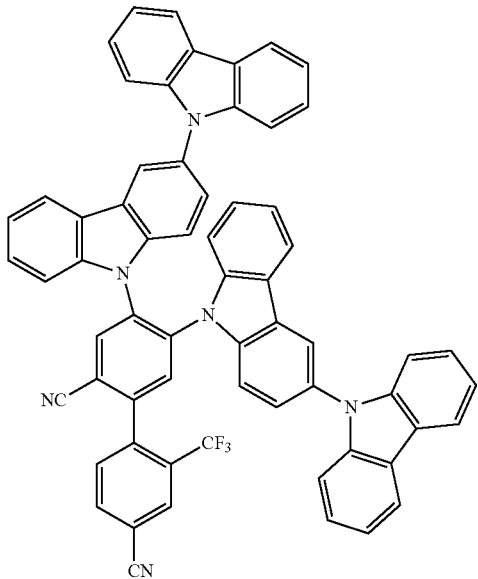
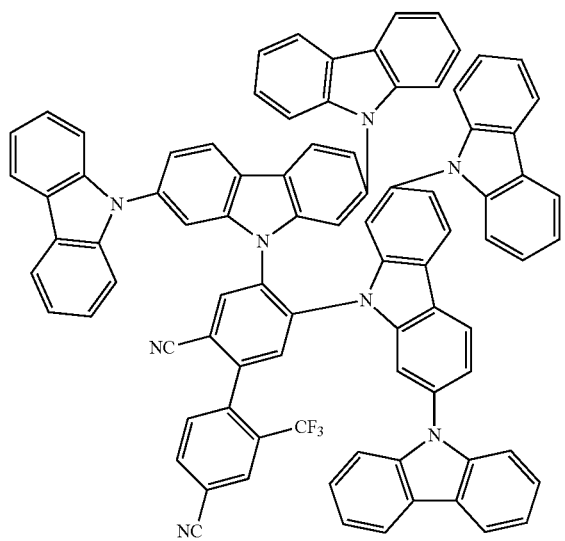
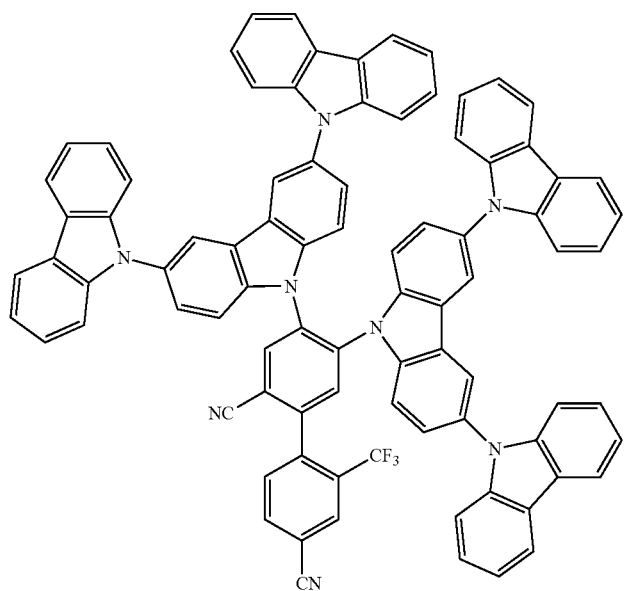
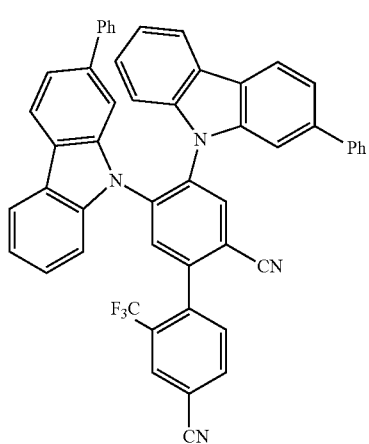

-continued
193
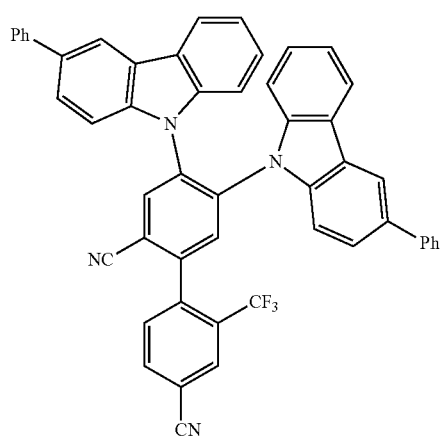
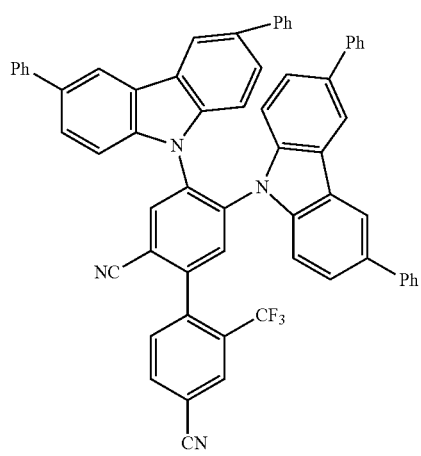
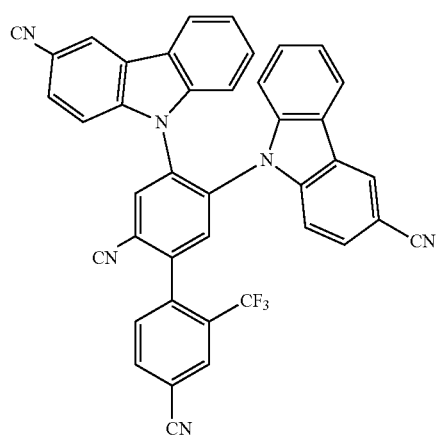
194
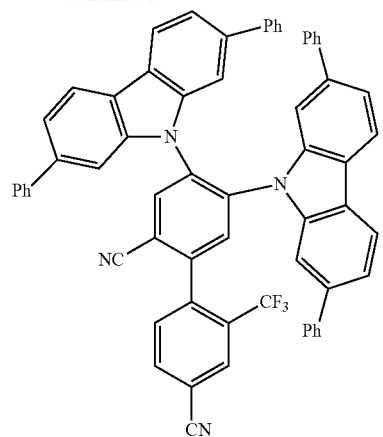
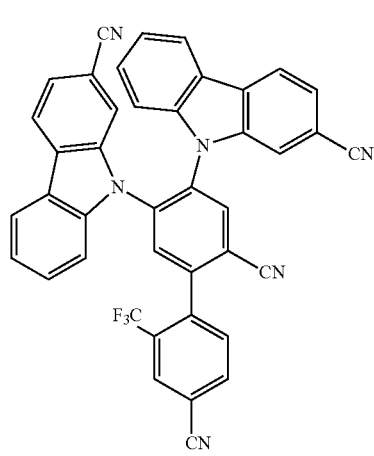
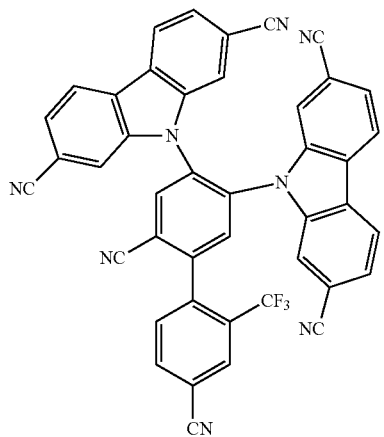

195
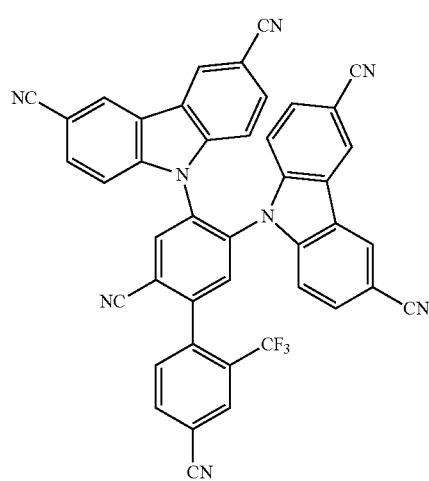
196
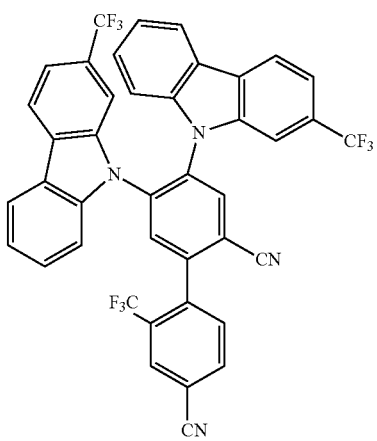
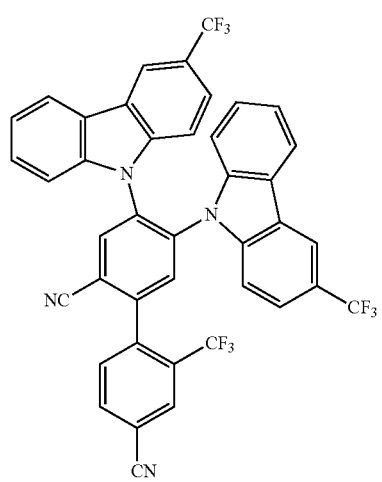
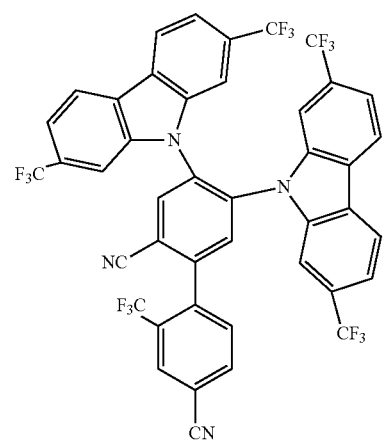
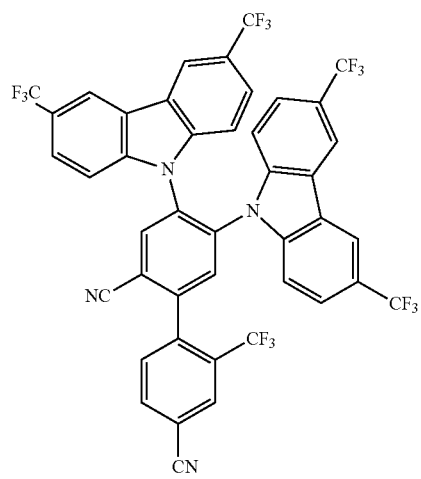
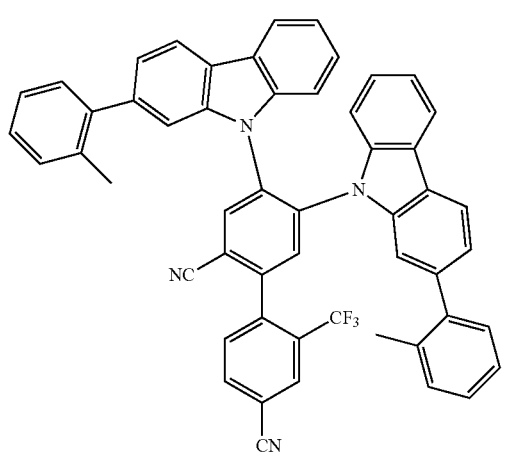

-continued
197
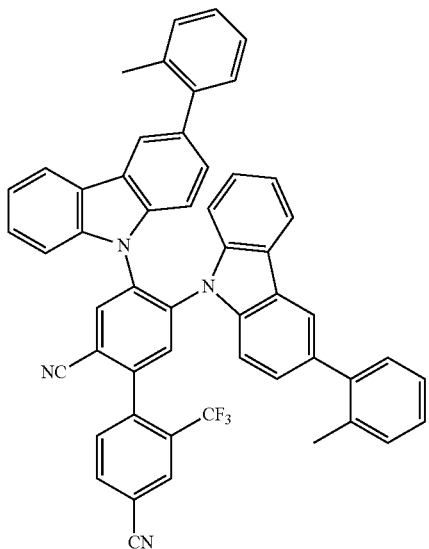
198
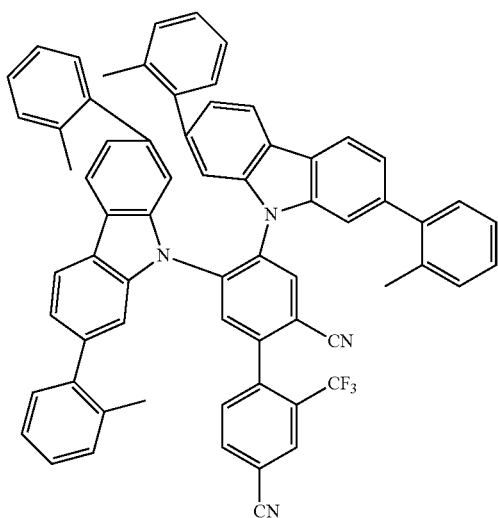
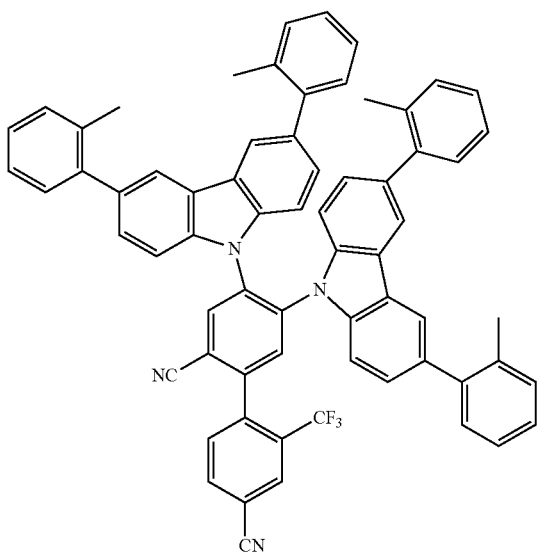
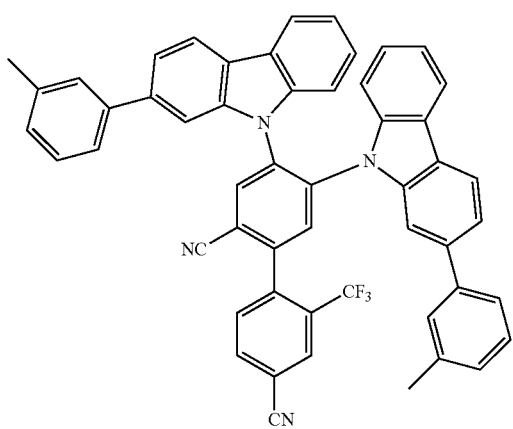
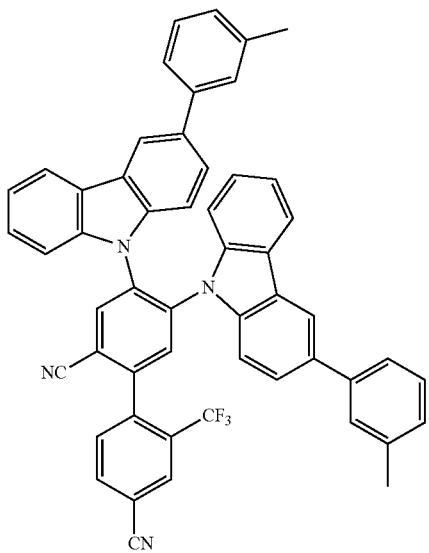
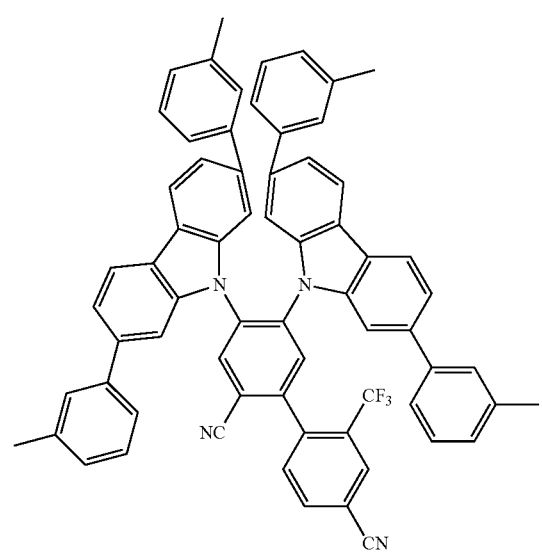

-continued
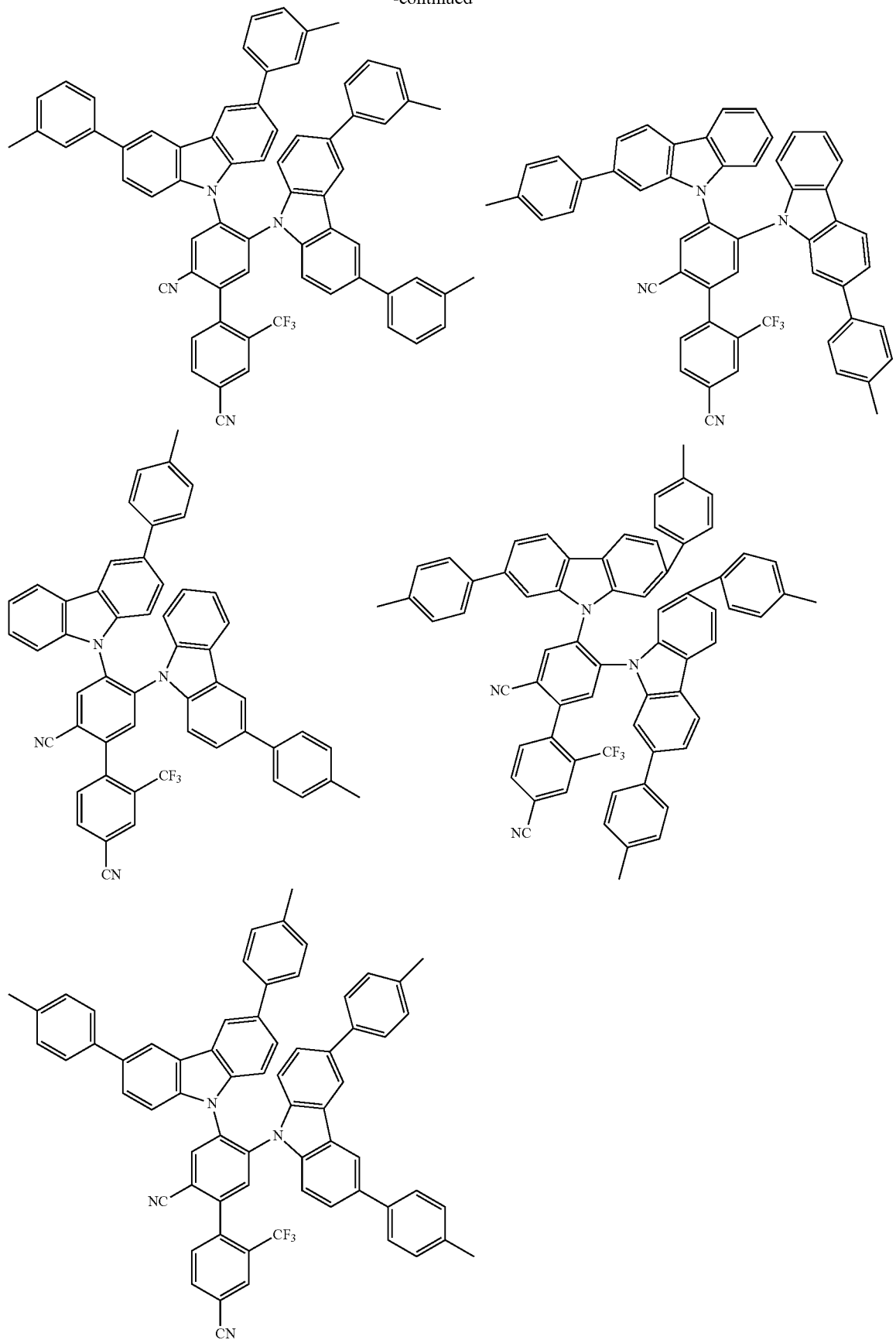

-continued
201
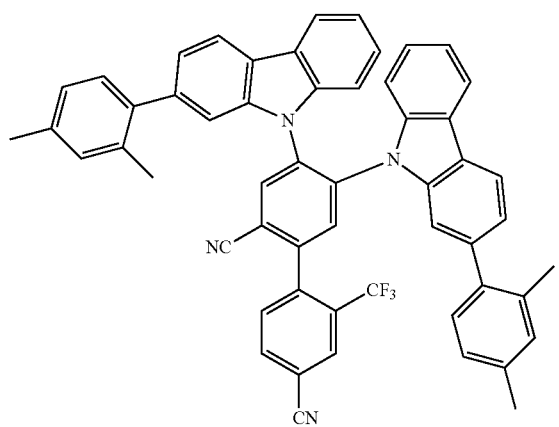
202
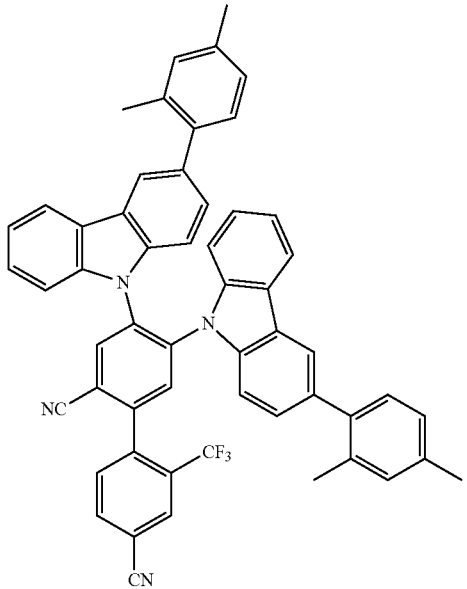
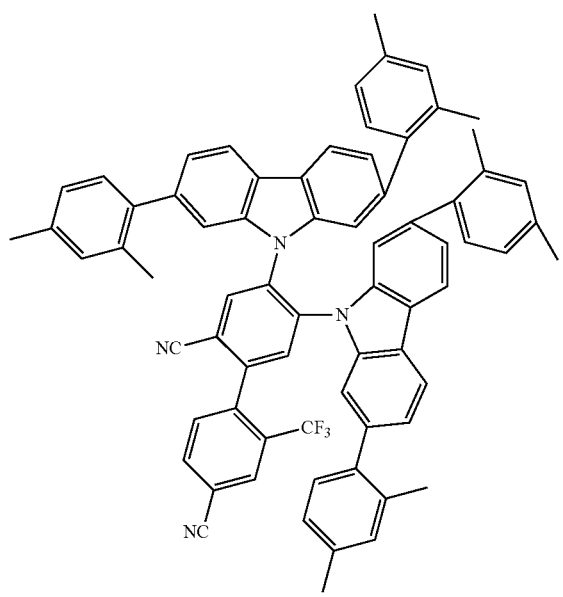

-continued
203 204
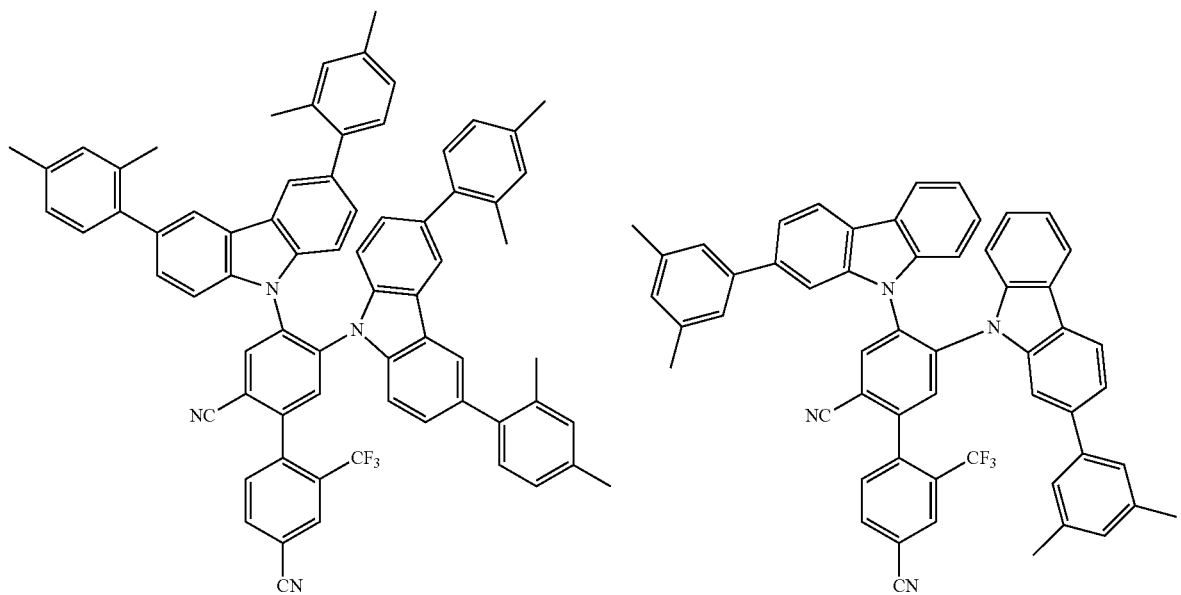
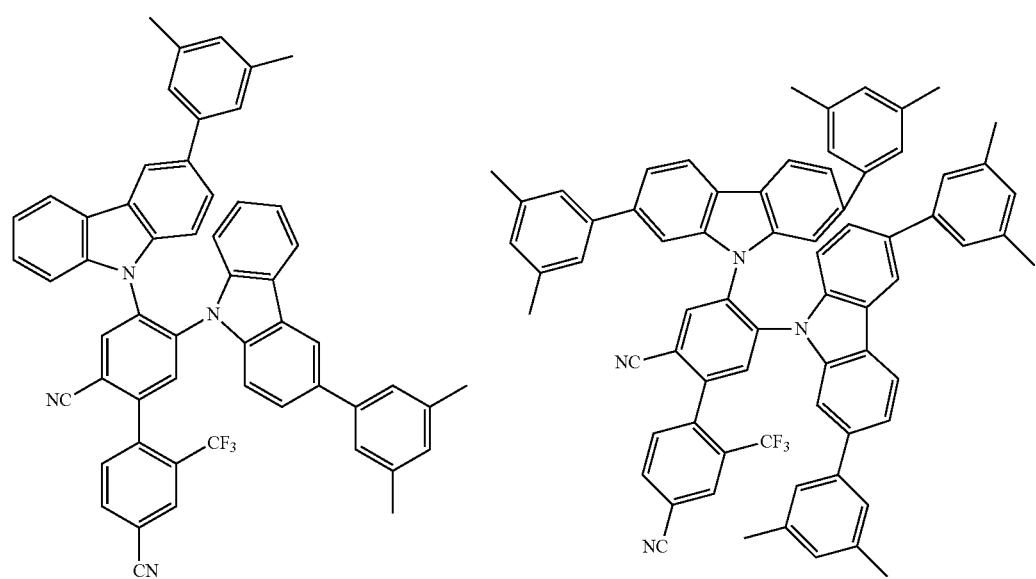

205
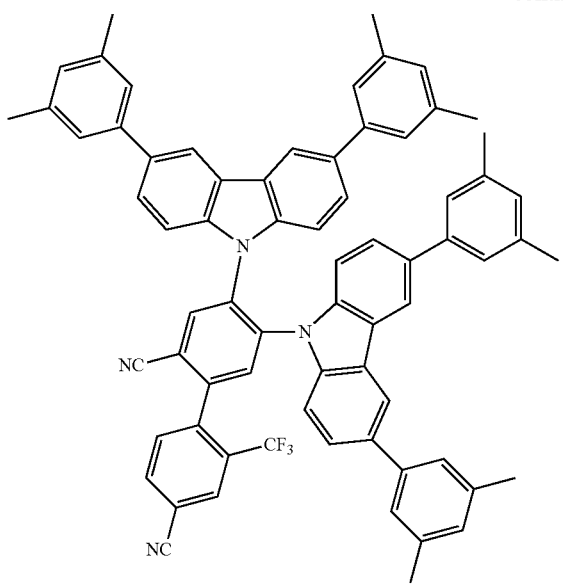
206
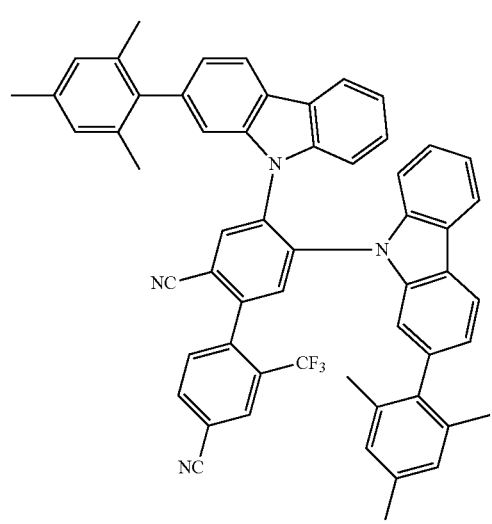
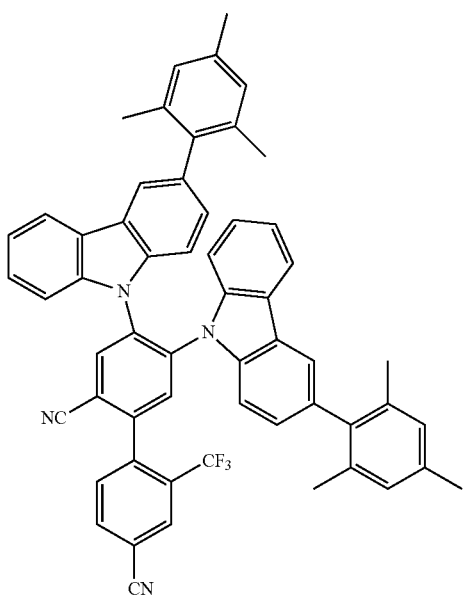
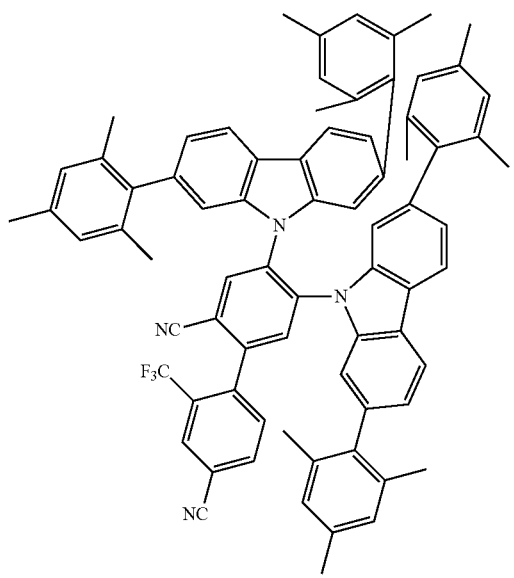

-continued
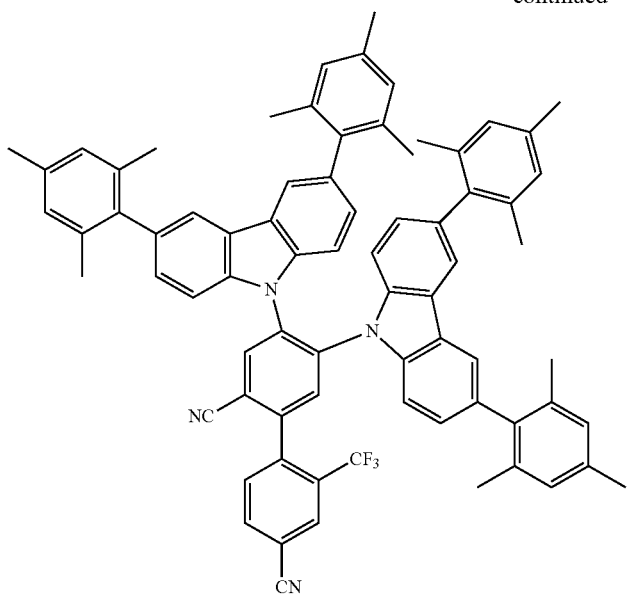
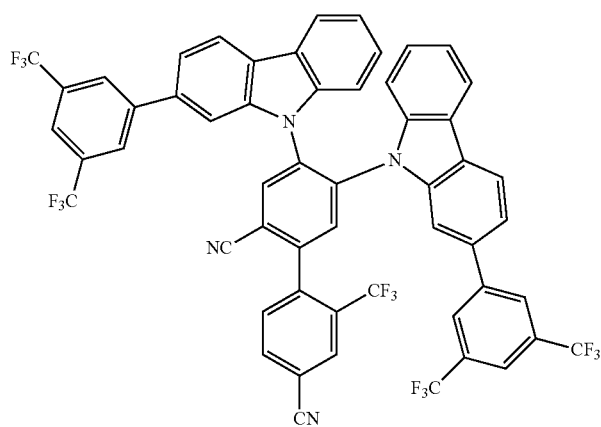
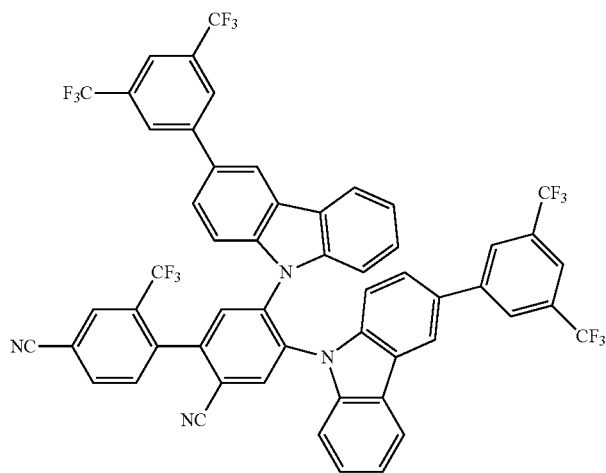

-continued
209
210
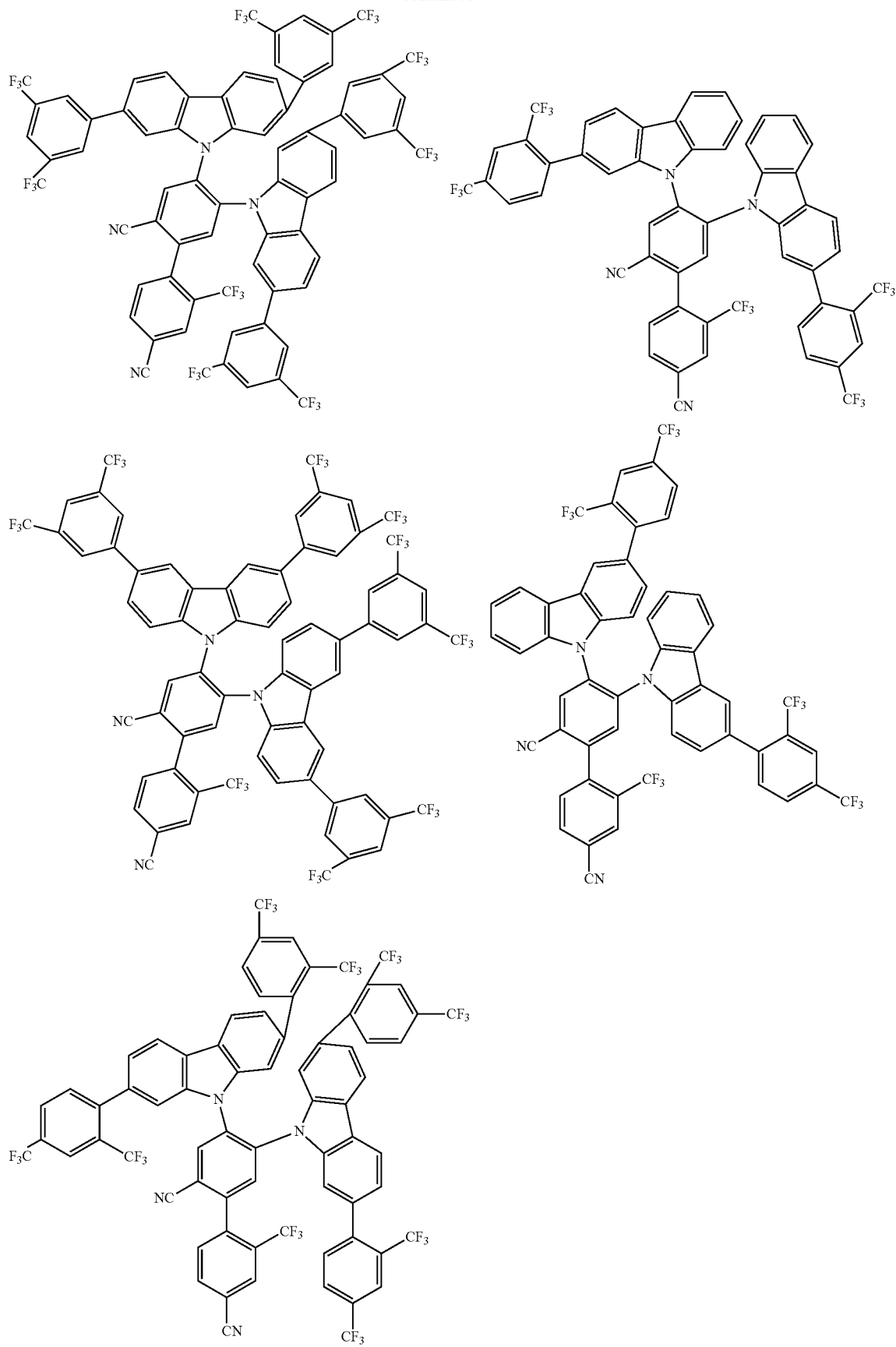

211 212
-continued
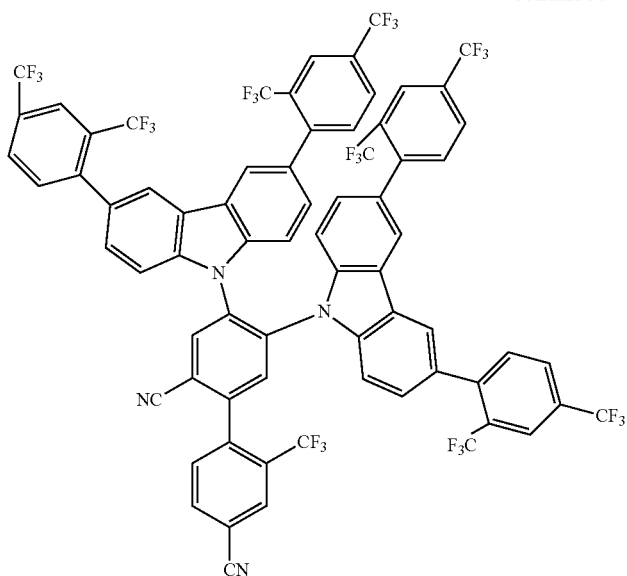
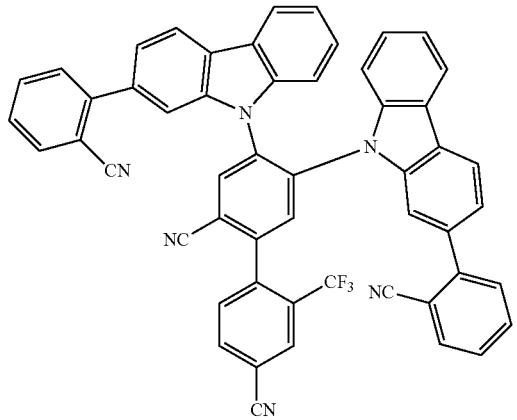
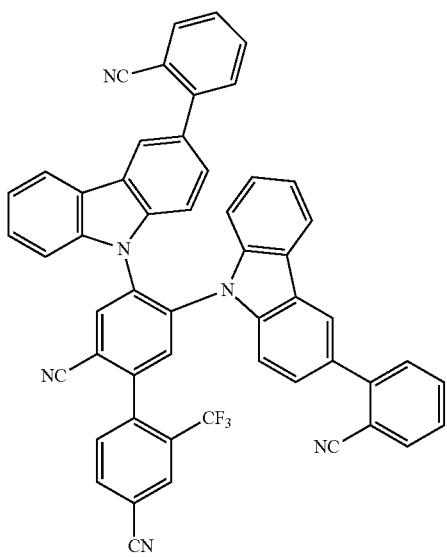
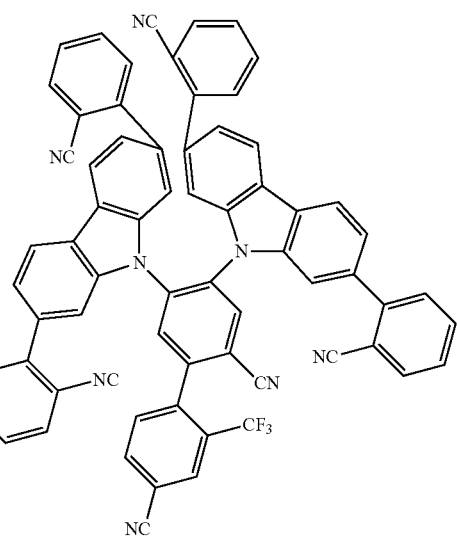
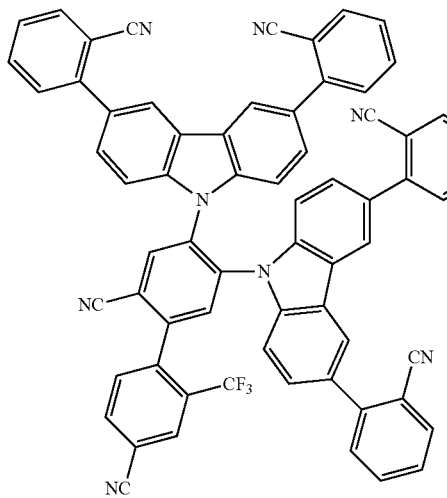
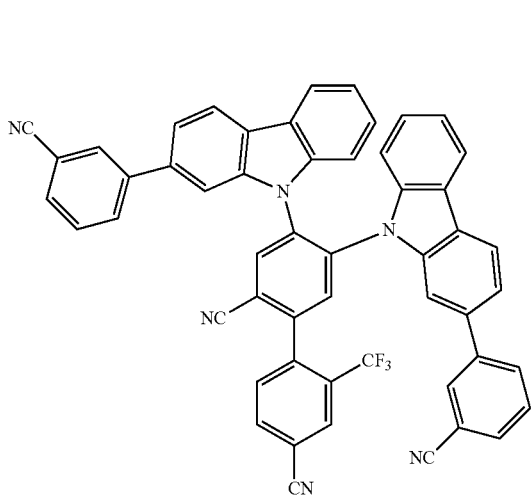

-continued
| 213 | 214 |
|---|---|
| 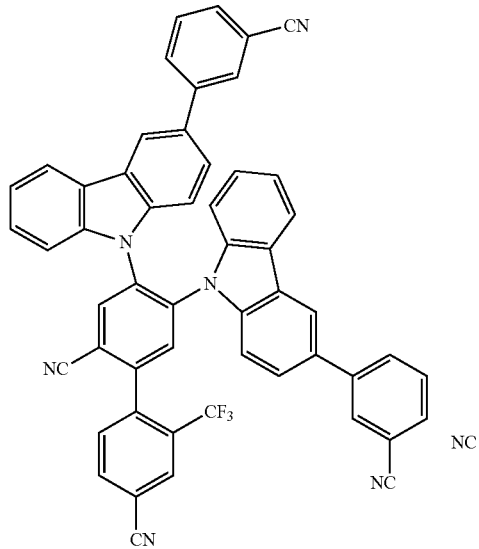 | 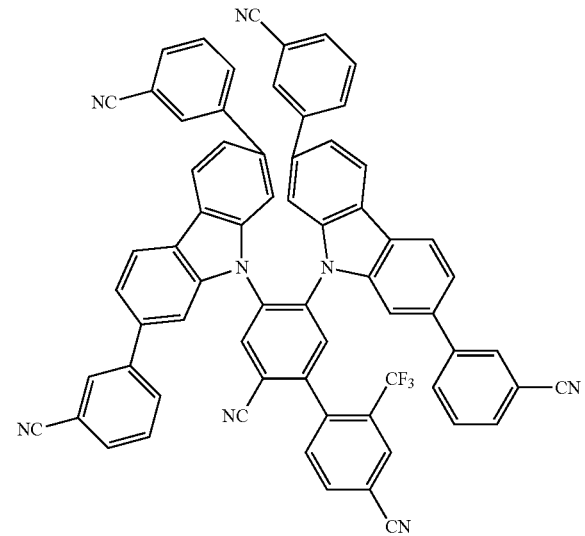 |
| 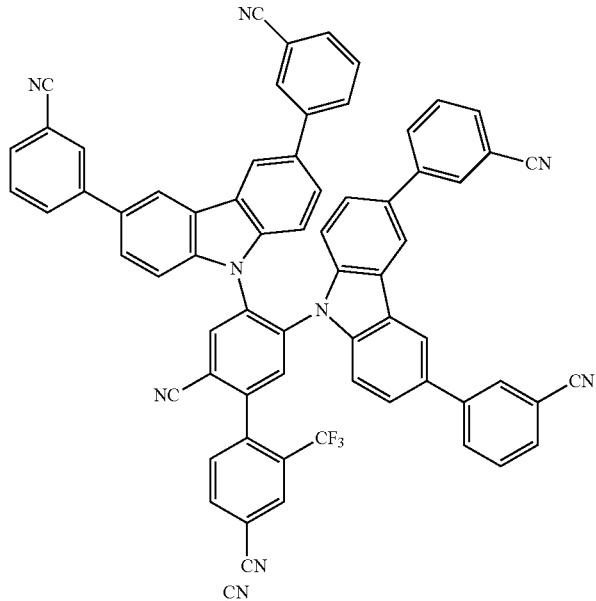 | 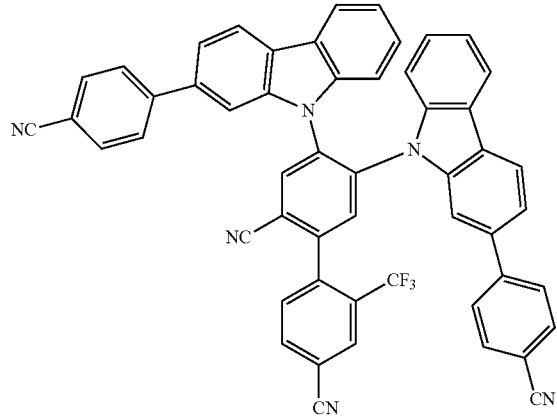 |
| 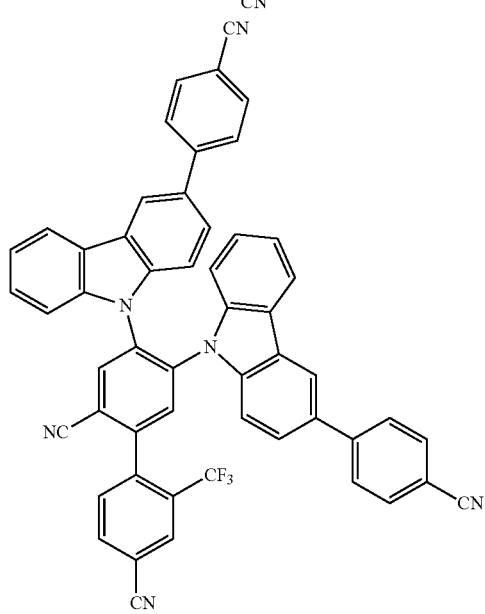 | 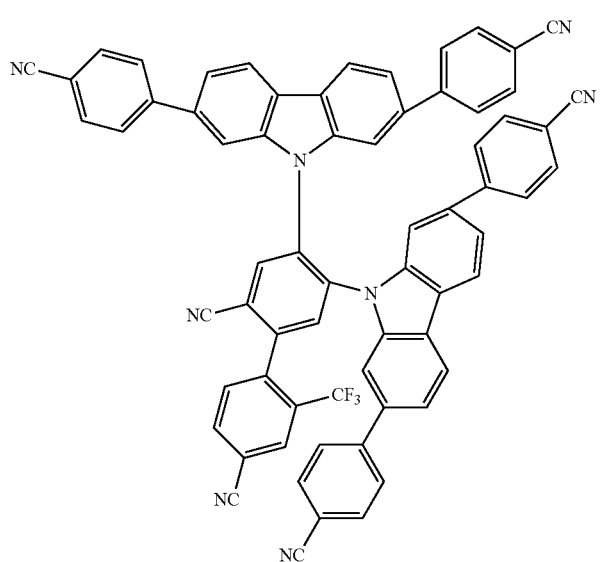 |

-continued
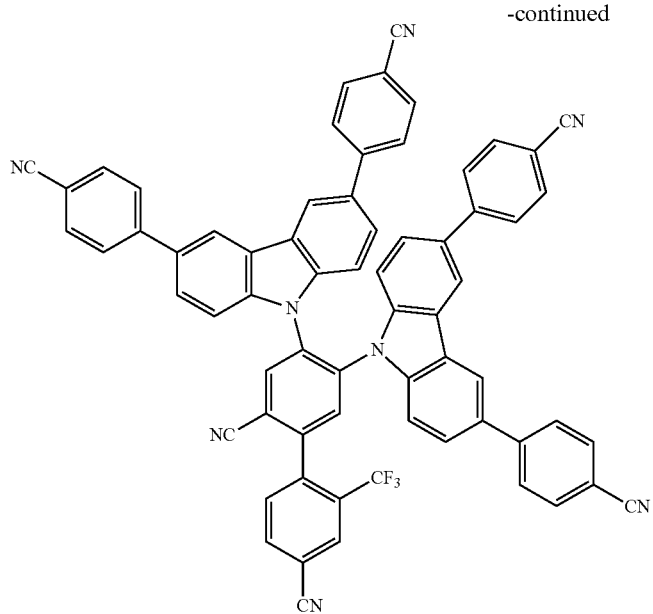
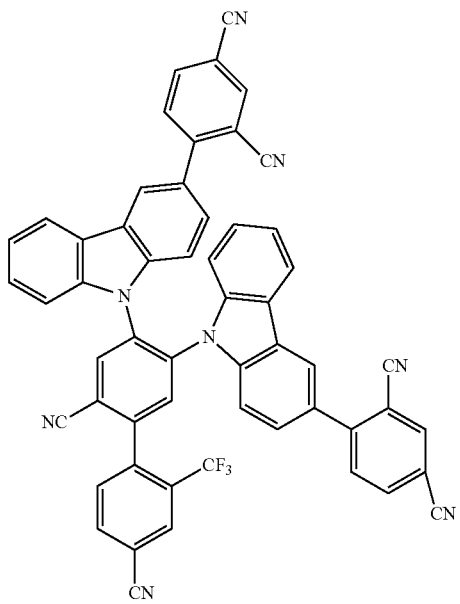
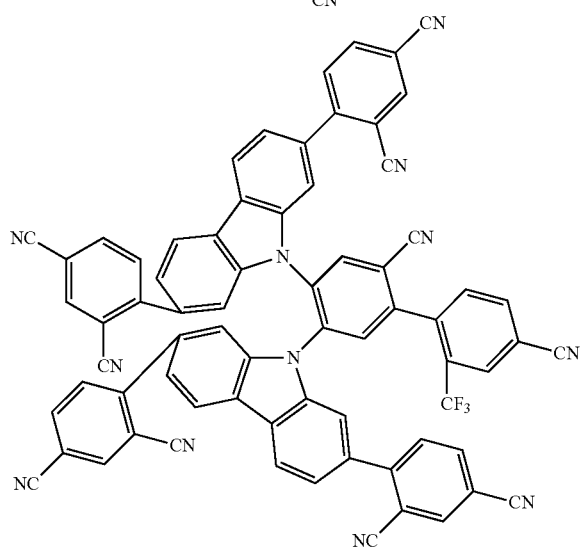

-continued
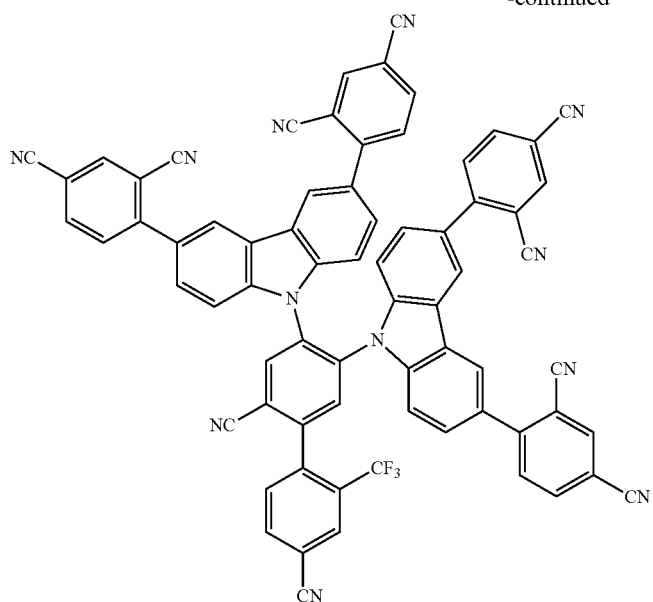
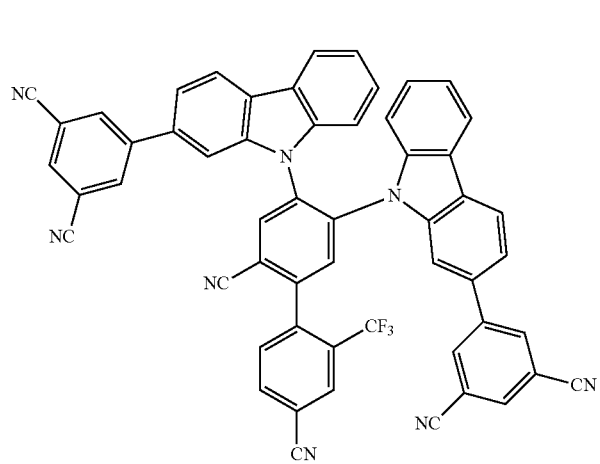
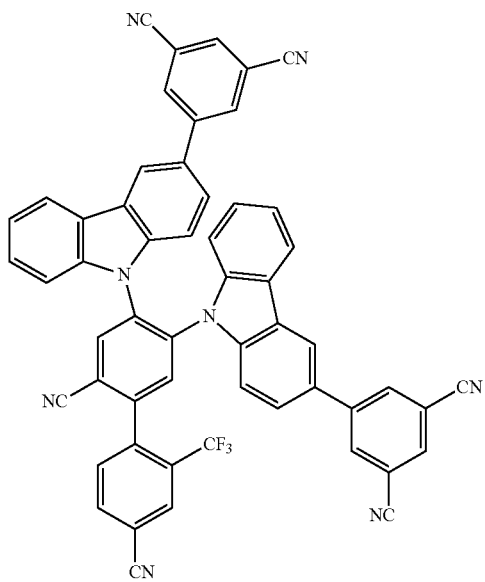
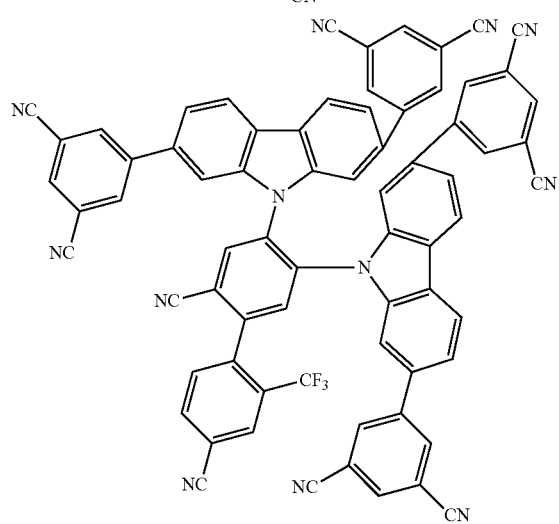

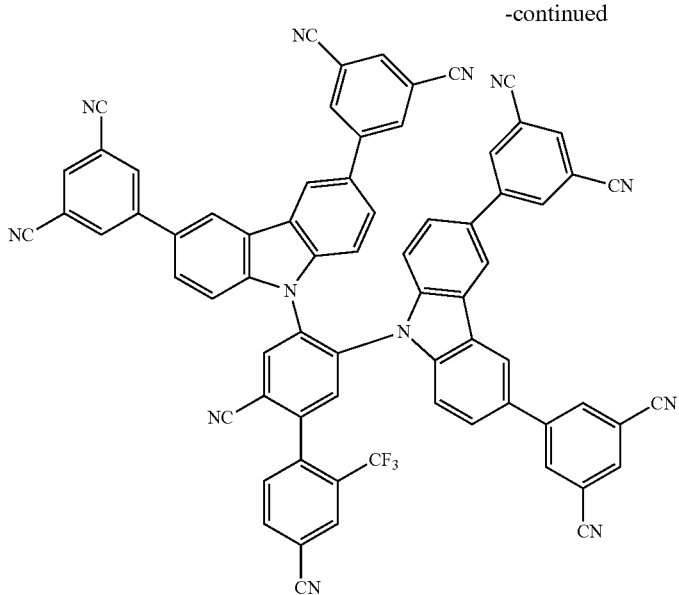
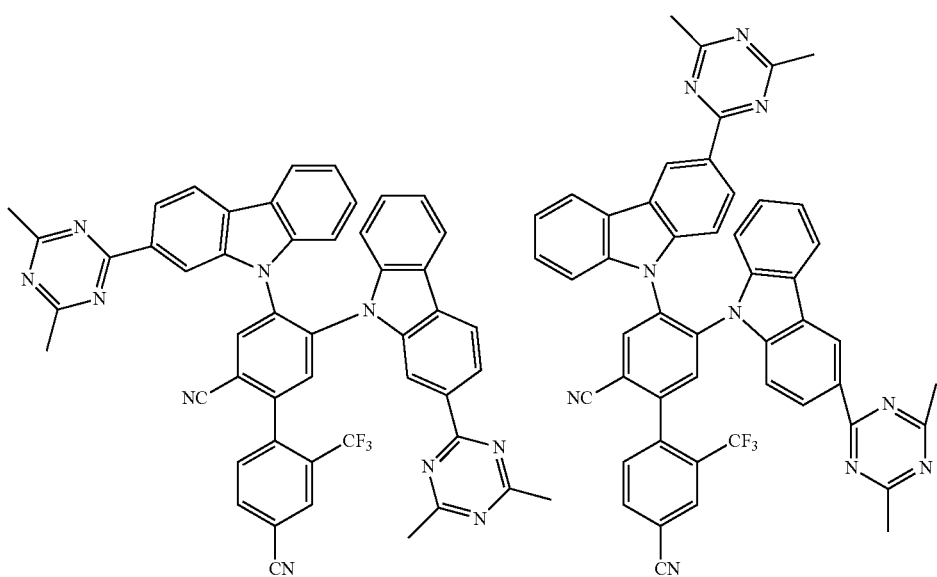
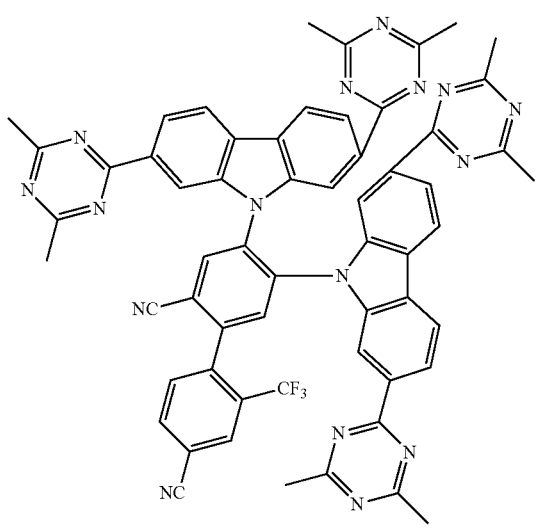

221 222
-continued
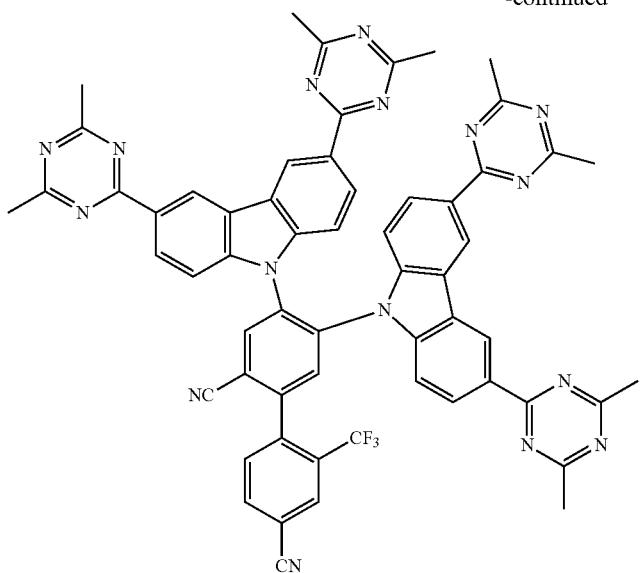
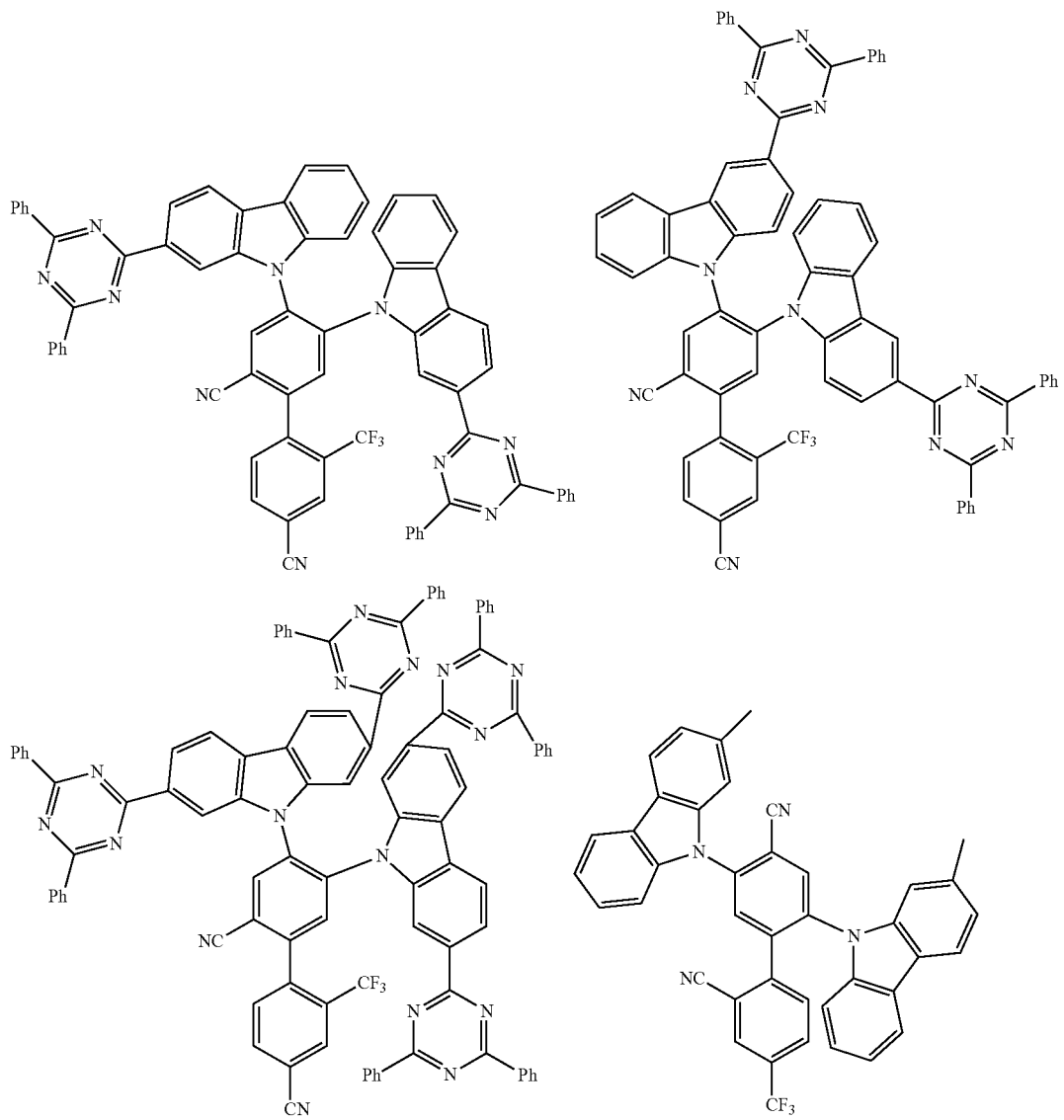

223 224
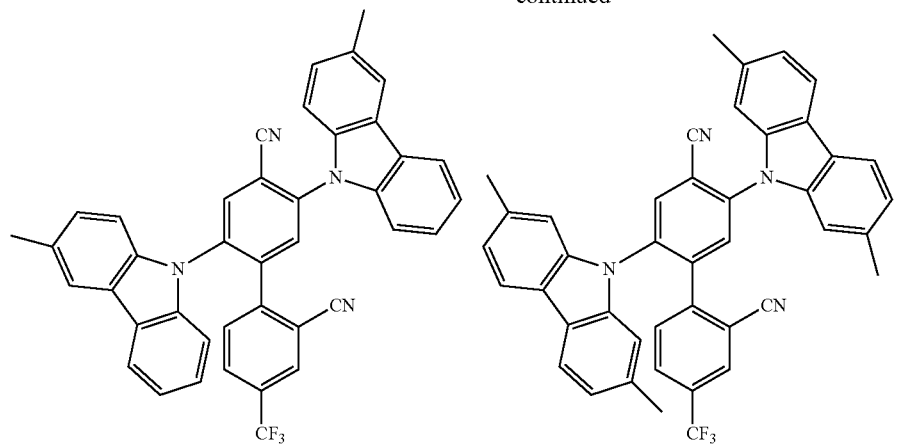
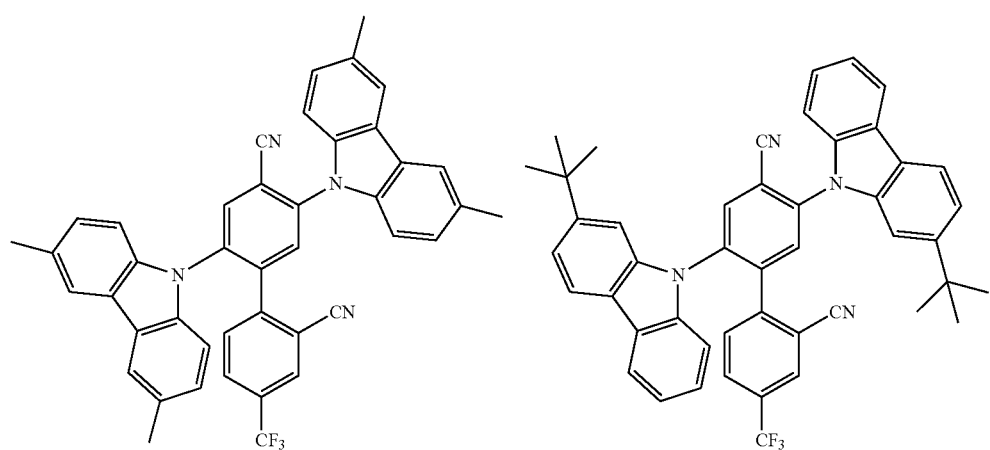
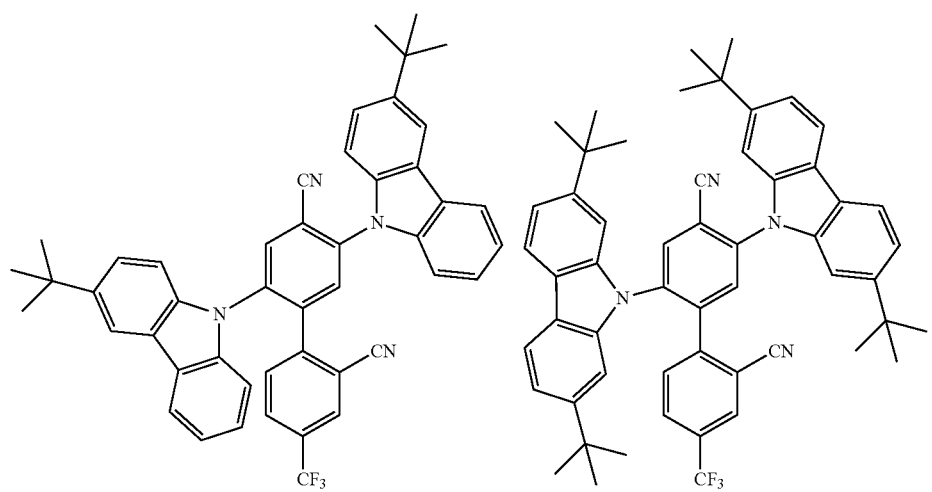

-continued
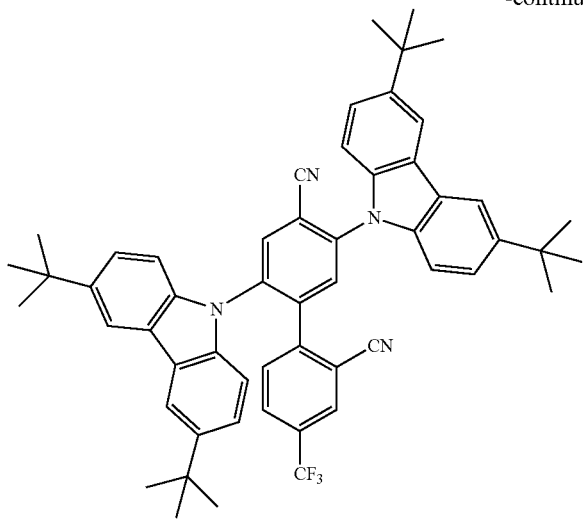
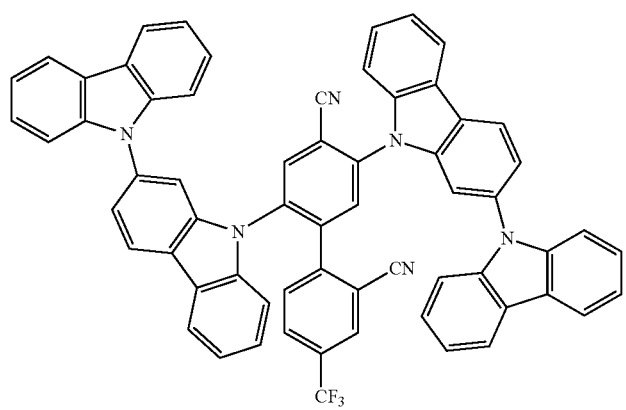
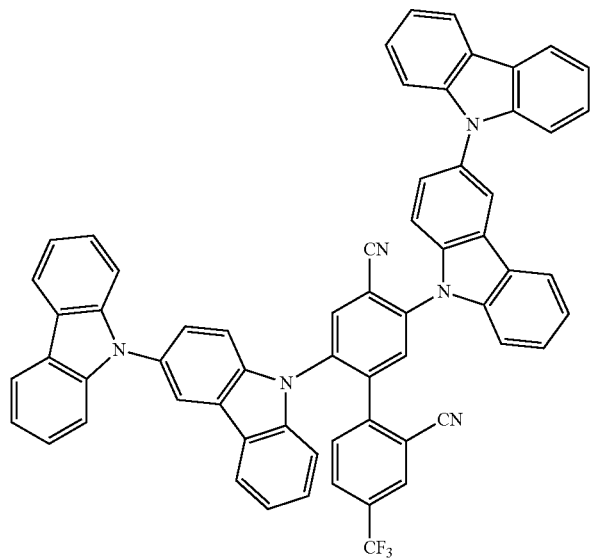

-continued
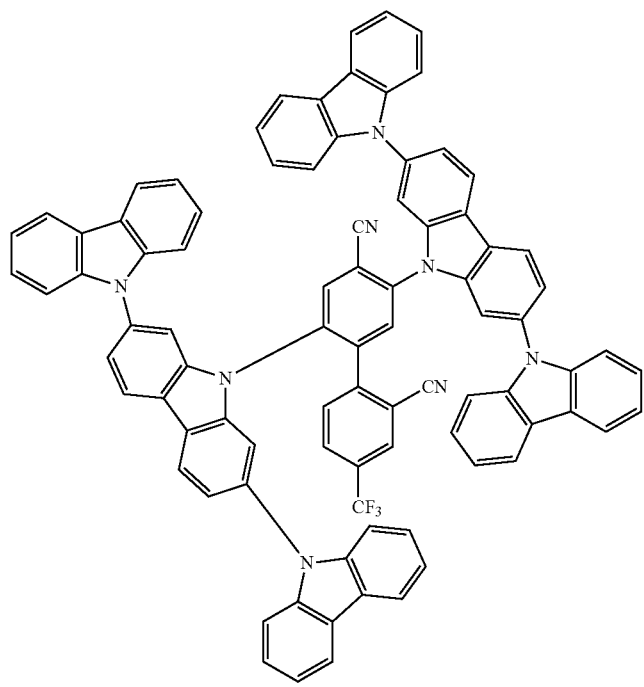
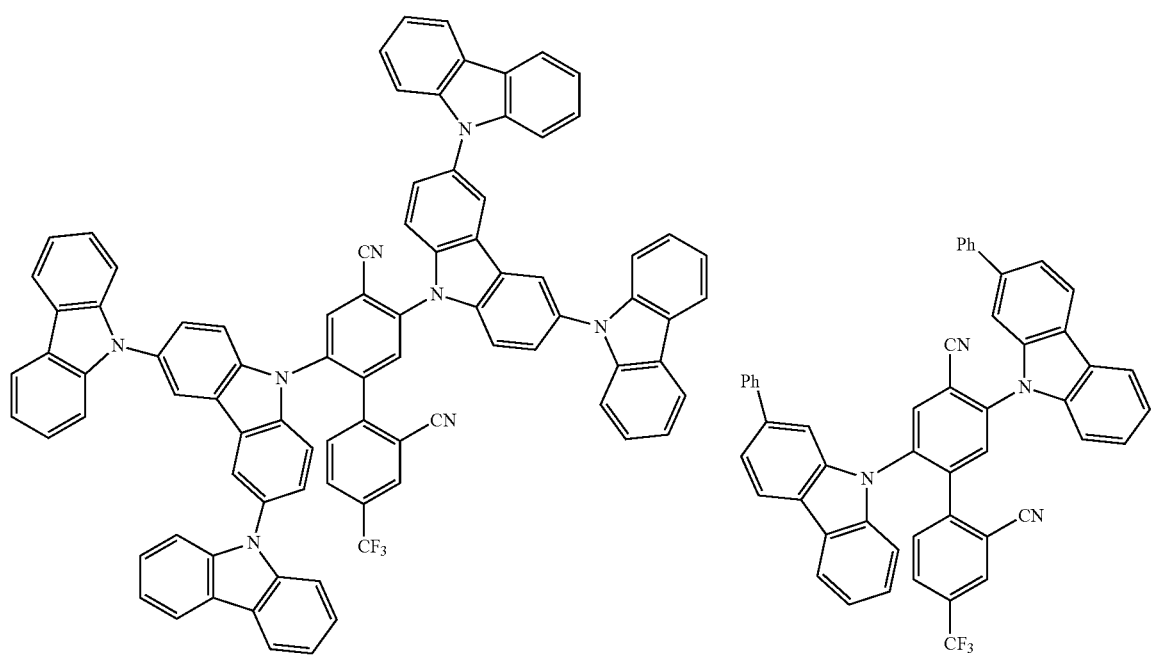

-continued
229 230
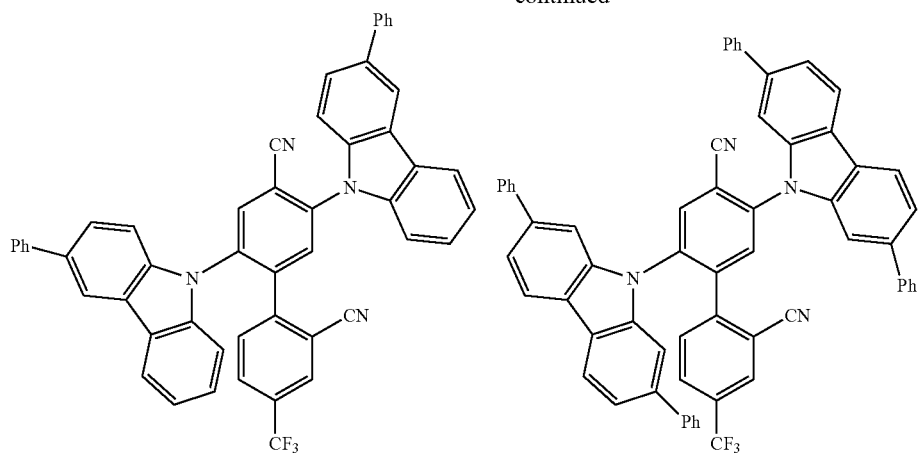
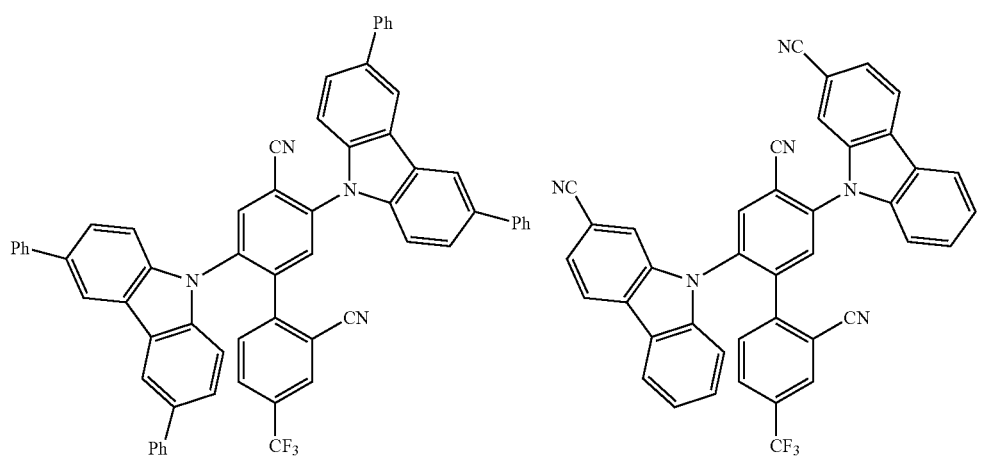
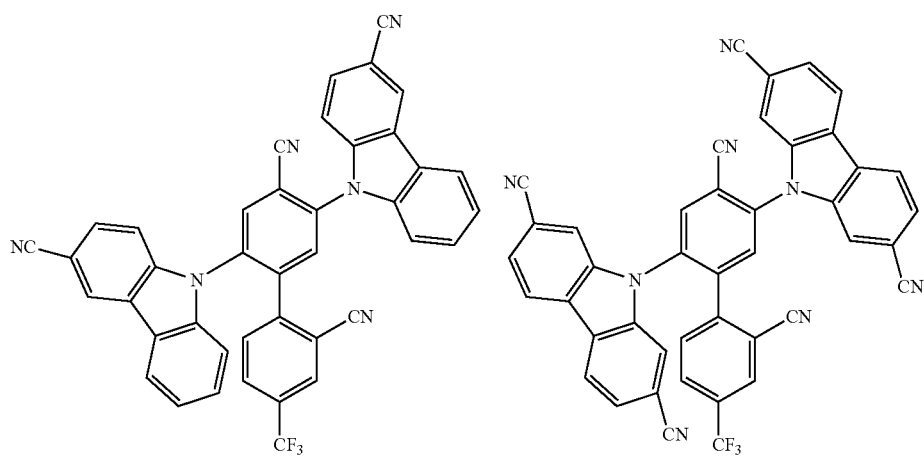

231 232
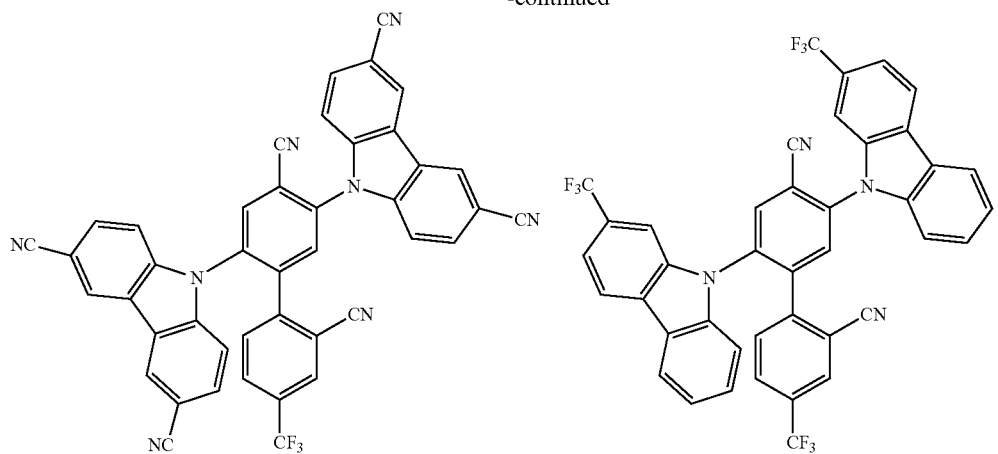
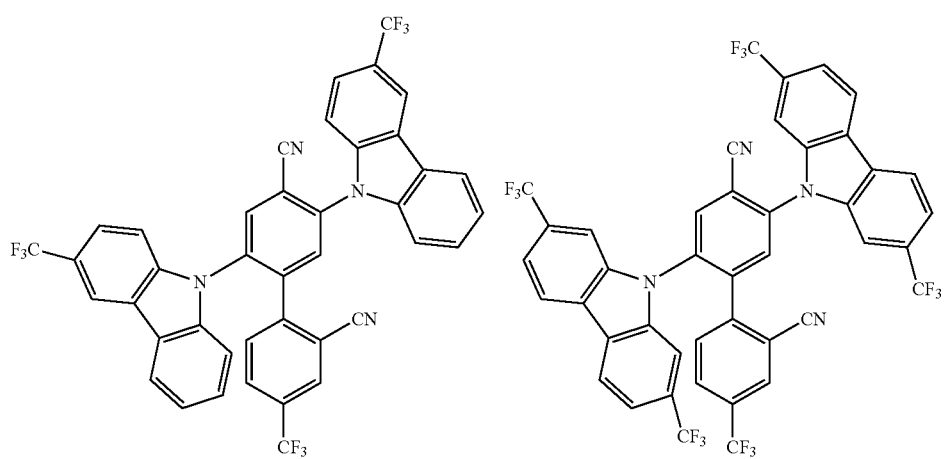
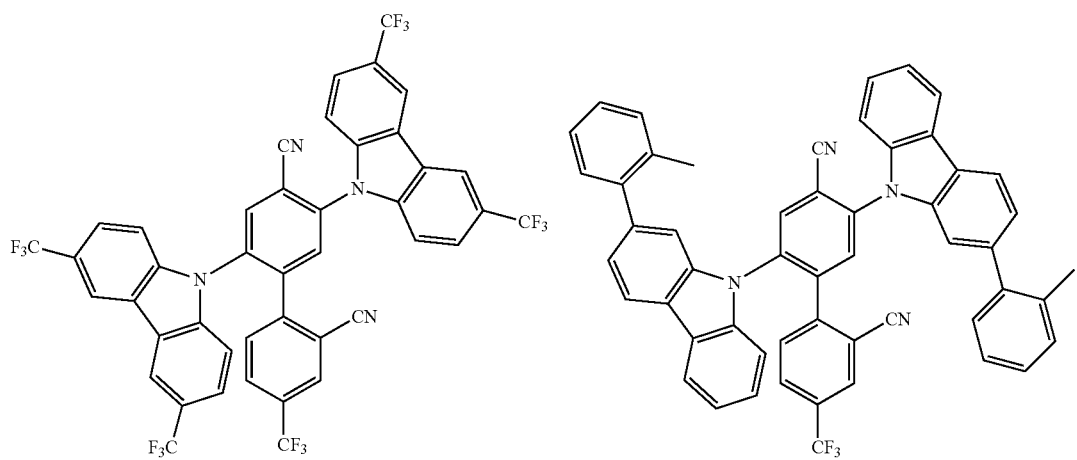

233 234
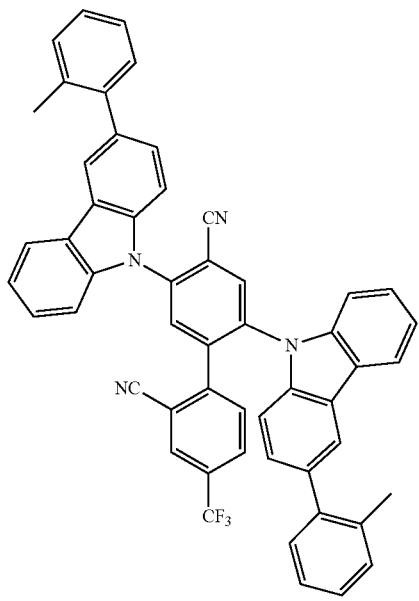 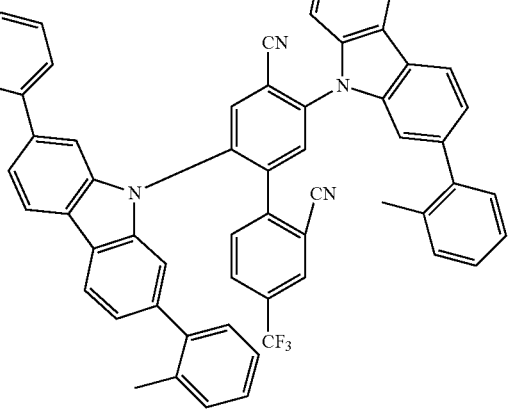
-continued
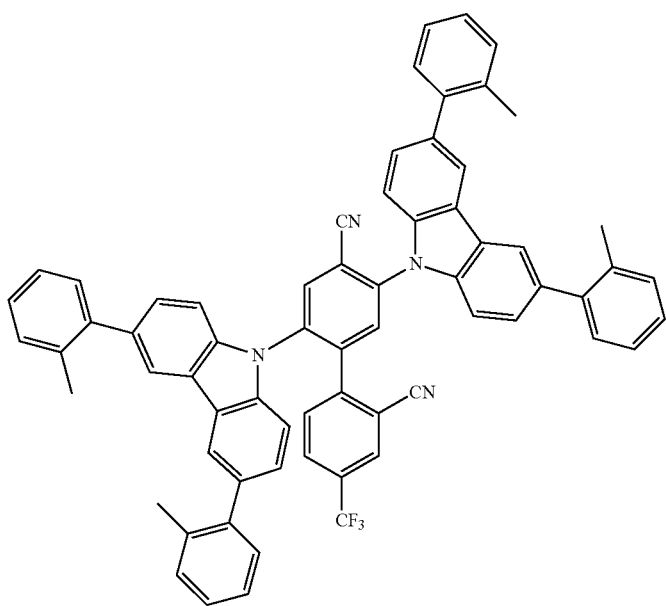

235
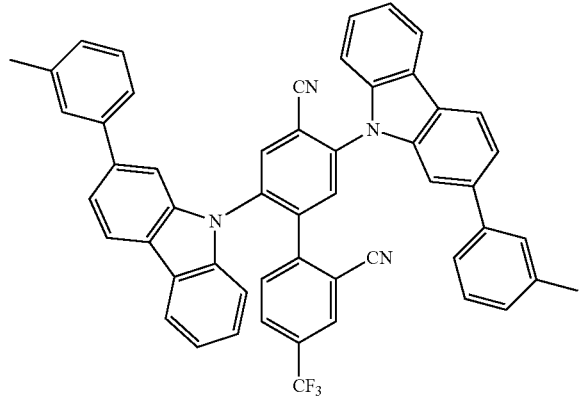
236
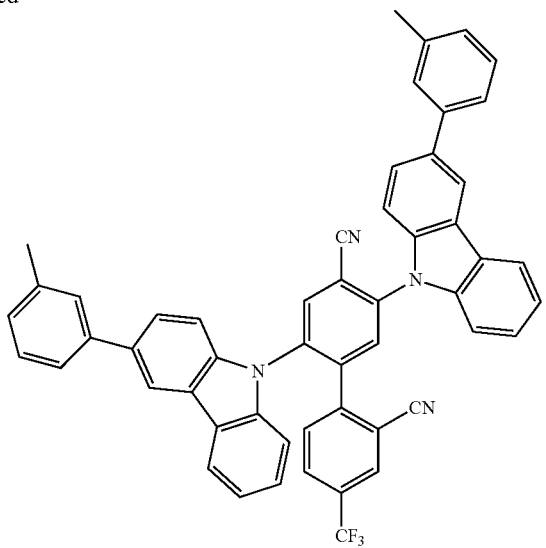
-continued
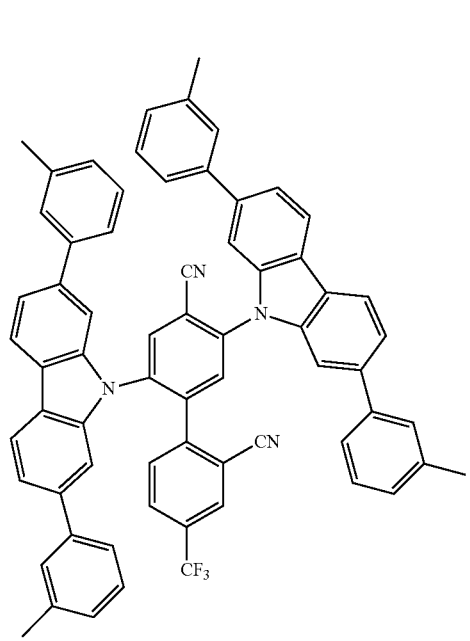
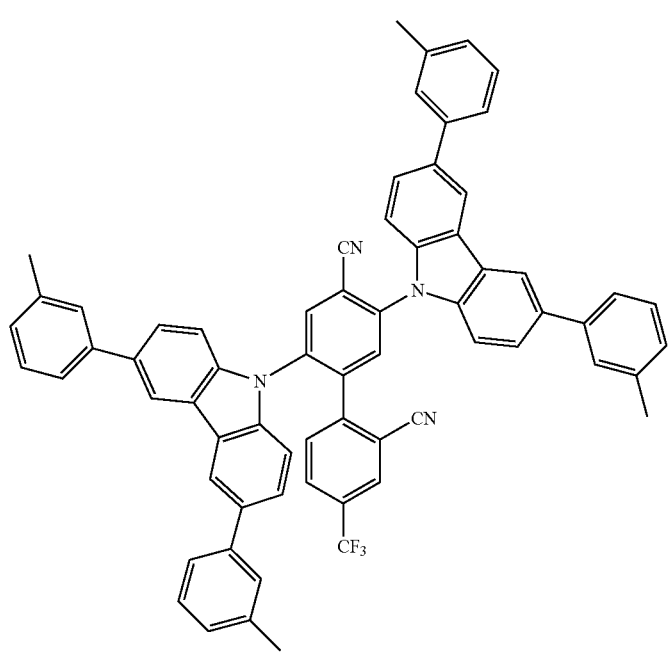

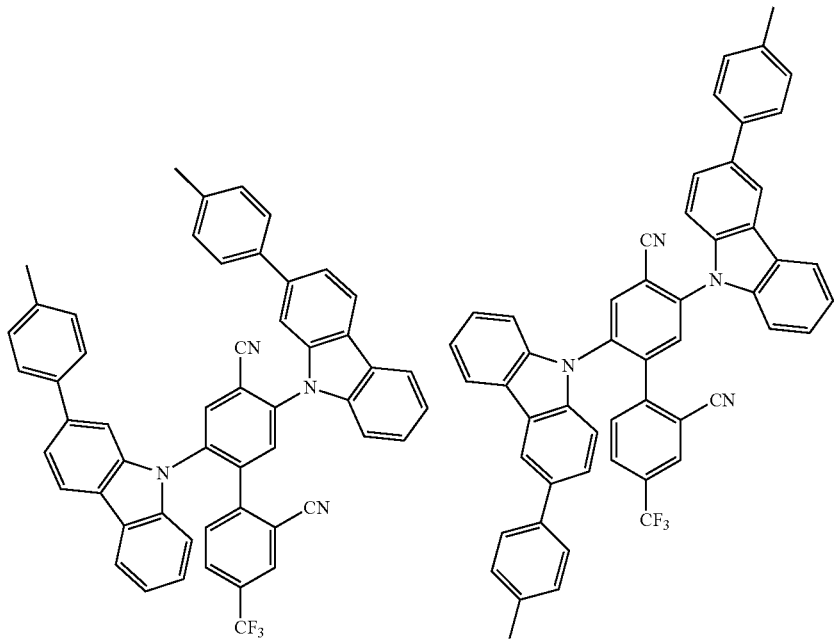
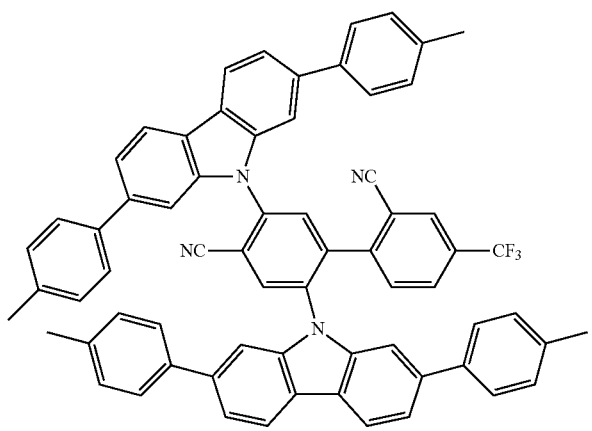
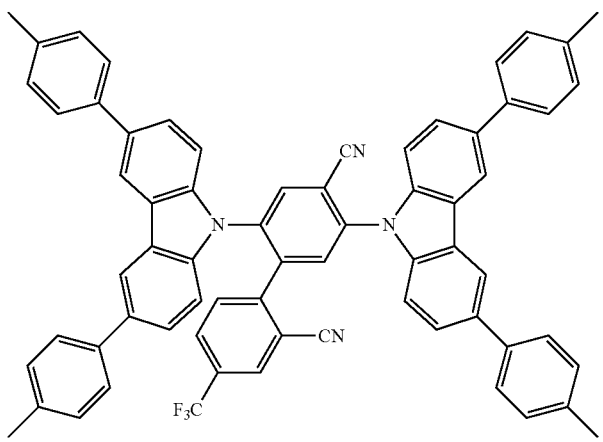

-continued
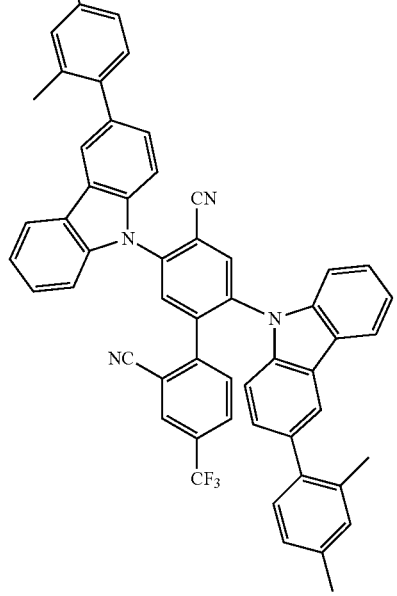
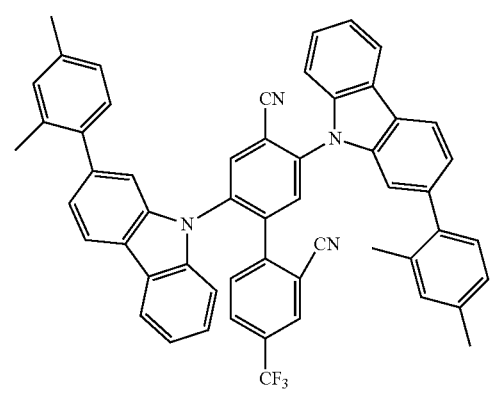
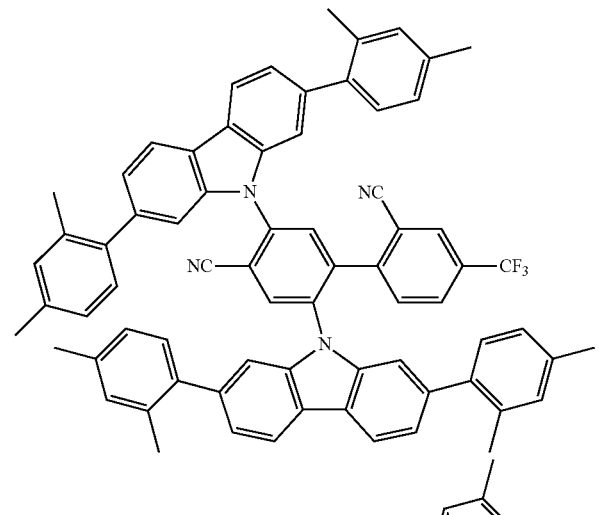
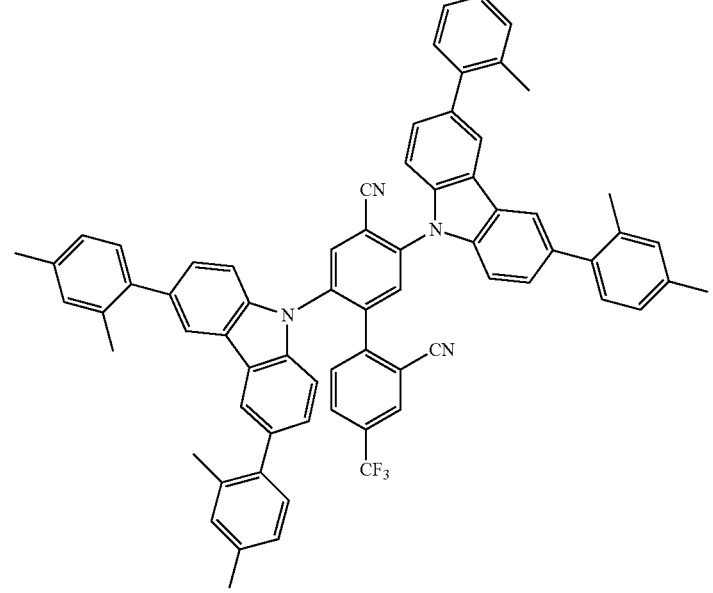

241 242
-continued
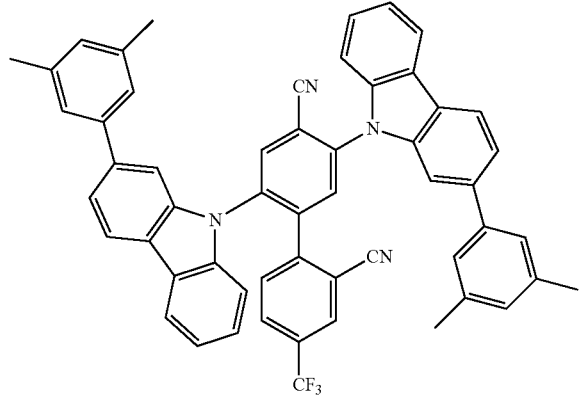
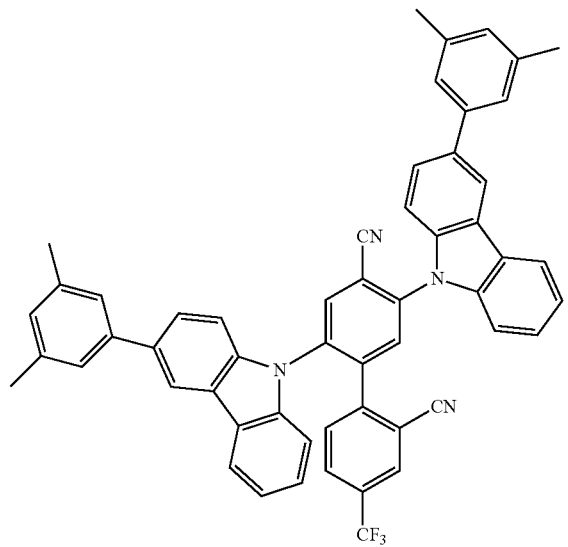
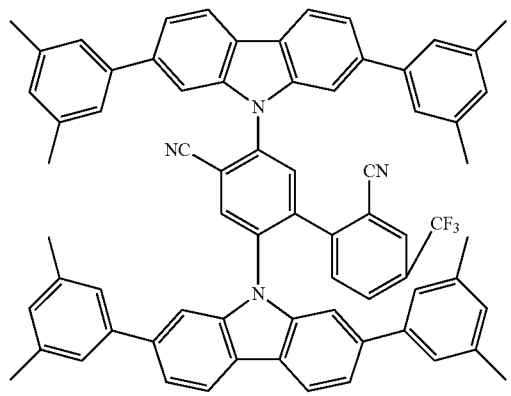
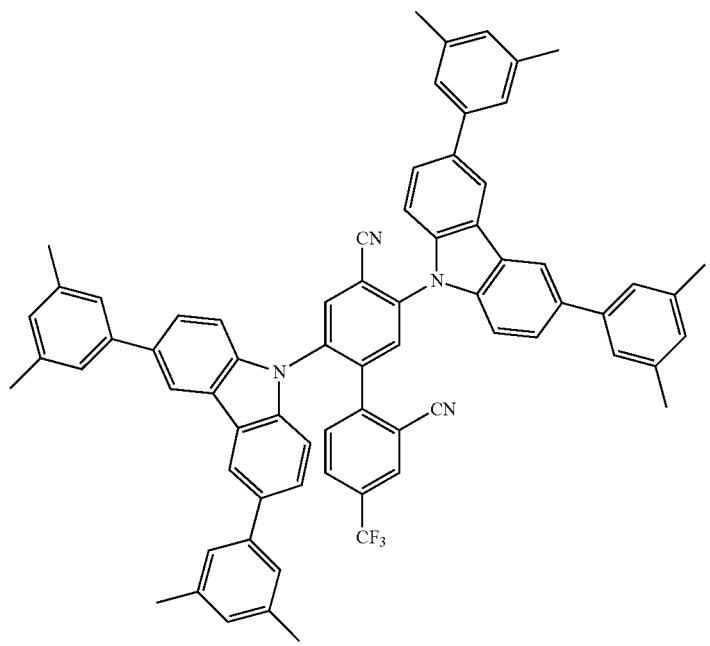

243 244
-continued
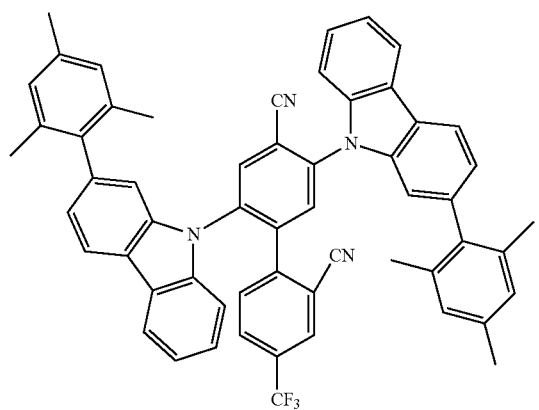
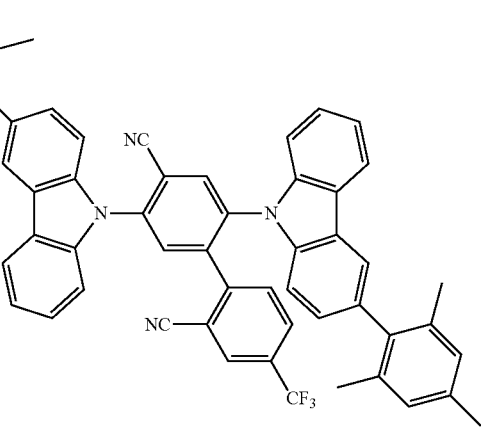
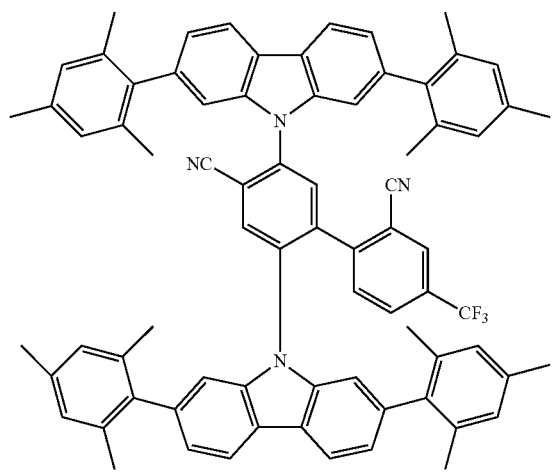
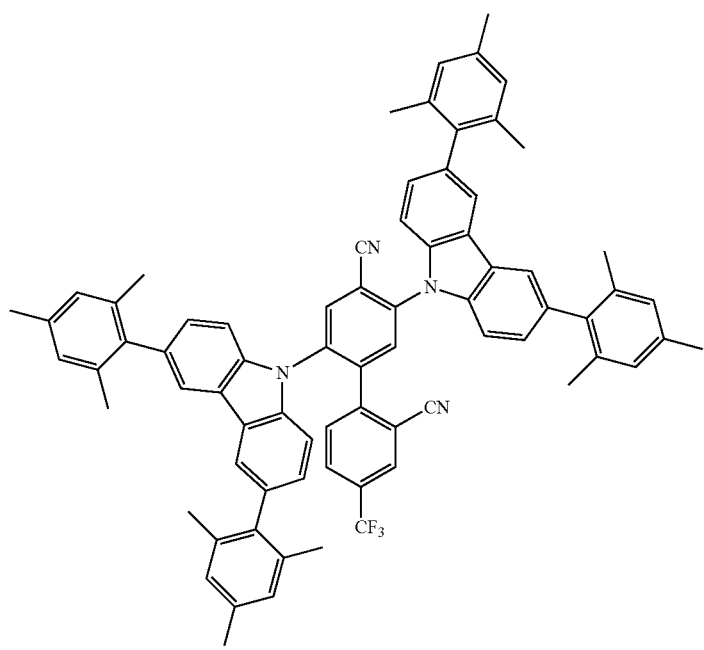

-continued
245
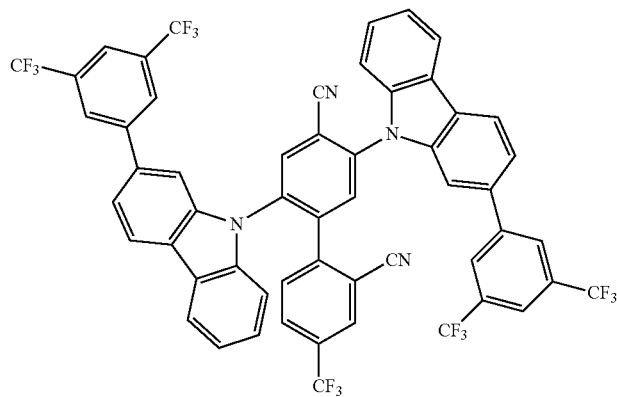
246
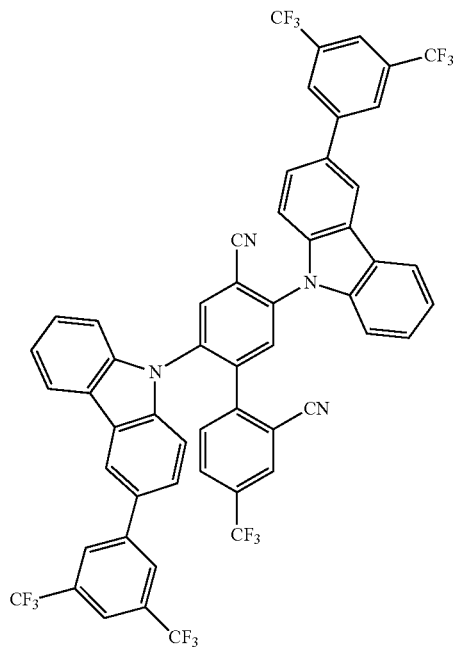
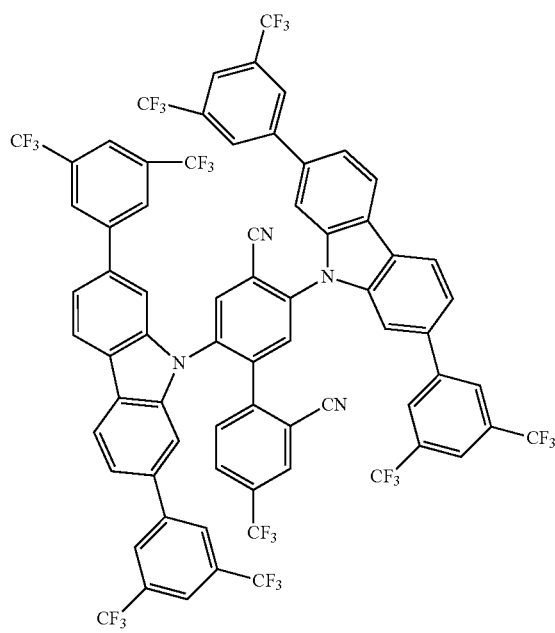
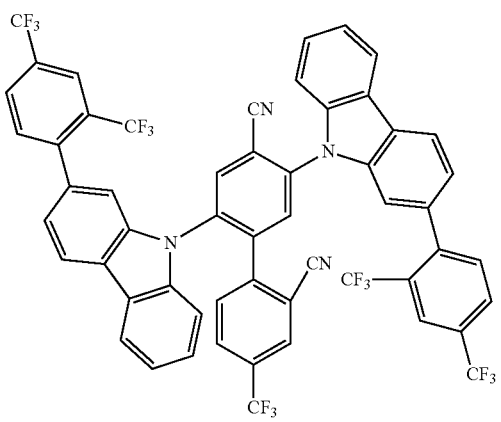

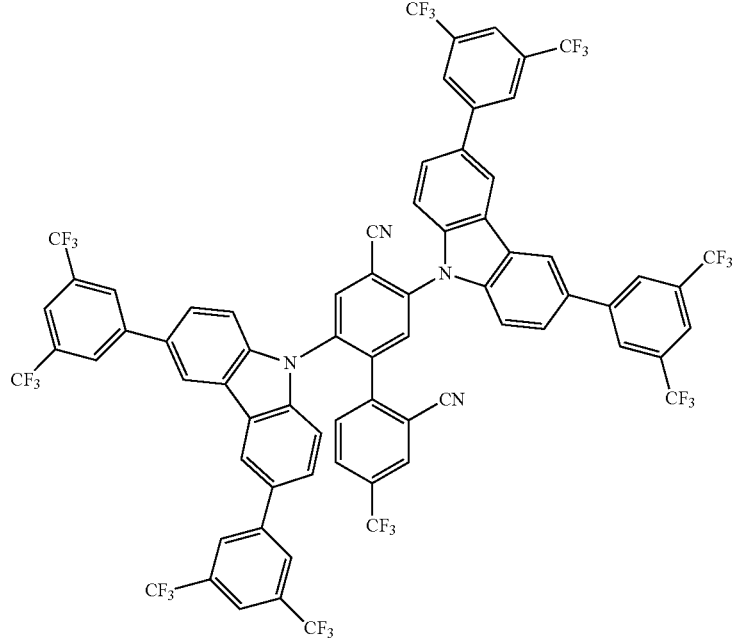
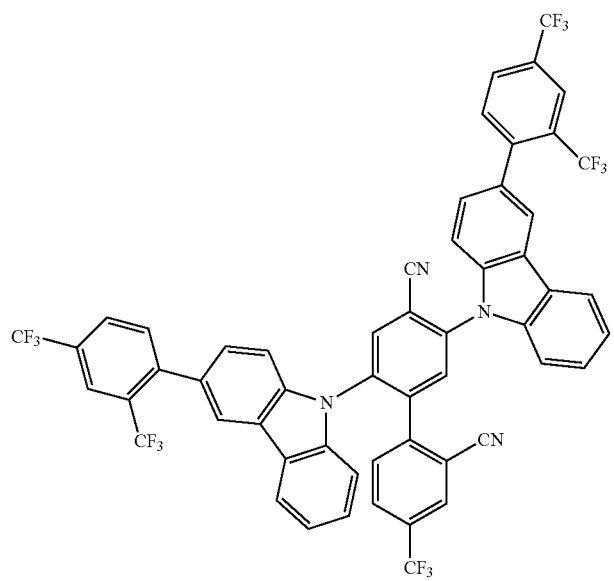
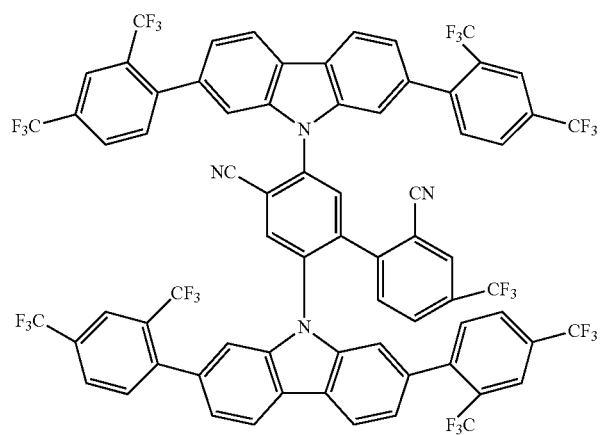

-continued
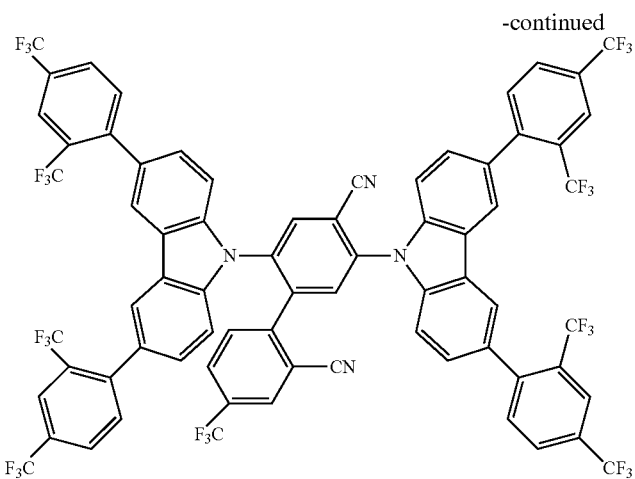
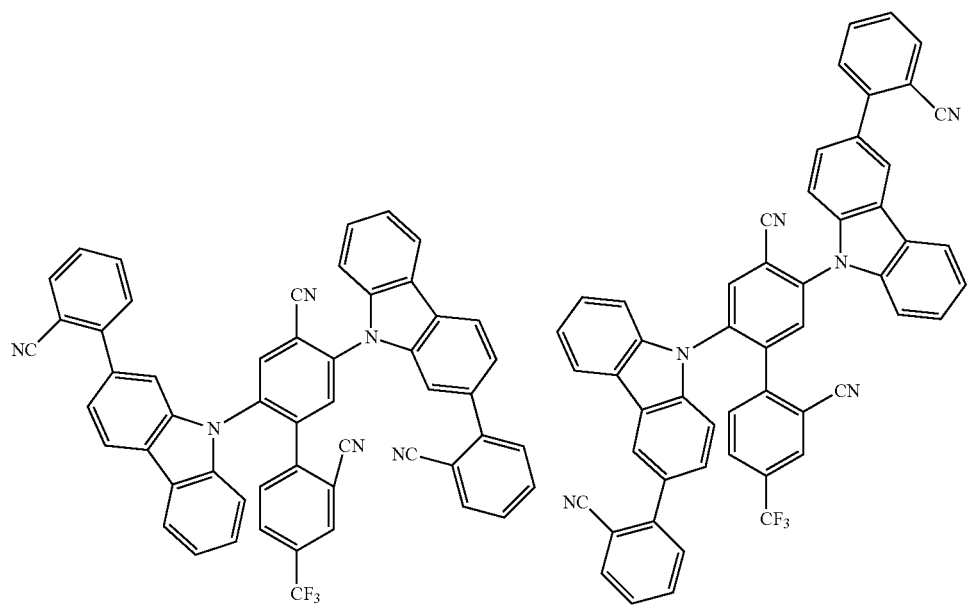
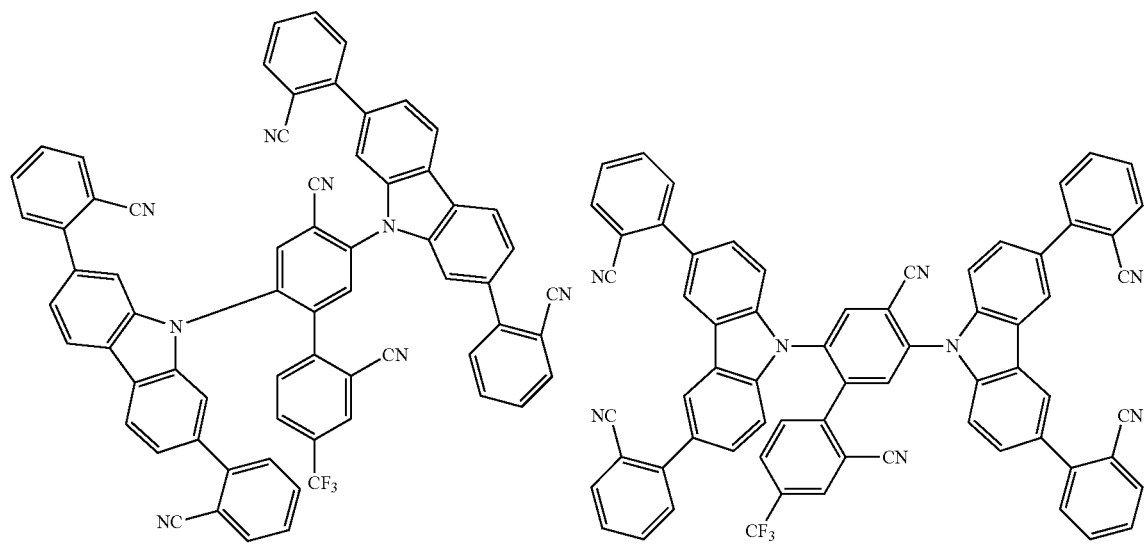

251
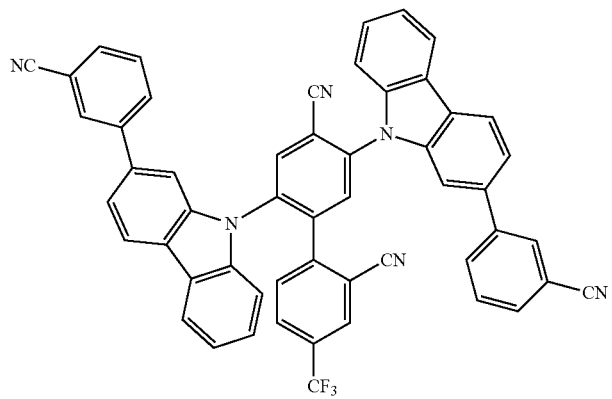
252
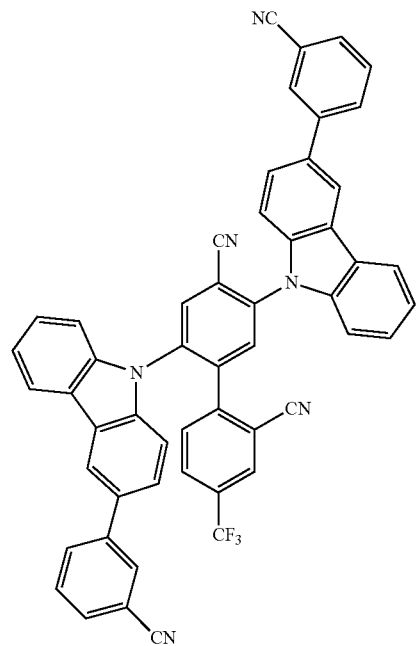
-continued
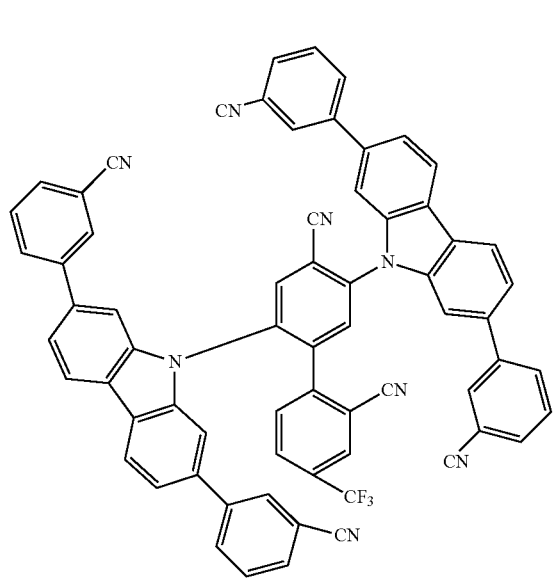
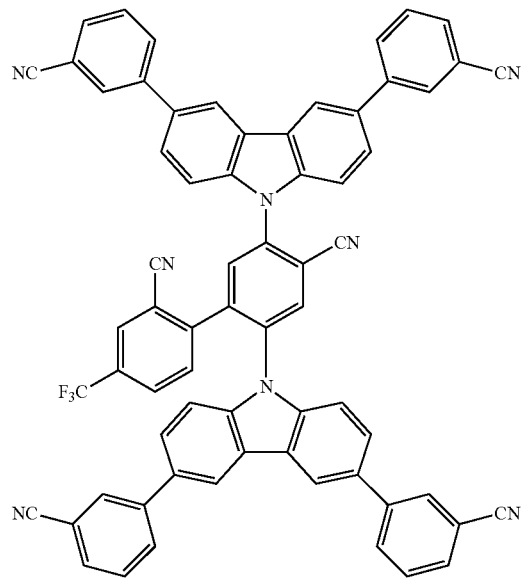

-continued
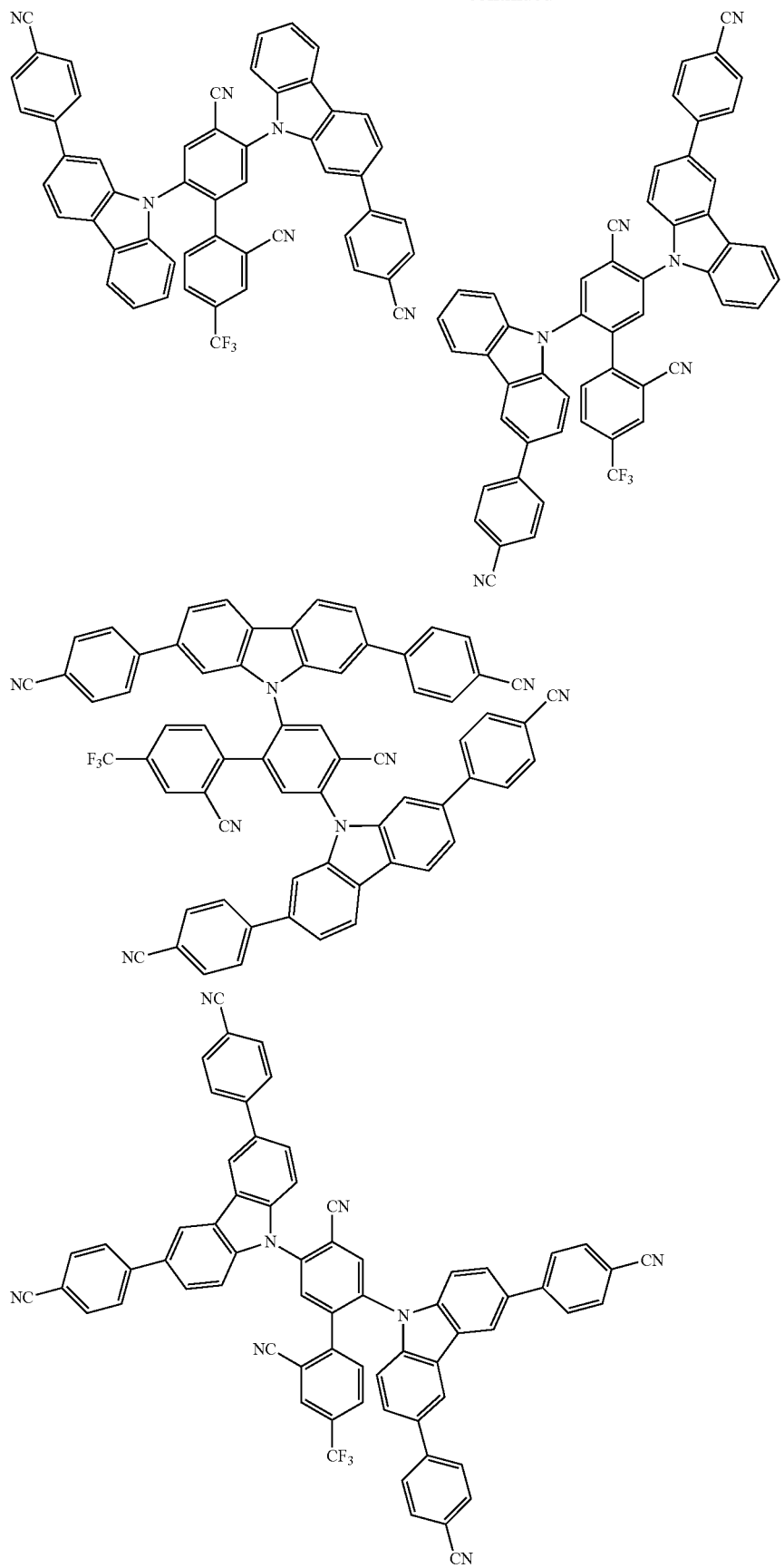

-continued
255
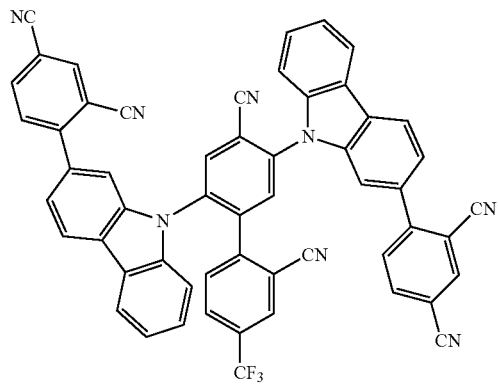
256
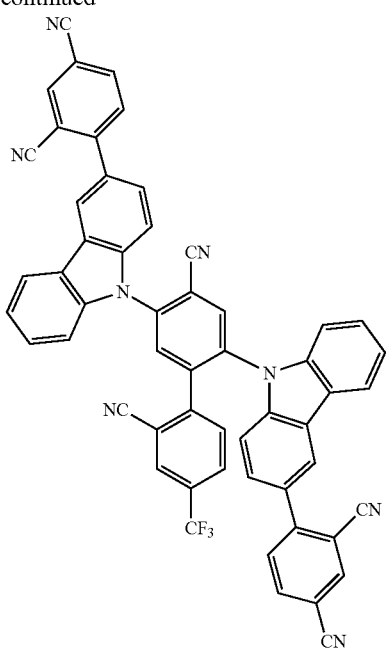
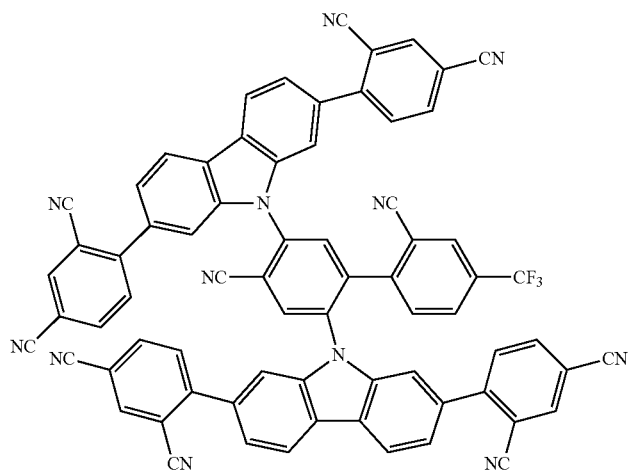
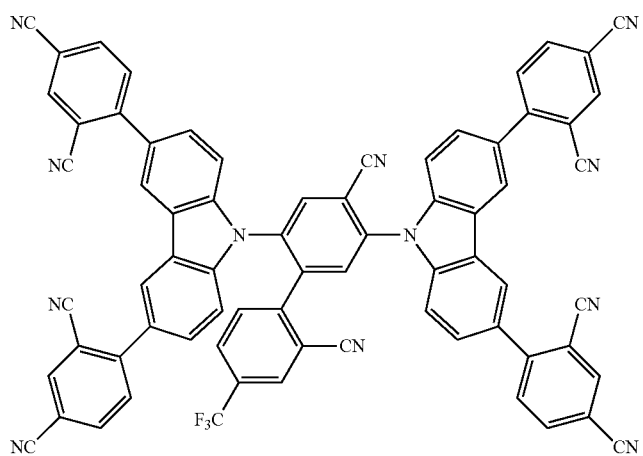

257 258
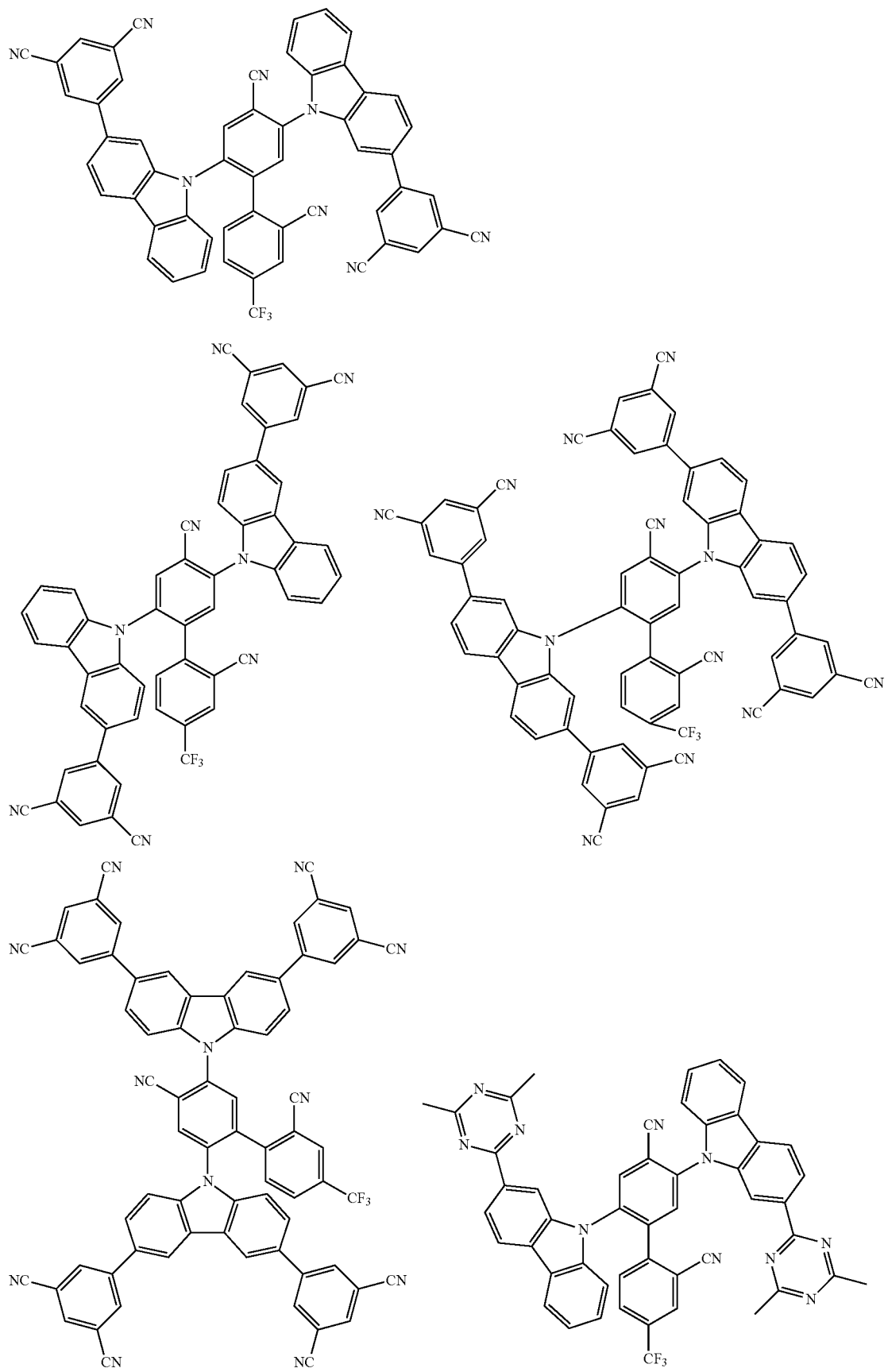

259
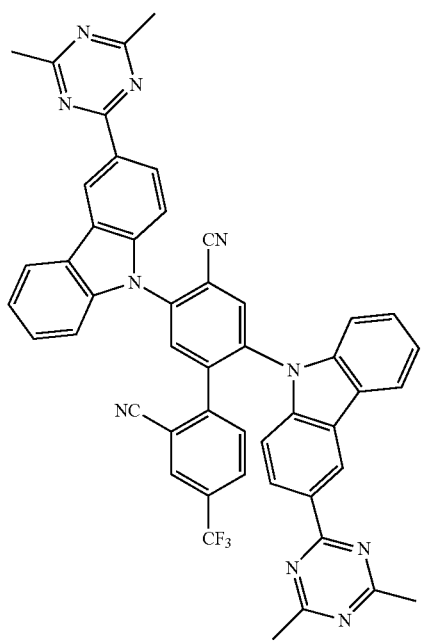
-continued
260
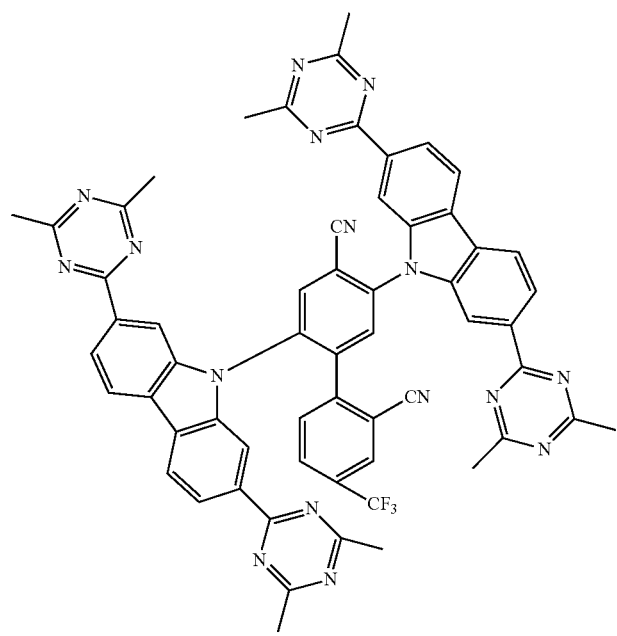
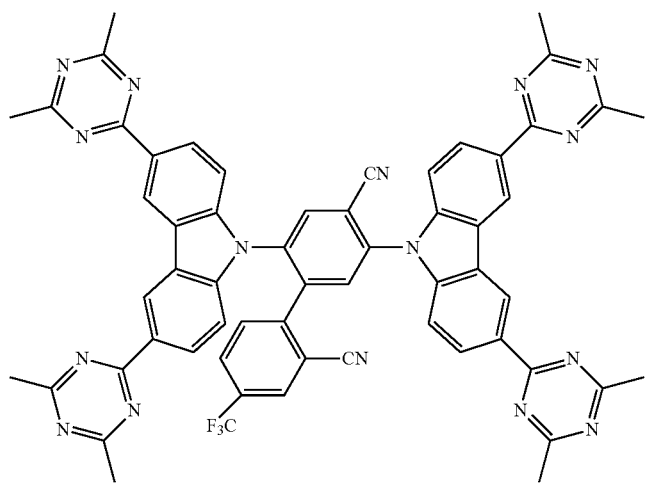
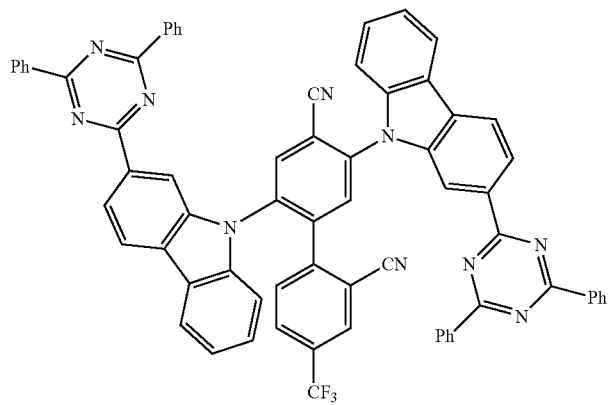

261
-continued
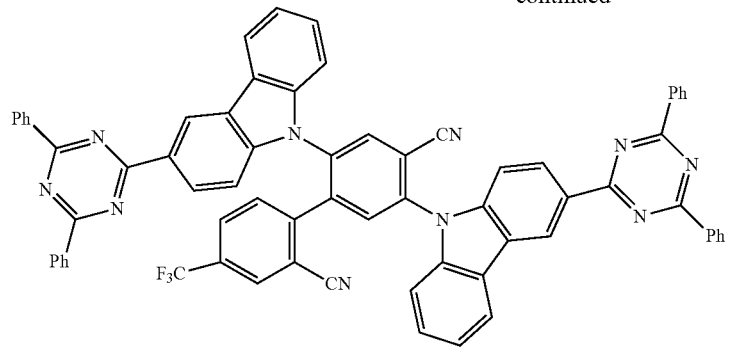
262
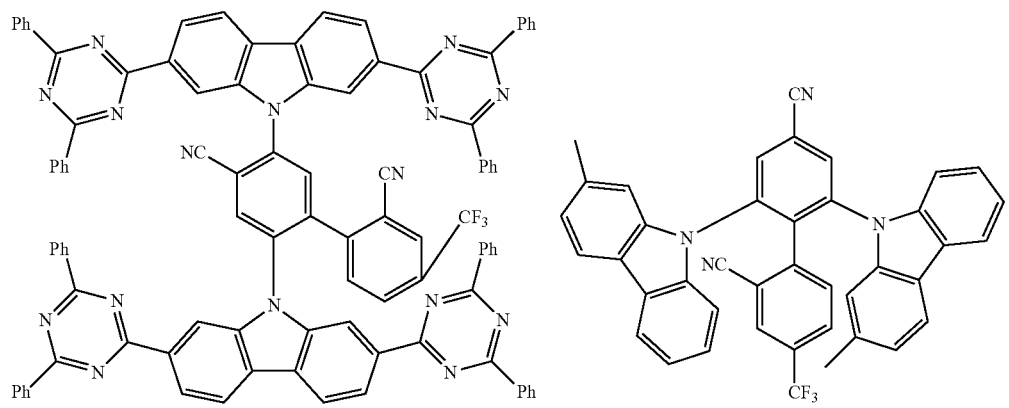
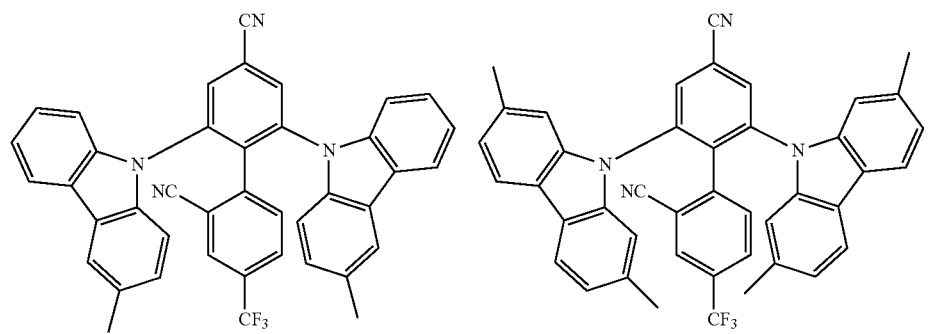
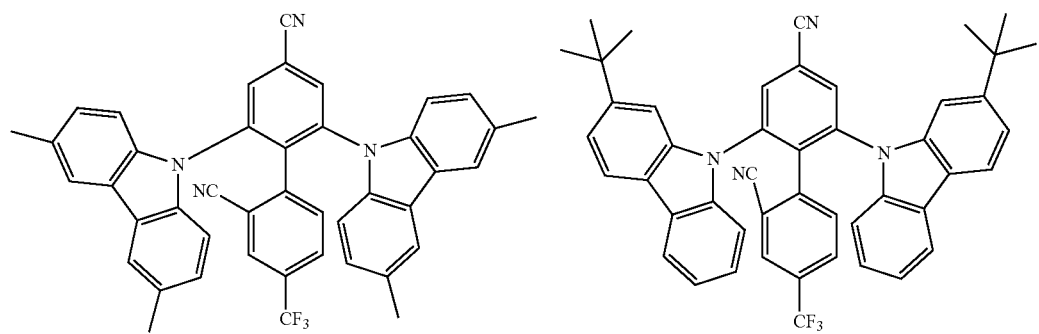

263 264
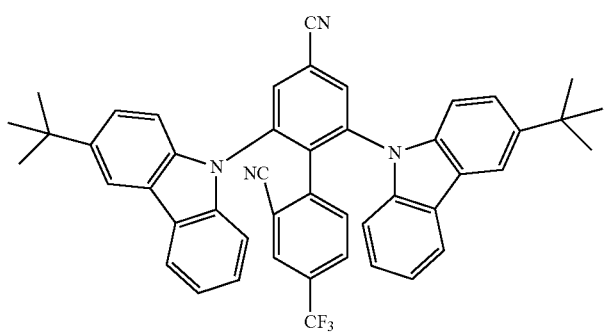
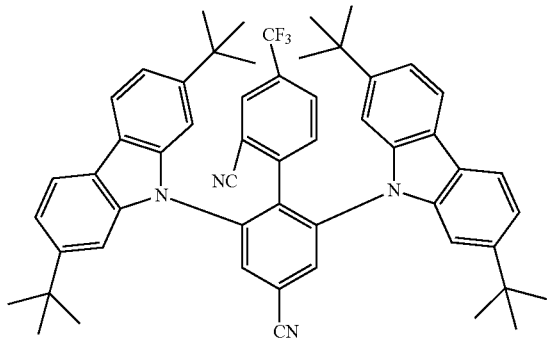
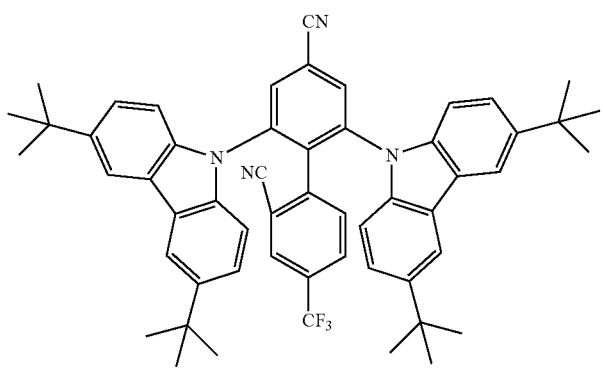
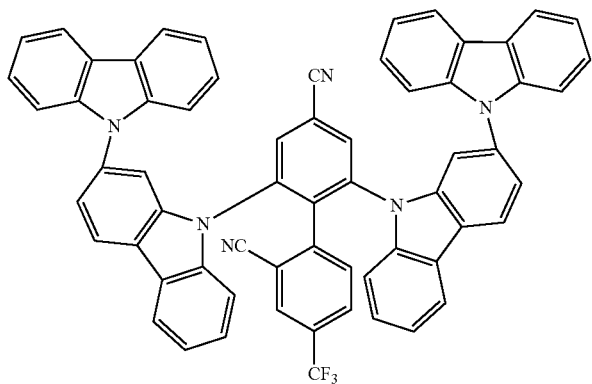
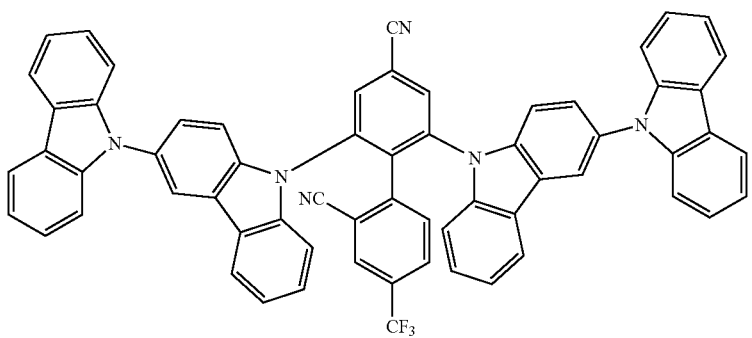

-continued
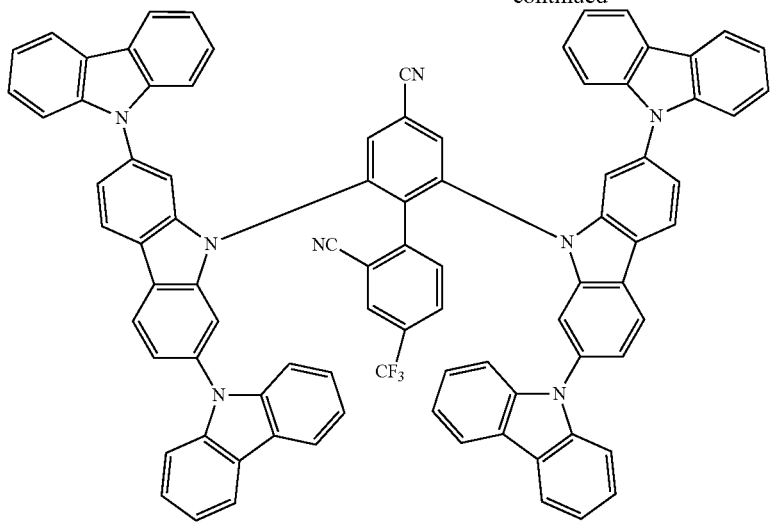
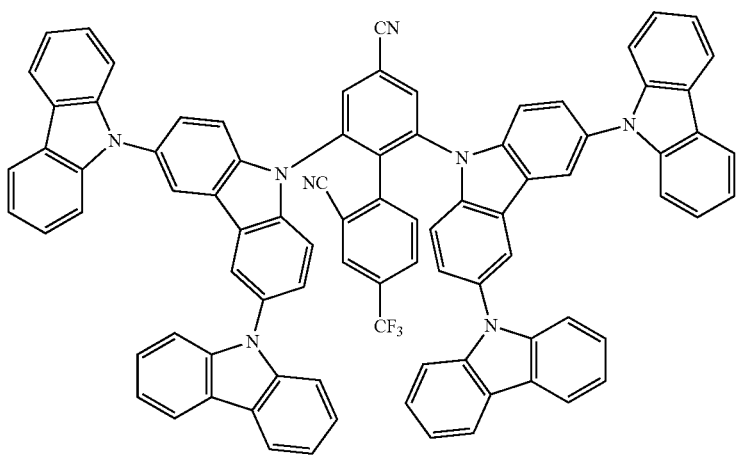
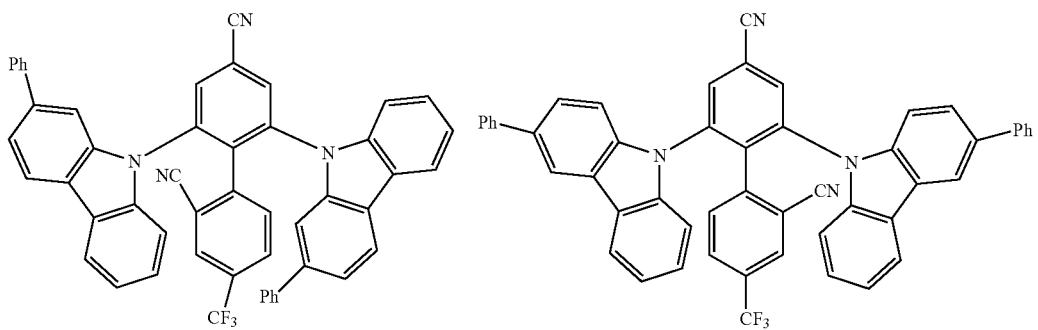
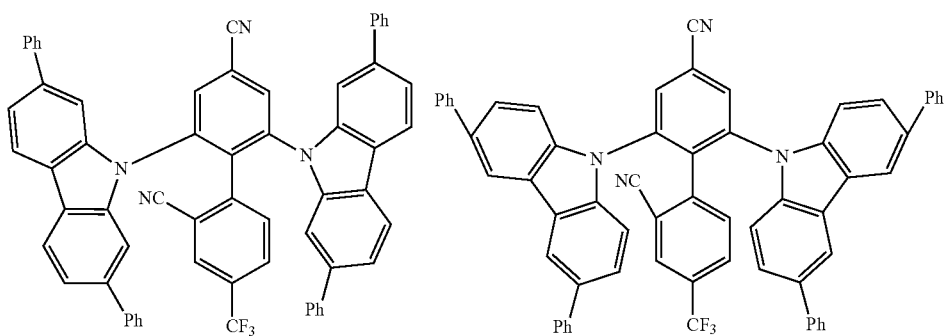

-continued
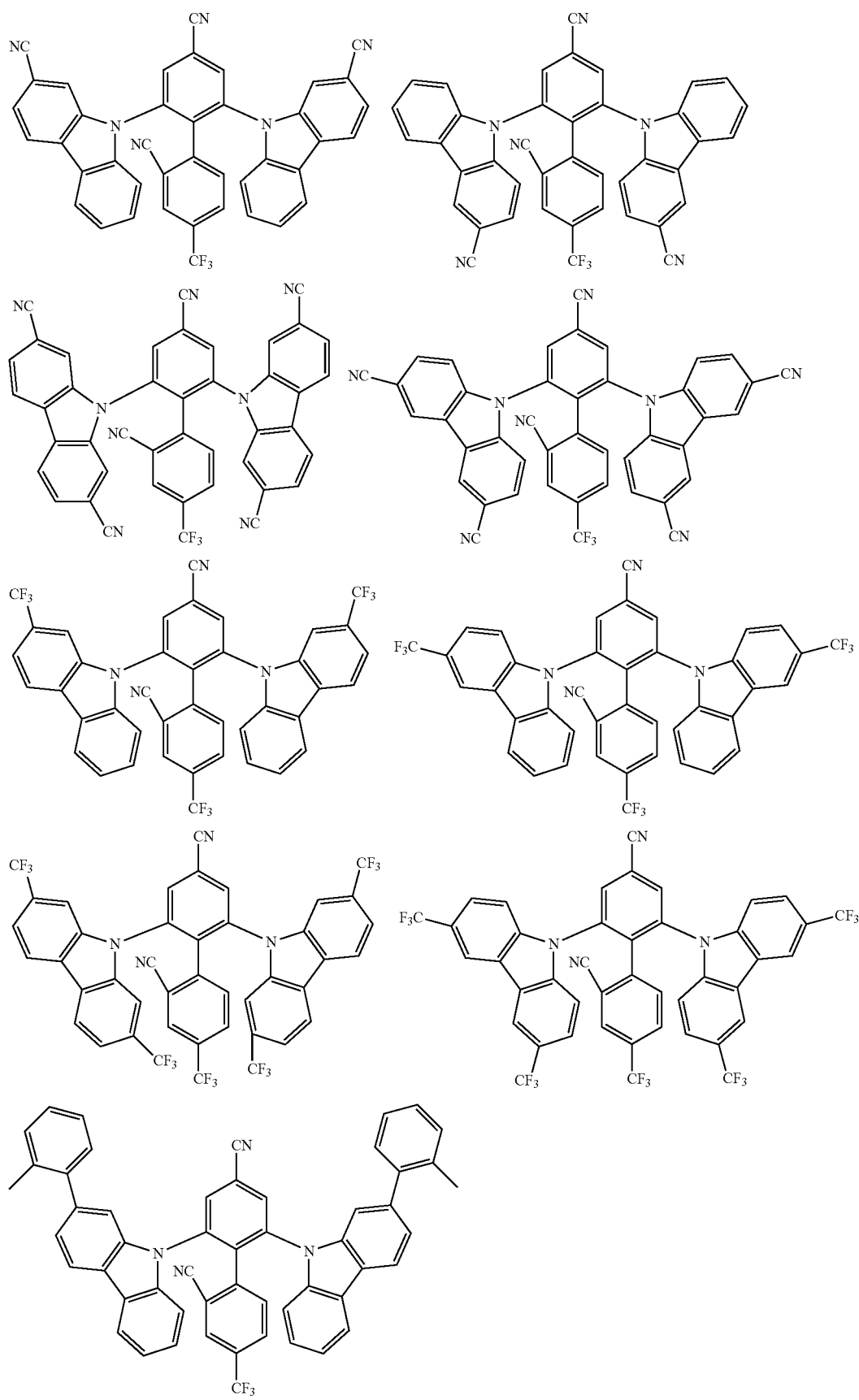

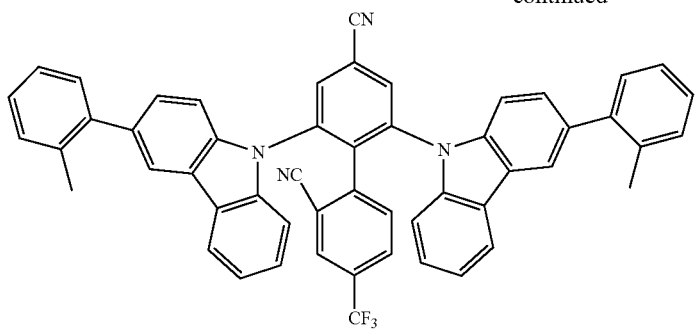
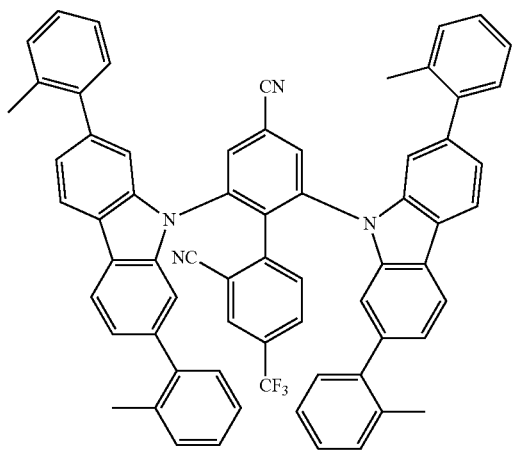
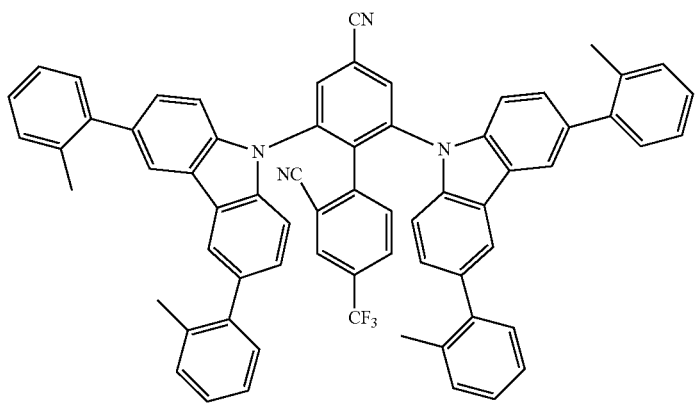
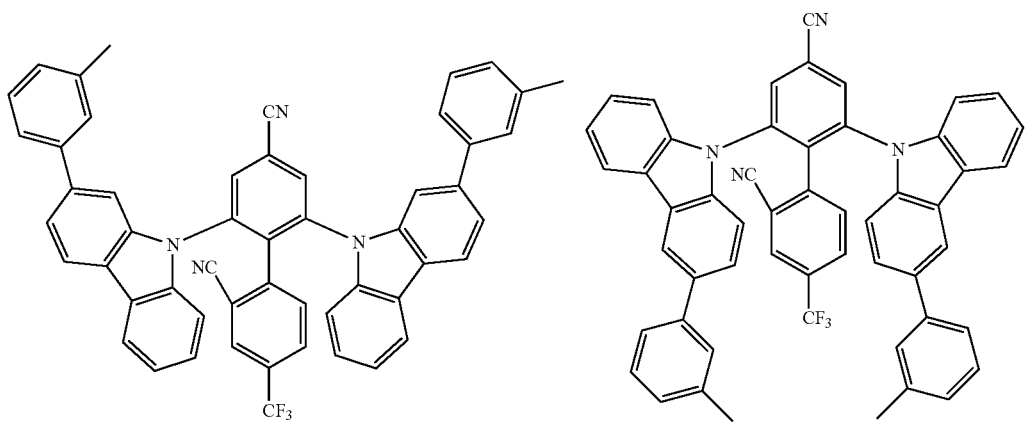

271
272
-continued
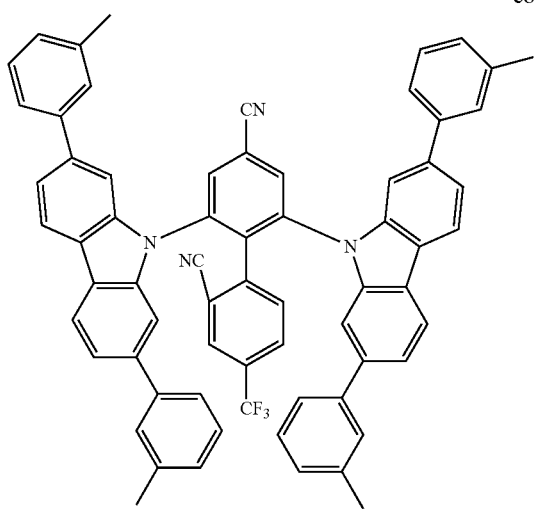
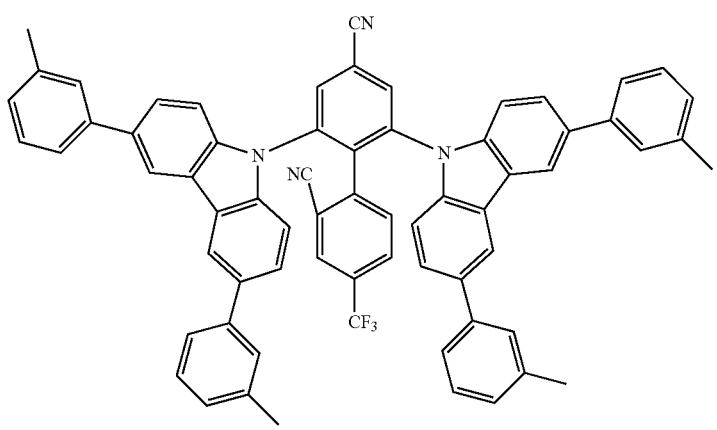
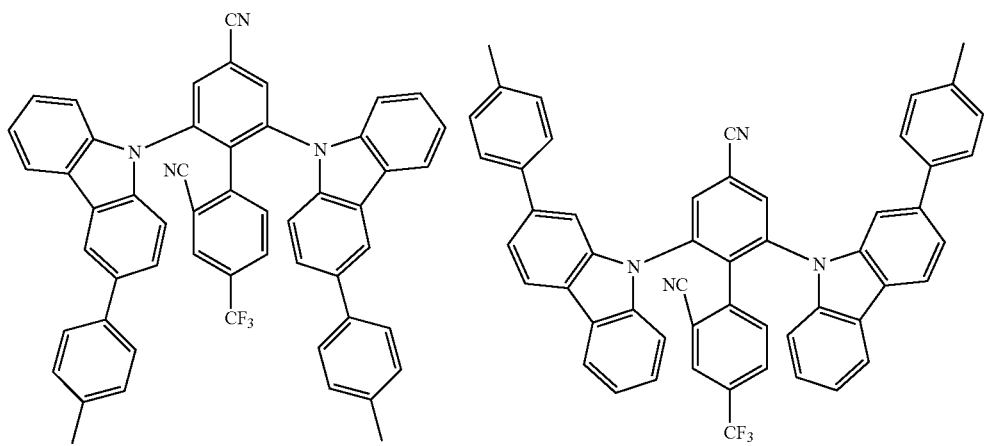

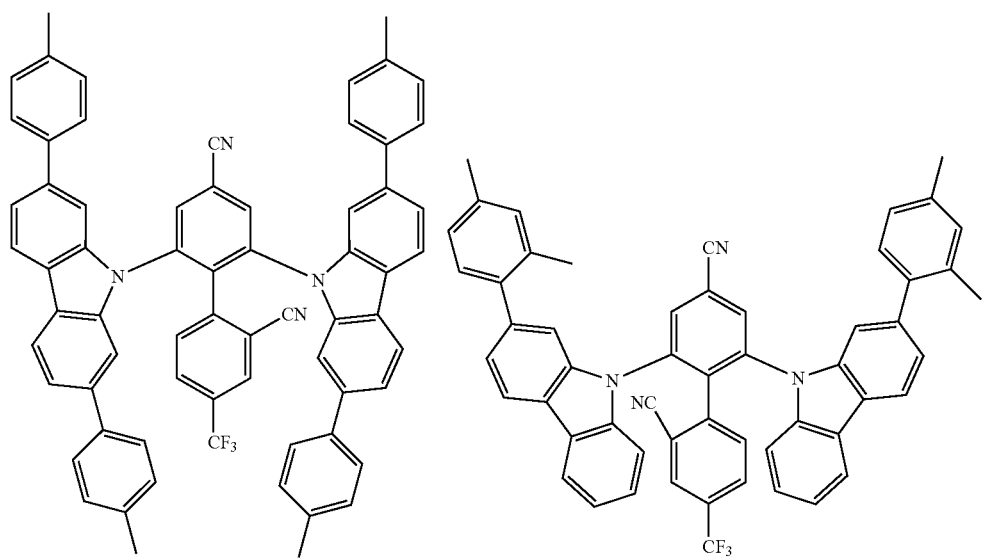
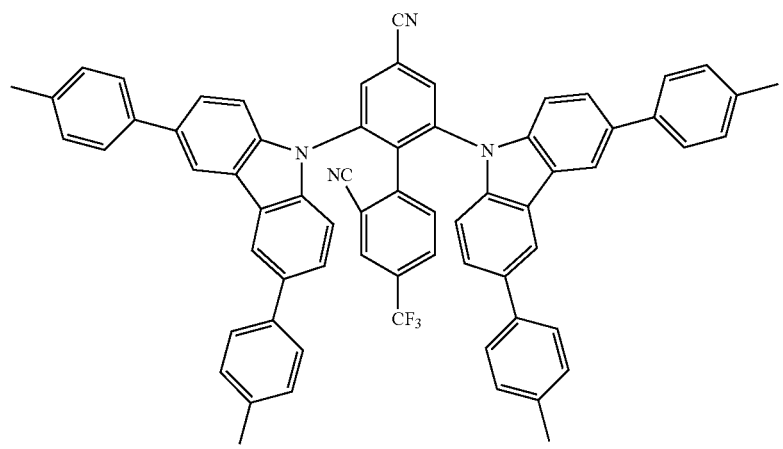
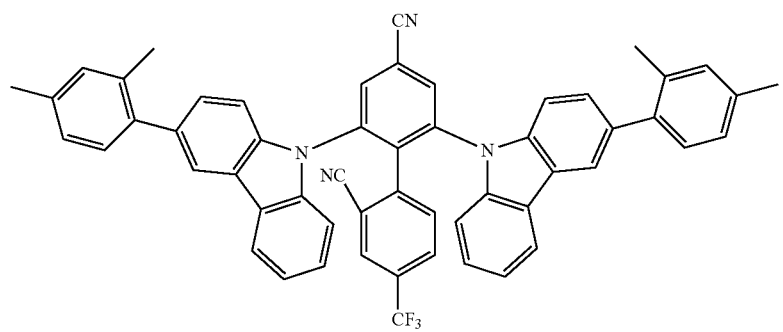

275 276
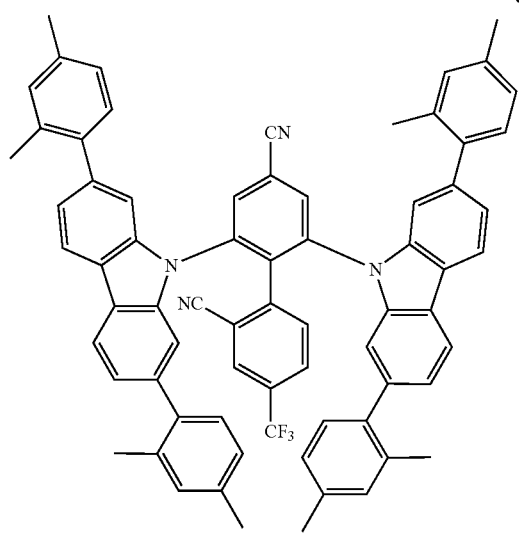
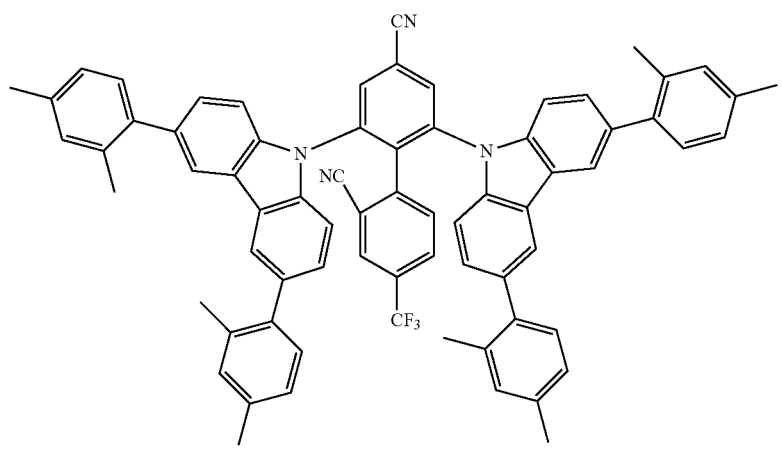
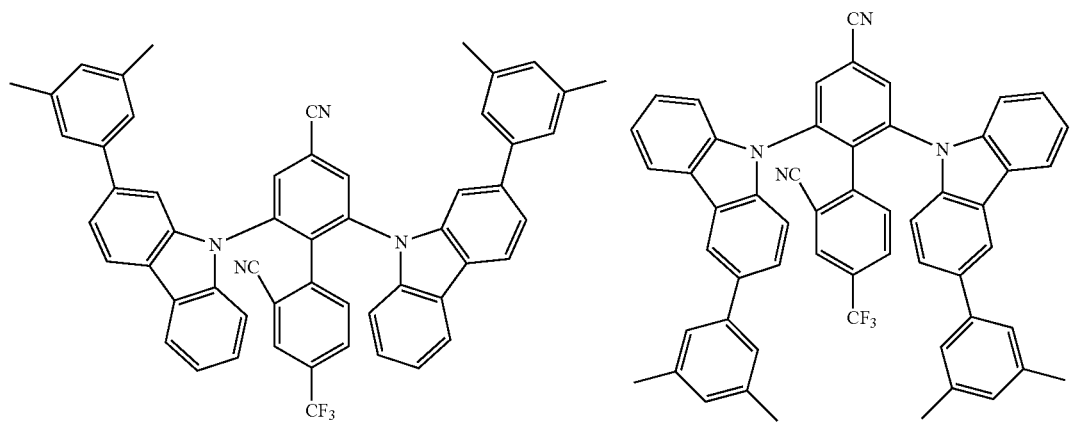

277
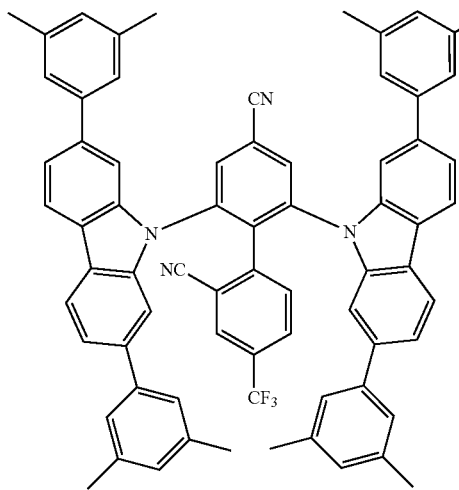
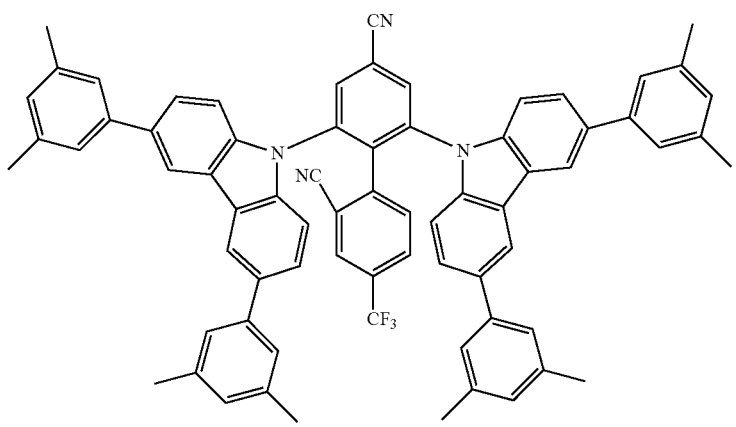
278 -continued
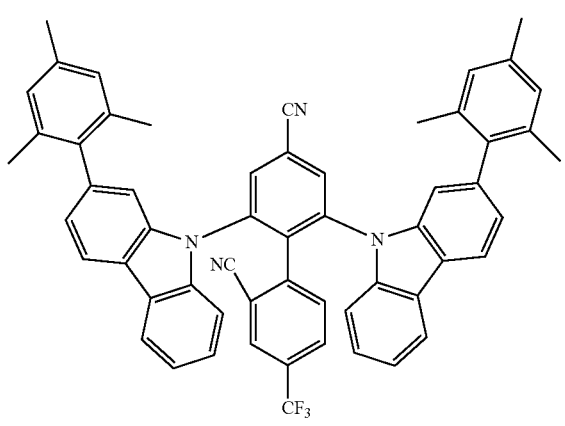
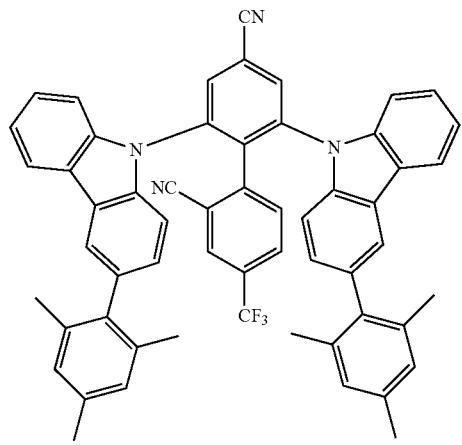

279
280
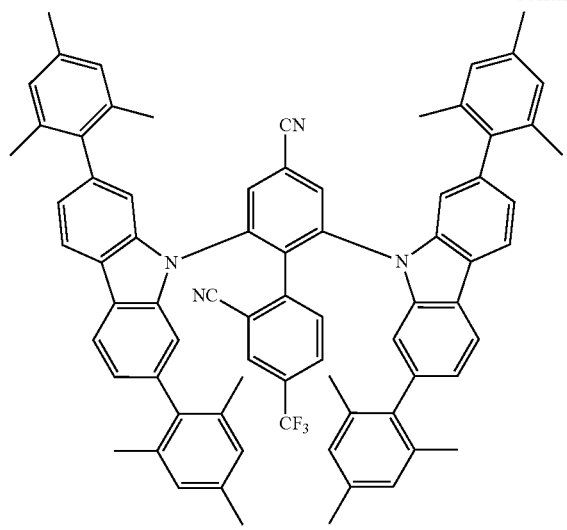
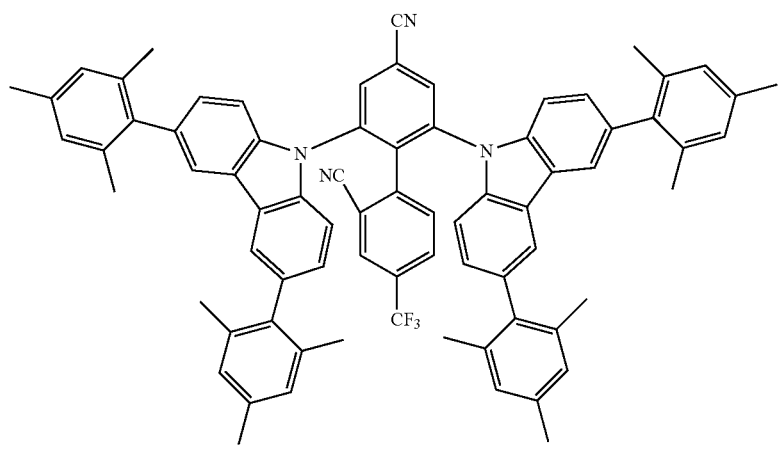
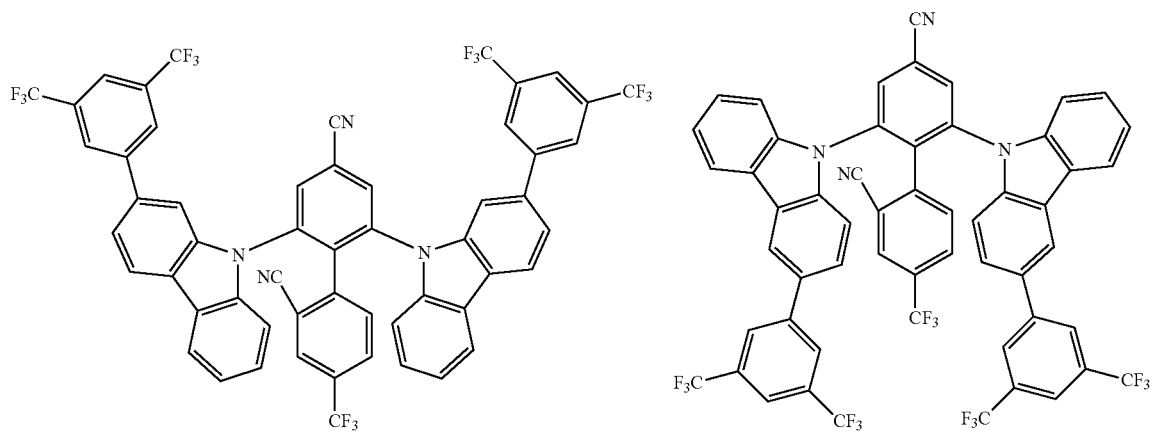

281 282
-continued
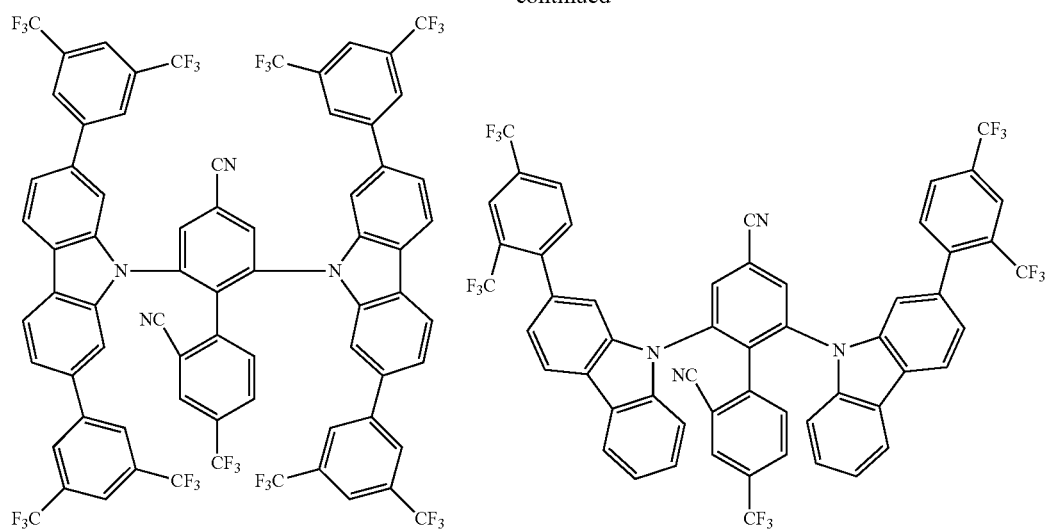
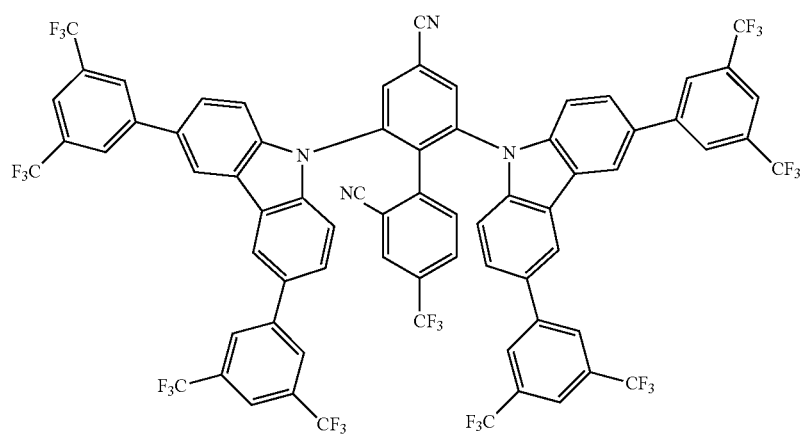
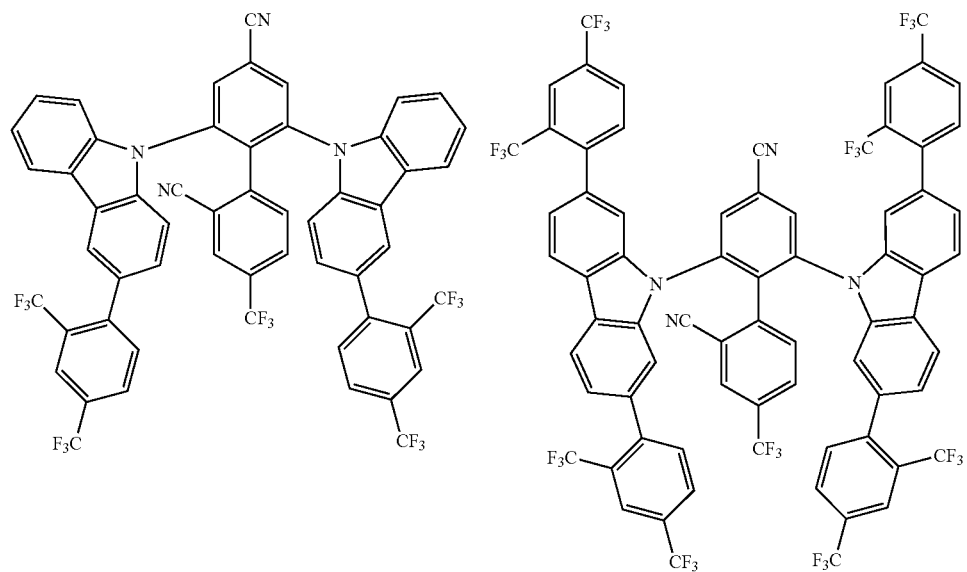

-continued
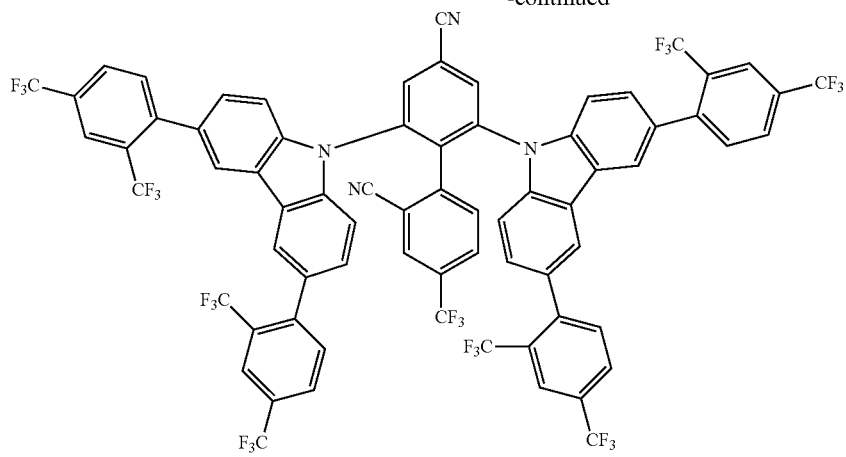
20
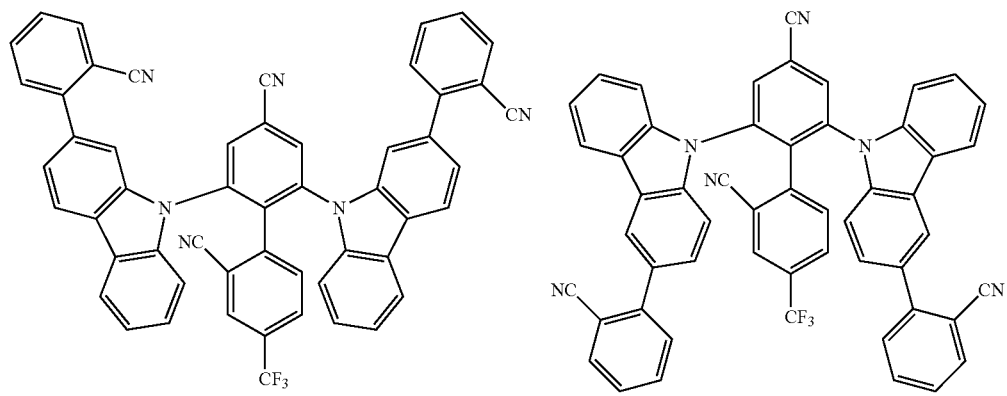
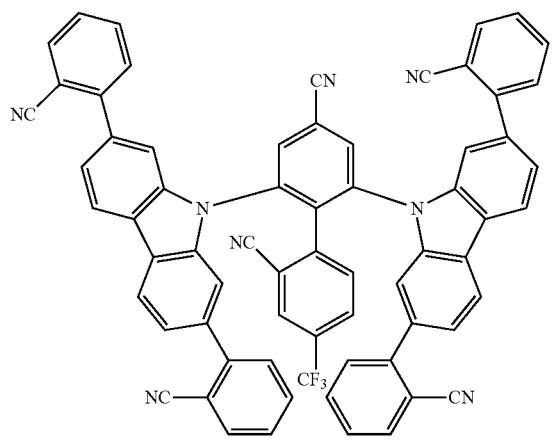

285
-continued
286
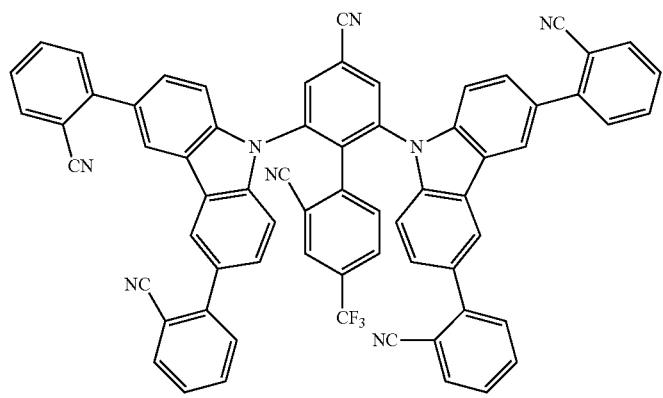
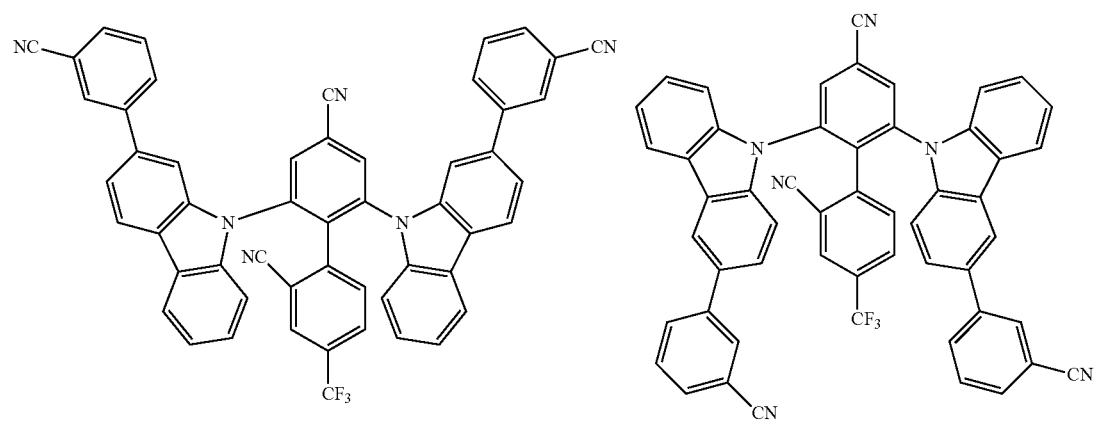
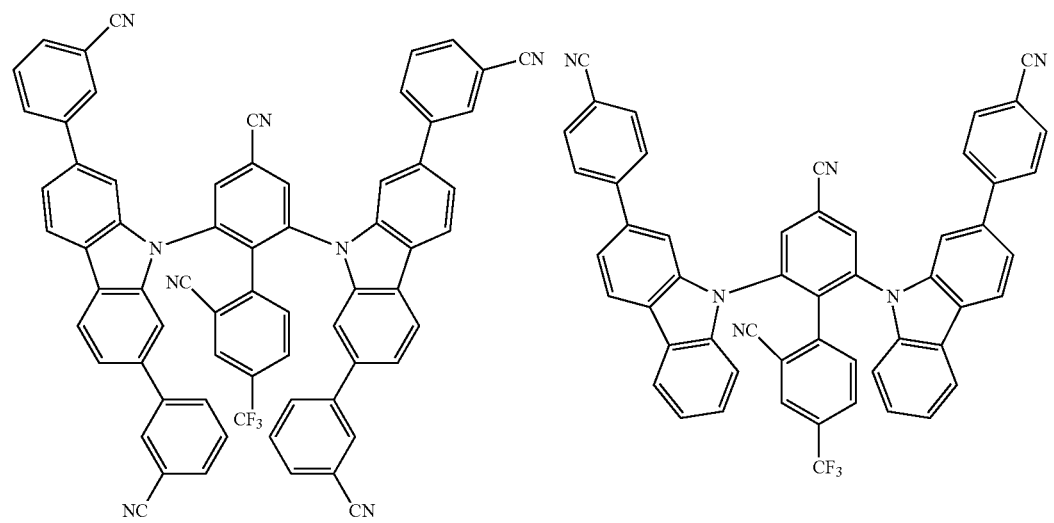

-continued
287
288
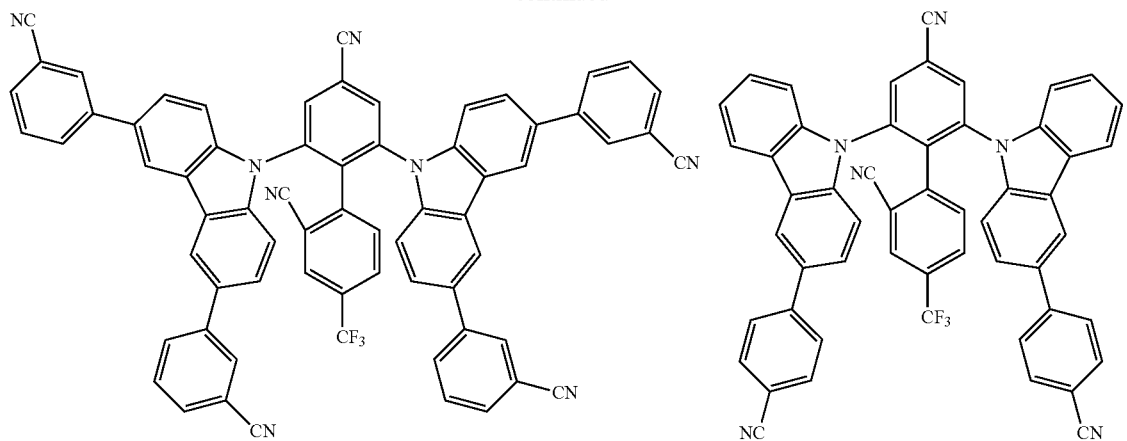
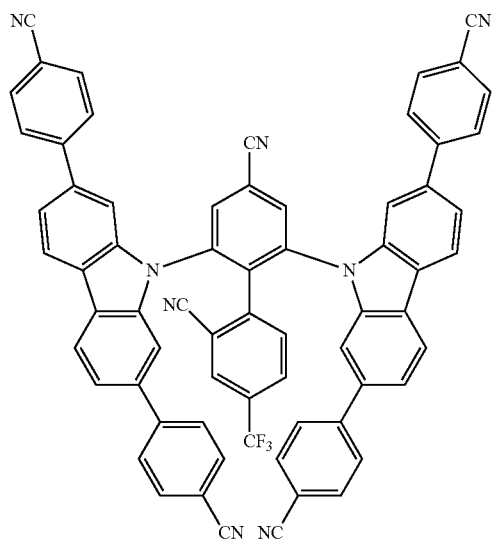
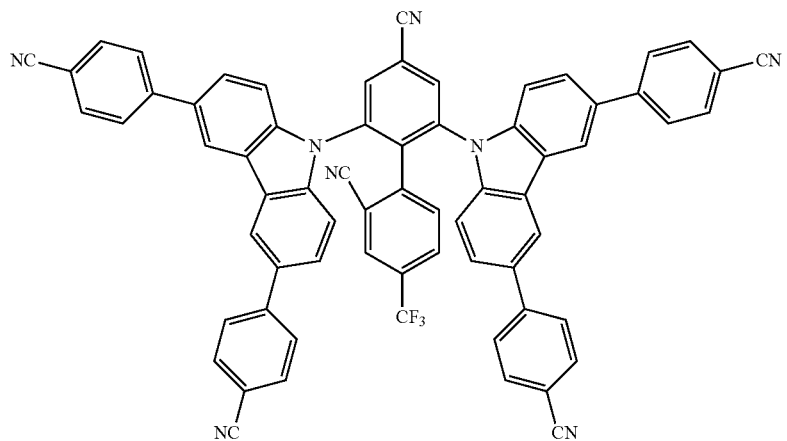

289 290
-continued
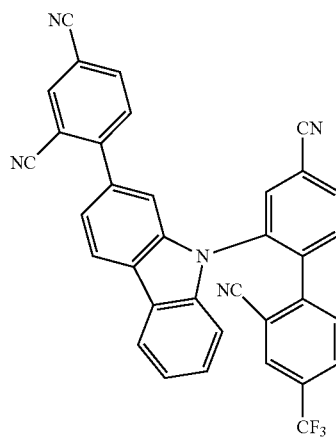
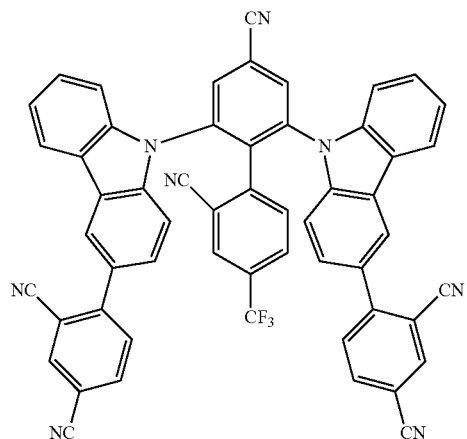
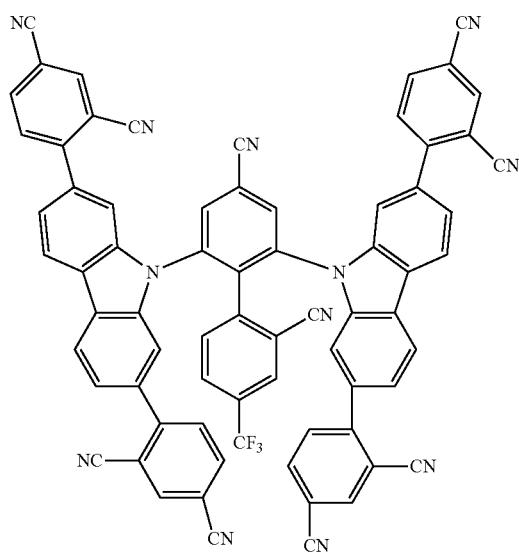
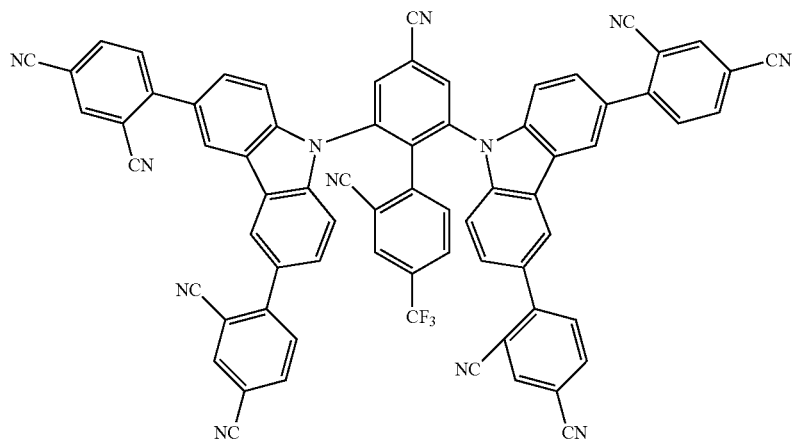

-continued
291 292
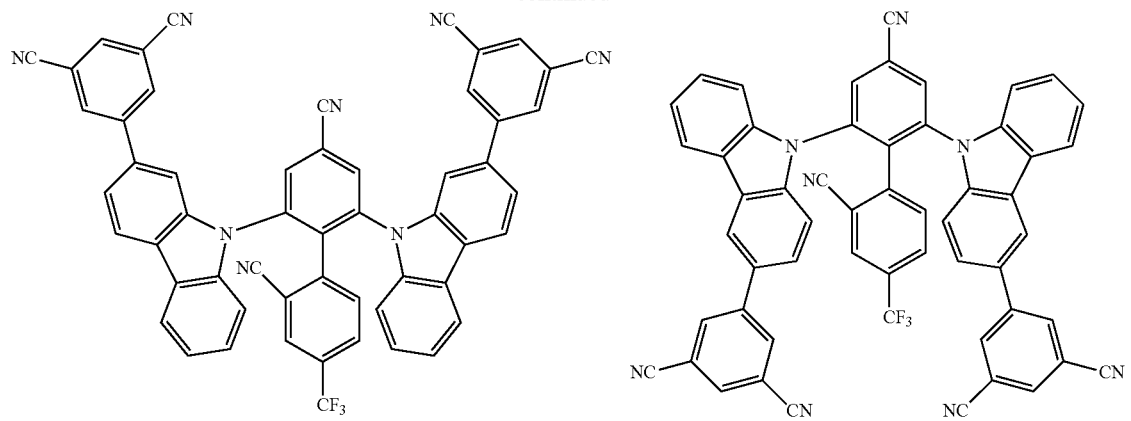
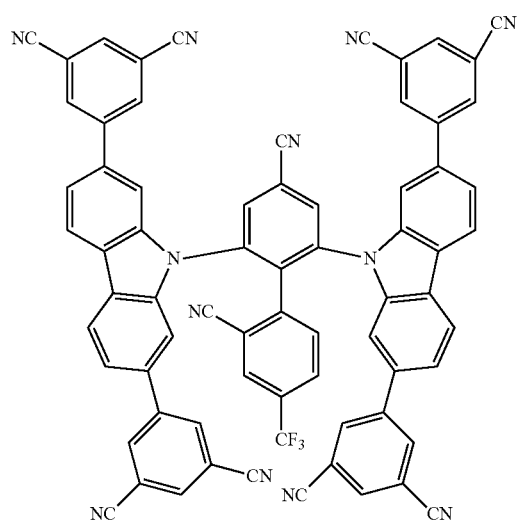
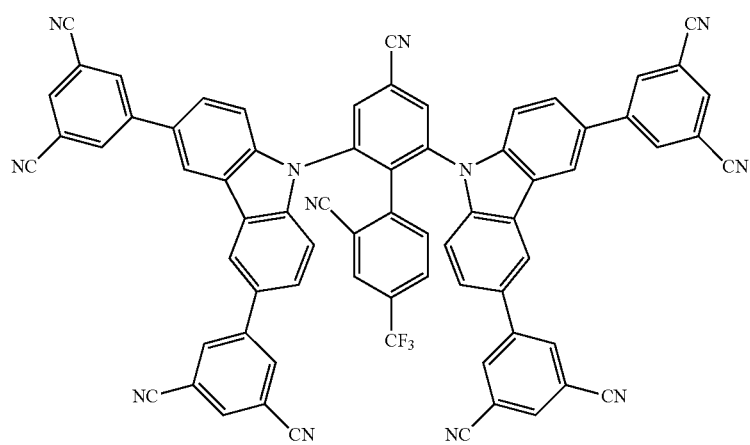

-continued
293 294
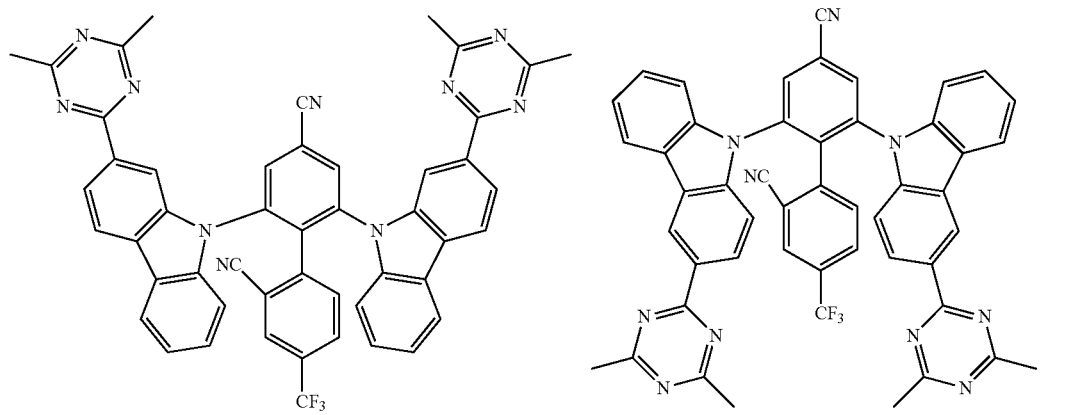
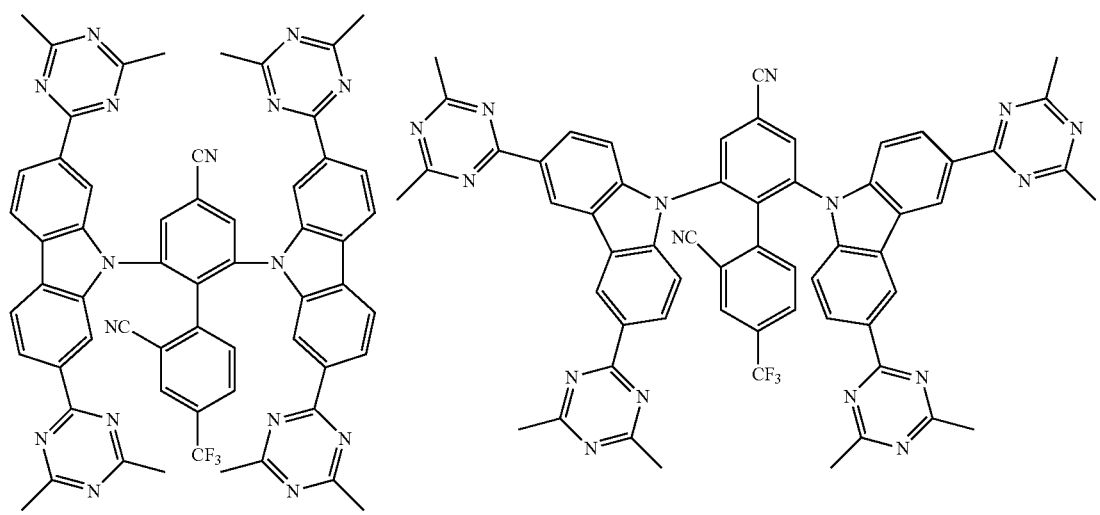
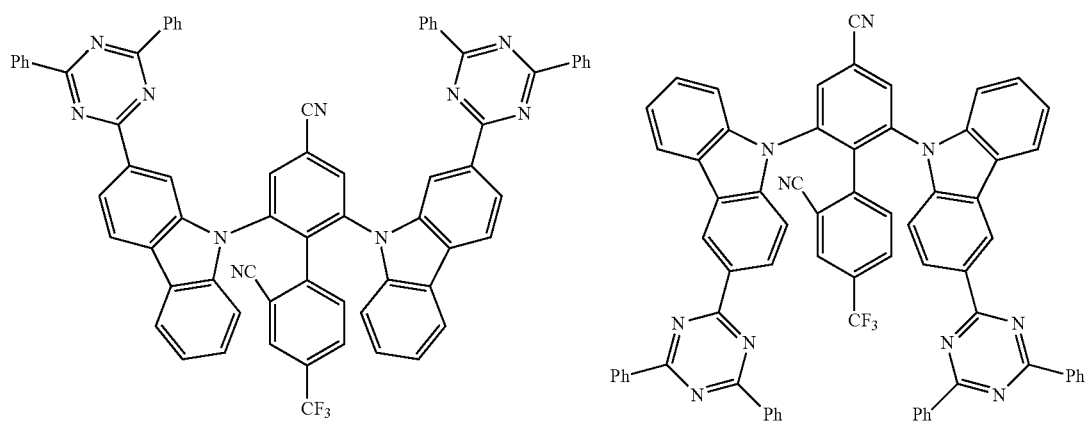

295 296
-continued
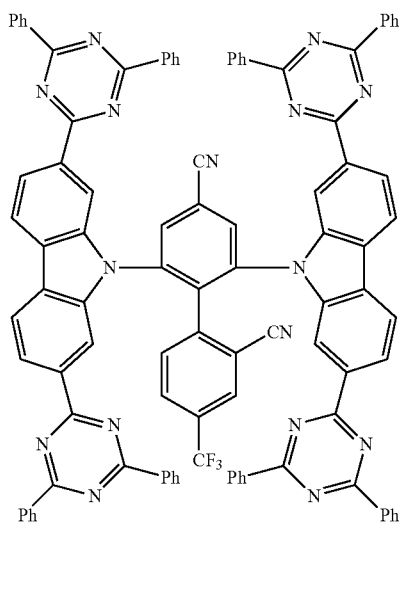
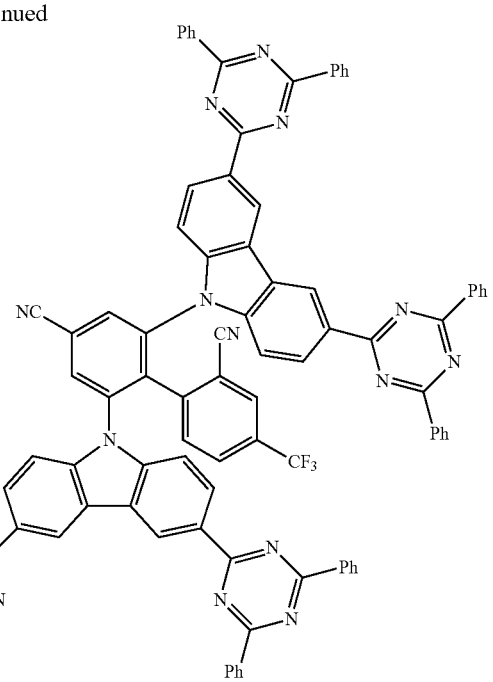
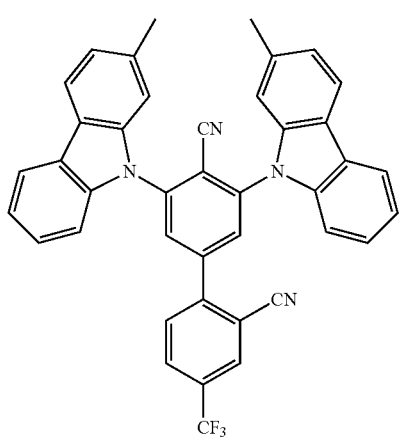
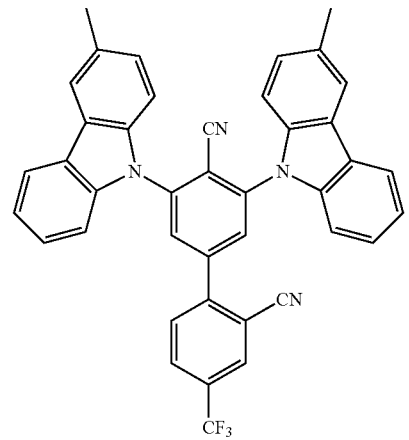
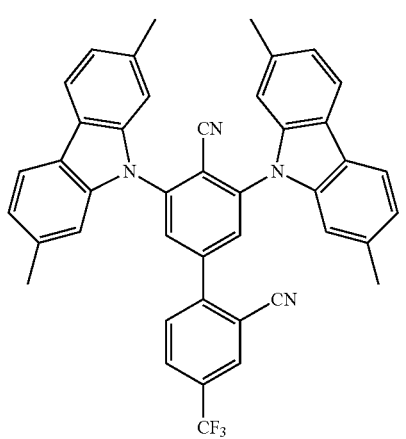
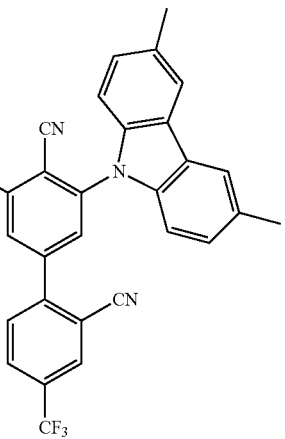

297
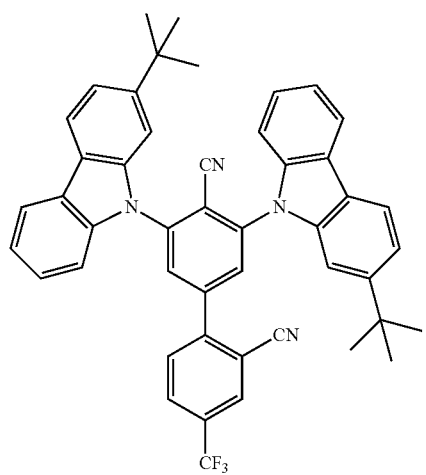
298
-continued
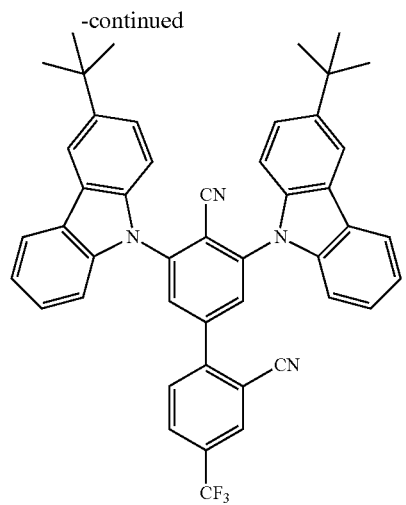
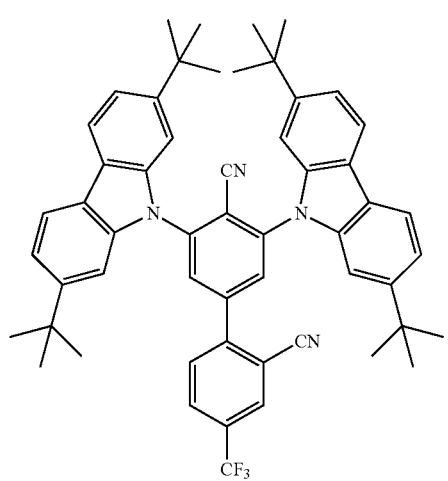
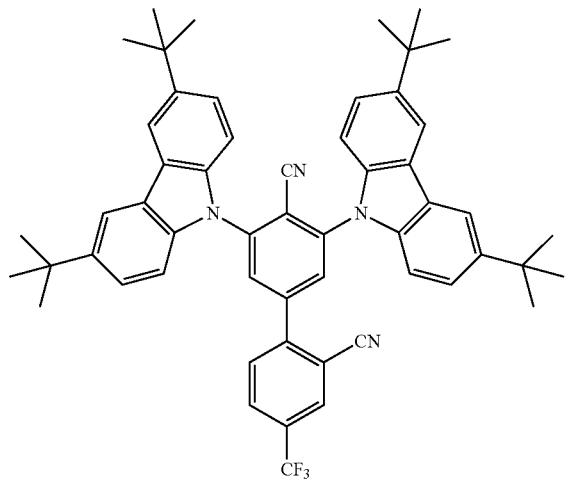
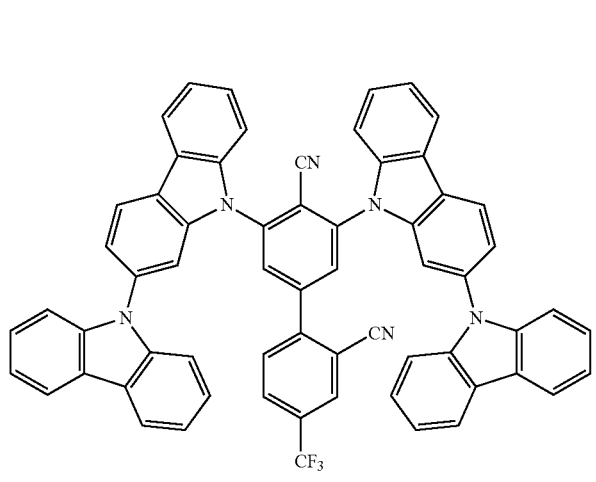
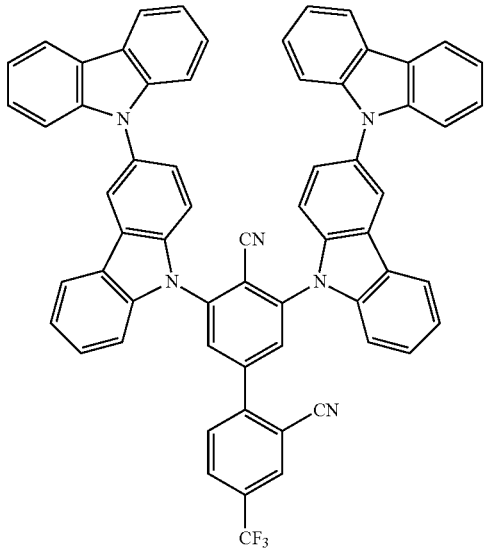

-continued
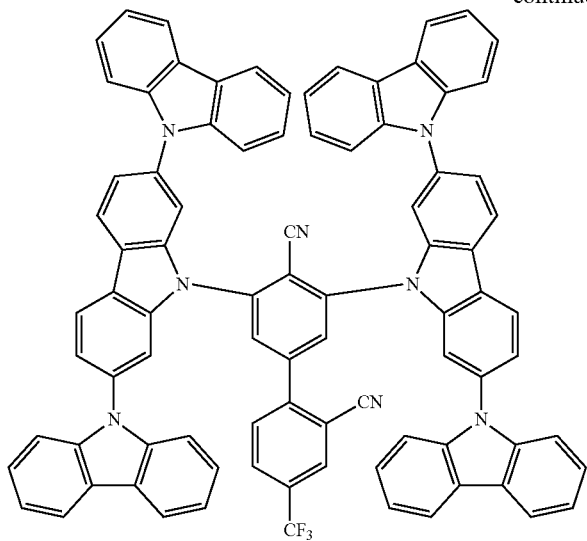
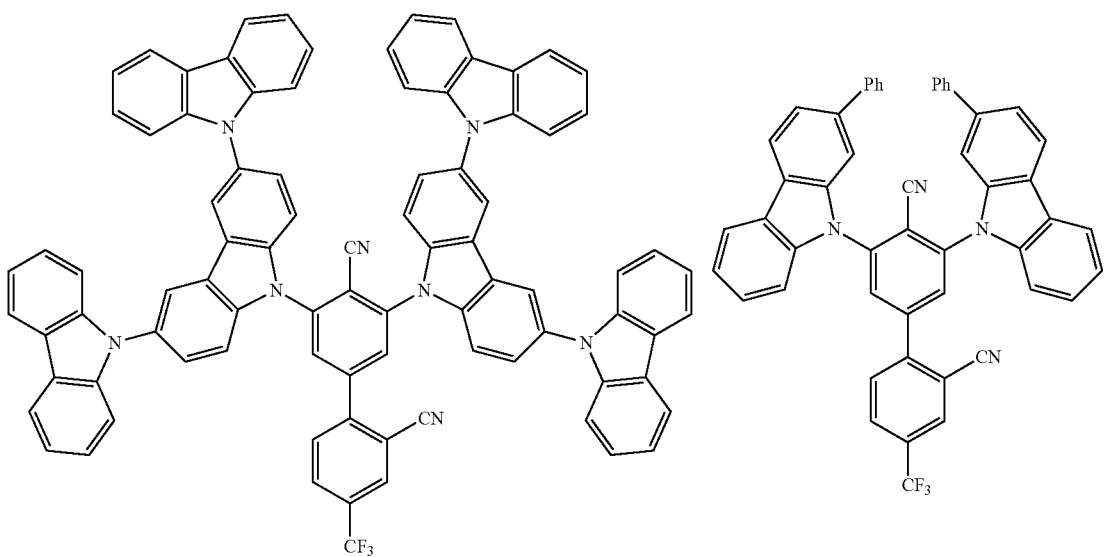
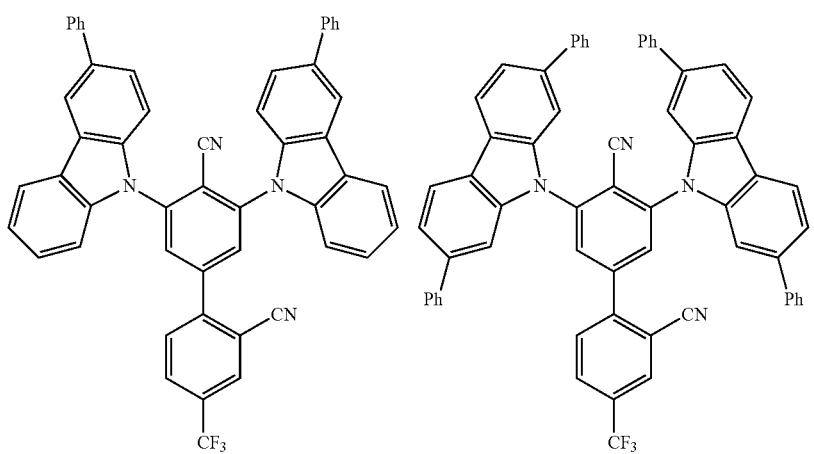

-continued
301
302
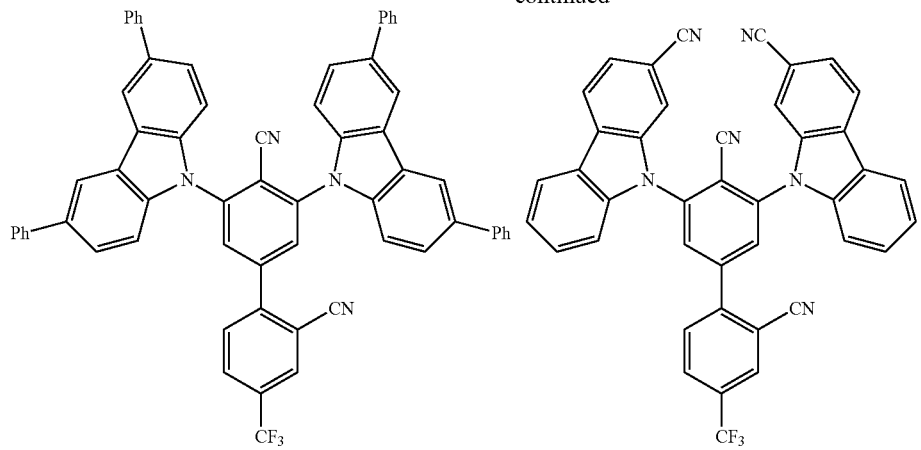
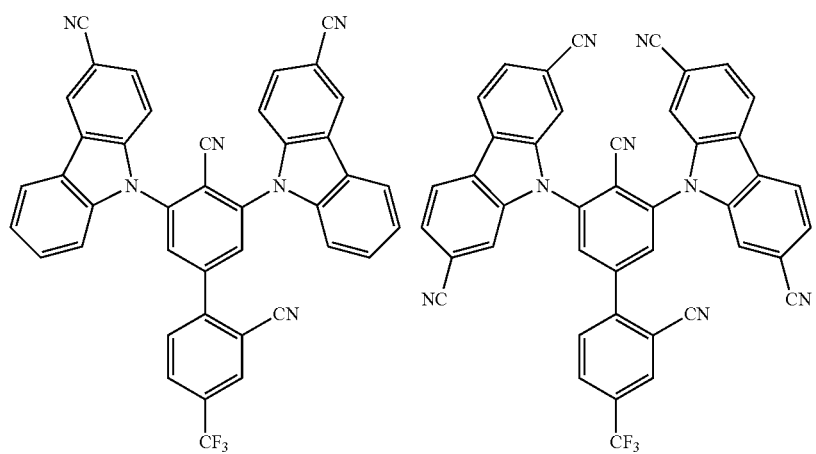
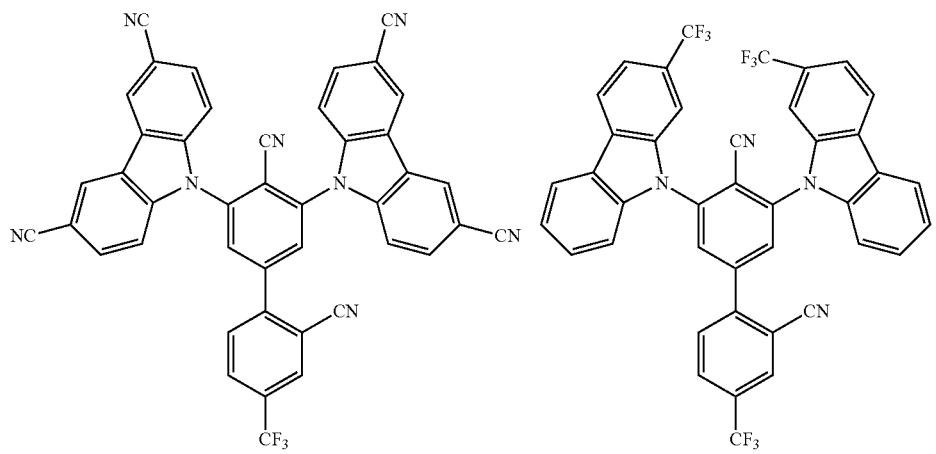

303
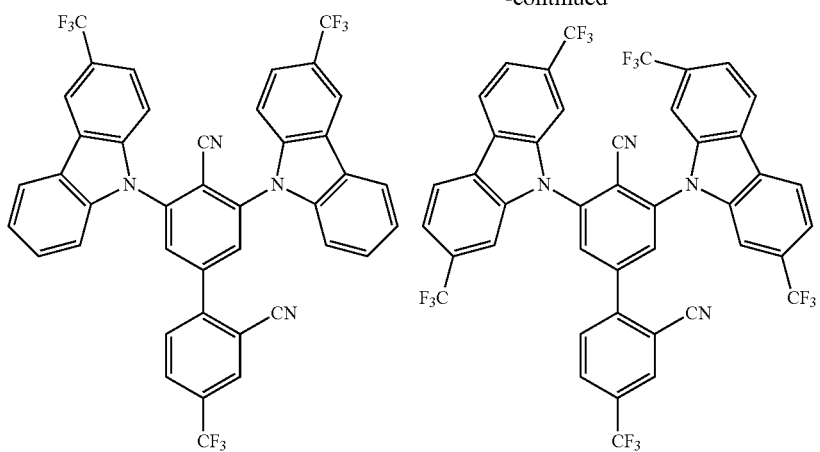
304
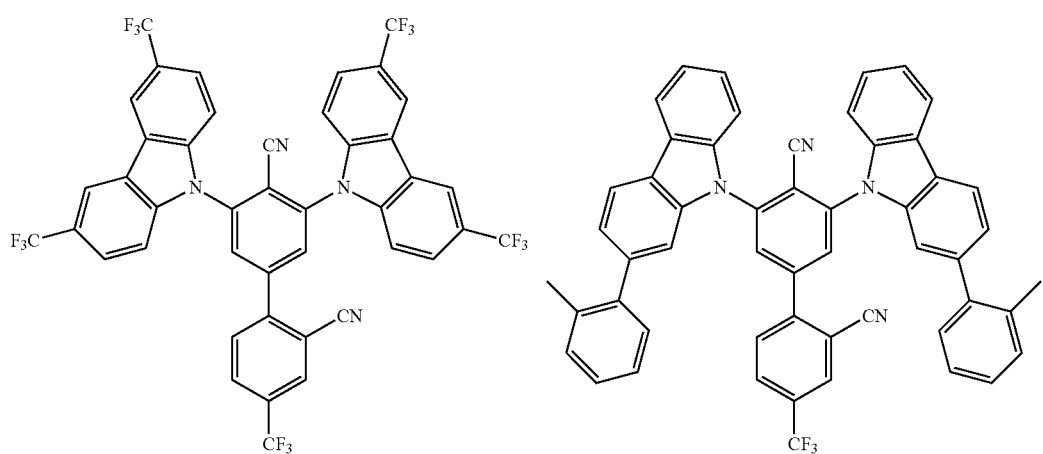
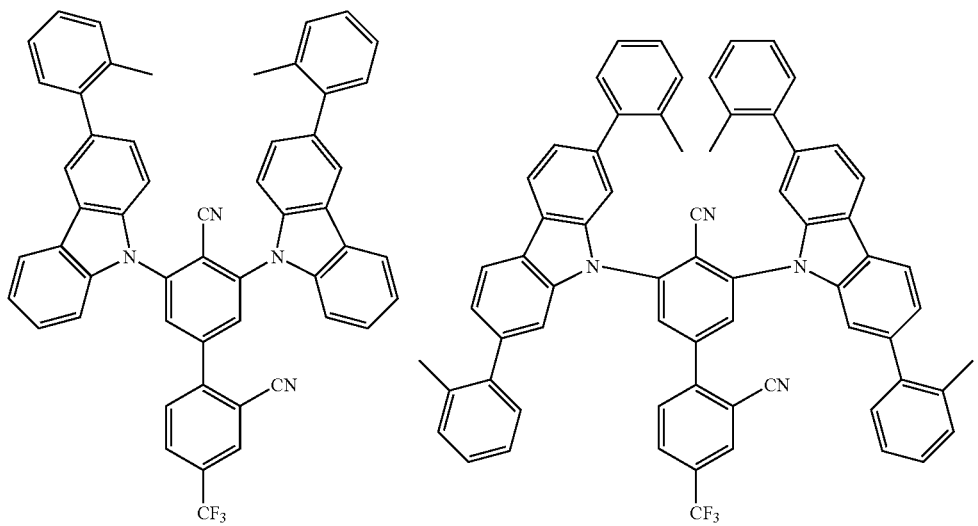

305
306
-continued
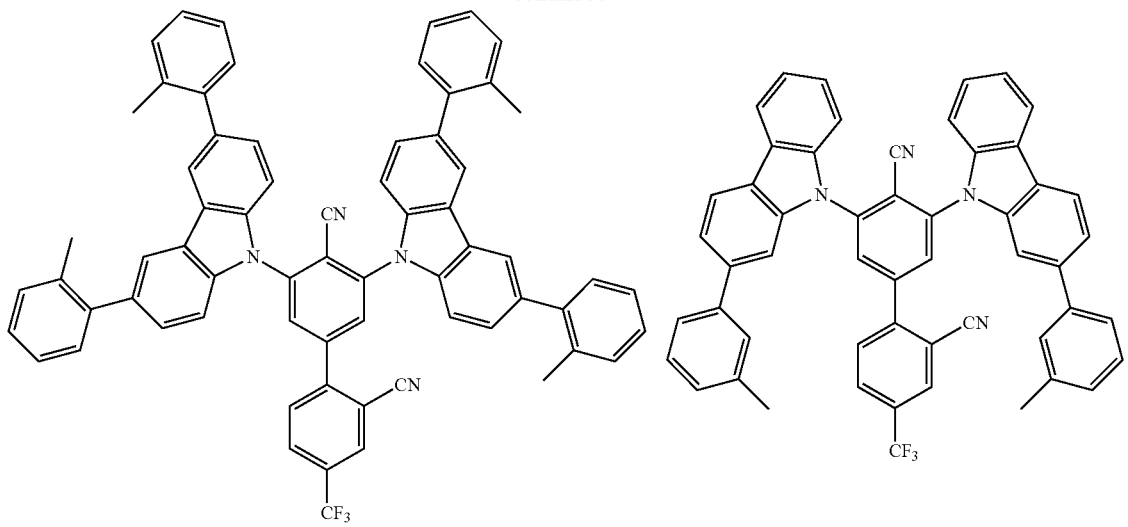
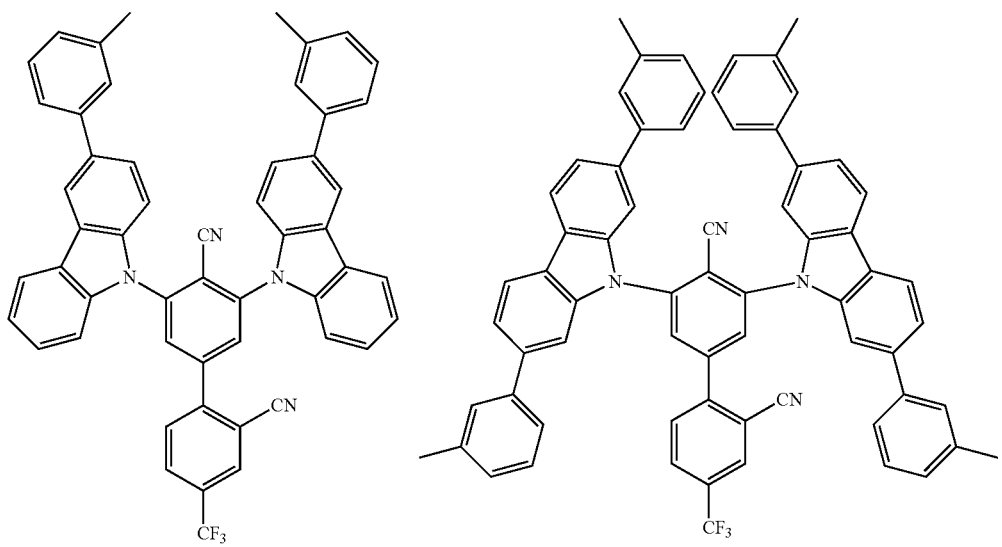
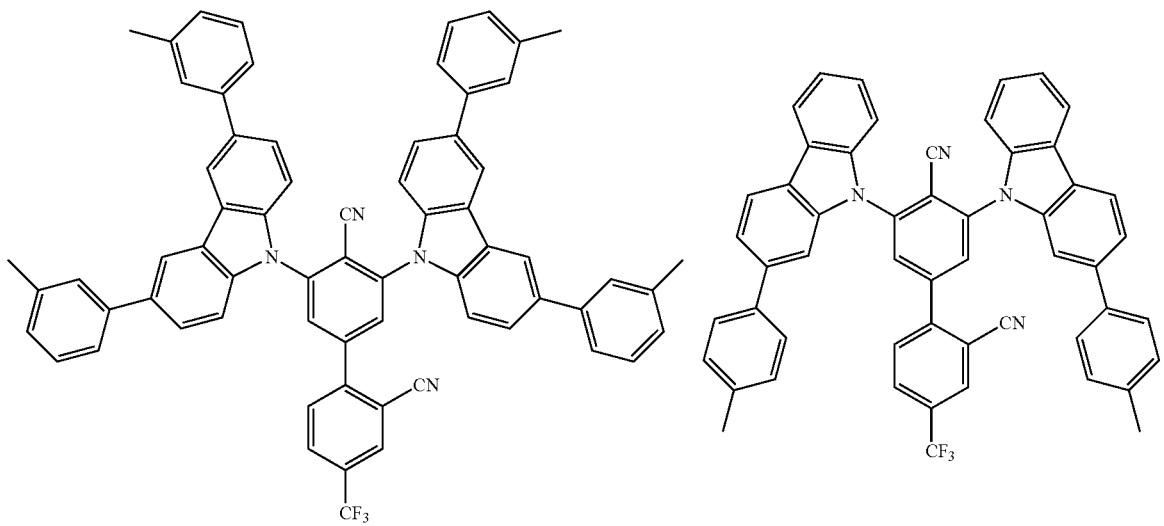

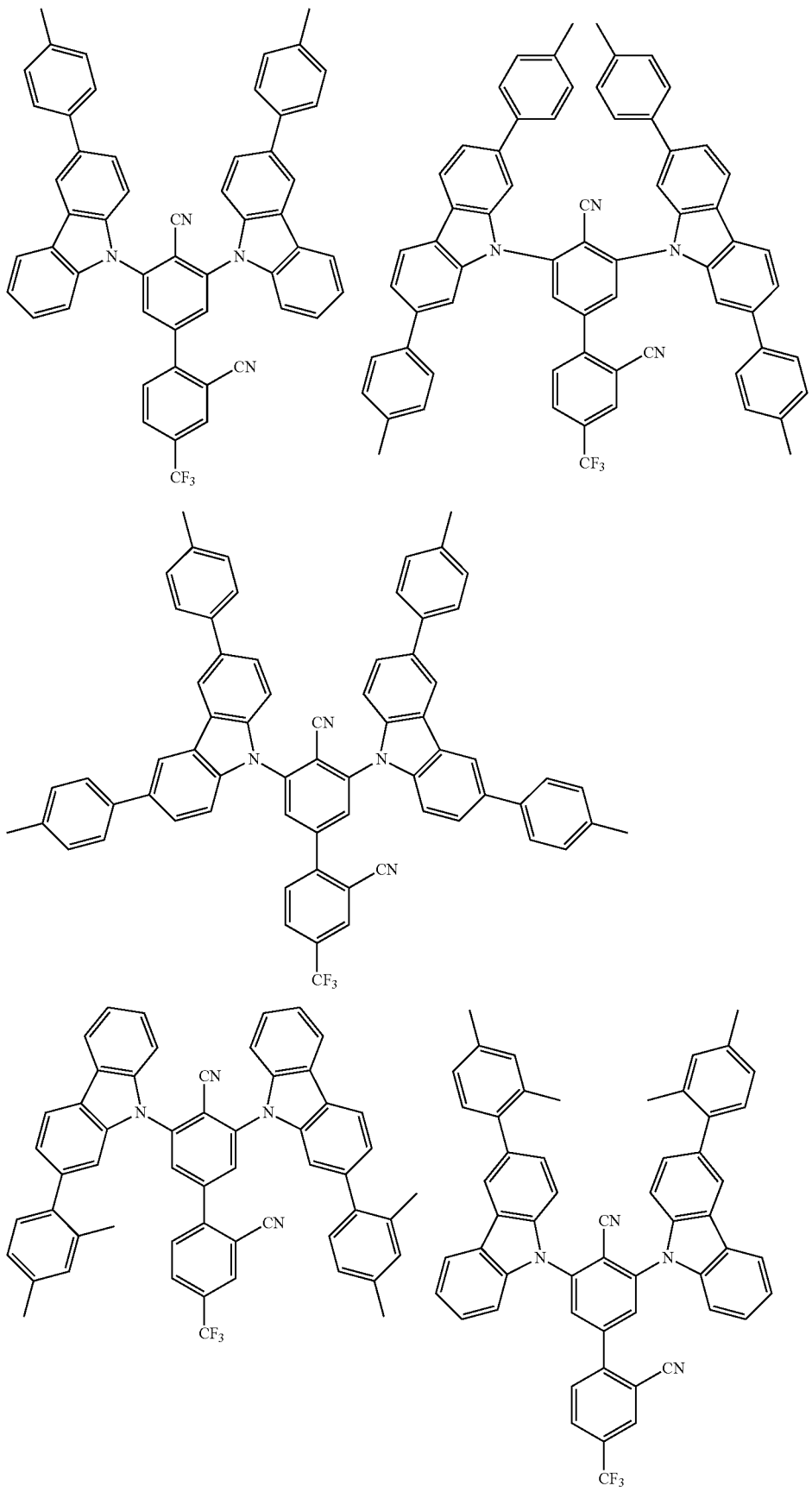

309
310
-continued
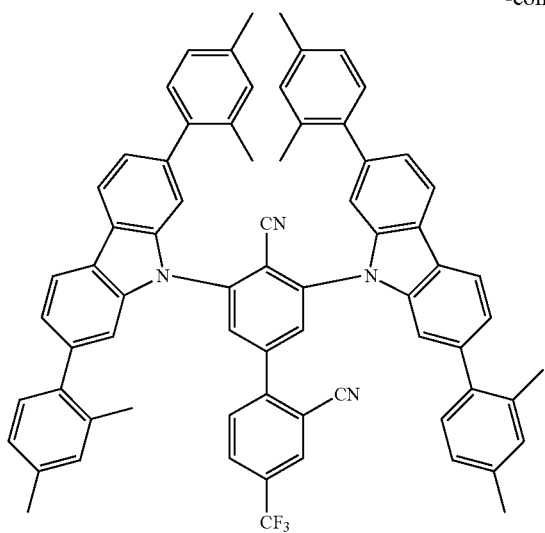
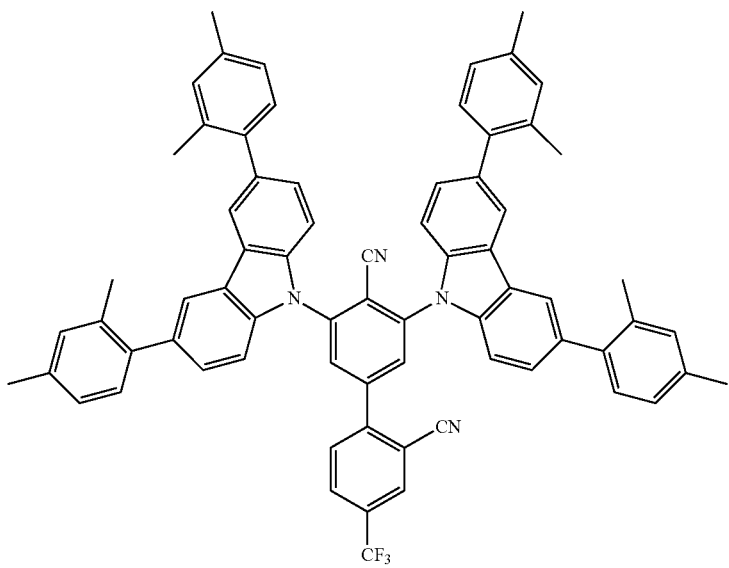
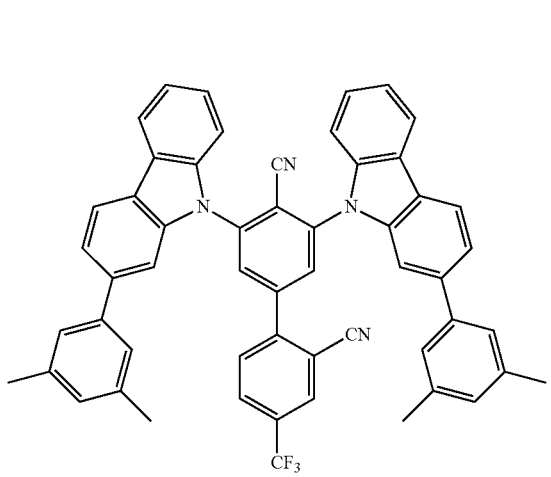
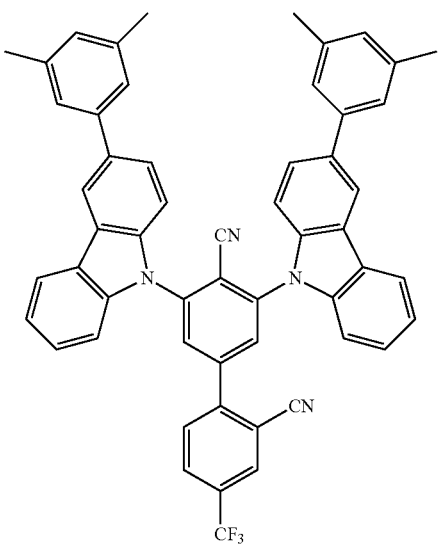

311
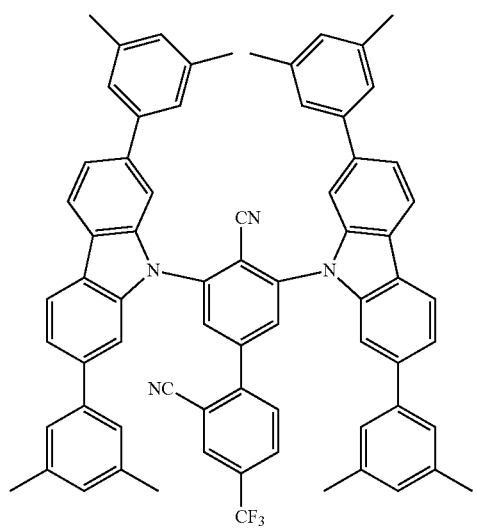
-continued
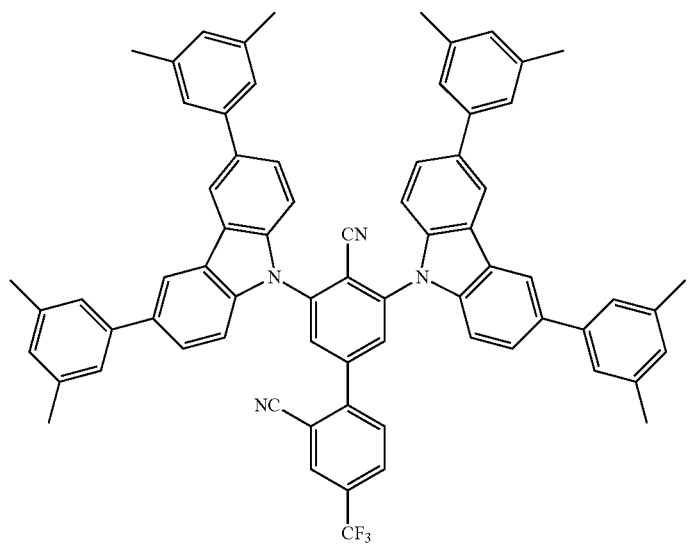
312
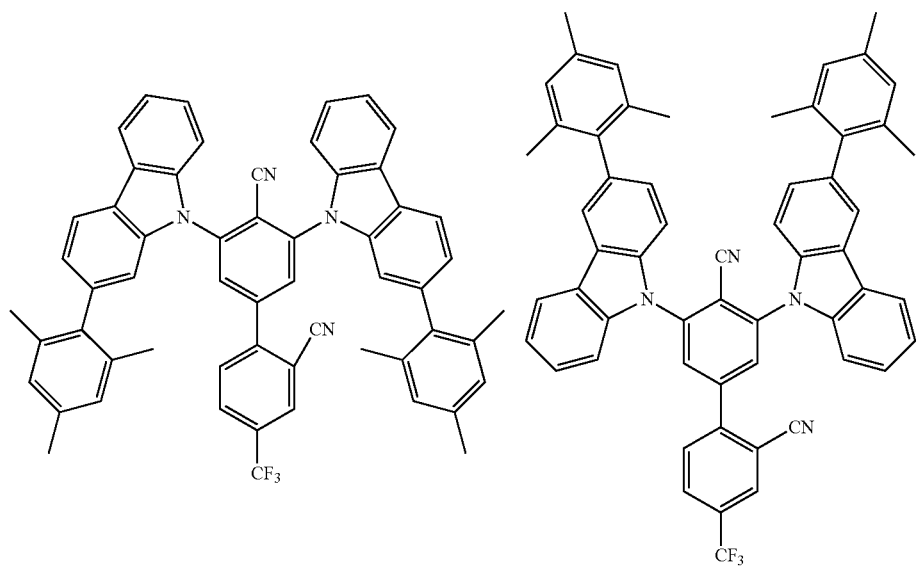

313
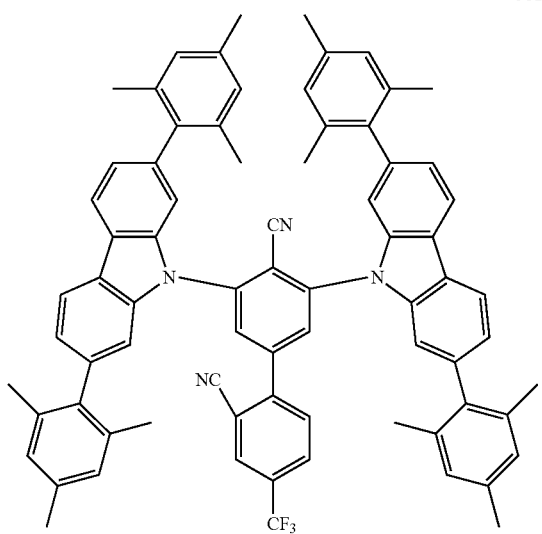
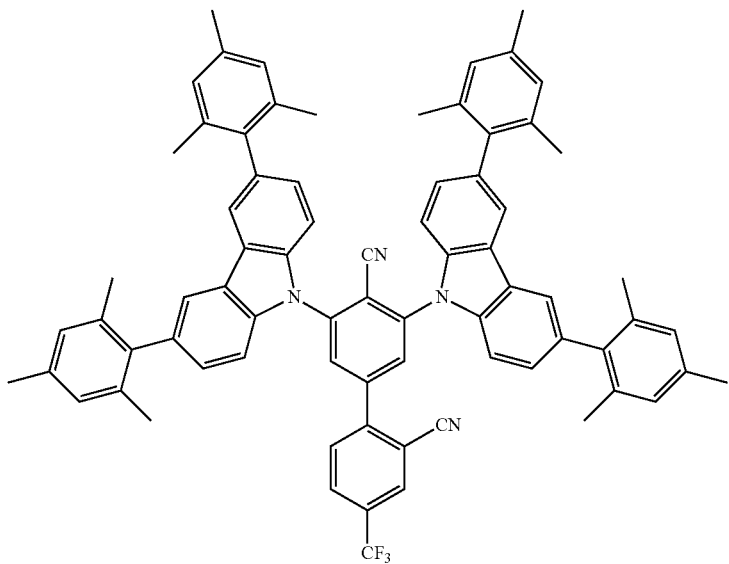
314
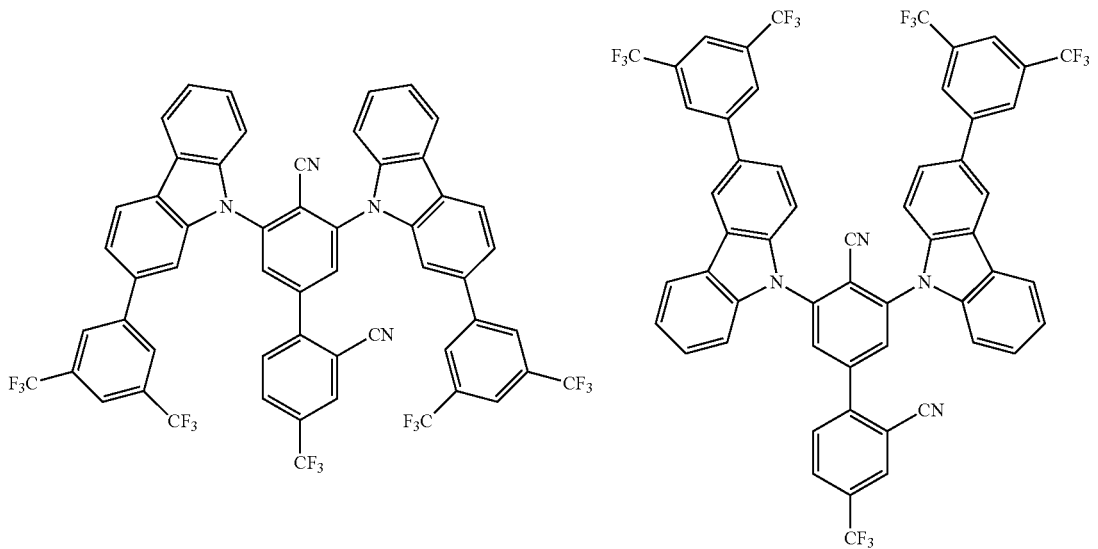

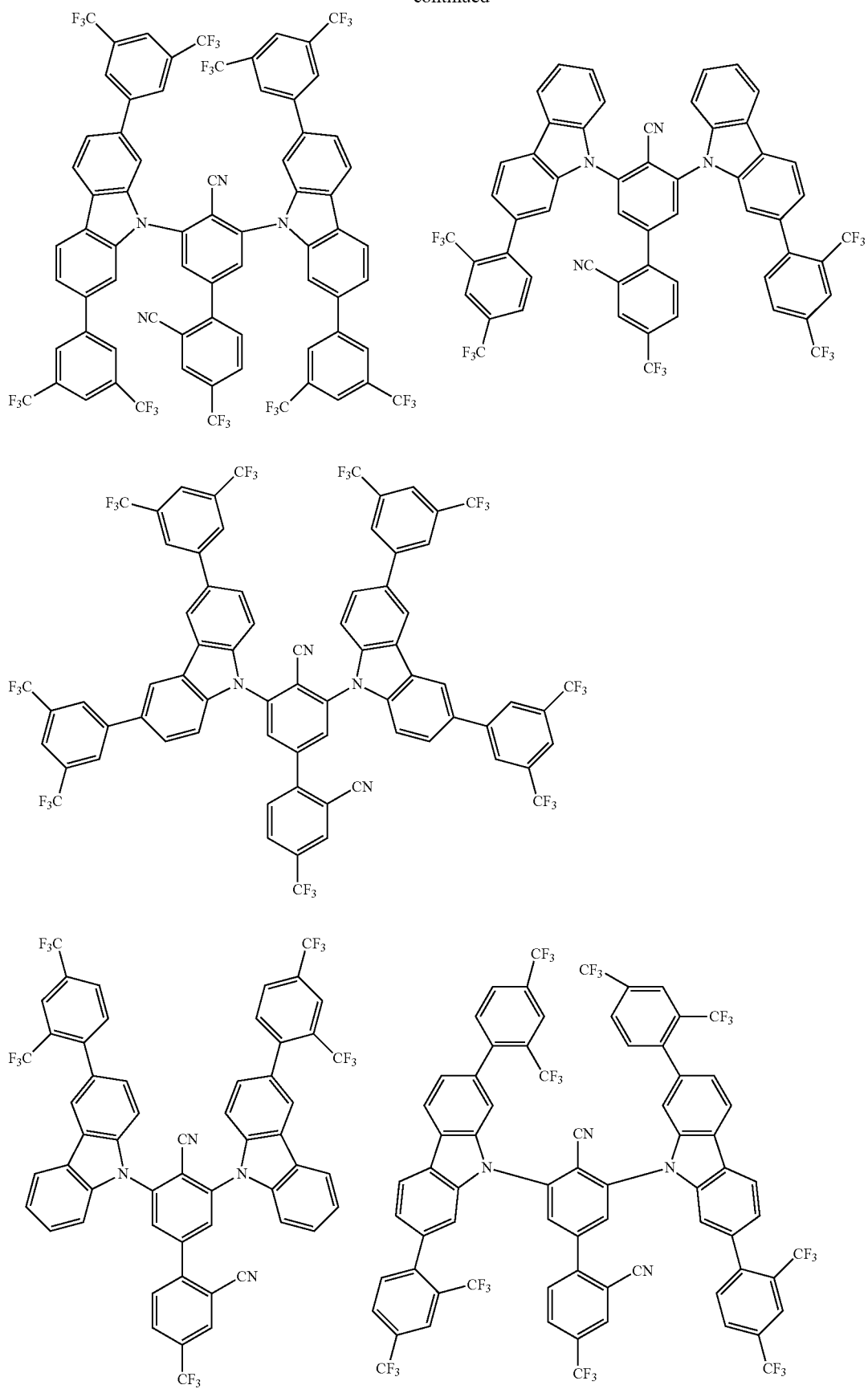

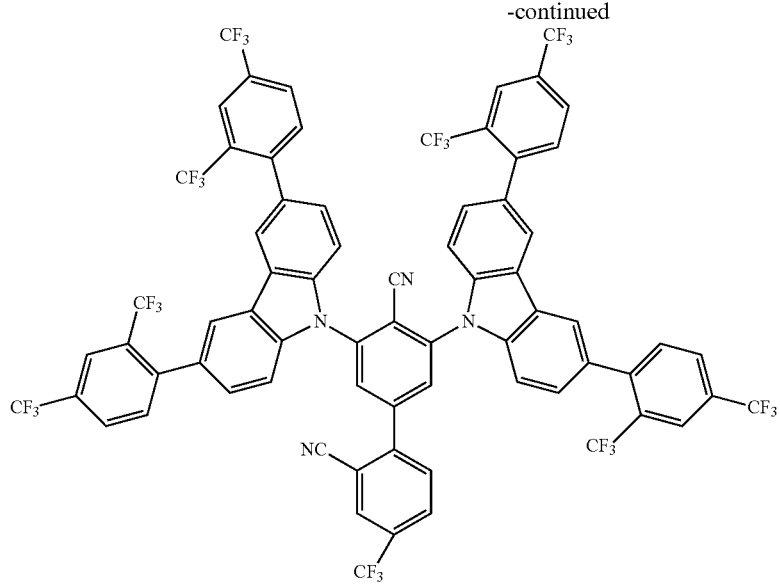
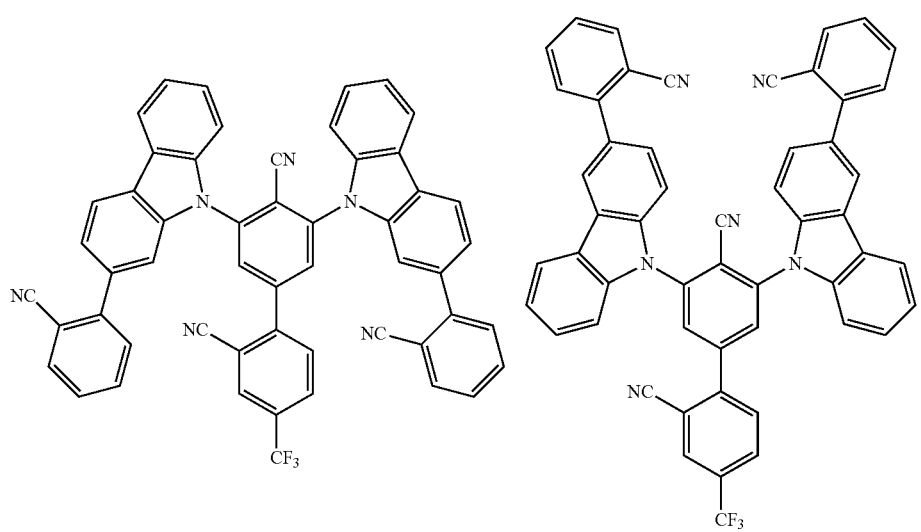
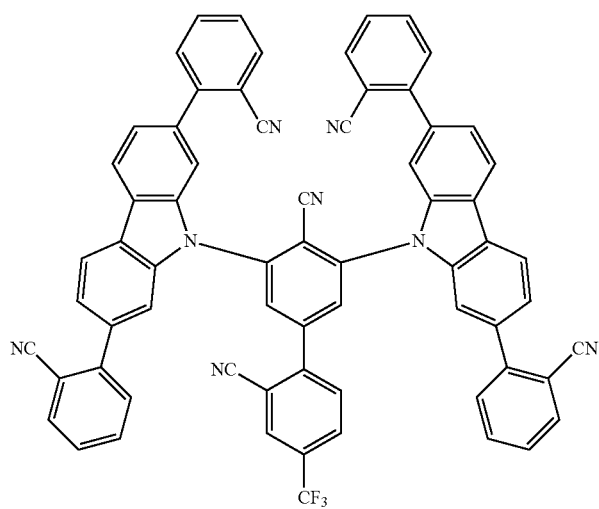

319
320
-continued
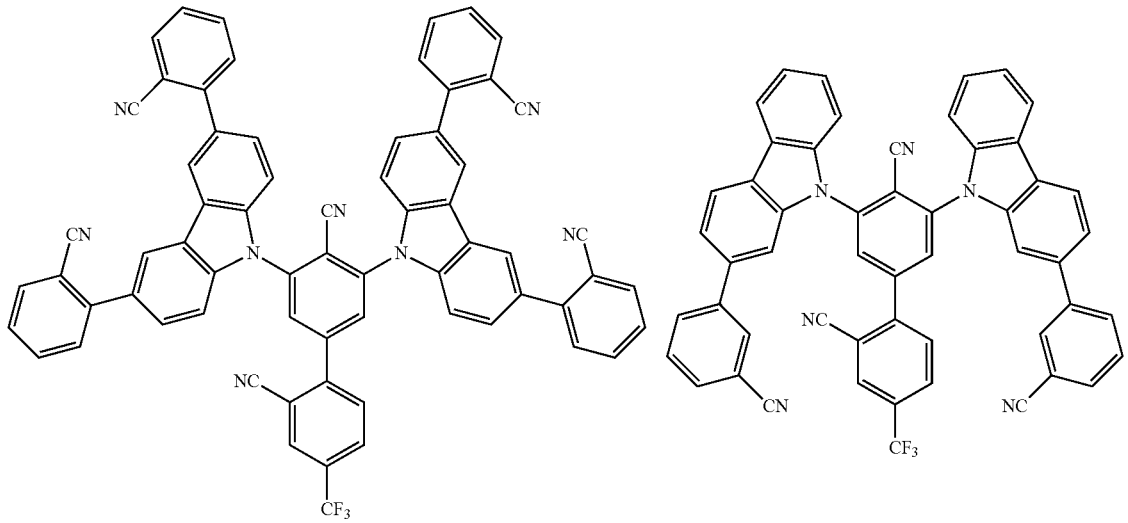
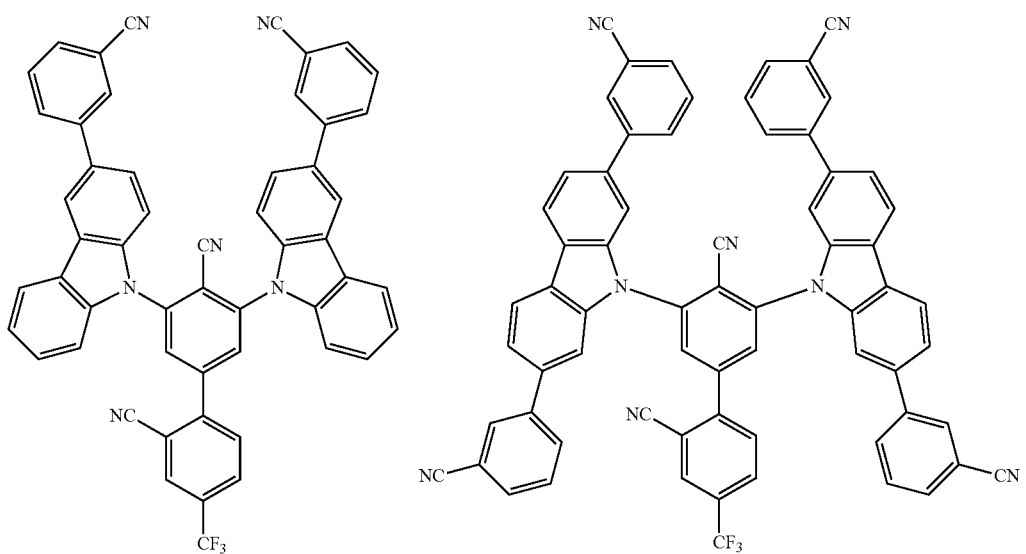
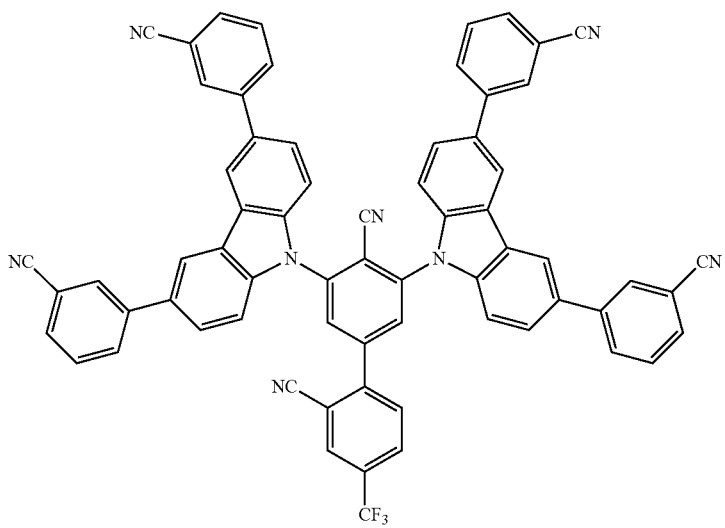

321
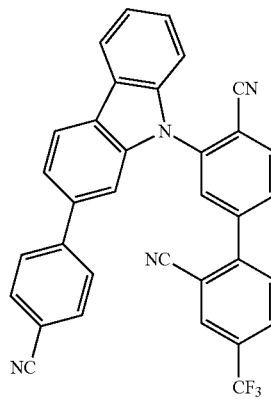
-continued
322
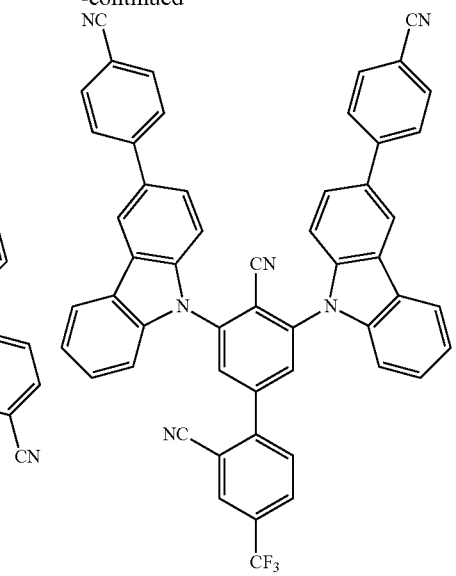
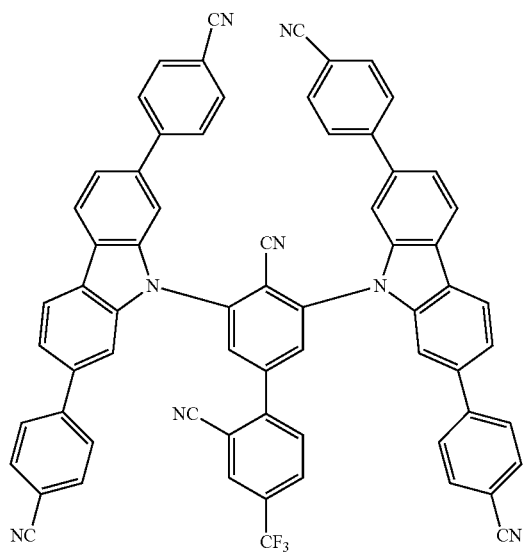
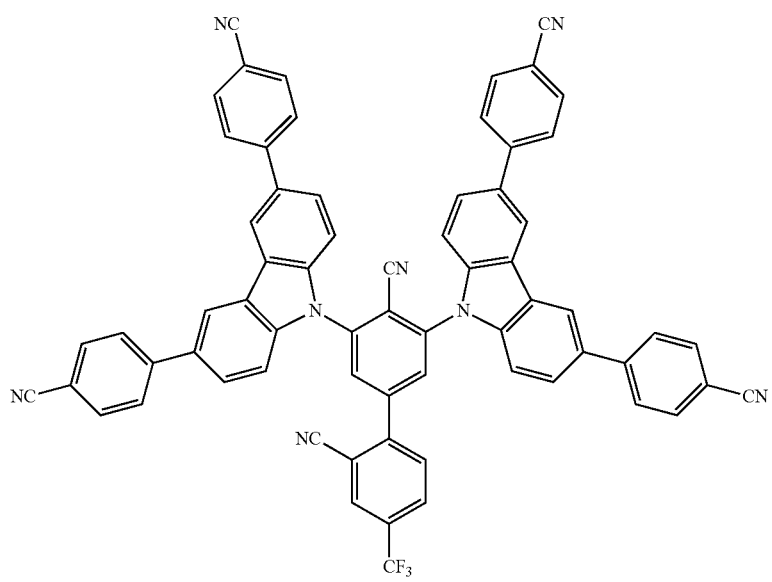

-continued
323
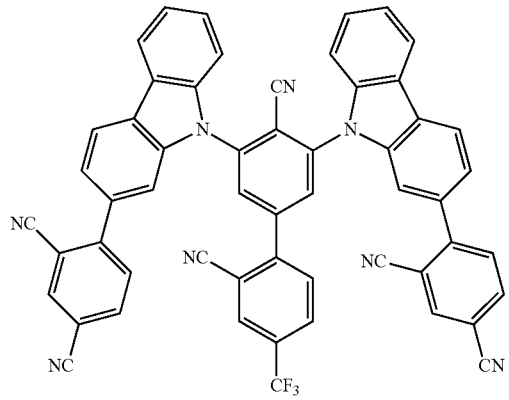
324
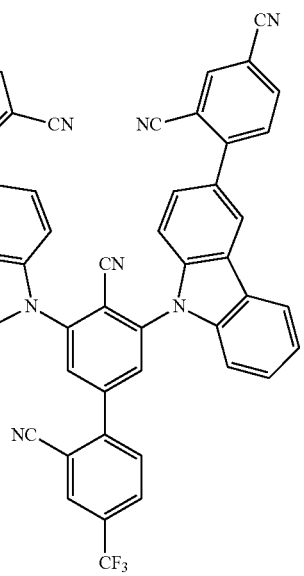
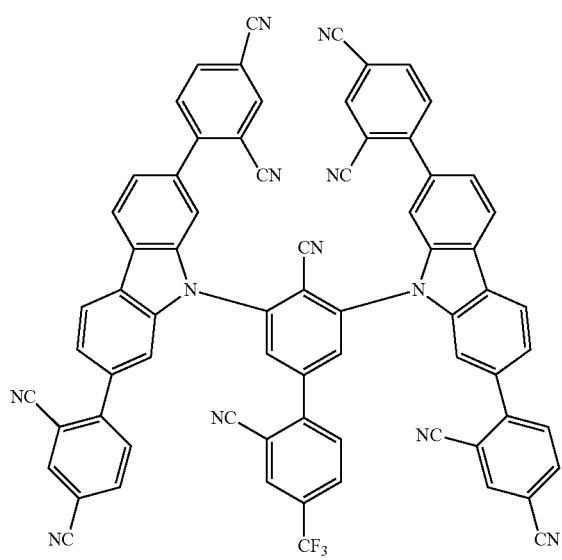
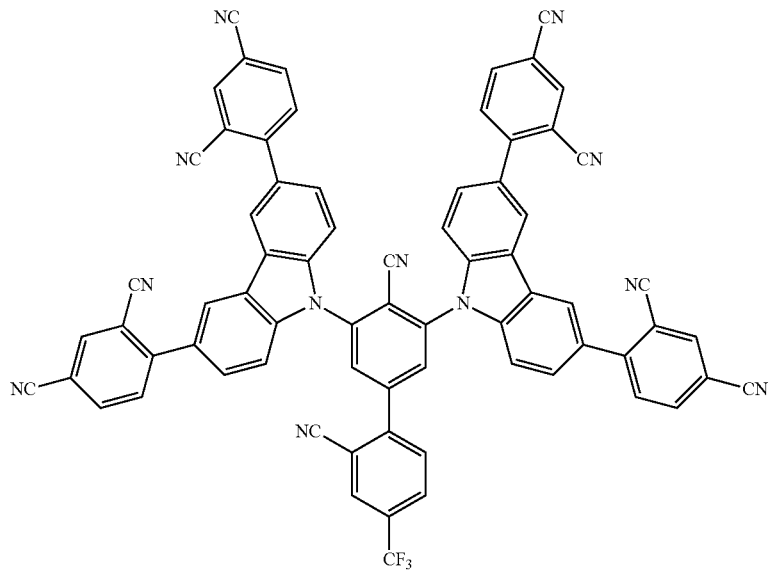

325
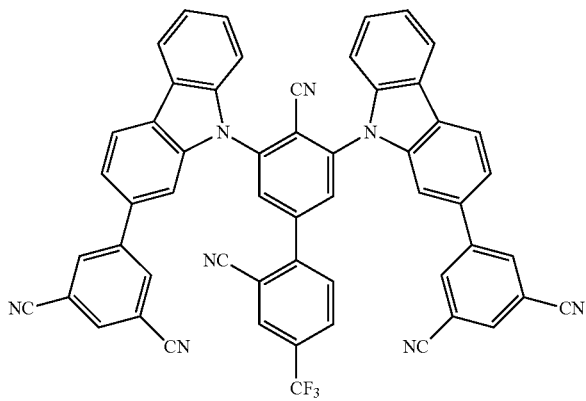
326
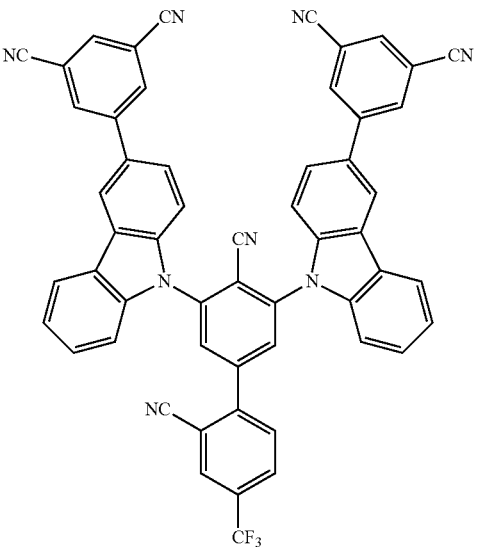
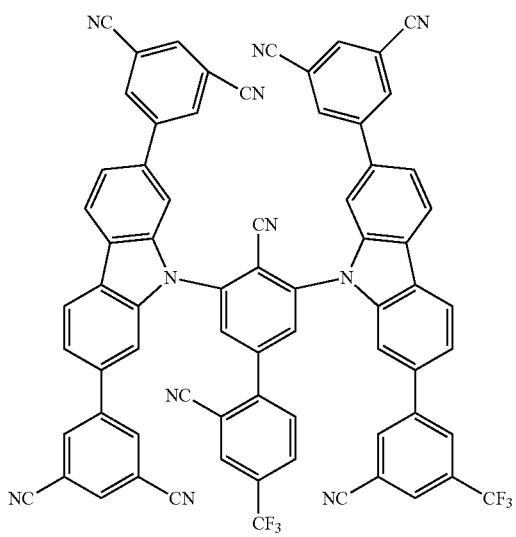
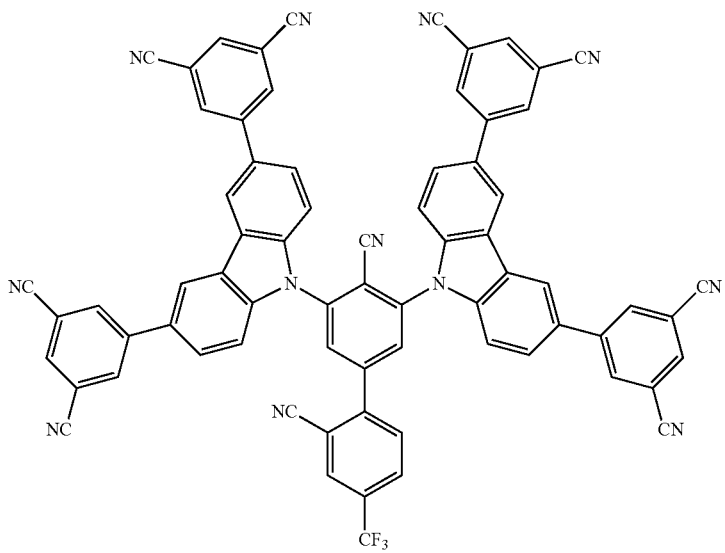

327 328
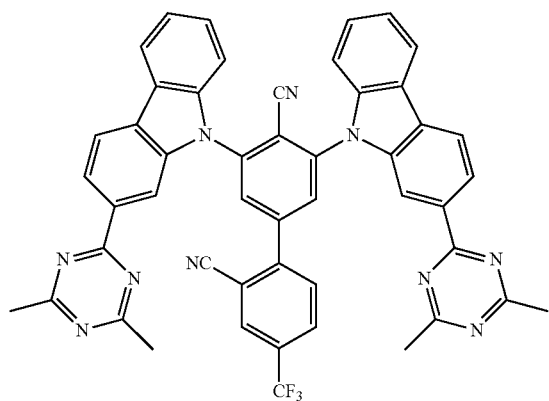 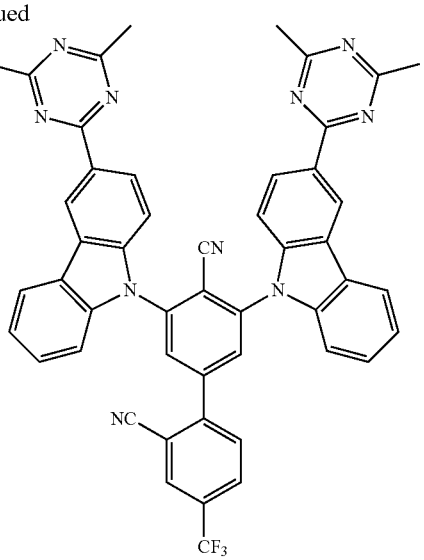
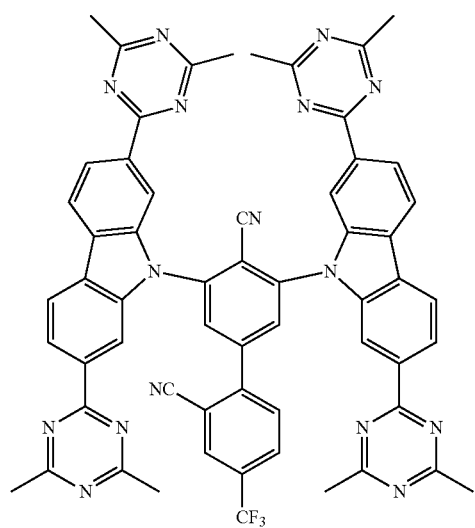
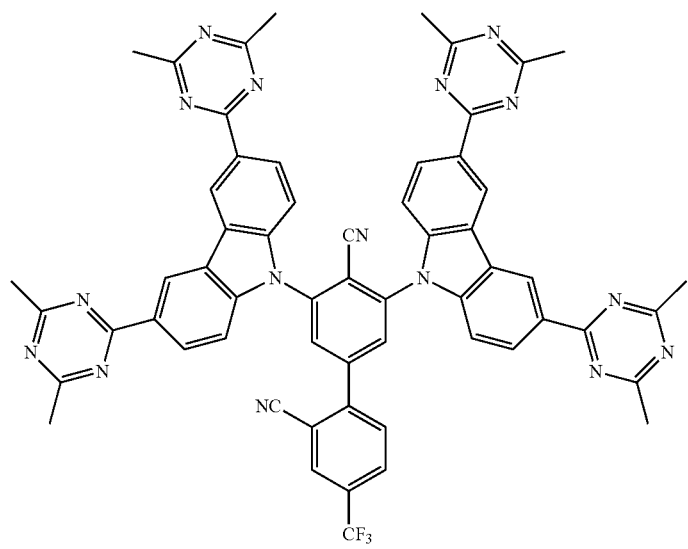

329
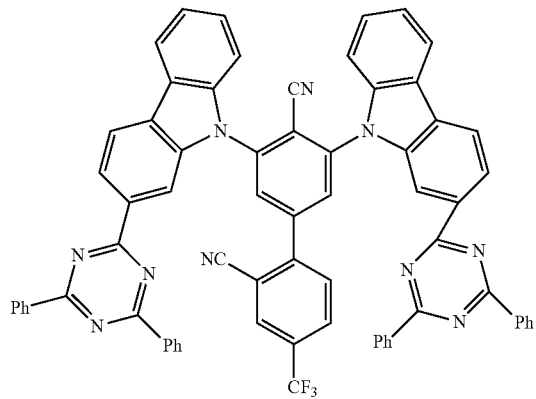
330
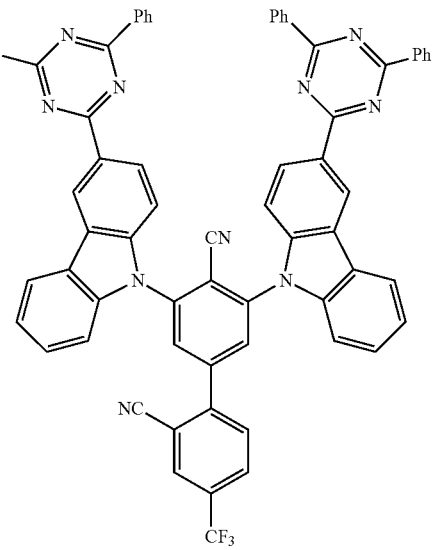
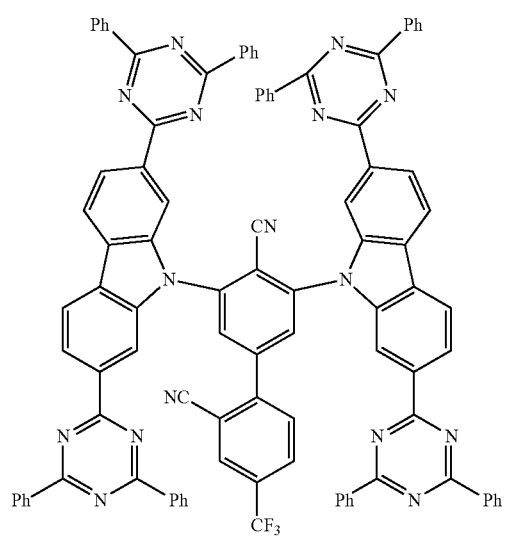
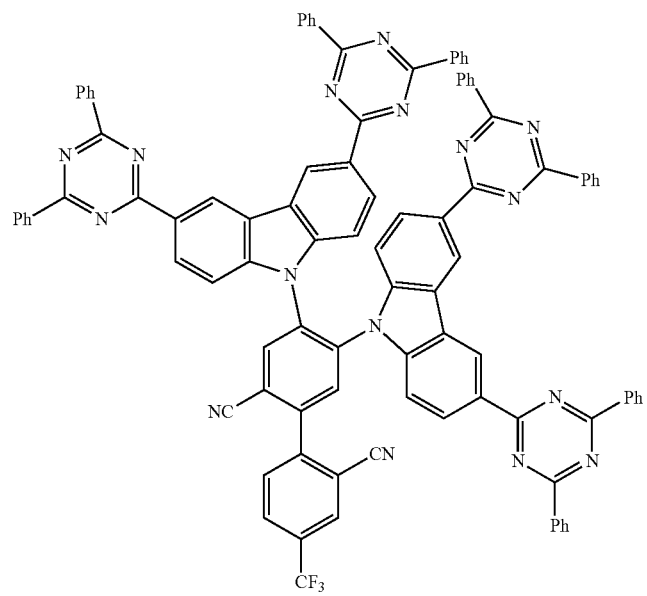
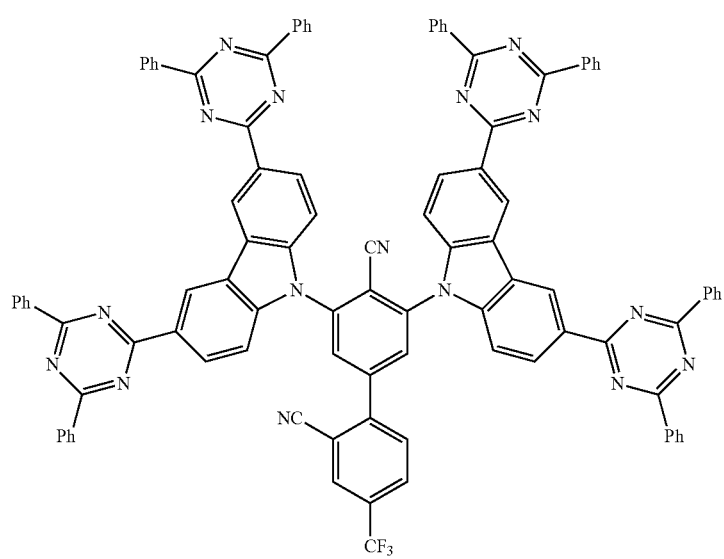

331
-continued
332
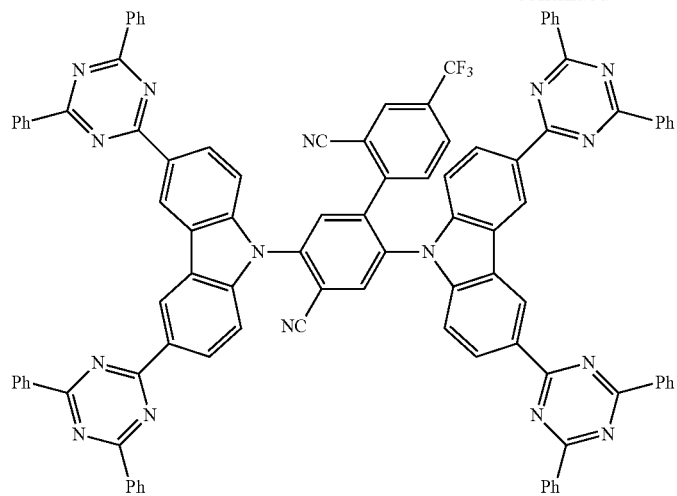
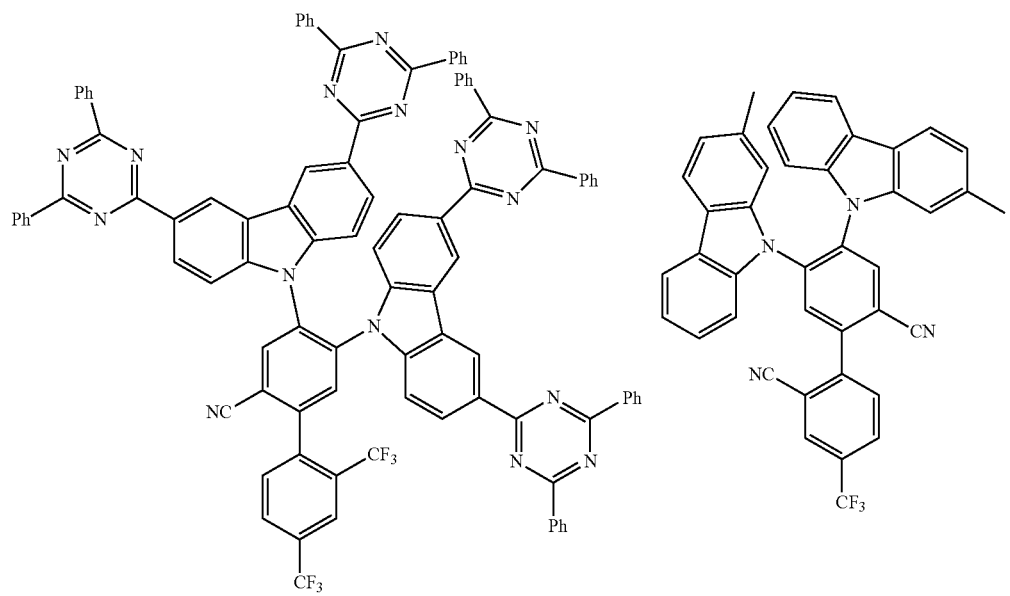
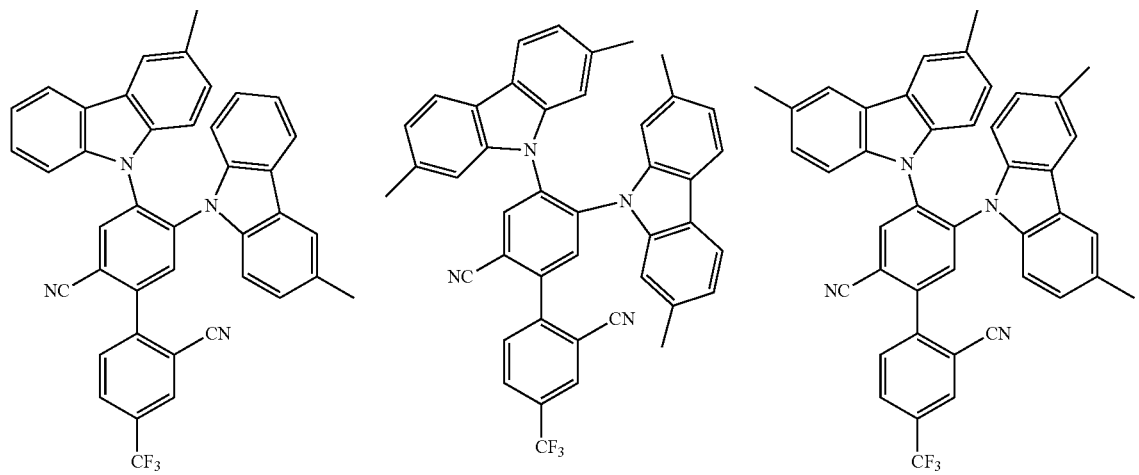

-continued
333
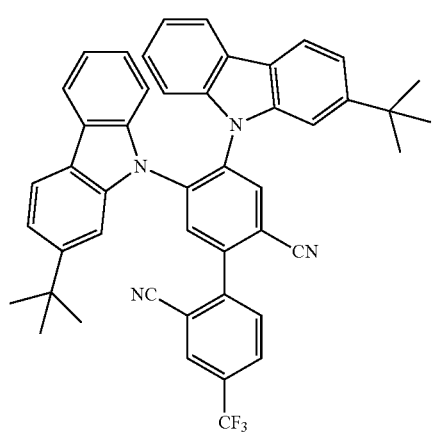
334
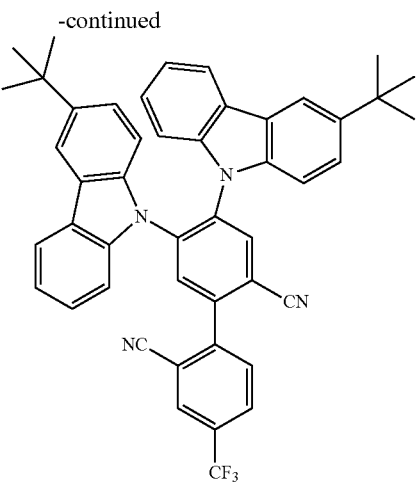
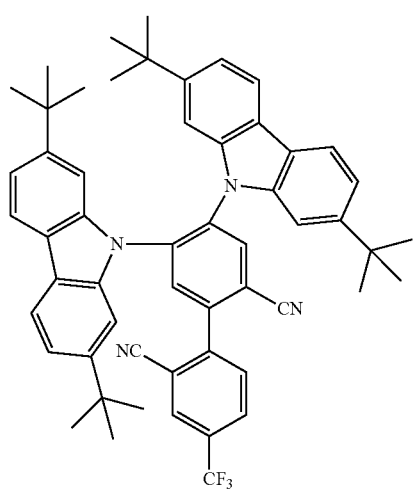
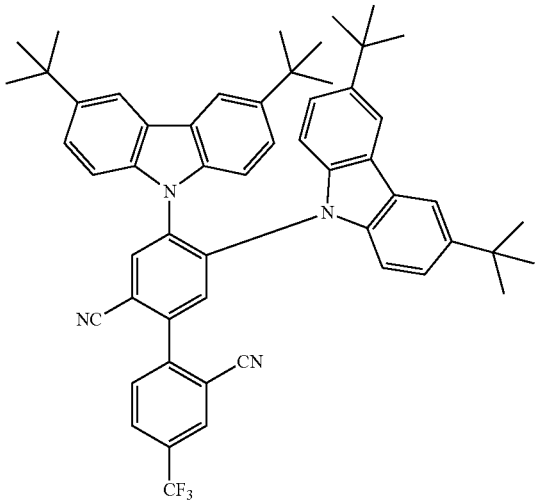
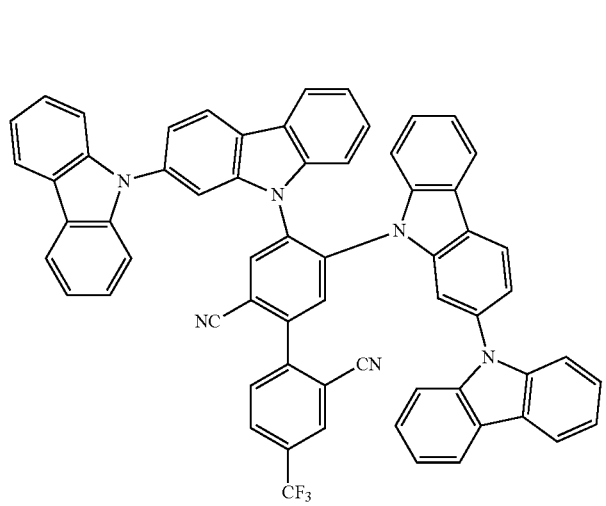
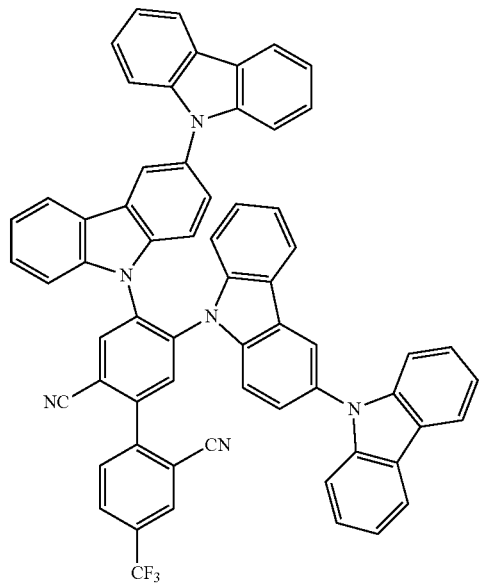

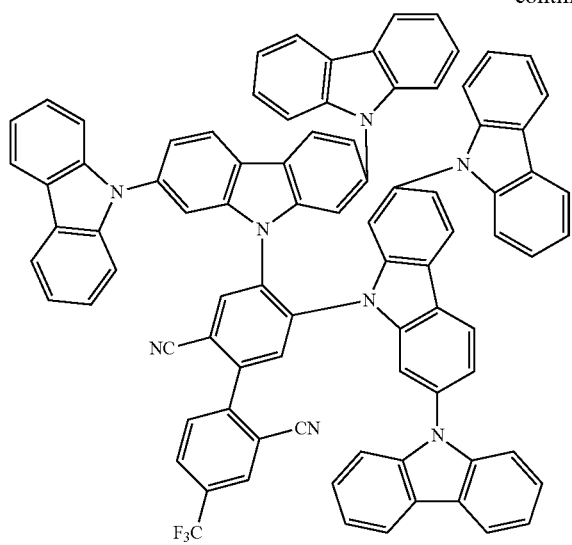
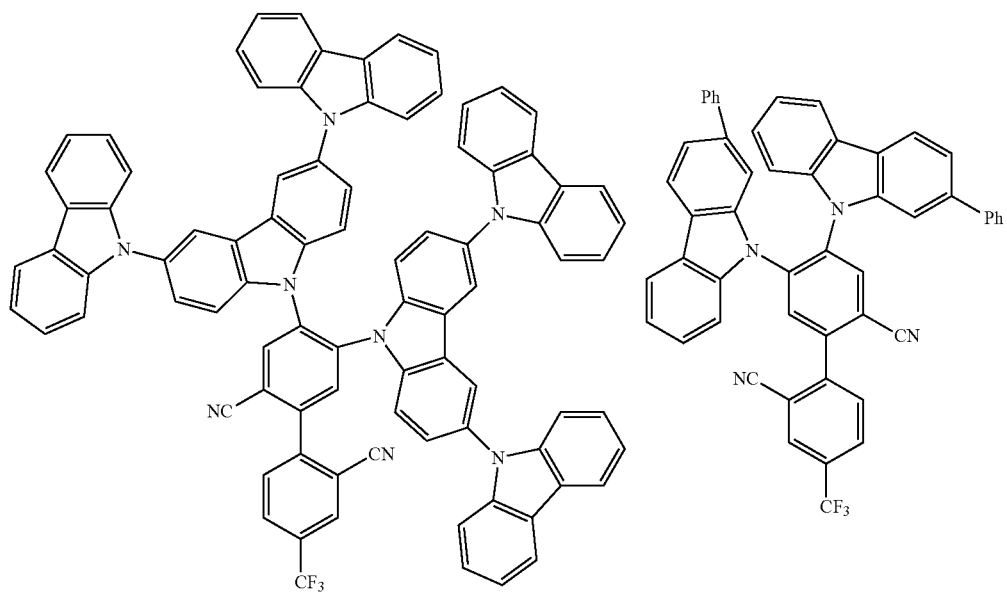
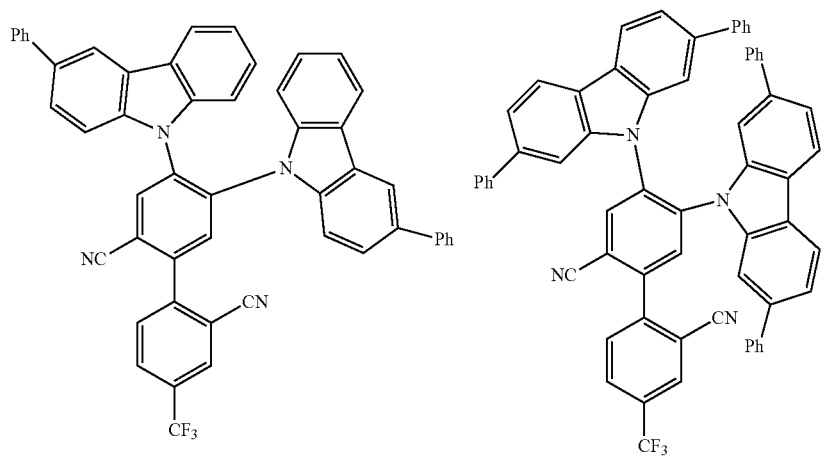

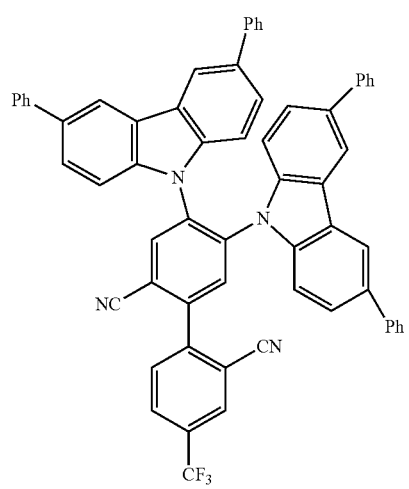
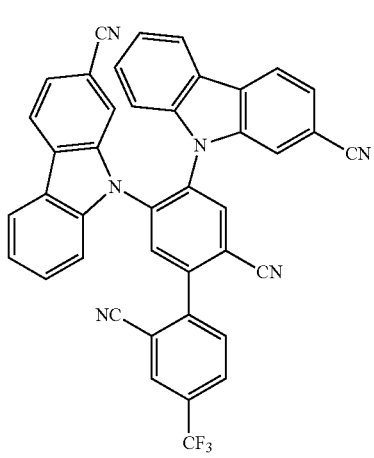
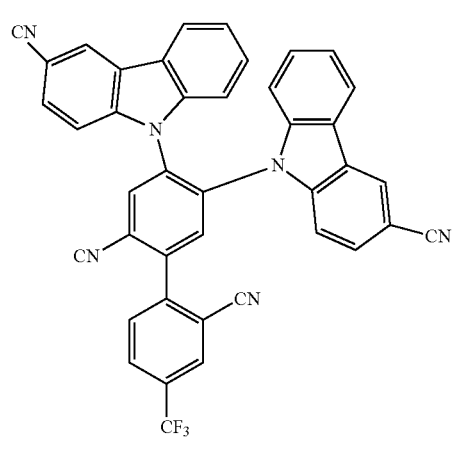
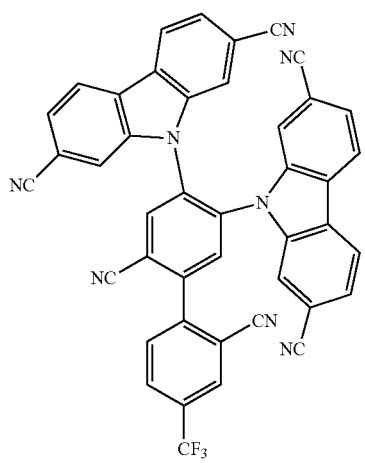
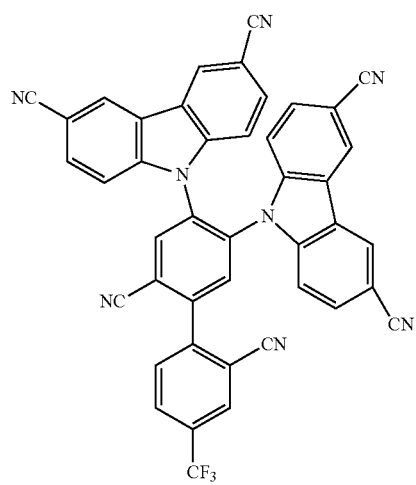
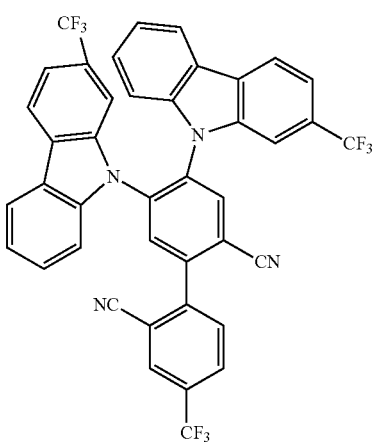

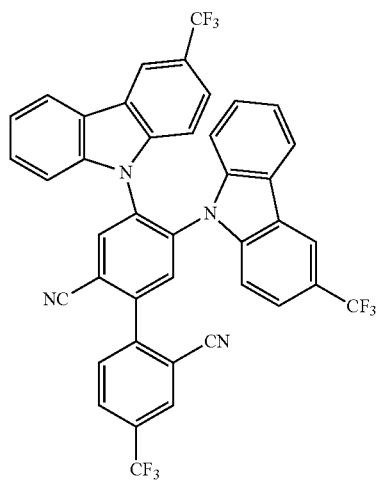
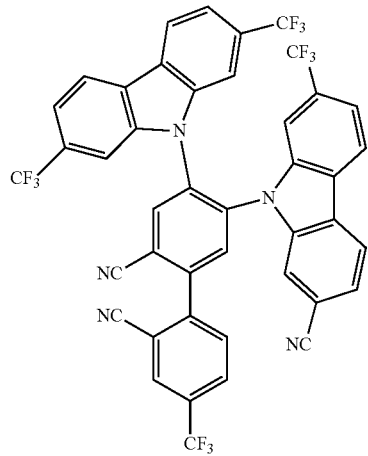
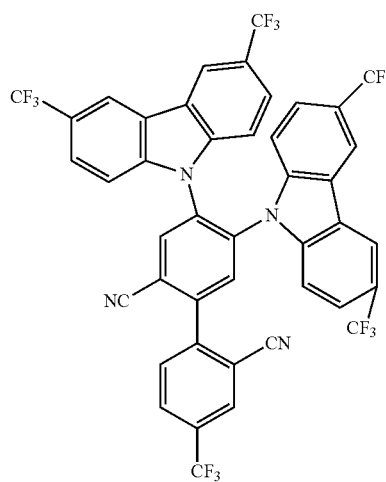
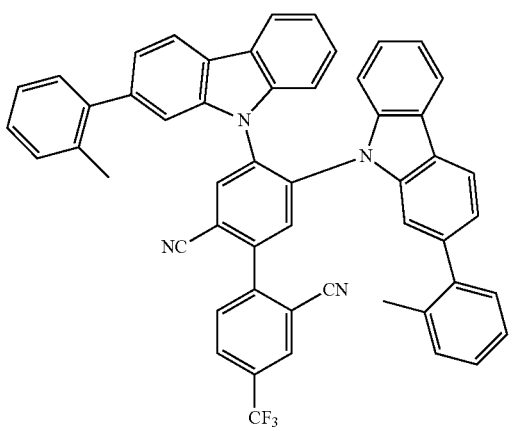
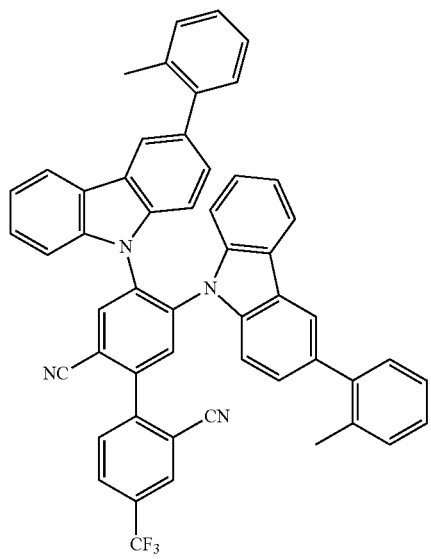
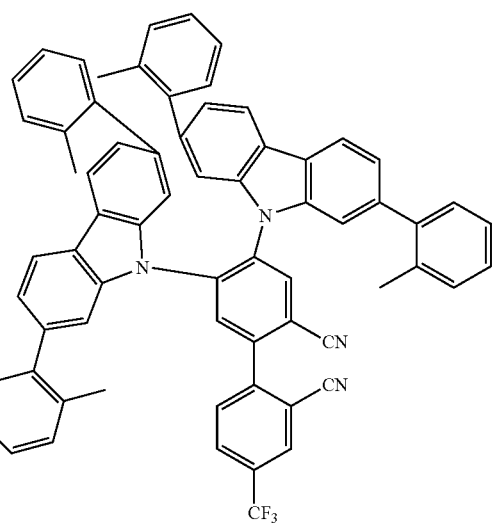

-continued
341
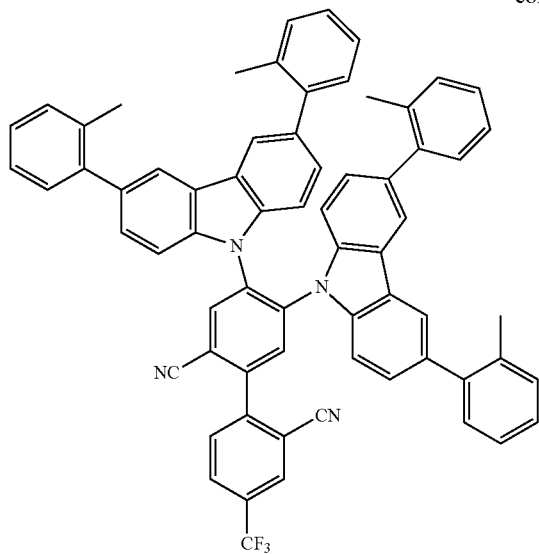
342
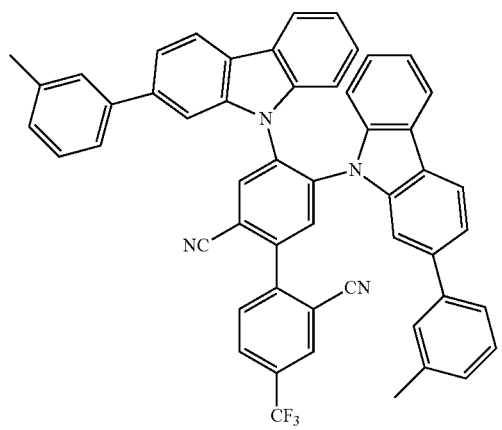
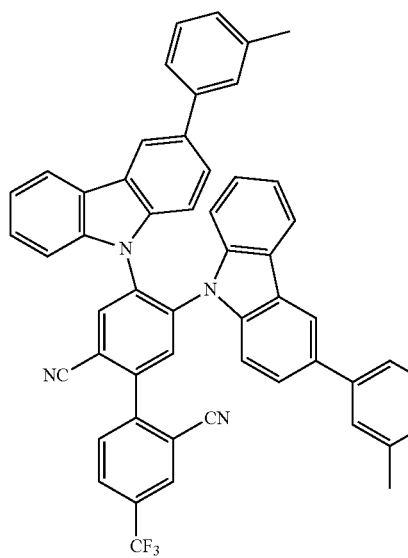
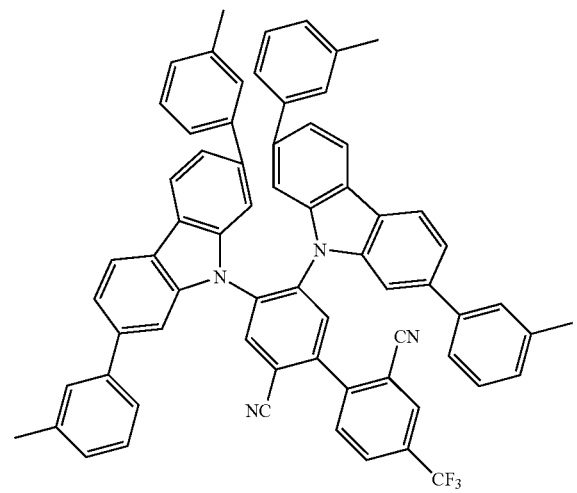
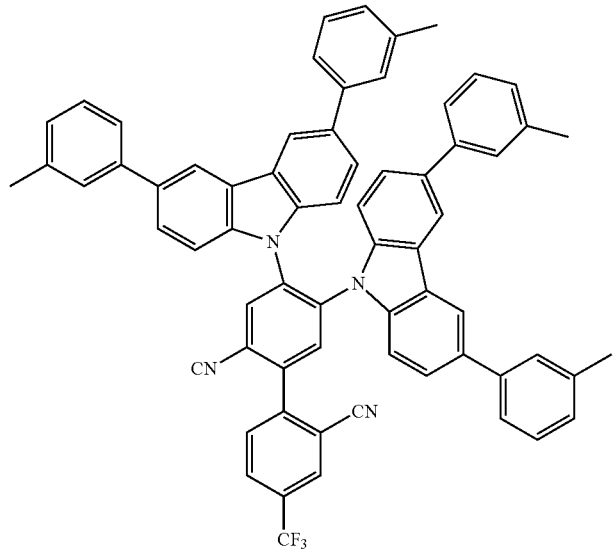
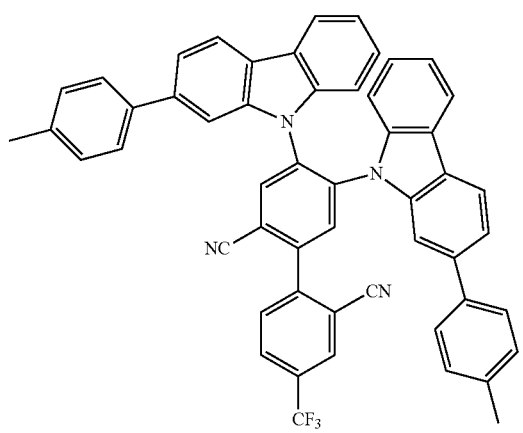

343
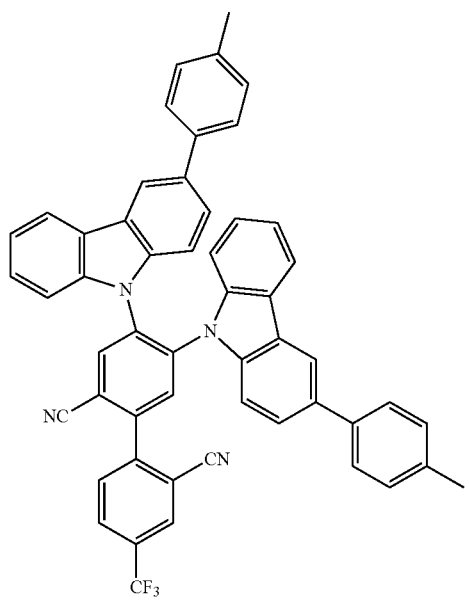
344
-continued
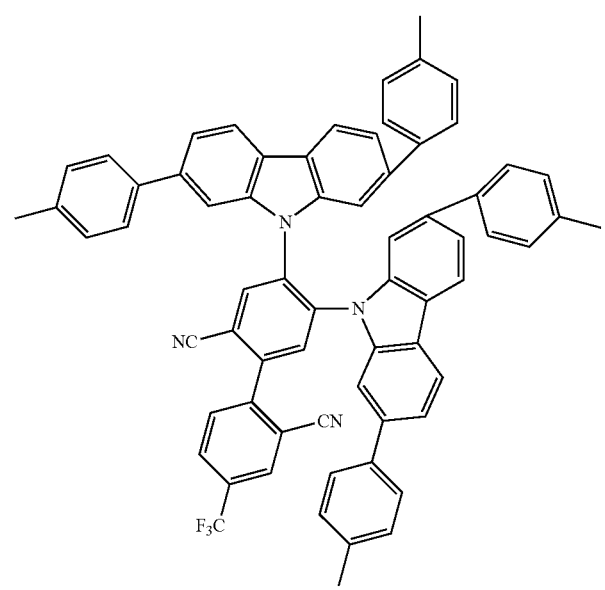
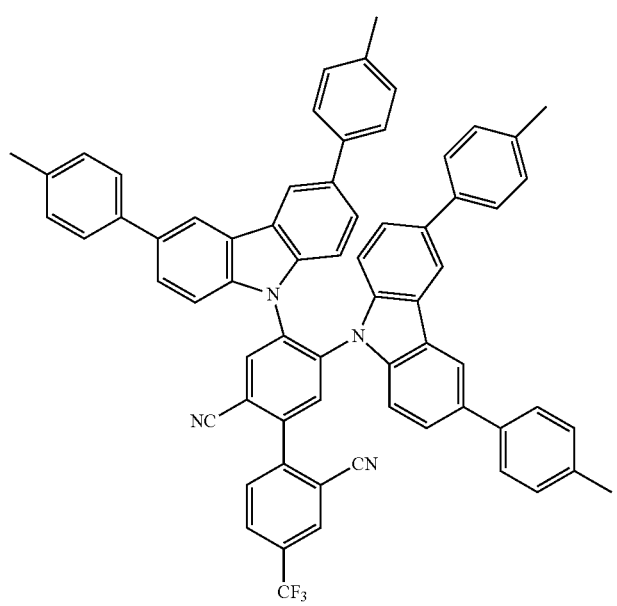
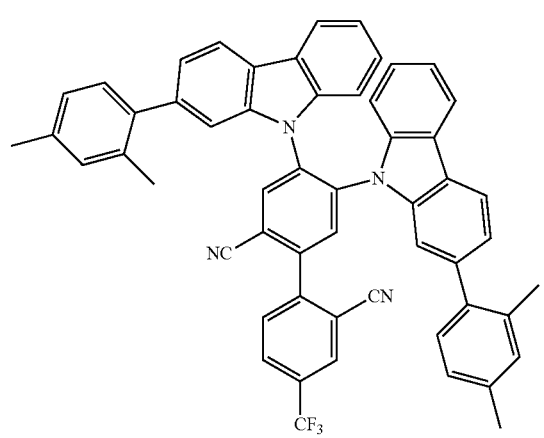

-continued
| 345 | 346 |
|---|---|
| 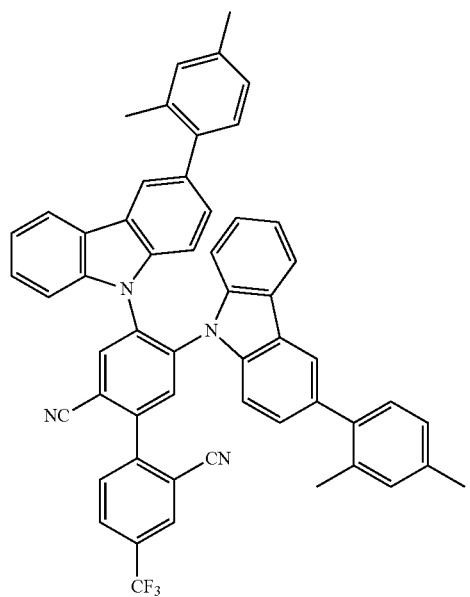 | 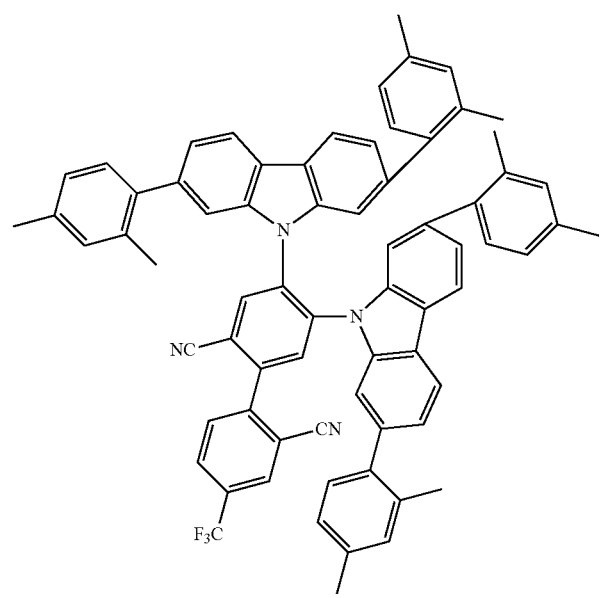 |
| 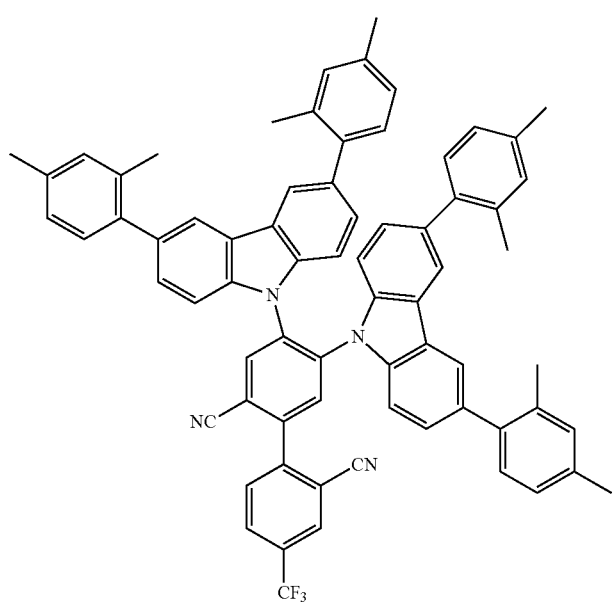 | 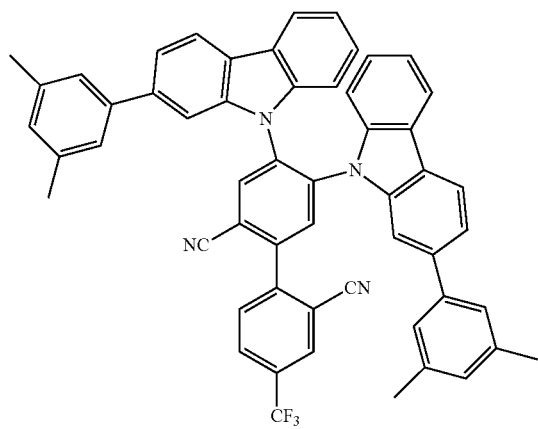 |

-continued
| 347 | 348 |
|---|---|
| 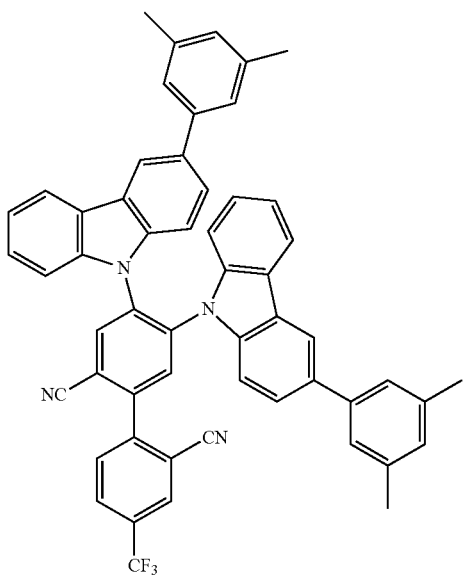 | 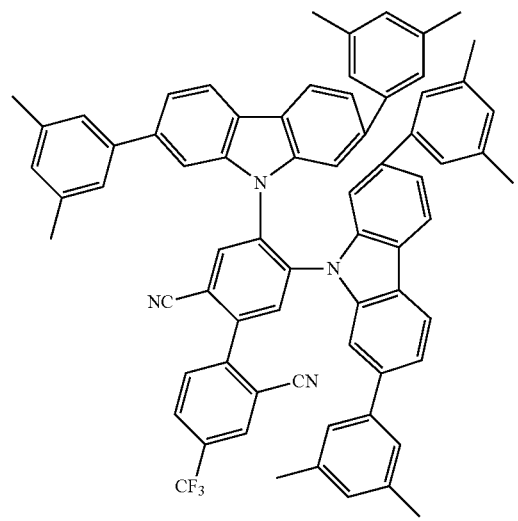 |
| 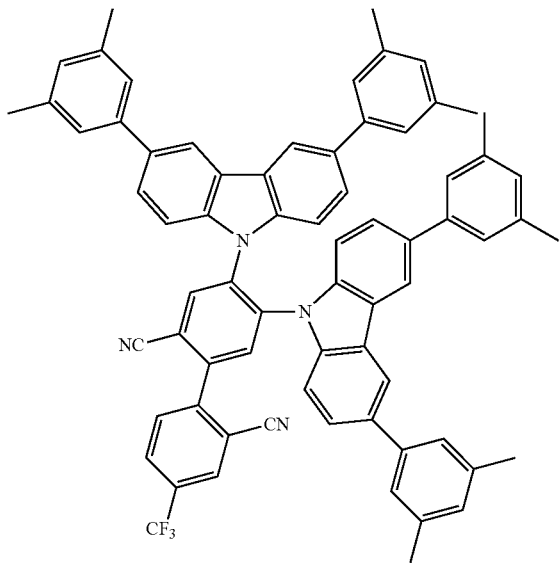 | 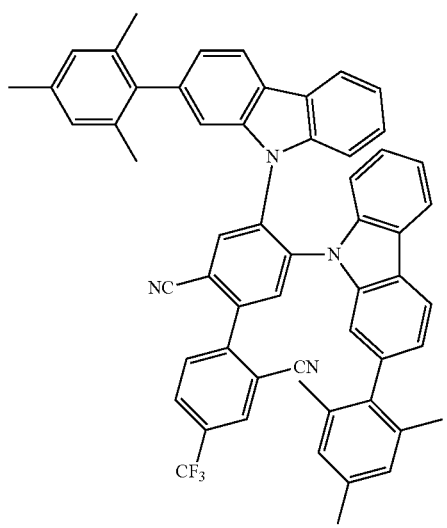 |
| 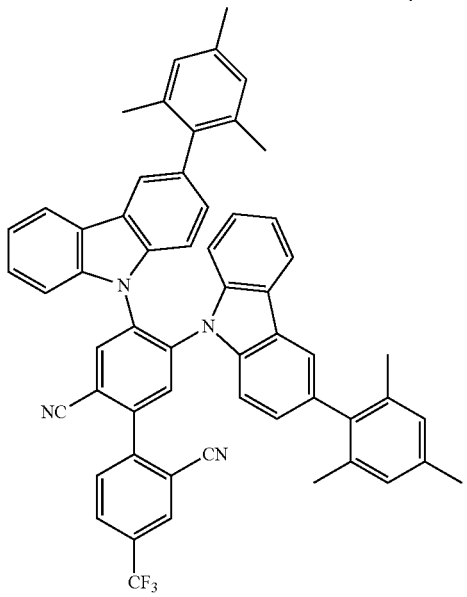 | 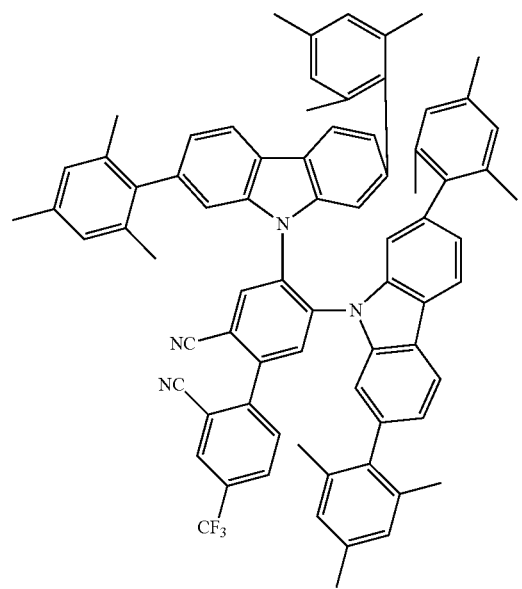 |

349
350
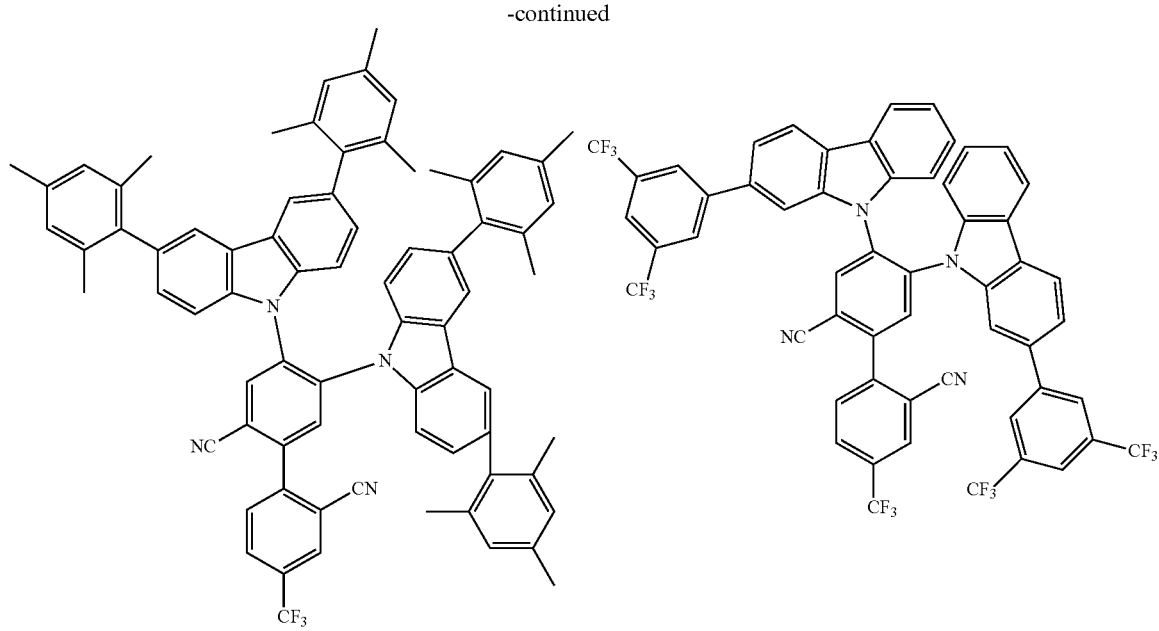
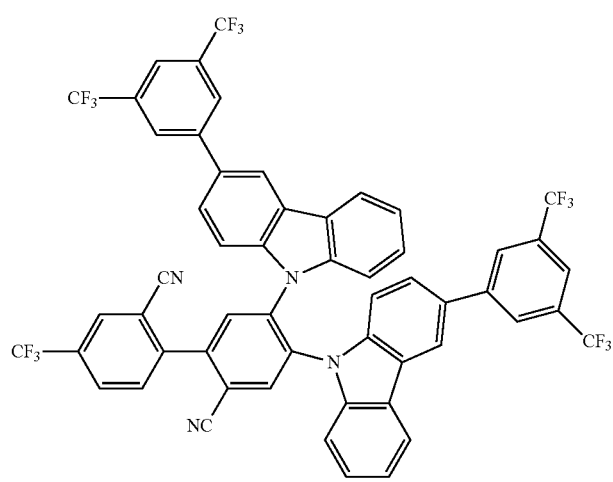
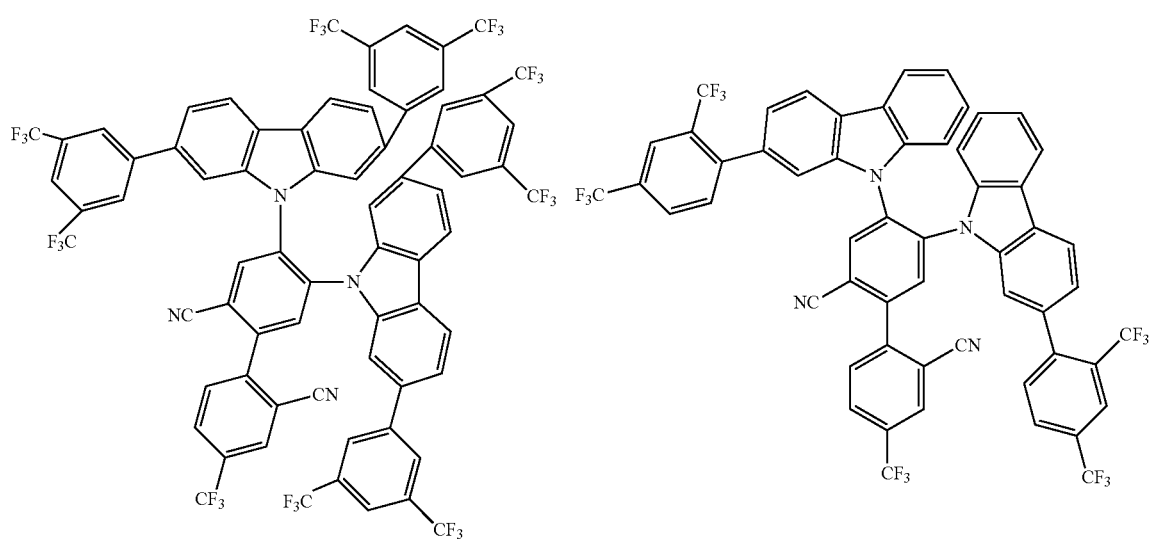

351 352
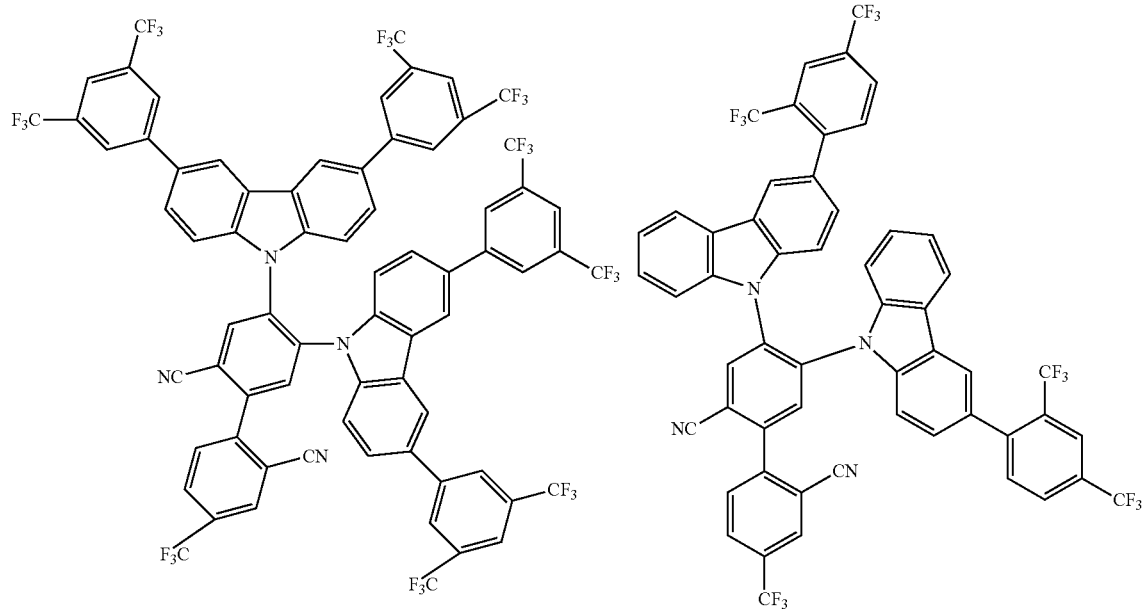
-continued
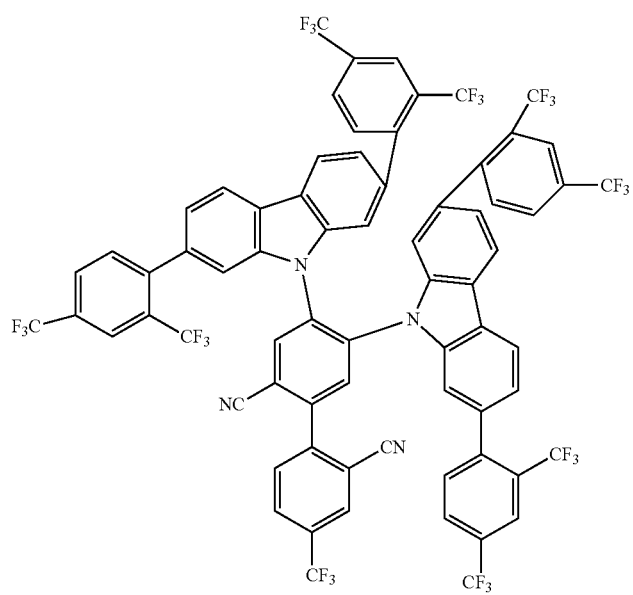

353    354
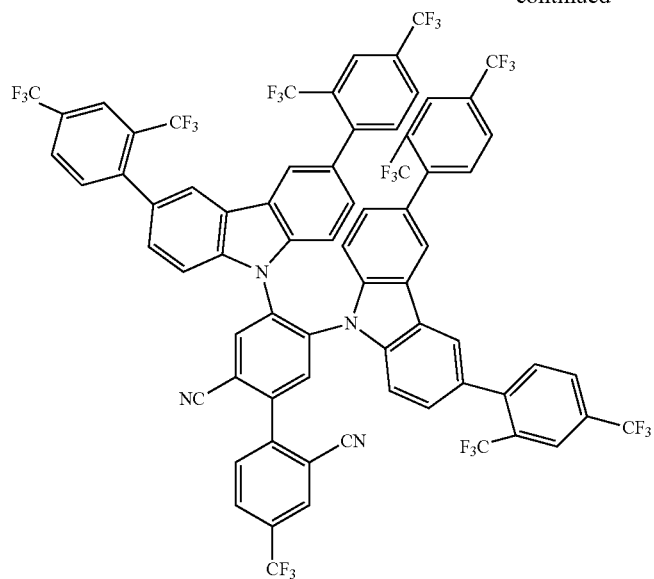
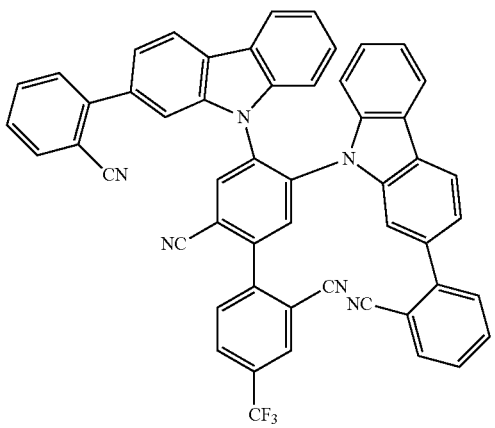
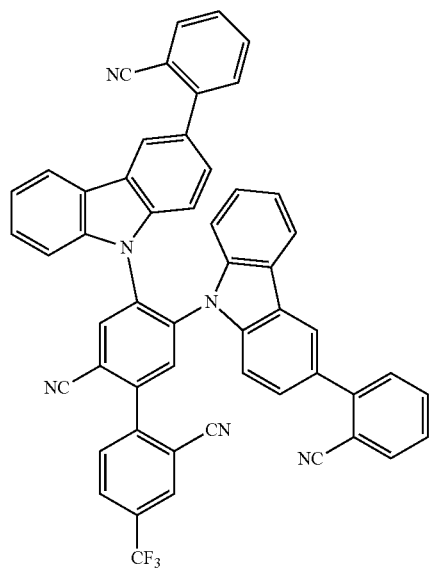
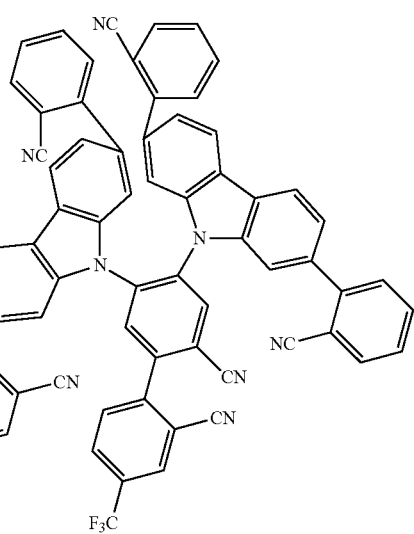
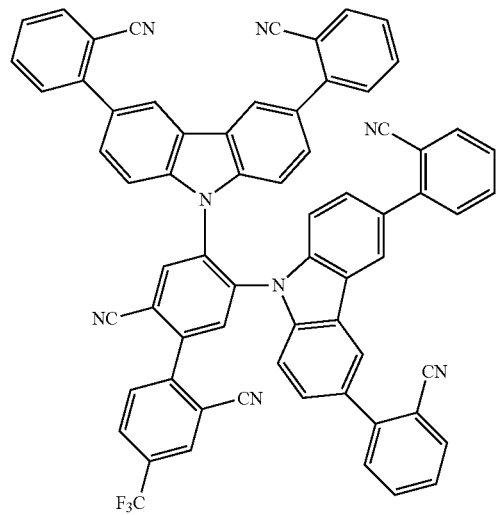
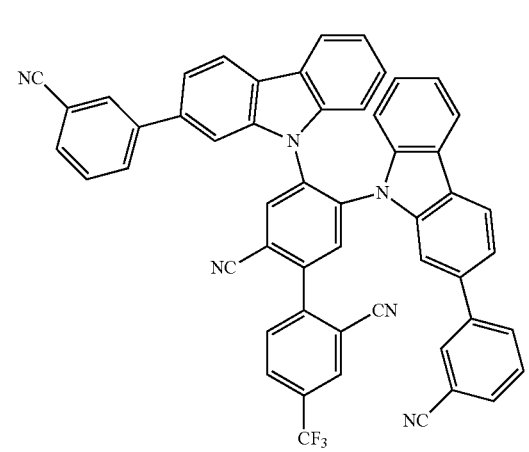

355
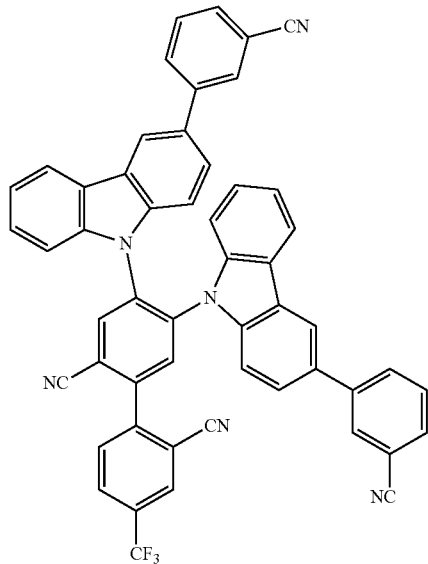
356
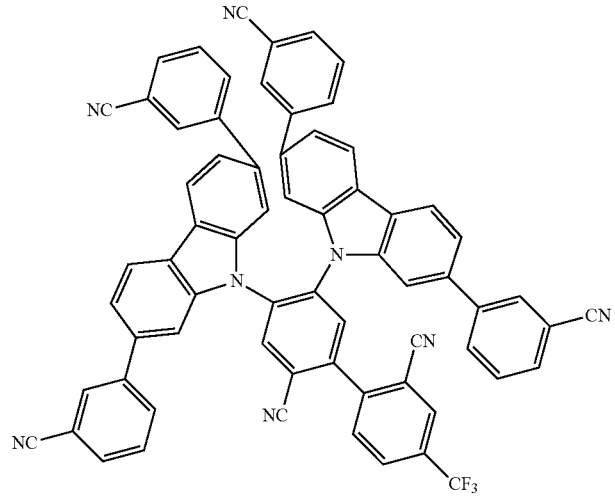
-continued
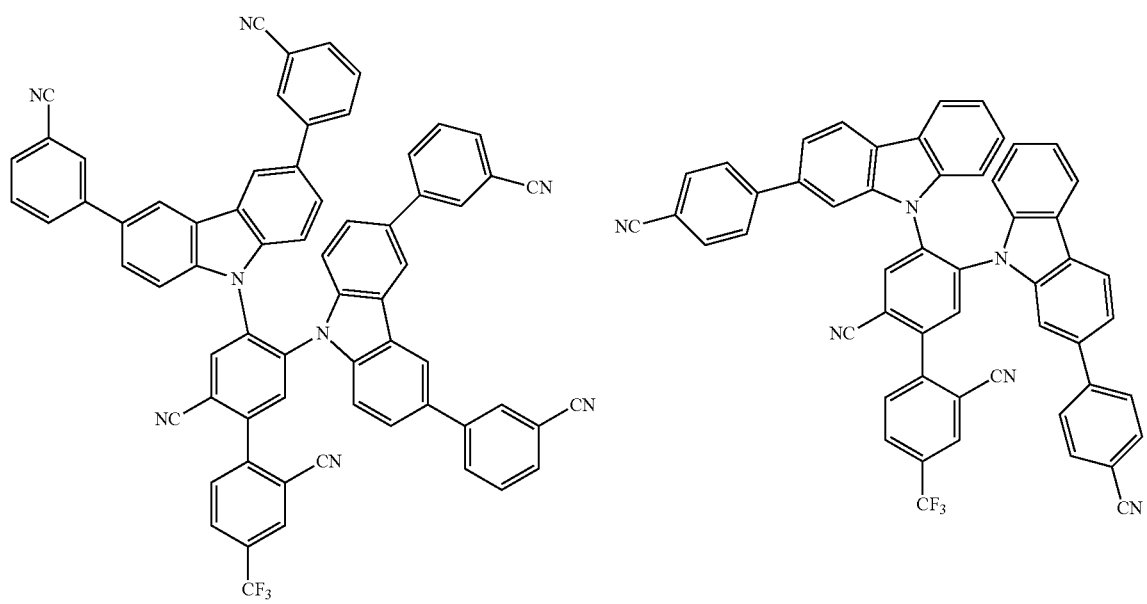

357
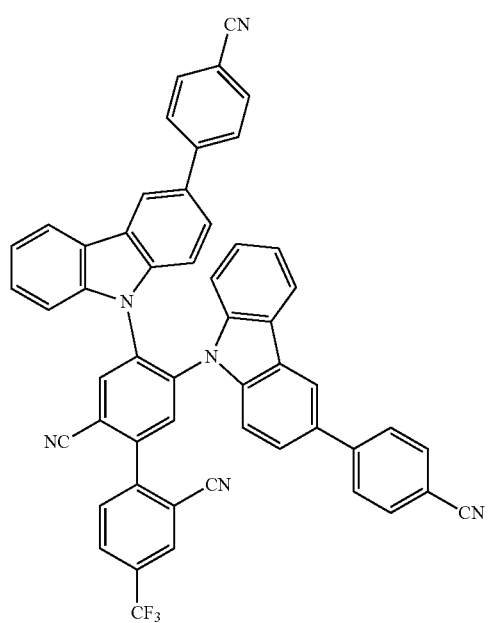
358
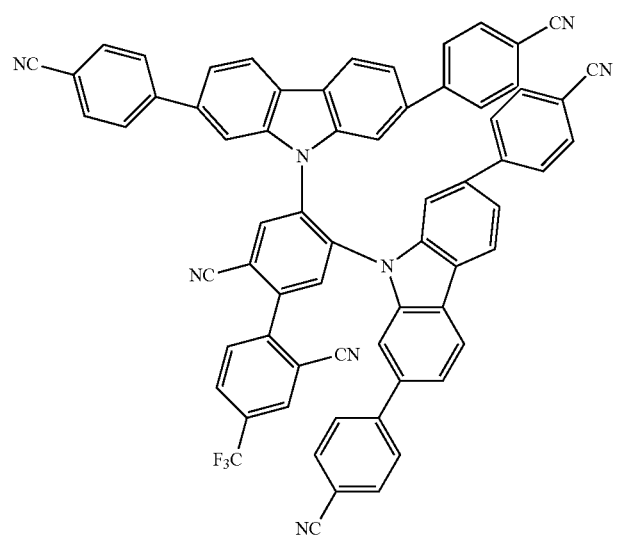
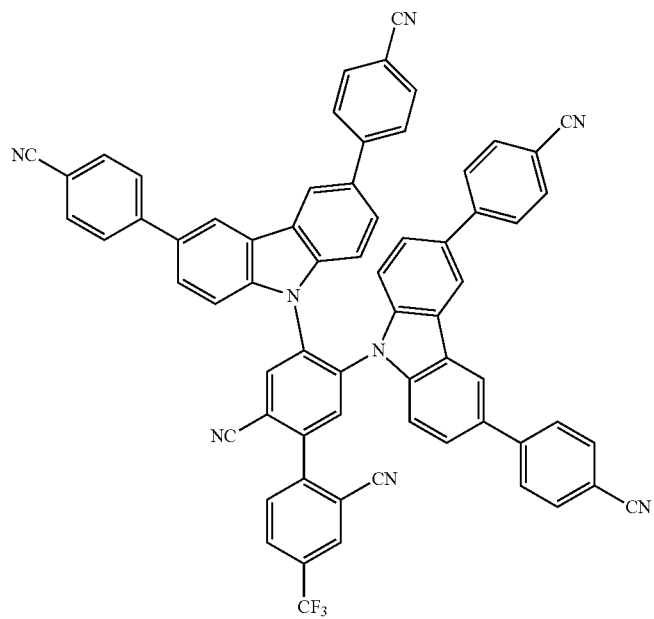

359
360
-continued
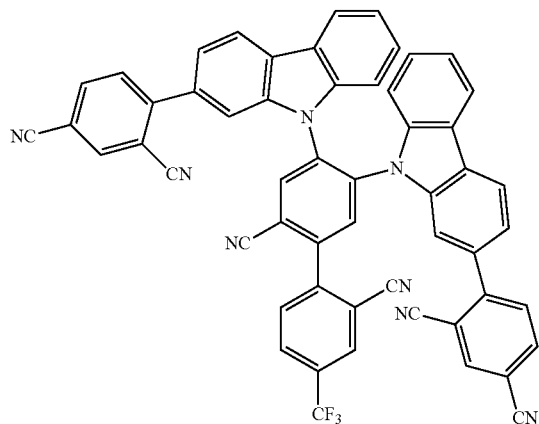
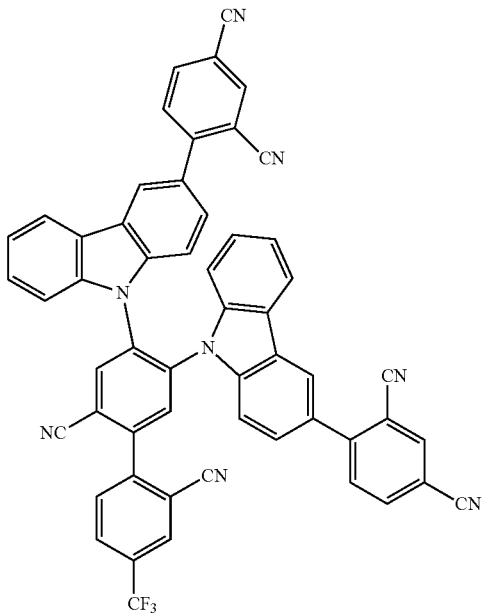
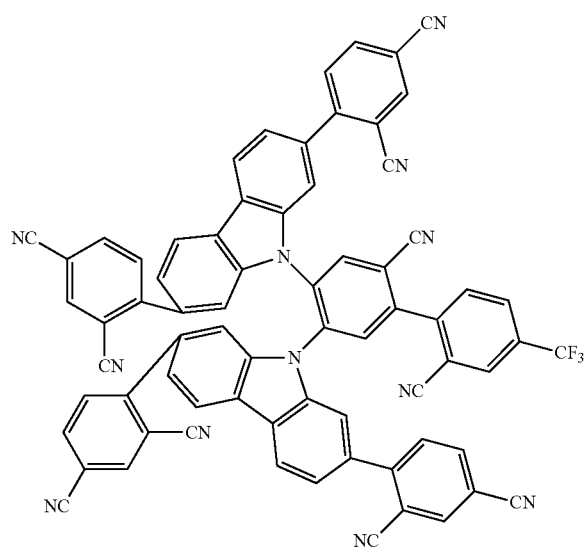

-continued
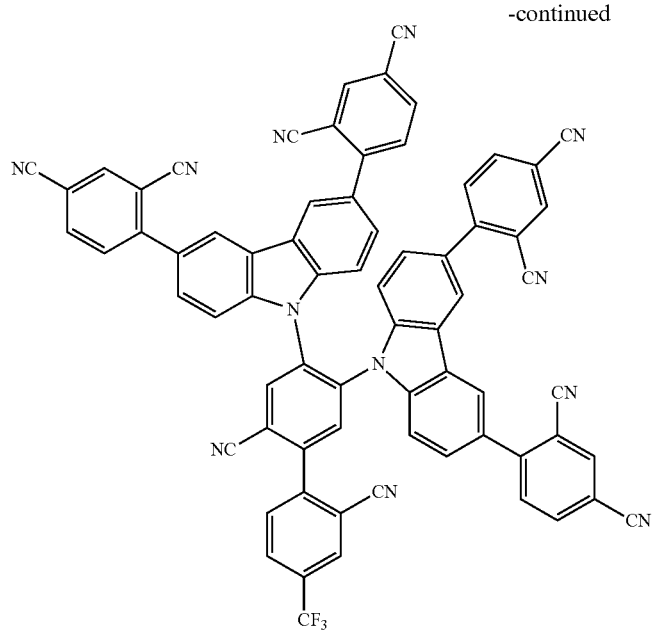
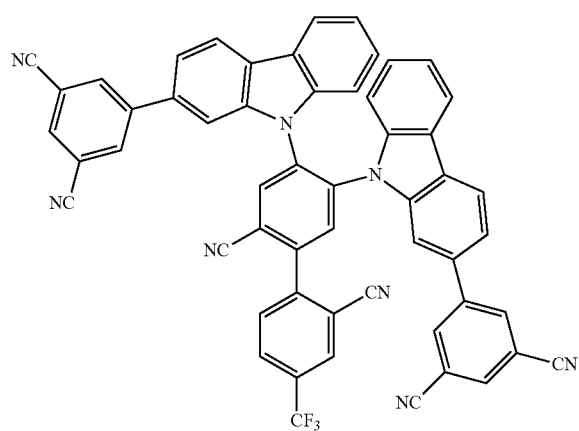
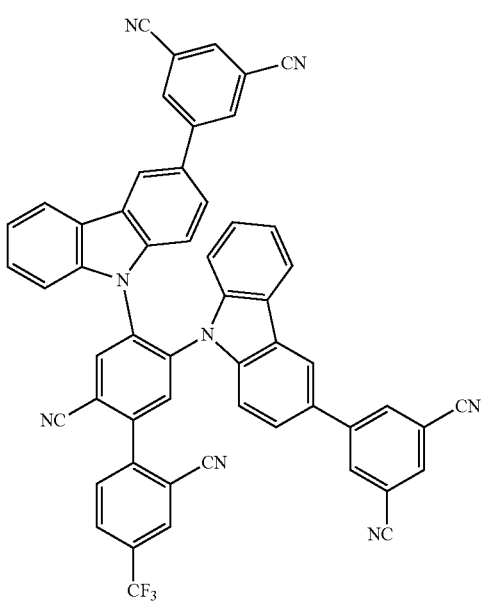
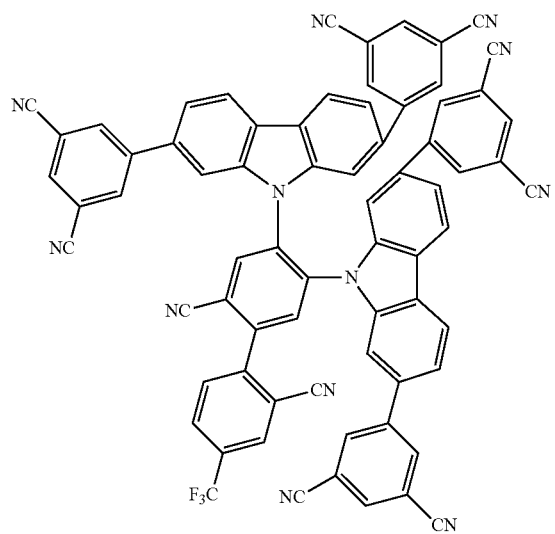

-continued
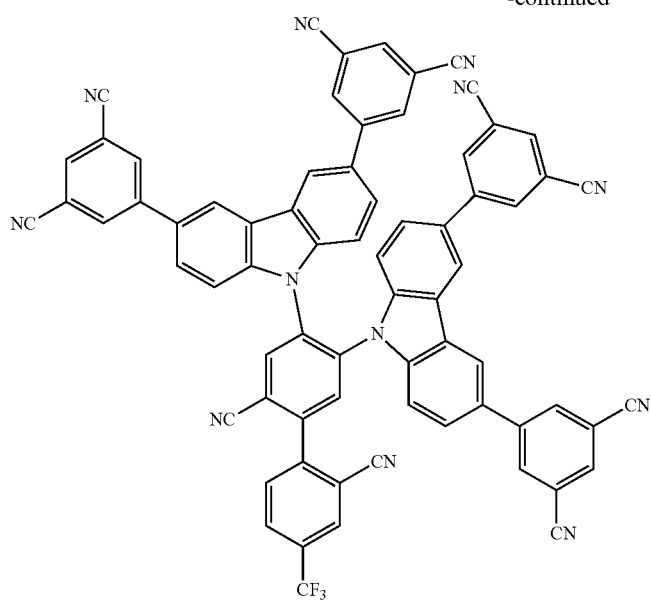
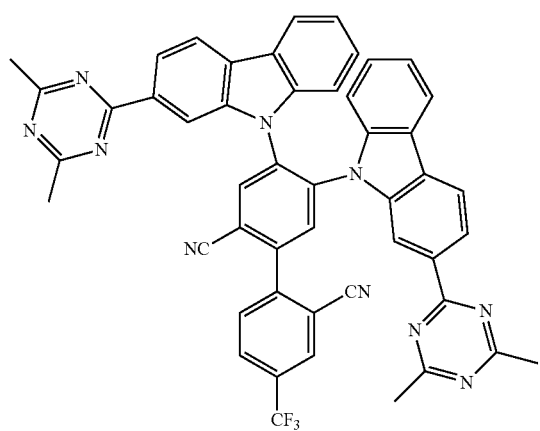
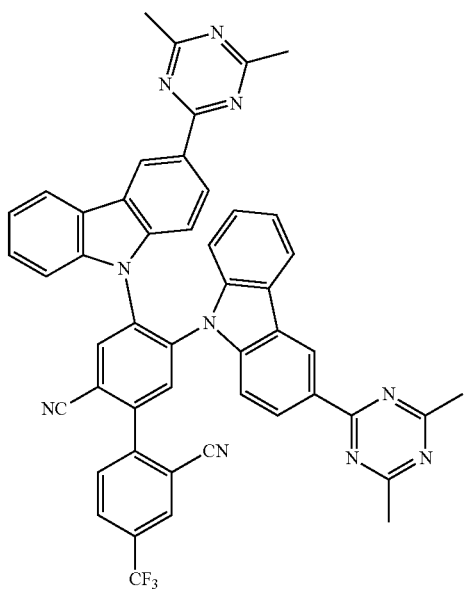
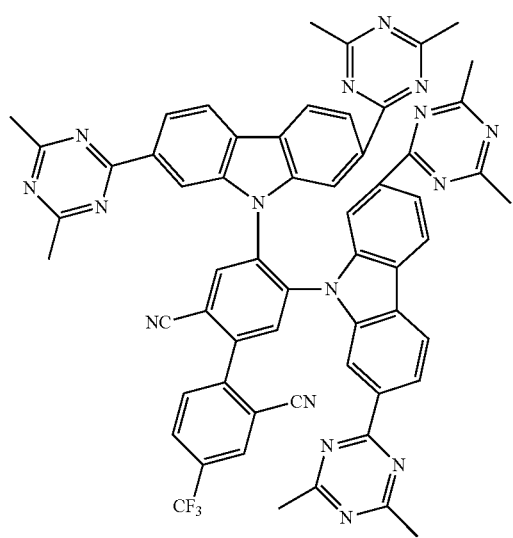

365
-continued
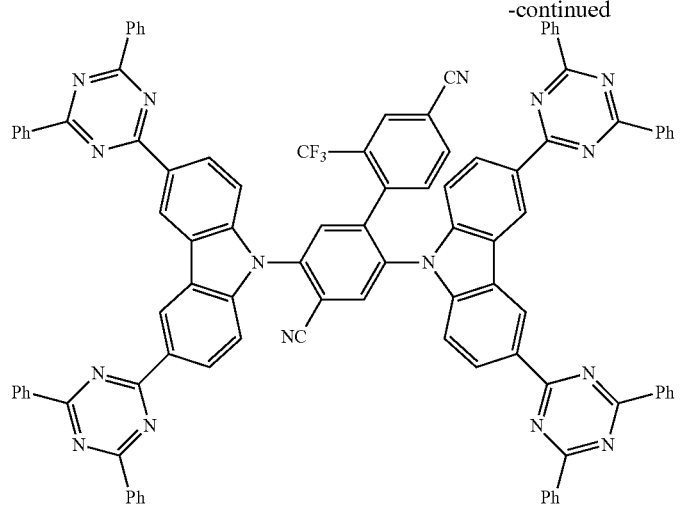
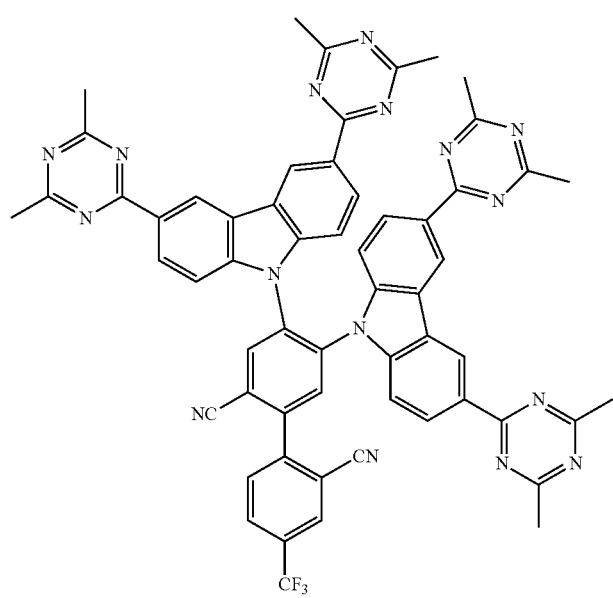
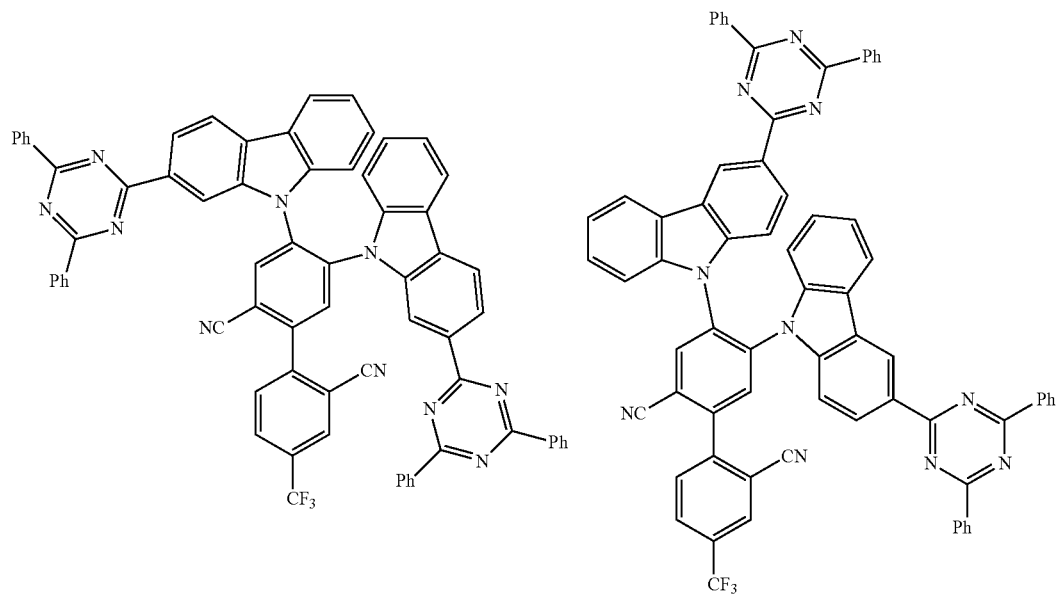
366

-continued
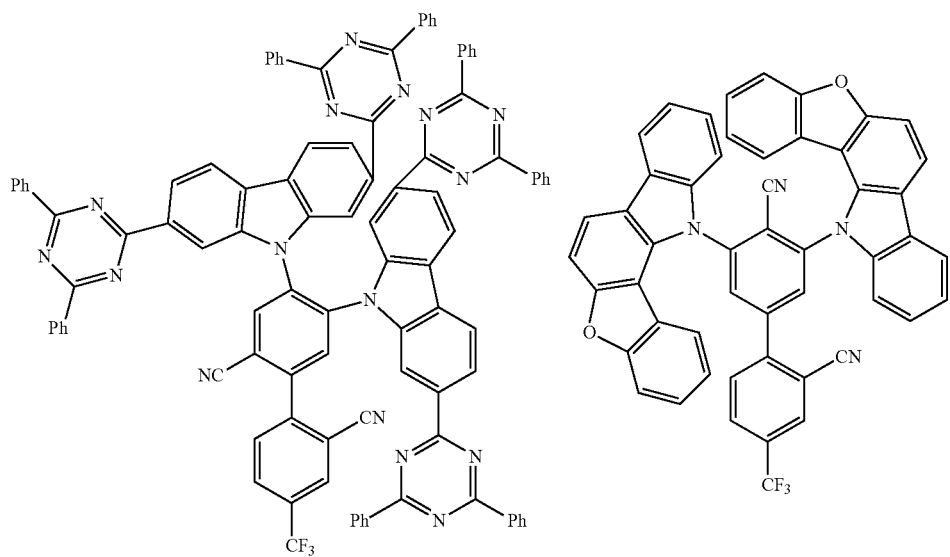
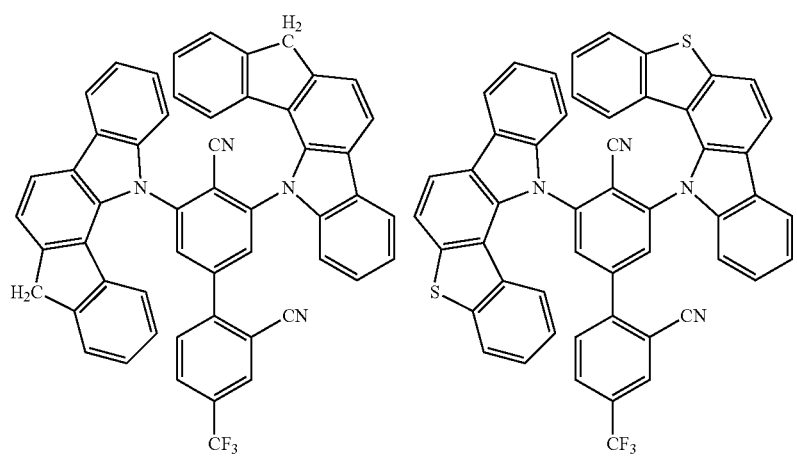
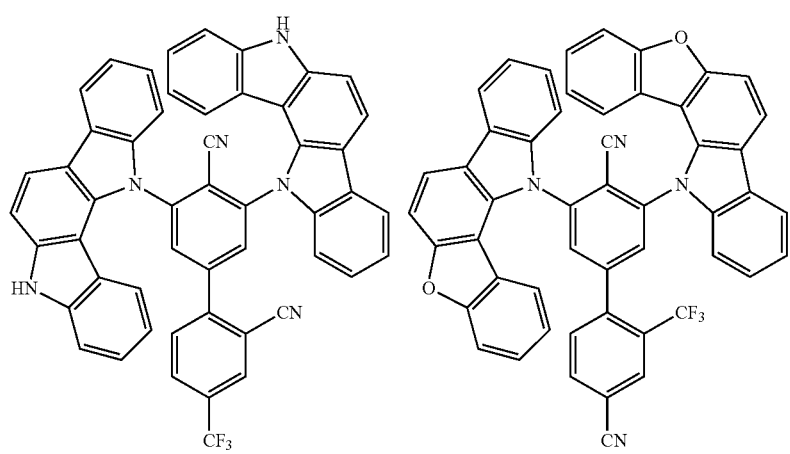

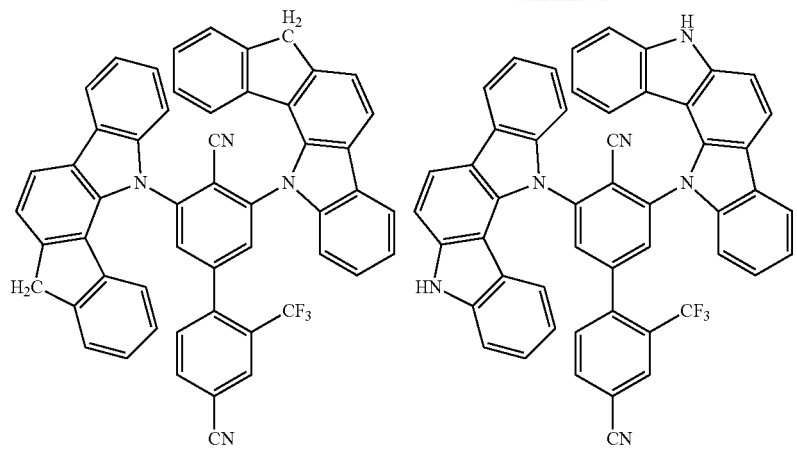
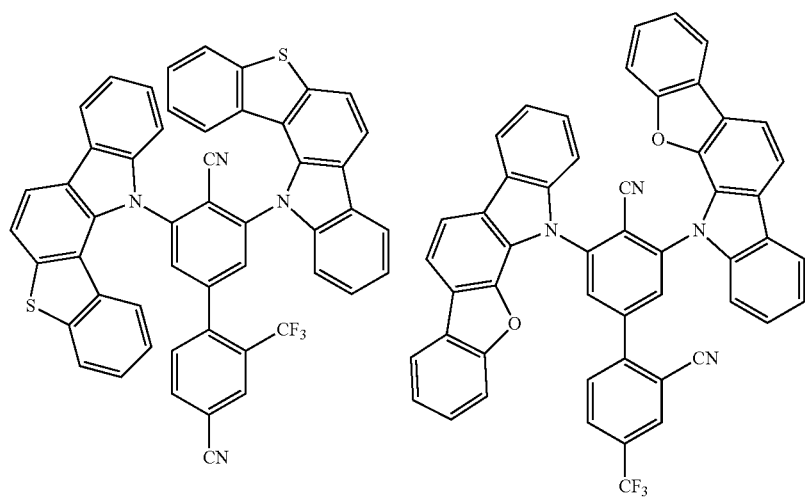
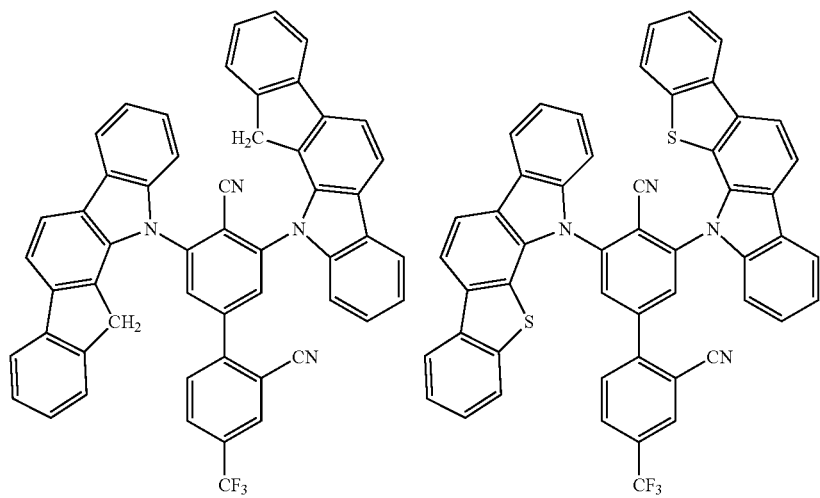

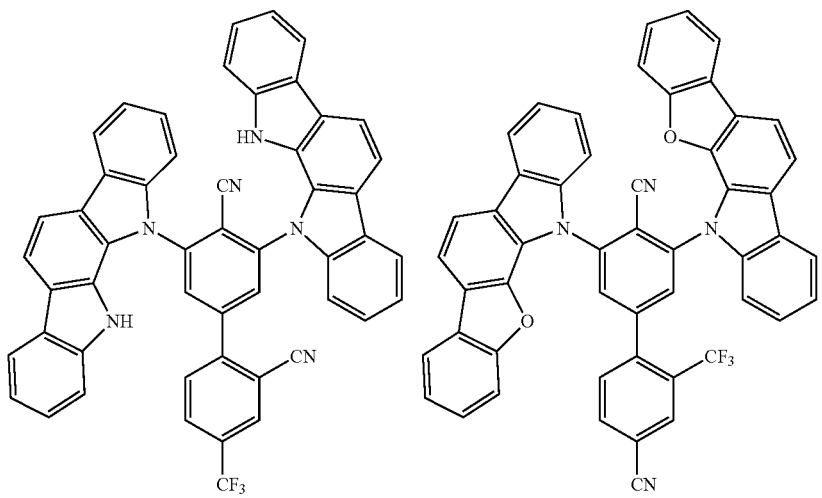
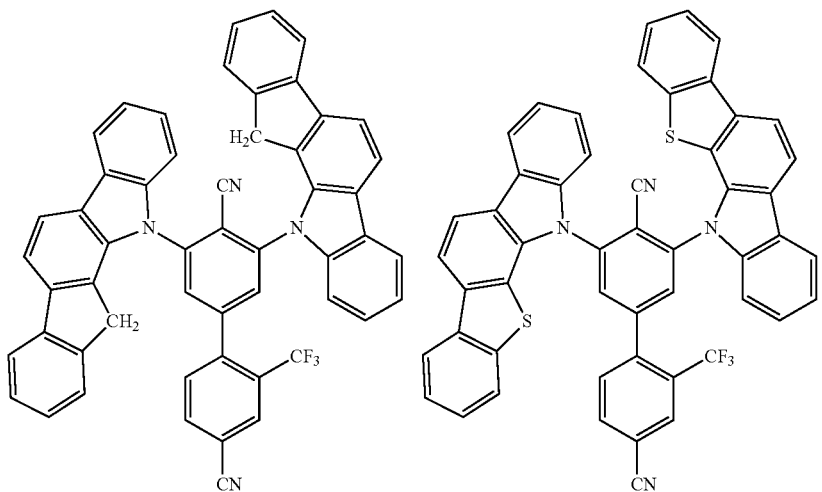
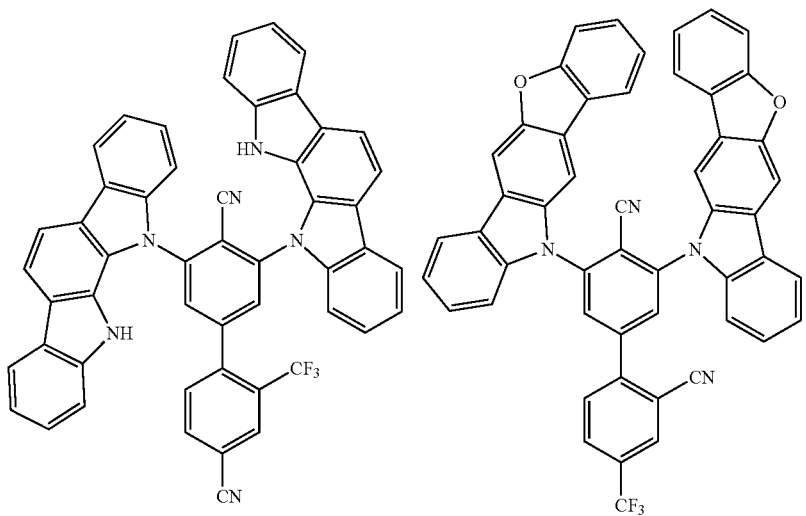

-continued
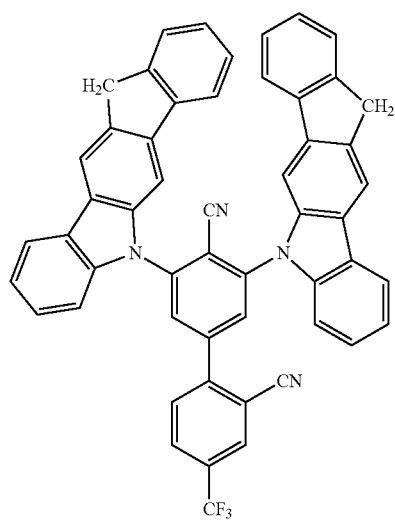
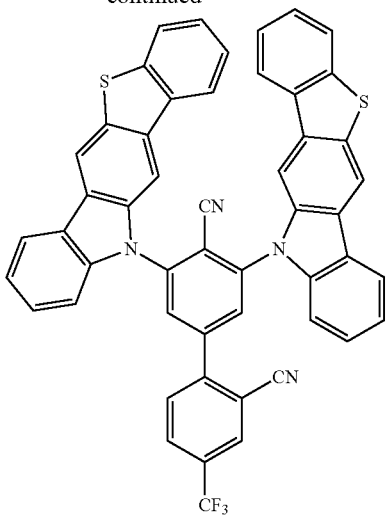
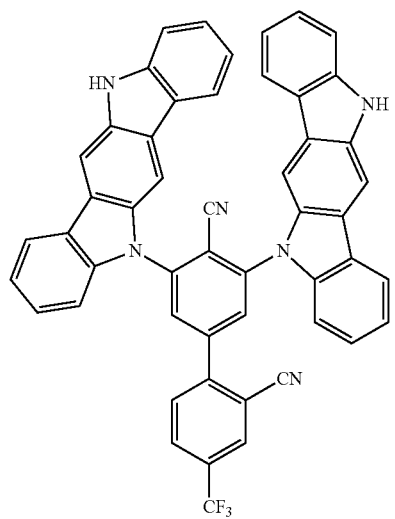
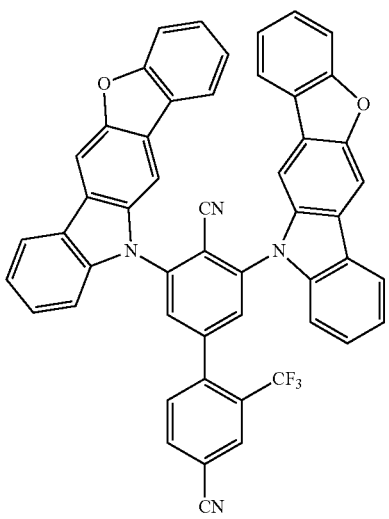
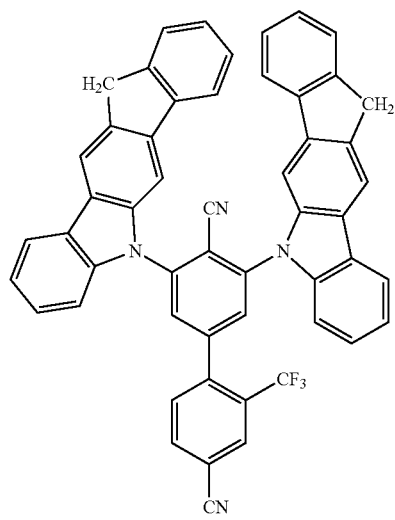
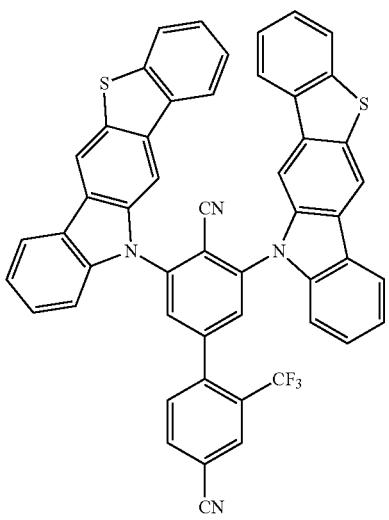

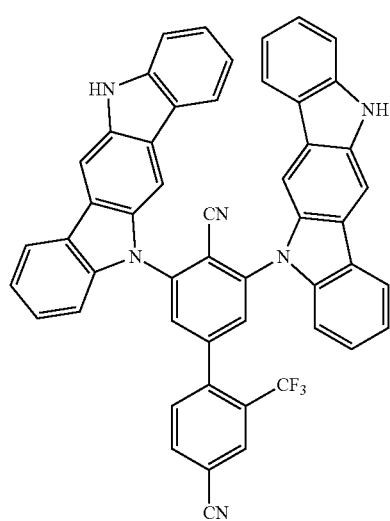
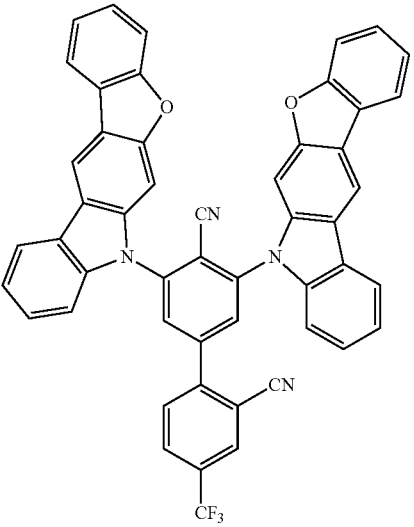
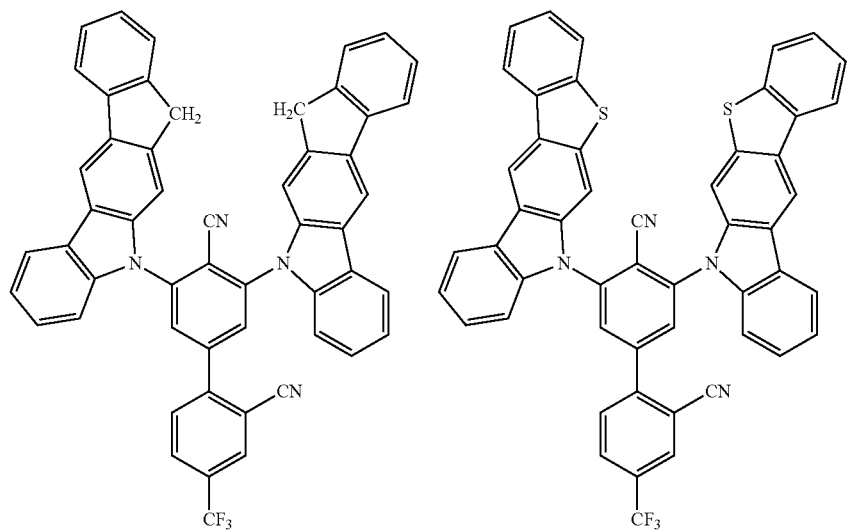
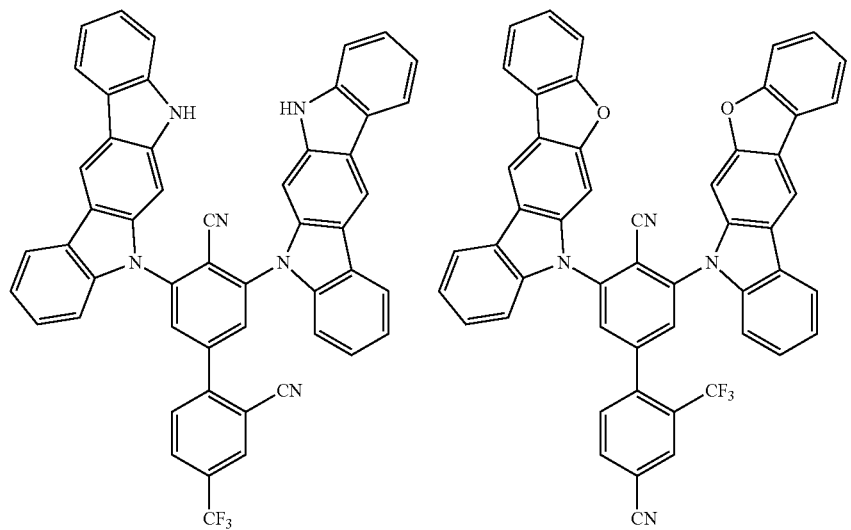

-continued
377
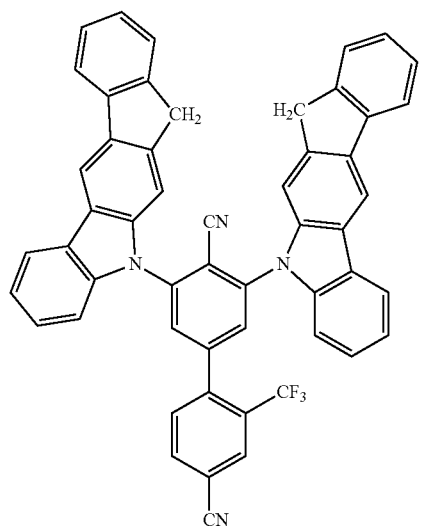
378
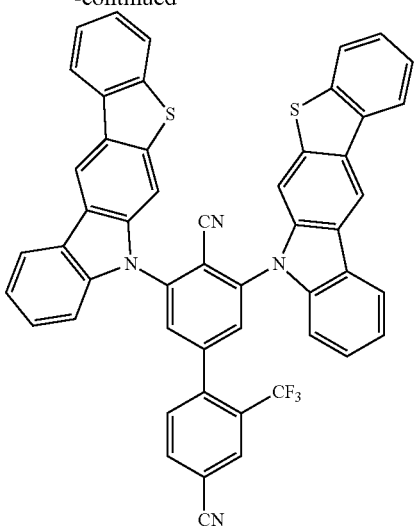
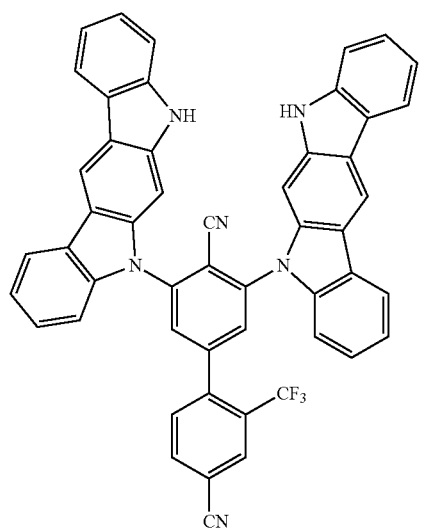
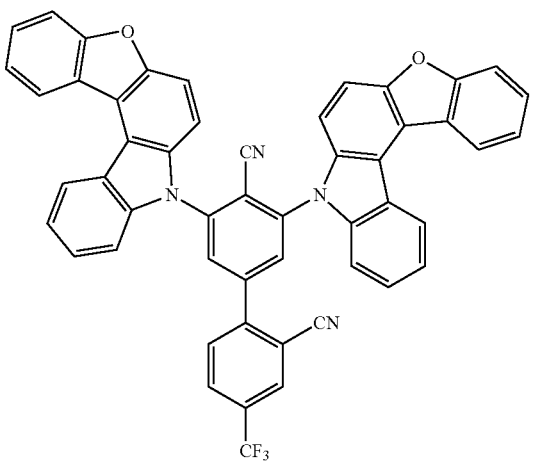
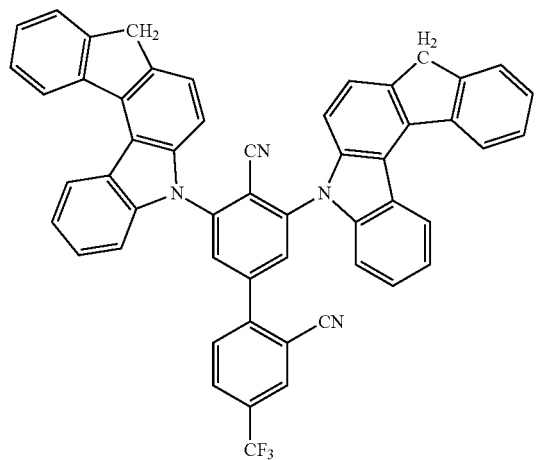
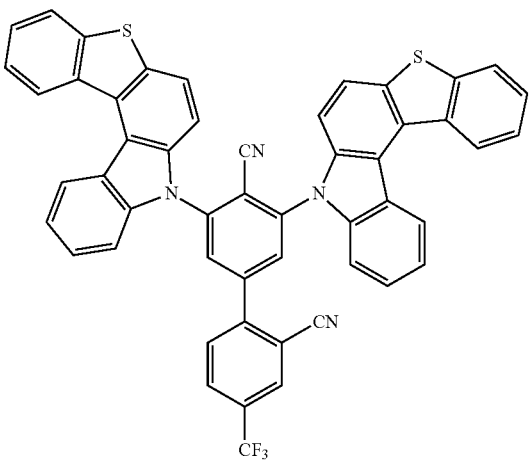

-continued
| 379 | 380 |
|---|---|
| 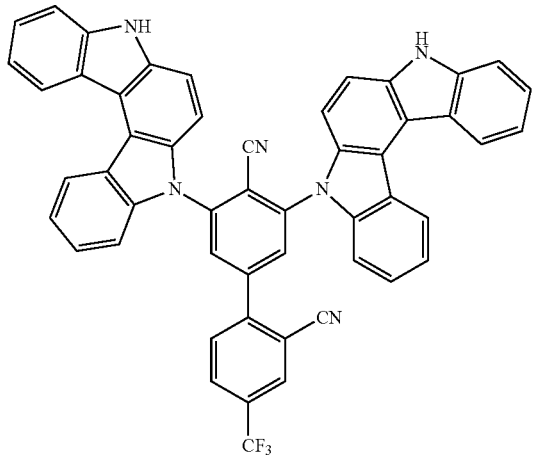 | 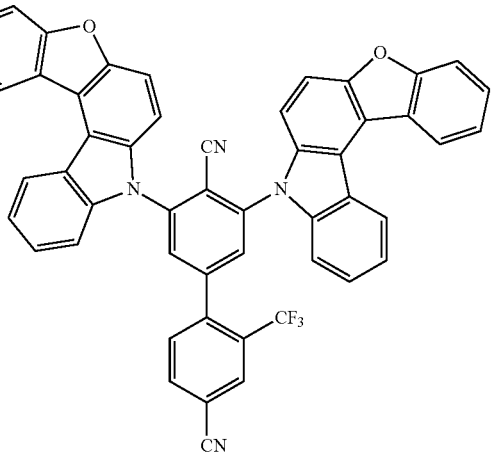 |
| 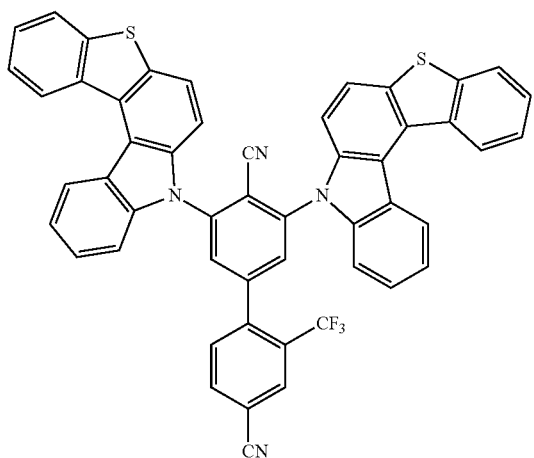 | 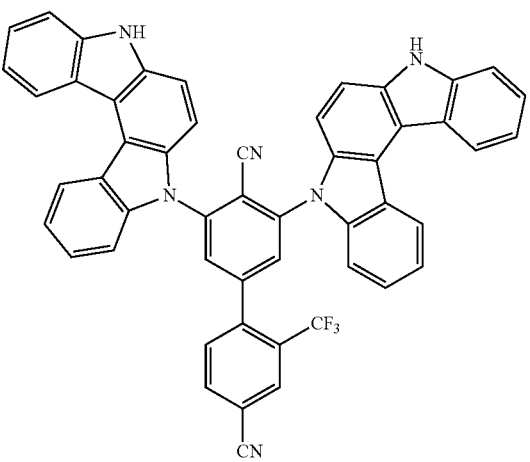 |
| 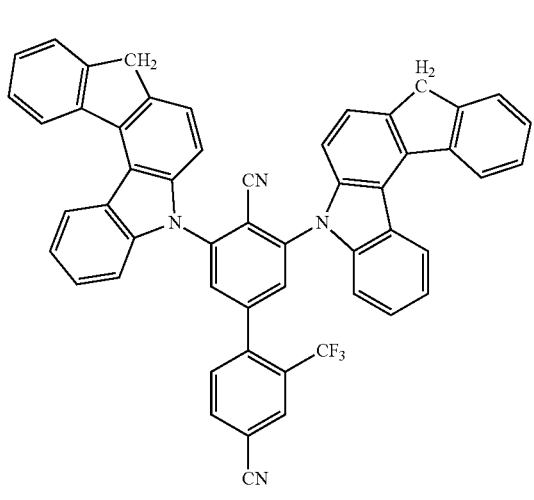 | 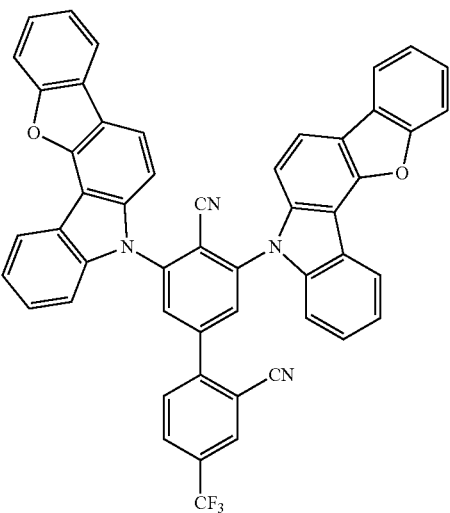 |

381
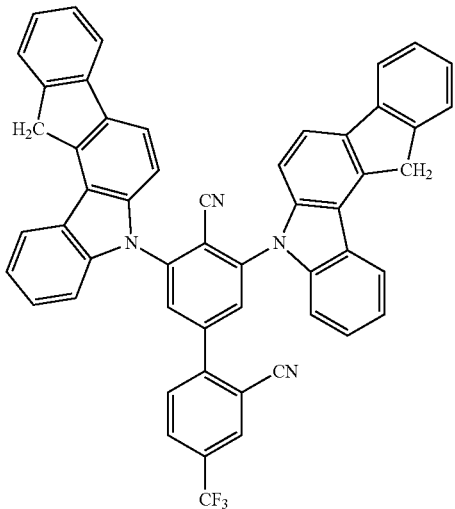
-continued
382
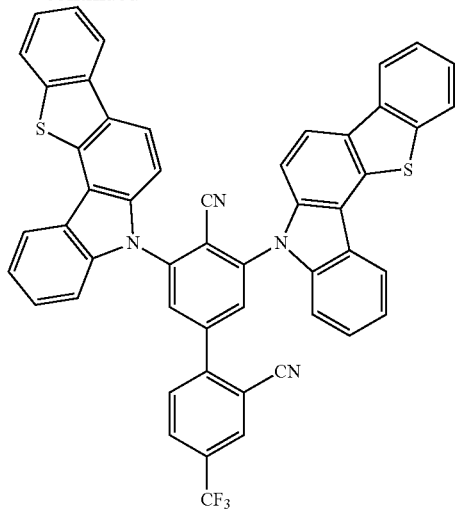
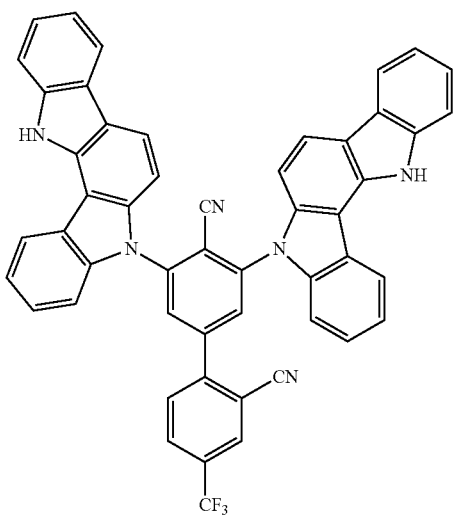
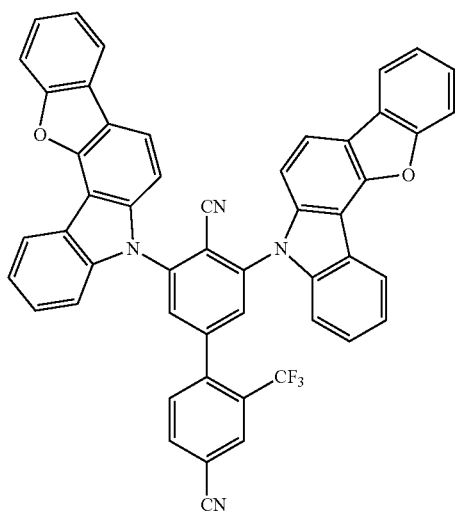
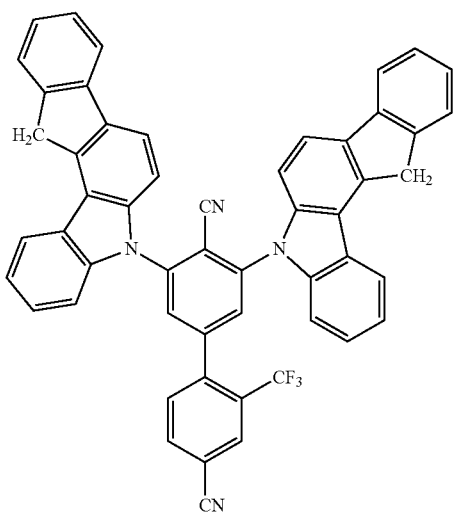
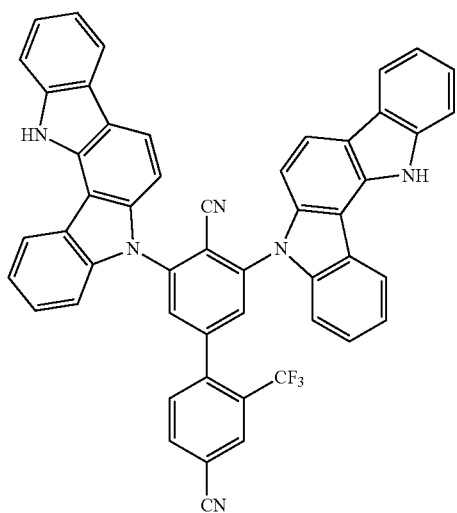

-continued

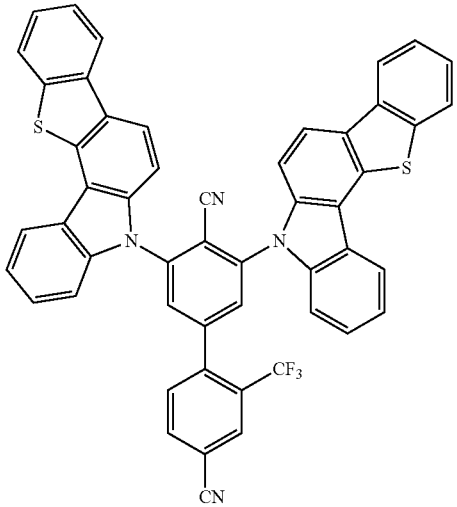

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:
1. An organic molecule, comprising:
a first chemical unit comprising or consisting of a structure according to Formula I,

Formula I

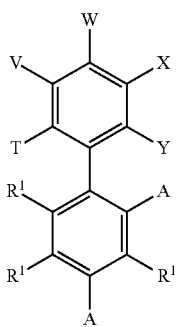

and
two second chemical units, which are respectively the same or different in each occurrence, having or consisting of a structure according to Formula II, Formula II

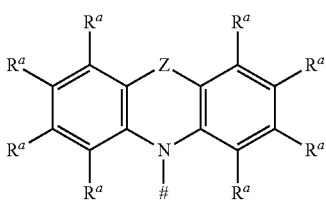

wherein, in each case, the first chemical unit is connected to the two second chemical units via a single bond;

with
T is the point of attachment of the single bond between the first chemical unit and a second chemical unit or is H;
V is the point of attachment of the single bond between the first chemical unit and a second chemical unit or is H;
W is the point of attachment of the single bond between the first chemical unit and a second chemical unit or is selected from the group consisting of H, CN and $CF_3$;
X is the point of attachment of the single bond between the first chemical unit and a second chemical unit or is selected from the group consisting of H, CN and $CF_3$, wherein when V is the point of attachment of the single bond between the first chemical unit and a second chemical unit, X is not the point of attachment of the single bond between the first chemical unit and another second chemical unit;
Y is the point of attachment of the single bond between the first chemical unit and a second chemical unit or is selected from the group consisting of H, CN and $CF_3$;
identifies the point of attachment of the single bond between a second chemical unit and the first chemical unit;
in each occurrence Z is the same or different, is a direct bond or is selected from the group consisting of $CR^3R^4$, $C=CR^3R^4$, $C=O$, $C=NR^3$, $NR^3$, O, $SiR^3R^4$, S, S(O) and $S(O)_2$;
in each occurrence, A is CN or $CF_3$;
in each occurrence $R^1$ is the same or different and is H, deuterium, a linear alkyl group having 1 to 5 C atoms, wherein in each case one or more H atoms can be replaced by deuterium; a linear alkenyl or alkynyl group having 2 to 8 C atoms, wherein in each case one or more H atoms can be replaced by deuterium; a branched or cyclic alkyl, alkenyl or alkynyl group having 3 to 10 C atoms, wherein in each case one or more H atoms can be replaced by deuterium; or an aromatic or heteroaromatic ring system having 5 to 15 aromatic ring atoms, which can in each case be substituted with one or more radicals $R^6$;
in each occurrence, $R^a$, $R^3$ and $R^4$ is the same or different and is H, deuterium, $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 C atoms, which can in each case be substituted with one or more radicals $R^5$, wherein one or more non-adjacent $CH_2$ groups can be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or CONR⁵ and wherein one or more H atoms can be replaced by deuterium, CN, CF₃ or NO₂; or a linear alkenyl or alkynyl group having 2 to 40 C atoms, which can in each case be substituted with one or more radicals R⁵, wherein one or more non-adjacent CH₂ groups can be replaced by R⁵C=CR⁵, C≡C, Si(R⁵)₂, Ge(R⁵)₂, Sn(R⁵)₂, C=O, C=S, C=Se, C=NR⁵, P(=O)(R⁵), SO, SO₂, NR⁵, O, S or CONR⁵ and wherein one or more H atoms can be replaced by deuterium, CN, CF₃ or NO₂; or a branched or cyclic alkyl, alkenyl, alkynyl, alkoxy or thioalkoxy group having 3 to 40 C atoms, which can in each case be substituted with one or more radicals R⁵, wherein one or more non-adjacent CH₂ groups can be replaced by R⁵C=CR⁵, C≡C, Si(R⁵)₂, Ge(R⁵)₂, Sn(R⁵)₂, C=O, C=S, C=Se, C=NR⁵, P(=O)(R⁵), SO, SO₂, NR⁵, O, S or CONR⁵ and wherein one or more H atoms can be replaced by deuterium, CN, CF₃ or NO₂; or an aromatic or heteroaromatic ring system having 5 to 60 aromatic ring atoms, which can in each case be substituted with one or more radicals R⁵, or an aryloxy or heteroaryloxy group having 5 to 60 aromatic ring atoms, which can in each case be substituted with one or more radicals R⁵, or a diarylamino group, diheteroarylamino group or arylheteroarylamino group having 10 to 40 aromatic ring atoms, which can in each case be substituted with one or more radicals R⁵;

in each occurrence, R⁵ is the same or different and is H, deuterium, N(R⁶)₂, OH, Si(R⁶)₃, B(OR⁶)₂, OSO₂R⁶, CF₃, CN, F, Br, I, a linear alkyl, alkoxy or thioalkoxy group having 1 to 40 C atoms, which can in each case be substituted with one or more radicals R⁶, wherein one or more non-adjacent CH₂ groups can be replaced by R⁶C=CR⁶, C≡C, Si(R⁶)₂, Ge(R⁶)₂, Sn(R⁶)₂, C=O, C=S, C=Se, C=NR⁶, P(=O)(R⁶), SO, SO₂, NR⁶, O, S or CONR⁶ and wherein one or more H atoms can be replaced by deuterium, CN, CF₃ or NO₂; or a linear alkenyl or alkynyl group having 2 to 40 C atoms, which can in each case be substituted with one or more radicals R⁶, wherein one or more non-adjacent CH₂ groups can be replaced by R⁶C=CR⁶, C≡C, Si(R⁶)₂, Ge(R⁶)₂, Sn(R⁶)₂, C=O, C=S, C=Se, C=NR⁶, P(=O)(R⁶), SO, SO₂, NR⁶, O, S or CONR⁶ and wherein one or more H atoms can be replaced by deuterium, CN, CF₃ or NO₂; or a branched or cyclic alkyl, alkenyl, alkynyl, alkoxy or thioalkoxy group having 3 to 40 C atoms, which can in each case be substituted with one or more radicals R⁶, wherein one or more non-adjacent CH₂ groups can be replaced by R⁶C=CR⁶, C≡C, Si(R⁶)₂, Ge(R⁶)₂, Sn(R⁶)₂, C=O, C=S, C=Se, C=NR⁶, P(=O)(R⁶), SO, SO₂, NR⁶, O, S or CONR⁶ and wherein one or more H atoms can be replaced by deuterium, CN, CF₃ or NO₂, or an aromatic or heteroaromatic ring system having 5 to 60 aromatic ring atoms, which can in each case be substituted with one or more radicals R⁶, or an aryloxy or heteroaryloxy group having 5 to 60 aromatic ring atoms, which can in each case be substituted with one or more radicals R⁶, or a diarylamino group, diheteroarylamino group or arylheteroarylamino group having 10 to 40 aromatic ring atoms, which can in each case be substituted with one or more radicals R⁶;

in each occurrence R⁶ is the same or different, is H, deuterium, OH, CF₃, CN, F, a linear alkyl, alkoxy or thioalkoxy group having 1 to 5 C atoms, wherein one or more H atoms can respectively be replaced by deuterium, CN, CF₃ or NO₂; or a linear alkenyl or alkynyl group having 2 to 5 C atoms, wherein one or more H atoms can respectively be replaced by deuterium, CN, CF₃ or NO₂; or a branched or cyclic alkyl, alkenyl, alkynyl, alkoxy or thioalkoxy group having 3 to 5 C atoms, wherein one or more H atoms can respectively be replaced by deuterium, CN, CF₃ or NO₂; or an aromatic or heteroaromatic ring system having 5 to 60 aromatic ring atoms or an aryloxy or heteroaryloxy group having 5 to 60 aromatic ring atoms or a diarylamino group, diheteroarylamino group or arylheteroarylamino group having 10 to 40 aromatic ring atoms;

wherein each of the radicals $R^a$, $R^3$, $R^4$ or $R^5$ can also form a mono- or polycyclic, aliphatic, aromatic and/or benzoannelated ring system with one or more further radicals $R^a$, $R^3$, $R^4$ or $R^5$;

wherein one A is CF₃ and the other A is CN;

wherein exactly one radical selected from the group consisting of W, X and Y is CN or is CF₃; and wherein exactly two radicals selected from the group consisting of T, V, W, X and Y are a point of attachment of the single bond between the first chemical unit and a second chemical unit D.

2. The organic molecule according to claim 1, wherein the first chemical unit has a structure of Formula Ia:

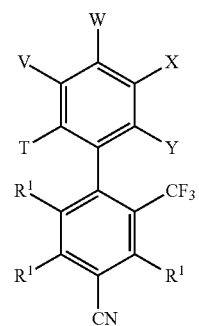

Formula Ia wherein R¹, T, V, W, X, and Y have the aforestated meanings.

3. The organic molecule according to claim 1, wherein, in each occurrence, R¹ is the same or different and is H, methyl or phenyl.

4. The organic molecule according to claim 1, wherein W is CN.

5. The organic molecule according to claim 1, wherein, in each occurrence, the second chemical unit is the same or different and has a structure of Formula IIa:

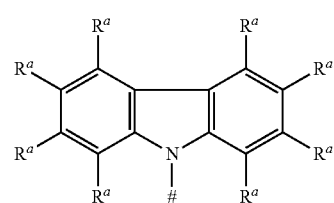

Formula IIa wherein # and $R^a$ have the aforestated meanings.

6. The organic molecule according to claim 1, wherein, in each case, the second chemical unit has a structure of Formula IIb:

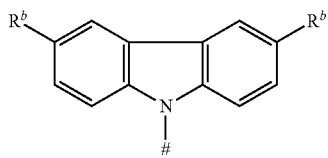

Formula IIb wherein
in each occurrence, $R^b$ is the same or different and is $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 C atoms, which can in each case be substituted with one or more radicals $R^5$, wherein one or more non-adjacent $CH_2$ groups can be replaced by $R^5C=CR^5$, $C\equiv C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$; or a linear alkenyl or alkynyl group having 2 to 40 C atoms, which can in each case be substituted with one or more radicals $R^5$, wherein one or more non-adjacent $CH_2$ groups can be replaced by $R^5C=CR^5$, $C\equiv C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$; or a branched or cyclic alkyl, alkenyl, alkynyl, alkoxy or thioalkoxy group having 3 to 40 C atoms, which can in each case be substituted with one or more radicals $R^5$, wherein one or more non-adjacent $CH_2$ groups can be replaced by $R^5C=CR^5$, $C\equiv C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$; or an aromatic or heteroaromatic ring system having 5 to 60 aromatic ring atoms, which can in each case be substituted with one or more radicals $R^5$, or an aryloxy or heteroaryloxy group having 5 to 60 aromatic ring atoms, which can in each case be substituted with one or more radicals $R^5$, or a diarylamino group, diheteroarylamino group or arylheteroarylamino group having 10 to 40 aromatic ring atoms, which can in each case be substituted with one or more radicals $R^5$; and # and $R^5$ have the aforestated meanings.

7. The organic molecule according to claim 1, wherein, in each case, the second chemical unit D has a structure of Formula IIc:

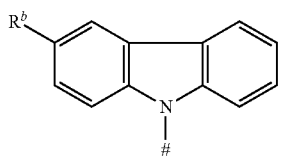

Formula IIc wherein
in each occurrence, $R^b$ is the same or different and is $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 C atoms, which can in each case be substituted with one or more radicals $R^5$, wherein one or more non-adjacent $CH_2$ groups can be replaced by $R^5C=CR^5$, $C\equiv C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$; or a linear alkenyl or alkynyl group having 2 to 40 C atoms, which can in each case be substituted with one or more radicals $R^5$, wherein one or more non-adjacent $CH_2$ groups can be replaced by $R^5C=CR^5$, $C\equiv C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$; or a branched or cyclic alkyl, alkenyl, alkynyl, alkoxy or thioalkoxy group having 3 to 40 C atoms, which can in each case be substituted with one or more radicals $R^5$, wherein one or more non-adjacent $CH_2$ groups can be replaced by $R^5C=CR^5$, $C\equiv C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$; or an aromatic or heteroaromatic ring system having 5 to 60 aromatic ring atoms, which can in each case be substituted with one or more radicals $R^5$, or an aryloxy or heteroaryloxy group having 5 to 60 aromatic ring atoms, which can in each case be substituted with one or more radicals $R^5$, or a diarylamino group, diheteroarylamino group or arylheteroarylamino group having 10 to 40 aromatic ring atoms, which can in each case be substituted with one or more radicals $R^5$; and # and $R^5$ have the aforestated meanings.

8. The organic molecule according to claim 6, wherein, in each occurrence, $R^b$ is the same or different and is Me, $^i$Pr, $^t$Bu, CN, $CF_3$ or Ph, which can in each case be substituted with one or more radicals selected from Me, $^i$Pr, $^t$Bu, CN, $CF_3$ or Ph, pyridinyl, which can in each case be substituted with one or more radicals selected from Me, $^i$Pr, $^t$Bu, CN, $CF_3$ or Ph, pyrimidinyl, which can in each case be substituted with one or more radicals selected from Me, $^i$Pr, $^t$Bu, CN, $CF_3$ or Ph, triazinyl, which can in each case be substituted with one or more radicals selected from Me, $^i$Pr, $^t$Bu, CN, $CF_3$ or Ph, or carbazolyl, which can in each case be substituted with one or more radicals selected from Me, $^i$Pr, $^t$Bu, CN, $CF_3$ or Ph.

9. A composition comprising:
(a) at least one organic molecule according to claim 1 as an emitter and/or a host;
(b) one or more emitter and/or host materials different from the at least one organic molecule according to claim 1, and
(c) optionally one or more dyes and/or one or more solvents.

10. An optoelectronic device comprising an organic molecule according to claim 1.

11. The optoelectronic device according to claim 10, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

12. The optoelectronic device according to claim 10, wherein the organic molecule is one of an emitter and an absorber in the optoelectronic device.

13. The optoelectronic device according to claim 10, comprising:
- a substrate;
- an anode;
- a cathode, wherein the anode or the cathode is applied to the substrate; and
- at least one light-emitting layer disposed between the anode and the cathode and which comprises the organic molecule.

14. The optoelectronic device according to claim 13, wherein a proportion of the organic molecule in the emitter or the absorber is in the range of 1% to 80%.

15. An optoelectronic device comprising an organic molecule according to claim 2.

16. The optoelectronic device according to claim 15, comprising:
- a substrate;
- an anode;
- a cathode, wherein the anode or the cathode is applied to the substrate; and
- at least one light-emitting layer disposed between the anode and the cathode and which comprises the organic molecule.

17. The optoelectronic device according to claim 16, wherein a proportion of the organic molecule in the emitter or the absorber is in the range of 1% to 80%.

18. An optoelectronic device comprising the composition according to claim 9.

19. The optoelectronic device according to claim 18, comprising:
- a substrate;
- an anode;
- a cathode, wherein the anode or the cathode is applied to the substrate; and
- at least one light-emitting layer disposed between the anode and the cathode and which comprises the composition.

20. The optoelectronic device according to claim 18, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

* * * * *